US010358628B2

(12) United States Patent
Rezania

(10) Patent No.: US 10,358,628 B2
(45) Date of Patent: Jul. 23, 2019

(54) DIFFERENTIATION OF HUMAN EMBRYONIC STEM CELLS INTO SINGLE HORMONAL INSULIN POSITIVE CELLS

(71) Applicant: Janssen Biotech, Inc., Horsham, PA (US)

(72) Inventor: Alireza Rezania, Skillman, NJ (US)

(73) Assignee: JANSSEN BIOTECH, INC., Horsham, PA (US)

(*) Notice: Subject to any disclaimer, the term of this patent is extended or adjusted under 35 U.S.C. 154(b) by 0 days.

(21) Appl. No.: 14/831,115

(22) Filed: Aug. 20, 2015

(65) Prior Publication Data

US 2015/0353895 A1    Dec. 10, 2015

Related U.S. Application Data

(62) Division of application No. 13/708,369, filed on Dec. 7, 2012, now Pat. No. 9,388,386.

(60) Provisional application No. 61/579,351, filed on Dec. 22, 2011.

(51) Int. Cl.
*C12N 5/071* (2010.01)

(52) U.S. Cl.
CPC ........ *C12N 5/0676* (2013.01); *C12N 2500/34* (2013.01); *C12N 2500/38* (2013.01); *C12N 2501/117* (2013.01); *C12N 2501/15* (2013.01); *C12N 2501/155* (2013.01); *C12N 2501/16* (2013.01); *C12N 2501/19* (2013.01); *C12N 2501/385* (2013.01); *C12N 2501/41* (2013.01); *C12N 2501/415* (2013.01); *C12N 2501/727* (2013.01); *C12N 2506/02* (2013.01)

(58) Field of Classification Search
CPC .................................................. C12N 5/0676
See application file for complete search history.

(56) References Cited

U.S. PATENT DOCUMENTS

| | | |
|---|---|---|
| 3,209,652 A | 10/1965 | Burgsmueller |
| 3,845,641 A | 11/1974 | Waller |
| 3,935,067 A | 1/1976 | Thayer |
| 4,499,802 A | 2/1985 | Simpson |
| 4,537,773 A | 8/1985 | Shenvi |
| 4,557,264 A | 12/1985 | Hinsch |
| 4,737,578 A | 4/1988 | Evans et al. |
| 5,215,893 A | 6/1993 | Mason et al. |
| 5,449,383 A | 9/1995 | Chatelier et al. |
| 5,525,488 A | 6/1996 | Mason et al. |
| 5,567,612 A | 10/1996 | Vacanti et al. |
| 5,665,568 A | 9/1997 | Mason et al. |
| 5,686,090 A | 11/1997 | Schilder et al. |
| 5,713,957 A | 2/1998 | Steele et al. |
| 5,716,810 A | 2/1998 | Mason et al. |
| 5,718,922 A | 2/1998 | Herrero-Vanrell |
| 5,759,830 A | 6/1998 | Vacanti et al. |
| 5,770,417 A | 6/1998 | Vacanti et al. |
| 5,780,454 A | 7/1998 | Adams et al. |
| 5,834,308 A | 11/1998 | Peck et al. |
| 5,843,780 A | 12/1998 | Thomson |
| 5,888,816 A | 3/1999 | Coon et al. |
| 5,908,782 A | 6/1999 | Marshank et al. |
| 5,914,262 A | 6/1999 | MacMichael et al. |
| 5,942,435 A * | 8/1999 | Wheeler ............ A01K 67/0271 435/325 |
| 6,001,647 A | 12/1999 | Peck et al. |
| 6,022,743 A | 2/2000 | Naughton et al. |
| 6,087,113 A | 6/2000 | Caplan et al. |
| 6,083,903 A | 7/2000 | Adams et al. |
| 6,200,806 B1 | 3/2001 | Thomson |
| 6,261,549 B1 | 6/2001 | Fernandez et al. |
| 6,281,012 B1 | 8/2001 | McIntosh et al. |
| 6,297,217 B1 | 10/2001 | Adams et al. |
| 6,306,424 B1 | 10/2001 | Vyakaman et al. |
| 6,328,960 B1 | 12/2001 | McIntosh et al. |
| 6,331,298 B1 | 12/2001 | Ferguson et al. |
| 6,333,029 B1 | 12/2001 | Vyakamam et al. |
| 6,365,149 B2 | 2/2002 | Vyakamam et al. |
| 6,413,773 B1 | 7/2002 | Ptasznik et al. |
| 6,436,704 B1 | 8/2002 | Roberts et al. |
| 6,458,589 B1 | 10/2002 | Rambhatla |
| 6,458,593 B1 | 10/2002 | Musick et al. |
| 6,509,369 B2 | 1/2003 | Scott et al. |
| 6,521,427 B1 | 2/2003 | Evans |
| 6,534,084 B1 | 3/2003 | Vyakamam et al. |
| 6,599,323 B2 | 7/2003 | Melican et al. |
| 6,617,152 B2 | 9/2003 | Bryhan et al. |
| 6,617,317 B1 | 9/2003 | Adams et al. |
| 6,626,950 B2 | 9/2003 | Brown et al. |
| 6,642,048 B2 | 11/2003 | Xu |
| 6,656,488 B2 | 12/2003 | Yi et al. |
| 6,670,127 B2 | 12/2003 | Evans |
| 6,703,017 B1 | 3/2004 | Peck et al. |
| 6,713,446 B2 | 3/2004 | Gupta |
| 6,793,945 B2 | 9/2004 | Bathurst et al. |
| 6,800,480 B1 | 10/2004 | Bodnar et al. |
| 6,815,203 B1 | 11/2004 | Bonner-Weir et al. |
| 6,958,319 B2 | 10/2005 | Gupta |
| 6,987,110 B2 | 1/2006 | Zhang et al. |
| 7,005,252 B1 | 2/2006 | Thomson et al. |
| 7,033,831 B2 | 4/2006 | Fisk et al. |

(Continued)

FOREIGN PATENT DOCUMENTS

| | | |
|---|---|---|
| CN | 1389565 A | 7/2002 |
| CN | 1602351 A | 3/2005 |

(Continued)

OTHER PUBLICATIONS

Zhang et al. (2009, Cell Research, vol. 19, pp. 429-438).*

(Continued)

*Primary Examiner* — Thaian N Ton
*Assistant Examiner* — David A. Montanari
(74) *Attorney, Agent, or Firm* — Klarquist Sparkman, LLP

(57) ABSTRACT

The present invention provides methods to promote the differentiation of pluripotent stem cells. In particular, the present invention provides methods to produce a population of cells, wherein greater than 10% of the cells in the population express markers characteristic of single hormonal pancreatic beta cells.

35 Claims, 79 Drawing Sheets

(56) References Cited

U.S. PATENT DOCUMENTS

| | | |
|---|---|---|
| 7,157,275 B2 | 1/2007 | Guarino et al. |
| 7,297,539 B2 | 11/2007 | Mandalam et al. |
| 7,326,572 B2 | 2/2008 | Fisk et al. |
| 7,371,576 B2 | 5/2008 | Tsang et al. |
| 7,410,798 B2 | 8/2008 | Mandalam et al. |
| 7,413,734 B2 | 8/2008 | Mistry et al. |
| 7,442,548 B2 | 10/2008 | Thomson et al. |
| 7,449,334 B2 | 11/2008 | Thomsom et al. |
| 7,510,873 B2 | 3/2009 | Mistry et al. |
| 7,510,876 B2 | 3/2009 | D'Amour et al. |
| 7,534,608 B2 | 5/2009 | Martinson et al. |
| 7,541,185 B2 | 6/2009 | D'Amour et al. |
| 7,569,385 B2 | 8/2009 | Haas |
| 7,585,672 B2 | 9/2009 | Odorico et al. |
| 7,704,738 B2 | 4/2010 | D'Amour et al. |
| 7,993,920 B2 | 8/2011 | Martinson et al. |
| 8,187,878 B2 | 5/2012 | Dalton et al. |
| 8,859,286 B2 | 10/2014 | Agulnick |
| 8,987,471 B2 | 3/2015 | Takeuchi et al. |
| 9,528,090 B2 | 12/2016 | Rezania |
| 10,066,210 B2 | 9/2018 | Rezania |
| 2002/0072117 A1 | 6/2002 | Xu |
| 2003/0082155 A1 | 5/2003 | Habener |
| 2003/0138948 A1 | 7/2003 | Fisk et al. |
| 2003/0180268 A1 | 9/2003 | Atala |
| 2003/0180903 A1 | 9/2003 | Bryhan et al. |
| 2004/0015805 A1 | 1/2004 | Kidd |
| 2004/0058412 A1 | 3/2004 | Ho et al. |
| 2004/0062753 A1 | 4/2004 | Rezania |
| 2004/0106196 A1 | 6/2004 | Fraser et al. |
| 2004/0121460 A1 | 6/2004 | Lumelsky et al. |
| 2004/0121461 A1 | 6/2004 | Honmou et al. |
| 2004/0132729 A1 | 7/2004 | Salituro et al. |
| 2004/0161419 A1 | 8/2004 | Strom et al. |
| 2004/0171623 A1 | 9/2004 | Reynolds et al. |
| 2004/0209901 A1 | 10/2004 | Adams et al. |
| 2004/0220393 A1 | 11/2004 | Ward et al. |
| 2004/0241761 A1 | 12/2004 | Sarvetnick |
| 2005/0037491 A1 | 2/2005 | Mistry et al. |
| 2005/0053588 A1 | 3/2005 | Yin et al. |
| 2005/0054093 A1 | 3/2005 | Haas |
| 2005/0054098 A1 | 3/2005 | Mistry et al. |
| 2005/0054102 A1 | 3/2005 | Wobus et al. |
| 2005/0058631 A1 | 3/2005 | Kihm et al. |
| 2005/0063961 A1 | 3/2005 | Friedlander et al. |
| 2005/0118148 A1 | 6/2005 | Stein et al. |
| 2005/0148070 A1 | 7/2005 | Thomson et al. |
| 2005/0158852 A1 | 7/2005 | Wang et al. |
| 2005/0187298 A1 | 8/2005 | Vasudevan et al. |
| 2005/0037488 A1 | 9/2005 | Mitalipova |
| 2005/0208029 A1 | 9/2005 | Umezawa et al. |
| 2005/0233446 A1 | 10/2005 | Parsons |
| 2005/0244962 A1 | 11/2005 | Thomson et al. |
| 2005/0260749 A1 | 11/2005 | Odorico et al. |
| 2005/0266554 A1 | 12/2005 | D'Amour |
| 2006/0003313 A1 | 1/2006 | D'Amour et al. |
| 2006/0003446 A1 | 1/2006 | Keller |
| 2006/0030042 A1 | 2/2006 | Brivaniou et al. |
| 2006/0040387 A1 | 2/2006 | Fisk |
| 2006/0148081 A1 | 7/2006 | Kelly et al. |
| 2006/0194315 A1 | 8/2006 | Condie et al. |
| 2006/0194321 A1 | 8/2006 | Colman et al. |
| 2006/0281174 A1 | 12/2006 | Xu et al. |
| 2007/0010011 A1 | 1/2007 | Parsons |
| 2007/0082397 A1 | 4/2007 | Hasson et al. |
| 2007/0122903 A1 | 5/2007 | Rezania et al. |
| 2007/0122905 A1 | 5/2007 | D'Amour et al. |
| 2007/0141702 A1 | 6/2007 | Revazova et al. |
| 2007/0154981 A1 | 7/2007 | Hori et al. |
| 2007/0155013 A1 | 7/2007 | Akaike et al. |
| 2007/0155661 A1 | 7/2007 | Kim |
| 2007/0254359 A1 | 11/2007 | Rezania et al. |
| 2007/0259421 A1 | 11/2007 | D'Amour et al. |
| 2007/0259423 A1 | 11/2007 | Odorico |
| 2007/0264713 A1 | 11/2007 | Terstegge et al. |
| 2008/0091234 A1 | 4/2008 | Kladakis et al. |
| 2008/0139662 A1 | 6/2008 | Brinkmann et al. |
| 2008/0159994 A1 | 7/2008 | Mantalaris et al. |
| 2008/0241107 A1 | 10/2008 | Copland, III et al. |
| 2008/0260700 A1 | 10/2008 | Accili et al. |
| 2008/0267926 A1 | 10/2008 | Martinson et al. |
| 2008/0268533 A1 | 10/2008 | Dalton et al. |
| 2008/0268534 A1 | 10/2008 | Robins et al. |
| 2009/0004152 A1 | 1/2009 | Martinson et al. |
| 2009/0029462 A1 | 1/2009 | Beardsley et al. |
| 2009/0029947 A1 | 1/2009 | Wallace et al. |
| 2009/0053182 A1 | 2/2009 | Ichim et al. |
| 2009/0093055 A1 | 4/2009 | Fisk et al. |
| 2009/0170198 A1 | 7/2009 | Rezania |
| 2009/0203141 A1 | 8/2009 | Lin et al. |
| 2009/0263896 A1 | 10/2009 | Kelly et al. |
| 2009/0269845 A1 | 10/2009 | Rezania et al. |
| 2009/0298178 A1 | 12/2009 | D'Amour |
| 2009/0325293 A1 | 12/2009 | Davis et al. |
| 2010/0003749 A1 | 1/2010 | Uchida et al. |
| 2010/0015100 A1 | 1/2010 | Xu |
| 2010/0015711 A1 | 1/2010 | Davis et al. |
| 2010/0028307 A1 | 2/2010 | O'Neil |
| 2010/0093053 A1 | 4/2010 | Oh et al. |
| 2010/0112691 A1 | 5/2010 | Green et al. |
| 2010/0112693 A1 | 5/2010 | Rezania et al. |
| 2010/0255580 A1 | 10/2010 | Rezania |
| 2011/0014702 A1 | 1/2011 | Xu et al. |
| 2011/0014703 A1 | 1/2011 | Xu et al. |
| 2011/0104805 A1 | 5/2011 | Fung et al. |
| 2011/0151560 A1 | 6/2011 | Xu |
| 2011/0151561 A1 | 6/2011 | Davis et al. |
| 2011/0229441 A1 | 9/2011 | Benchoua et al. |
| 2011/0280842 A1 | 11/2011 | Melton et al. |
| 2011/0281355 A1 | 11/2011 | Xu |
| 2012/0045830 A1 | 2/2012 | Green et al. |
| 2012/0052576 A1 | 3/2012 | Rezania |
| 2012/0190111 A1 | 7/2012 | Davis et al. |
| 2012/0264209 A1 | 10/2012 | Odorico et al. |
| 2013/0109092 A1 | 5/2013 | Matsuyama et al. |
| 2013/0189777 A1 | 7/2013 | Rezania |
| 2013/0224156 A1 | 8/2013 | Takahashi et al. |
| 2014/0186953 A1 | 7/2014 | Rezania |
| 2014/0228324 A1 | 8/2014 | Takeuchi et al. |

FOREIGN PATENT DOCUMENTS

| | | |
|---|---|---|
| CN | 1671835 A | 9/2005 |
| CN | 1946838 A | 4/2007 |
| CN | 101092606 A | 12/2007 |
| CN | 101310012 A | 11/2008 |
| CN | 101410509 A | 4/2009 |
| CN | 101541953 A | 9/2009 |
| CN | 101611016 A | 12/2009 |
| EP | 0363125 A2 | 4/1990 |
| EP | 348969 B1 | 5/1993 |
| EP | 0617126 B1 | 9/1994 |
| EP | 0800829 B1 | 10/1997 |
| EP | 0092302 B1 | 11/2006 |
| EP | 1873237 A1 | 1/2008 |
| EP | 1391505 B1 | 1/2009 |
| EP | 2088190 A1 | 8/2009 |
| EP | 2559756 A1 | 2/2013 |
| EP | 2674485 A1 | 12/2013 |
| EP | 2479260 B1 | 6/2016 |
| GB | 2484873 B2 | 4/2014 |
| JP | 2005506074 A2 | 3/2003 |
| JP | 2005537803 A | 12/2005 |
| JP | 2006-500003 A2 | 1/2006 |
| JP | 2008500809 A2 | 1/2008 |
| JP | 2009513143 A2 | 4/2009 |
| JP | A-2011-172586 | 9/2011 |
| JP | 2013528356 A | 7/2013 |
| KR | 10-2008-0020098 A | 3/2008 |
| KR | 10-2012-0039025 A | 4/2012 |
| KZ | 18625 | 7/2007 |
| RU | 1767433 A1 | 10/1992 |
| RU | 2215029 C2 | 2/2000 |
| RU | 2359030 C1 | 6/2009 |

(56) References Cited

FOREIGN PATENT DOCUMENTS

| | | |
|---|---|---|
| RU | 2359671 C2 | 6/2009 |
| WO | WO199219759 A2 | 2/1992 |
| WO | 1996040172 A1 | 12/1996 |
| WO | 199830679 A1 | 7/1998 |
| WO | 199847892 A1 | 10/1998 |
| WO | WO199920741 A1 | 4/1999 |
| WO | 200029549 A1 | 5/2000 |
| WO | WO 2000/47717 | 8/2000 |
| WO | 200123528 A1 | 4/2001 |
| WO | WO200151616 A2 | 7/2001 |
| WO | WO200181549 A3 | 11/2001 |
| WO | 200246183 A2 | 6/2002 |
| WO | 200246197 A1 | 6/2002 |
| WO | 2002086107 A2 | 10/2002 |
| WO | 02092756 A2 | 11/2002 |
| WO | 03033697 A1 | 4/2003 |
| WO | 2003026584 A2 | 4/2003 |
| WO | 2003029445 A1 | 4/2003 |
| WO | 2003042405 A2 | 5/2003 |
| WO | WO200305049 A1 | 6/2003 |
| WO | 2003054169 A1 | 7/2003 |
| WO | 2003062405 A2 | 7/2003 |
| WO | 2003095452 A1 | 11/2003 |
| WO | 03103972 A1 | 12/2003 |
| WO | WO2003102134 A2 | 12/2003 |
| WO | 2004016747 A2 | 2/2004 |
| WO | WO2004011621 A2 | 2/2004 |
| WO | 2004044158 | 5/2004 |
| WO | 2004050827 A2 | 6/2004 |
| WO | 2004055155 A2 | 7/2004 |
| WO | 2004073633 A1 | 9/2004 |
| WO | 2004087885 | 10/2004 |
| WO | WO2004090110 A2 | 10/2004 |
| WO | 2004067001 A1 | 12/2004 |
| WO | 2005080598 A1 | 1/2005 |
| WO | WO2005001077 A2 | 1/2005 |
| WO | 2005017117 A2 | 2/2005 |
| WO | WO2005014799 A1 | 2/2005 |
| WO | 2005058301 A1 | 6/2005 |
| WO | 2005063971 A1 | 7/2005 |
| WO | 2005065354 A2 | 7/2005 |
| WO | 2005080551 A2 | 9/2005 |
| WO | 2005086845 A2 | 9/2005 |
| WO | 2005097977 A2 | 10/2005 |
| WO | 2005097980 A2 | 10/2005 |
| WO | WO2005116073 A3 | 12/2005 |
| WO | 2006020919 A2 | 2/2006 |
| WO | 2006088867 A2 | 2/2006 |
| WO | WO2006016999 A1 | 2/2006 |
| WO | 2006026473 A1 | 3/2006 |
| WO | 2006029197 A1 | 3/2006 |
| WO | 2006036925 A1 | 4/2006 |
| WO | 2006080952 A2 | 8/2006 |
| WO | 2006083782 A2 | 8/2006 |
| WO | 2006100490 A1 | 9/2006 |
| WO | WO2006094286 A2 | 9/2006 |
| WO | 2006108361 A1 | 10/2006 |
| WO | 2006113470 A2 | 10/2006 |
| WO | 2006114098 A2 | 11/2006 |
| WO | 2006126574 A1 | 11/2006 |
| WO | 2006135824 A1 | 12/2006 |
| WO | 2006137787 A1 | 12/2006 |
| WO | 2006138433 A2 | 12/2006 |
| WO | 2007002086 A2 | 1/2007 |
| WO | 2007003525 A2 | 1/2007 |
| WO | 2007012144 A1 | 2/2007 |
| WO | 2007016485 A2 | 2/2007 |
| WO | 2007026353 A2 | 3/2007 |
| WO | 2007030870 A1 | 3/2007 |
| WO | WO2007027157 A1 | 3/2007 |
| WO | 2007047509 A1 | 4/2007 |
| WO | 2007051038 A2 | 5/2007 |
| WO | 2007069666 A1 | 6/2007 |
| WO | WO2007082963 A1 | 7/2007 |
| WO | 2007101130 A2 | 9/2007 |
| WO | WO2007103282 A1 | 9/2007 |
| WO | 2007127927 A2 | 11/2007 |
| WO | 2007136673 A2 | 11/2007 |
| WO | 2007143193 A1 | 12/2007 |
| WO | 2007149182 A2 | 12/2007 |
| WO | WO2007139929 A2 | 12/2007 |
| WO | 2008004990 A2 | 1/2008 |
| WO | 2008013664 A1 | 1/2008 |
| WO | 2008015682 A2 | 2/2008 |
| WO | 2008035110 A1 | 3/2008 |
| WO | 2008036447 A2 | 3/2008 |
| WO | 2008048671 A1 | 4/2008 |
| WO | WO2008048647 A1 | 4/2008 |
| WO | 2009096049 A1 | 5/2008 |
| WO | 2008086005 A1 | 7/2008 |
| WO | 2008094597 | 8/2008 |
| WO | 2008102118 A1 | 8/2008 |
| WO | 2009012428 A1 | 1/2009 |
| WO | WO 2009/006399 A1 | 1/2009 |
| WO | 2009018453 A1 | 2/2009 |
| WO | 2009027644 A2 | 3/2009 |
| WO | WO2009048675 A1 | 4/2009 |
| WO | 2009061442 A1 | 5/2009 |
| WO | 2009070592 A1 | 6/2009 |
| WO | 2009096902 A1 | 8/2009 |
| WO | 2009101407 A2 | 8/2009 |
| WO | WO2009105570 A2 | 8/2009 |
| WO | 2009110215 A1 | 9/2009 |
| WO | 2009131568 A1 | 10/2009 |
| WO | 2009132083 A2 | 10/2009 |
| WO | 2009154606 A1 | 12/2009 |
| WO | 2010000415 A1 | 1/2010 |
| WO | 2010002846 A1 | 1/2010 |
| WO | 2010051213 A1 | 5/2010 |
| WO | 2010051223 A1 | 5/2010 |
| WO | 2010053472 A1 | 5/2010 |
| WO | 2010057039 A2 | 5/2010 |
| WO | 2010059775 A1 | 5/2010 |
| WO | 2011011300 A2 | 1/2011 |
| WO | WO 2011/019092 A1 | 2/2011 |
| WO | WO 2011/058558 A2 | 5/2011 |
| WO | 2011067465 A1 | 6/2011 |
| WO | WO 2011/079017 A2 | 6/2011 |
| WO | WO 2011/081222 A1 | 7/2011 |
| WO | 2011096223 A1 | 8/2011 |
| WO | 2011108993 A1 | 9/2011 |
| WO | 2011123572 A1 | 10/2011 |
| WO | 2011139628 A1 | 11/2011 |
| WO | WO 2011/158960 A1 | 12/2011 |
| WO | WO 2011/160066 A1 | 12/2011 |
| WO | 2012019122 A2 | 2/2012 |
| WO | WO 2012/030540 A2 | 3/2012 |
| WO | 2012117333 A2 | 9/2012 |
| WO | 2013055397 A1 | 4/2013 |
| WO | 2013055834 A2 | 4/2013 |
| WO | WO 2013/056072 A1 | 4/2013 |
| WO | 2013095953 A1 | 6/2013 |
| WO | 2013184888 A1 | 12/2013 |
| WO | 2014033322 A1 | 3/2014 |
| WO | 2014105546 A1 | 7/2014 |
| WO | 2014152321 A1 | 9/2014 |

OTHER PUBLICATIONS

Munoz et al. (2008, Theriogenology, vol. 69, pp. 1159-1164).*
Paris et al. (2010, Theriogenology, vol. 74, pp. 516-524).*
Brevini et al., 2010, Theriogenology, vol. 74, pp. 544-550.*
Baetge, Production of B-Cells from Human Embryonic Stem Cells, Diabetes, Obesity, Metabolism, 2008, pp. 186-194, vol. 10, Supplement 4.
Bocian-Sobkowska, et al., Polyhormonal Aspect of the Endocrine Cells of the Human Fetal Pancreas, Histochem Cell Biol, 1999, pp. 147-153, vol. 112, Issue 2.
Borowiak, et al., How to Make AB Cells, Current Opinion Cell Biology, 2009, pp. 727-732, vol. 21, Issue 6.
Cao, et al., High Glucose is Necssary for Complete Maturation of Pdx1-VP16-Expressing Hepatic Cells into Functional Insulin-Producing Cells, Diabetes, 2004, pp. 3168-3176, vol. 53.

(56) References Cited

OTHER PUBLICATIONS

Chen, et al., A Small Molecule that Directs Differentiation of Human ESCs into the Pancreatic Lineage, Nature Chemical Biology, Apr. 11, 2009, pp. 258-265, vol. 5, No. 4.
D'Amour et al., Efficient differentiation of human embryonic stem cells to definitive endoderm, Nature Biotechnology, Oct. 28, 2005, 1-8, :W.1038/nbt1163, Nature Publishing Group.
D'Amour et al., Production of pancreatic hormone-expressing endocrine cells from human embryonic stem cells, Nature Biotechnology, Oct. 19, 2006, 1392-1401, 24-11, Nature Publishing Group, US.
Jeon, et al., Endocrine Cell Clustering During Human Pancreas Development, J Histochem Cytochem, 2009, pp. 811-824, vol. 57, Issue 9.
Jiang, et al., Generation of Insulin-Producing Islet-Like Clusters from Human Embryonic Stem Cells, Stem Cells, 2007, pp. 1940-1953, vol. 25, Issue 8.
Jiang, et al., In Vitro Derivation of Functional Insulin-Producing Cells from Human Embryonic Stem Cells, Cell Research, 2007, pp. 333-344, vol. 17.
Kelly, et al., Cell-Surface Markers for the Isolation of Pancreatic Cell Types Derived from Human Embryonic Stem Cells, Nature Biotechnology, 2011, pp. 750-756, vol. 29, Issue 8.
Kroon, et al., Pancreatic Endoderm Derived from Human Embryonic Stem Cells Generates Glucose-Responsive Insulin-Secreting Cells in vivo, Nature Biotechnology, Apr. 2008, pp. 443-452, vol. 26, No. 4.
Loh, et al., Genomic Approaches to Deconstruct Puripotency, Annu Rev Genomics Hum Genet, 2011, pp. 165-185, vol. 12.
McLin, et al., Repression of WNT/(szligbeta)-6atenin Signaling in the Anterior Endoderm is Essential for Liver and Pancreas Development, Development, 2007, pp. 2207-2217, vol. 134, Issue 12.
Nostro, et al., Stage-Specific Signaling Through TGF Family Members and WNT Regulates Patterning and Pancreatic Specification of Human Pluripotent Stem Cells, Development, 2011, pp. 861-871, vol. 138, Issue 5.
Rezania, et al., Enrichman of Human Embryonic Stem Cell-Derived NKX6.1—Expressing Pancreatic Progenitor Cells Accelerates the Maturation of Insulin-Secreting Cells in Vivo, Stem Cells, 2013, pp. 2432-2442, vol. 31.
Rezania, Production of Functional Glucagon-Secreting-Cells from Human Embryonic Stem Cells, Diabetes, 2011, pp. 239-247, vol. 60, Issue 1.
Sherwood, et al., Transcriptional Dynamics of Endodermal Organ Formation, Developmental Dynamics, 2009, pp. 29-42, vol. 238, Issue 1.
Shi et al., Inducing Embryonic Stem Cells to Differentiate into Pancreatic β Cells by a Novel Three-Step Approach with Activin A and All-Trans Retinoic Acid, Stem Cells, 2005, 656-662, 23, AlphaMed Press.
Stafford, et al., Retinoic Acid Signaling is Required for a Critical Early Step in Zebrafish Pancreatic Development, Current Biology, 2002, pp. 1215-1220, vol. 12, Issue 14.
Thomson et al., Embryonic Stem Cell Lines Derived from Human Blastocysts, Science, Nov. 6, 1998, 1145-1147, 282, HighWire Press.
Thomson et al., Isolation of a primate embryonic stem cell line, Developmental Biology, Aug. 1995, 7844-7848, 92, Proc. Natl. Acad. Sci, US.
Thomson et al., Primate Embryonic Stem Cells, Currenl Topics in Developmental Biology, 1998, 133-154, 38, Academic Press, US.
Wang, et al., Three-Dimensional Differentiation of Embryonic Stem Cells into islet-Like Insulin-Producing Clusters, Tissue Engineering: Part A, 2009, pp. 1941-1952, vol. 15, No. 8.
Wells, et al., Early Mouse Endoderm is Patterned by Soluble Factors from Adjacent Germ Layers, Development, 2000, pp. 1563-1572, vol. 127, Issue 8.
Wilson, et al., The HMG Box Transcription Factor Sox4 Contributes to the Development of the Endcrine Pancreas, Diabetes, 2005, pp. 3402-4309, vol. 54, Issue 12.
Zhang_et_al, Highly Efficient Differentiation of Human ES Cells and iPS Cells into Mature Pancreatic Insulin-Producing Cells, Cell Research, 2009, pp. 429-438, vol. 19, Issue 14.
Zorn, et al., Vertebrate Endoderm Development and Organ Formation, Annual Review Cell Development Biology, 2009, pp. 221-251, vol. 25.
European Search Report dated Jun. 8, 2015 for application No. EP 12860751.
Abe, et al., Evidence That PI3K, Rac, Rho, and Rho Kinase are Involved in Basic Fibroblast Growth Factor-Stimulated Fibroblast-Collagen Matrix Contraction, Journal of Cellular Biochemistry, 2007, pp. 1290-1299, vol. 102.
Abeyta, et al., Unique Gene Expression Signatures of Independently-Derived Human Embryonic Stem Cells Lines, Human Molecular Genetics, Jan. 28, 2004, pp. 601-608, vol. 13, No. 6, Oxford University Press.
Abranches, et al., Expansion of Mouse Embryonic Stem Cells on Microcarriers, Biotechnology Bioengineering, Apr. 15, 2007, pp. 1211-1221, vol. 96, No. 6, Wiley InterScience.
Ackermann, et al., Molecular Regulation of Pancreatic B-Cell Mass Development, Maintenance, and Expansion, Journal of Molecular Endocrinology, 2007, pp. 193-206, vol. 38.
Adams, et al., Proteasome Inhibition in Cancer: Development of PS-341, Seminars in Oncology, 2001, pp. 613-619, vol. 28, No. 6.
Age-Related Eye Disease Study Research Group, A Randomized, Palcebo-Controlled, Clinical Trial of High-Dose Supplementation with Vitamins C and E, Beta Carotene, and Zinc for Age-Related Macular Degeneration and Vision Loss, Arch Ophthalmology, 2001, pp. 1417-1436, AREDS Report No. 8, vol. 119.
Ali, et al., Exploitation of Protein Kinase C: A Useful Target for Cancer Therapy, Cancer Treatment Reviews, 2009, pp. 1-8, vol. 35.
Allegrucci, et al., Differences between Human Embryonic Stem Cell Lines, Human Reproduction Update, Aug. 26, 2006, pp. 1-18, Advance Access.
Almond, et al., The Proteasome: A Novel Target for Cancer Chemotherapy, Leukemia, 2002, pp. 433-443, vol. 16.
Amit et al., Human Feeder Layers for Human Embryonic Stem Cells, Biology of Reproduction, Jan. 22, 2003, 2150-2156, vol. 68, No. 6, Society for the Study of Reproduction, Inc.
Amit, et al., Clonally Derived Human Embryonic Stem Cell Lines Maintain Pluripotency and Proliferative Potential for Prolonged Periods of Culture, Developmental Biology, 2000, pp. 271-278, vol. 227.
Amit, et al., Dynamic Suspension Culture for Scalable Expansion of Undifferentiated Human Pluripotent Stem Cells, Nature Protocols, Apr. 7, 2011, pp. 572-579, vol. 6, No. 5.
Amit, et al., Feeder Layer-and Serum-Free Culture of Human Embryonic Stem Cells, Biology of Reproduction, 2004, pp. 837-845, vol. 70.
Arai, et al., Purification of Recombinant Activin A Using the Second Follistatin Domain of Follistatin-Related Gene (FLRG), Protein Expression & Purification, 2006, pp. 78-82, vol. 49.
Armstrong, et al., The Role of PI3K/AKT, MAPK/ERK and NFκβ Signalling in the Maintenance of Human Embryonic Stem Cell Pluripotency and Viability Highlighted by Transcriptional Profiling and Functional Analysis, Human Molecular Genetics, 2006, pp. 1894-1913, vol. 15, No. 11.
Assady, et al., Insulin Production by Human Embryonic Stem Cells, Diabetes, 2001, pp. 1691-1697, vol. 50.
Baertschiger, et al., Mesenchymal Stem Cells Derived From Human Exocrine Pancreas Express Transcription Factors Implicated in Beta-Cell Development, Pancreas, 2008, pp. 75-84, vol. 37, No. 1.
Bai, et al., Glucagon-Like Peptide-1 Enhances Production of Insulin in Insulin-Producing cells Derived from Mouse Embryonic Stem Cells, Journal of Endocrinology, 2005, pp. 343-352, vol. 186, No. 2.
Balsam, et al., Haematopoeitic Stem Cells Adopt Mature Haeatopoietic Fates in Ischaemic Myocardium, Nature, Apr. 8, 2004, pp. 668-673, ?, Nature Publishing Group.
Bandyopadhyay, et al., Inhibition of Pulmonary and Skeletal Metastasis by a Transforming Growth Factor-B Type I Receptor Kinase Inhibitor, Cancer Research, 2006, pp. 6714-6721, vol. 66, No. 13.

(56) References Cited

OTHER PUBLICATIONS

Barclay, et al., The Leucocyte Antigen Facts Book, The Leucocyte Antigen Facts Book, 1997, Textbook, 2[sup] edition, Academic Press.

Bellinger, et al, Swine Models of Type 2 Diabetes Mellitus: Insulin Resistance, Glucose Tolerance, and Cardiovascular Complications, ILAR Journal, 2006, pp. 243-258, vol. 47, No. 3.

Beltrami, et al., Adult Cardiac Stem Cells are Multipotent and Support Myocardial Regeneration, Cell, Sep. 19, 2003, pp. 763-776, vol. 114, Cell Press.

Best, et al., Embryonic Stem Cells to Beta-Cells by Understanding Pancreas Development, Molecular and Cellular Endorinology, 2008, pp. 86-94, vol. 288.

Bigdeli, et al., Adaptation of Human Embryonic Stem Cells to Feeder-Free and Matrix-Free Culture Conditions Directly on Plastic Surfaces, Journal of Biotechnology, 2008, pp. 146-153, vol. 133.

Blin, et al., A Purified Population of Multipotent Cardiovascular Progenitors Derived from Primate Pluripotent Stem Cells Engrafts in Postmyocardial Infarcted Nonhumans Primates, The Journal of Clinical Investigation, Apr. 2010, pp. 1125-1139, vol. 120, No. 4.

Blyszczuk et al., Expression of Pax4 in embryonic stem cells promotes differentiation of nestin-positive progenitor and insulin-producing cells, Proceedings of the National Academy of Sciences, Feb. 4, 2003, pp. 998-1003, vol. 100-3, National Academy of Sciences.

Bo, et al., Research Progress of Pancreatic Islet Development and Pancreatic Stem Cells, Journal of Clinical Surgery, 2009, pp. 208-210, vol. 17, No. 3.

Bonner-Weir et al., In vitro cultivation of human islets from expanded ductal tissue, Proceedings of the National Academy of Sciences, Jul. 5, 2000, pp. 7999-8004, vol. 97-14, National Academy of Sciences.

Borowitz, et al., Prognostic Significance of Fluorescence Intensity of Surface Marker . . . , Blood, Jun. 1, 1997, pp. 3960-3966, vol. 89-11, American Society of Hematology, Washington, D.C., US.

Braam, et al., Improved Genetic Manipulation of Human Embryonic Stem Cells, Nature Methods, May 2008, pp. 389-392, vol. 5, No. 5.

Brakenhoff et al., Development of a Human Interleukin-6 Receptor Antagonist, Journal of Biological Chemistry, Jan. 7, 1994, pp. 86-93, vol. 269-1, US.

Brambrink, et al., Sequential Expression of Pluripotency Markers During Direct Reprogramming of Mouse Somatic Cells, Cell Stem Cell, 2008, pp. 151-159, vol. 2.

Brevig, et al., The Recognition of Absorbed and Denatured Proteins of Different Topographies by β2 Integrins and Effects on Leukocyte Adhesion and Activation, Biomaterials, 2005, pp. 3039-3053, vol. 26.

Brevini, et al, No Shortcuts to Pig Embryonic Stem Cells, Theriogenology, 2010, pp. 544-550, vol. 74.

Bross, et al., Approval Summary for Bortezomib for Injection in the Treatment of Multiple Myeloma, Clinical Cancer Research, Jun. 15, 2004, pp. 3954-3964, vol. 10.

Brown, et al, Optimal Control of Blood Glucose: The Diabetic Patient or the Machine?, Science Translation Medicine, Apr. 14, 2010, pp. 1-5, vol. 2 Issue 27.

Burkard et al, Conditional Neuronal Nitric Oxide Synthase Overexpression Impairs Myocardial Contractility, Circulation Reseach, Jan. 18, 2007, pp. e32-e44, vol. 100.

Buzzard et al., Karyotype of human ES cells during extended culture, Nature Biotechnology, Apr. 1, 2004, pp. 381-382, vol. 22-4, Nature Publishing Group.

Cai, et al., Generation of Homogeneous PDX1+Pancreatic Progenitors from Human ES Cell-derived Endoderm Cells, Journal of Molecular Cell Biology, Nov. 12, 2009, pp. 50-60, vol. 2.

Castaing, et al., Blood Glucose Normalization Upon Transplantation of Human Embryonic Pancreas into Beta-Cell-Deficient SCID Mice, Diabetologica, 2001, pp. 2066-2076, vol. 44.

Chambers, et al., Functional Expression Cloning of Nanog, a Pluripotency Sustaining Factor in Embryonic Stem ells, Cell, May 30, 2003, pp. 643-655, vol. 113.

Chapple, et al., Unfolding Retinal Dystrophies: A Role for Molecular Chaperones?, Trends in Molecluar Medicine, 2001, pp. 414-421, vol. 7, No. 9.

Chen, et al., Chemically Defined Conditions for Human iPSC Derivation and Culture, Nature Methods, 2011, pp. 424-429, vol. 8, Issue 5.

Chen, et al., Differentiation of Embryonic Stem Cells Towards Pancreatic Progenitor Cells and their Transplantation Into Strepozotocin-Induced Diabetic Mice, Cell Biology International, 2008, pp. 456-461, vol. 32.

Chen, et al., Differentiation of Rat Marrow Mesencymal Stem Cells in Pancreatic Islet Beta-Cells, World Journal of Gastroenterology, Oct. 15, 2004, pp. 3016-3020, vol. 10.

Chen, et al., Retinoic Acid Signaling is Essential for Pancreas Development and Promotes Endocrine at the Expense of Exocrine Cell Differentiation in Xenopus, Developmental Biology, 2004, pp. 144-160, vol. 271.

Cheon et al., Secretory Leukocyte Protease Inhibitor (SLPI) Regulate the Embryonic Differentiation During Periimplantation Stage, Biology of Reproduction, 2007, pp. 64, vol. 77, Society for the Study of Reproduction, Inc.

Cheon, et al., Defined Feeder-Free Culture System of Human Embryonic Stem Cells, Biol Reprod, 2005, pp. 611, vol. 74.

Chetty, et al., A Simple Tool ti Improve Pluripotent Stem Cell Differentiation, Nature Methods, 2013, pp. 553-558, vol. 10, No. 6.

Choi, et al., In Vitro Trans-Differentiation of Rat Mesenchymal Cells into Insulin-Producing Cells by Rat Pancreatic Extract, Biochemical and Biophysical ResearchCommunications, 2005, pp. 1299-1305, vol. 330.

Chung, et al., Human Embryonic Stem Cell Lines Generated without Embryo Destruction, Cell Stem Cell, 2008, pp. 113-117, vol. 2.

Corbeil, et al., Rat Prominin, Like its Mouse and Human Orthologues, is a Pentaspan Membrane Glycoprotein, Biochemical and Biophysical Research Communications, 2001, pp. 939-944, vol. 285, No. 4.

Crane, et al., An Embryogenic Model to Explain Cytogenetic Inconsistencies Observed in Chorionic Villus Versus Fetal Tissue, Prenatal Diagnosis, 1988, pp. 119-129, vol. 8.

Cresta, et al., Phase I Study of Bortezomib with Weekly Paclitaxel in Patients with Advanced Solid Tumours, European Journal of Cancer, 2008, pp. 1829-1834, vol. 44.

Cure, et al., Improved Metabolic Control and Quality of Life in Seven Patients with Type 1 Diabetes Following Islet After Kidney Transplantation, Cell Therapy and Islet Transplantation, Mar. 27, 2008, pp. 801-812, vol. 85, No. 6.

D'Amour et al, Production of pancreatic hormone expressing endocrine cells from human embryonic stem cells, Nature Biotechnology, 2006, pp. 1392-1401, vol. 24.

Damy, et al., Increased Neuronal Nitric Oxide Synthase-Derived NO Production in the Failing Human Heart, Research Letters, Apr. 24, 2004, pp. 1365-1367, vol. 363.

David M. Chacko, et al., Survival and Differentiation of Cultured Retinal Progenitors Transplanted in the Subretinal Space of the Rat, Biochemical and Biophysical Research Communications, 2000, pp. 842-846, vol. 268, Academic Press.

De Coppi, et al., Isolation of Amniotic Stem Cell Lines with Potential for Therapy, Nature Biotechnology, 2007, pp. 100-106, vol. 25, No. 1.

De Rosa, 11-color, 13-parameter flow cytometry: Identification of . . . , Nature, Feb. 1, 2001, pp. 245-248, vol. 7-2, Nature Publishing Group, US.

Dekker, et al., Adhesion of Endothelial Cells and Adsorption of Serum Proteins on Gas Plasma-Treated Polytetrafluoroethylene, Biomaterials, 1991, pp. 130-138, vol. 12.

Denning, et al., Common Culture Conditions for Maintenance and Cardiomyocyte Differentiation of the Human Embryonic Stem Cell Lines, BG01 and HUES-7, Int. J. Del. Biol., 2006, pp. 27-37, vol. 50.

(56) References Cited

OTHER PUBLICATIONS

Deramaudt, et al., The PDX1 Flomeodomain Transcription Factor Negatively Regulates the Pancreatic Ductal Cell-specific Keratin 19 Promoter*, Journal of Biological Chemistry, 2006, pp. 38385-38395, vol. 281, No. 50.
Donovan, et al., The End of the Beginning for Pluripotent Stem Cells, Nature, Nov. 2001, pp. 92-97, vol. 414.
Dorrell, et al., Editorial, Stem Cell Research, 2008, pp. 155-156, vol. 1.
Doyle, et al., Cell and Tissue Culture: Laboratory Procedures in Biotechnology, Cell and Tiossue Culture: Laboratory Procedures in Biotechnology, 1995, Textbook, Textbook, Wiley.
Draper, et al., Recurrent Gain of Chromosomes 17q and 12 in Cultured Human Embryonic Stem Cells, Nature Biotechnology, 2004, pp. 53-54, vol. 22, No. 1.
Draper, et al., Surface Antigens of Human Embryonic Stem Cells: Changes Upon Differentiation in Culture, Journal Anatomy, 2002, pp. 249-258, vol. 200, Anatomical Society of Great Britain and Ireland.
Dufour, et al., Development of an Ectopic Site for Islet Transplantation Using Biodegradable Scaffolds, Tissue Engineering, 2005, pp. 1323-1331, vol. 11, No. 9/10.
Dupont-Gillain, et al., Plasma-Oxidized Polystyrene: Wetting Properties and Surface Reconstruction, Langmuir, 2000, pp. 8194-8200, vol. 16.
Edlund, Pancreatic Organogenisis—Pancreatic Mechanisims and Implications for Therapy, Nature, Jul. 1, 2002, pp. 524-532, vol. 3, Nature Publishing Group, US.
Eguizabal, et al., Embryonic Stem Cells/Induced Pluriptent Stem Complete Meiosis from Human Induced Pluripotent Stem Cells, Stem Cells, 2011, pp. 1186-1195, vol. 29.
Ellerstrom, et al., Derivation of a Xeno-Free Human Embryonic Stem Cell Line, Stem Cells, 2006, pp. 2170-2176, vol. 24.
Ellerstrom, et al., Facilitated Expansion of Human Embryonic Stem Cells by Single-Cell Enzymatic Dissociation, Stem Cells, 2007, pp. 1690-1696, vol. 25, No. 7.
Ellmers, et al., Transforming Growth Factor-B Blockade Down-Regulates the Renin-Angiotensin System and Modifies Cardiac Remodling after Myoardial Infarction, Endocrinology, Jul. 24, 2008, pp. 5828-5834, vol. 149—Issue 11, The Endocrine Society.
Enzmann, et al., Enhanced Induction of RPE Lineage Markers in Pluripootent Neural Stem Cells Engrafted into the Adult Rat Subretinal Space, Ophthamology & Visual Science, Dec. 2003, pp. 5417-5422, vol. 44, No. 12, Association for Research in Vision and Ophthamology.
Eventov-Friedman, et al., Embryonic Pig Pancreatic Tissue Transplantation for the Treatment of Diabetes, PLoS Medicine, Jul. 2006, e215, pp. 1165-1177, vol. 3, Issue 7.
Ezashi, et al., Low 02 Tensions and the Prevention of Differentiation of hES Cells, Proceedings of the National Academy of Sciences of USA, Mar. 29, 2005, pp. 4783-4788, vol. 102, No. 13.
Fauza, Amniotic Fluid and Placental Stem Cells, Ballieres Best Practice and Research Clinical Obsterics and Gynaecology, 2004, pp. 877-891, vol. 18, No. 6.
Fidler et al., Selective Immunomodulation by the Antineoplastic Agent Mitoxantrone, Journal of Immunology, Jul. 15, 1986, pp. 727-732, vol. 137-2, American Society of Immunologists, US.
Fischer, et al., Residues in the C-Terminal Region of Activin a Determine Specificity for Follistatin and Type II Receptor Binding, Journal of Endocrinology, 2003, pp. 61-68, vol. 176, Society for Endocrinology.
Florio, et al., Activin A Stimulates Insulin Secretion in Cultured Human Pancreatic Islets, J. Endocrinol. Invest., 2000, pp. 231-234, vol. 23.
Fok, et al., Shear-Controlled Single-Step Mouse Embryonic Stem Cell Expansion and Embryoid Body-Based Differentiation, Stem Cells, 2005, pp. 1333-1342, vol. 23.
Foster, et al., Differentiation of Transplanted Microencapsulated Fetal Pancreatic Cells, Experimental Transplantation, Jun. 15, 2007, pp. 1440-1448, vol. 83, No. 11.

Frandsen et al., Activin B mediated induction of Pdx1 in human embryonic stemcell derived embryoid bodies, Biochemical and Biophysical Research Communications, Aug. 15, 2007, 568-574, 362, Elsevier Inc.
Frigui, et al., A Robust Competitive Clustering Algorithm With Applications in Computer Vision, IEEE Transactions on Pattern Analysis and Machine Intelligence, May 1, 1999, pp. 450-465, vol. 21, No. 5, IEEE, US.
Fung, et al., The Effect of Medical Therapy and Islet Cell Transplantation on Diabetic Nephropathy: An Interim Report, Transplantation, Jul. 15, 2007, pp. 17-22, vol. 84, No. 1.
Furue, et al., Heparin Promotes the Growth of Human Embryonic Stem Cells in a Defined Serum-Free Medium, Proceedings of the National Academy of Sciences, Sep. 9, 2008, pp. 13409-13414, vol. 105, No. 36.
Gadue, et al, Wnt and TGB-B Signaling are Required for the Induction of an in vitro Model of Primitive Streak Formation Using Embryonic Stem Cells, Proceedings of the National Academy of Sciences, Nov. 7, 2006, pp. 16806-16811, vol. 103-45, National Academy of Sciences, US.
Gaspar, et al., Inhibition of Transforming Growth Factor Signaling Reduces Pancreatic Adenocarcinoma Growth and Invasiveness, Molecular Pharmacology, 2007, pp. 152-161, vol. 72, Issue 1.
Gellibert, et al., Identification of 1,5-Naphthyridine Derivatives as a Novel Series of Potent and Selective TGF-B Type I Receptor Inhibitor, J. Med. Chem, 2004, pp. 4494-4506, vol. 47, No. 18.
Gershengorn et al., Epithelial-to-Mesenchymal Transition Generates Proliferative Human Islet Precursor Cells, Science, Dec. 24, 2004, pp. 2261-2264, vol. 306, US.
Gibco, Solutions for Life Science Research and Drug Discovery, Catalogue Cell Culture Products, 2004-2005, pp. 1-4E, 281406 26 5 27.
Giltaire, et al., The CYP26 Inhibitor R115866 Potentiates the Effects of All-Trans Retinoic Acid on Cultured Human Epidermal Keratinocytes, British Journal of Dermatology, 2009, pp. 505-513, vol. 160.
Ginis, et al., Differences Between Human and Mouse Embryonic Stem Cells, Developmental Biology, 2004, pp. 360-380, vol. 269.
Gittes, Developmental Biology of the Pancreas: A comprehensive Review, Developmental Biology, 2009, pp. 4-35, vol. 326, No. 1.
Gordon Weir, Do stem cells hold the key to creation of a cure for diabetes?, Diabetes Voice, 2008, pp. 29-31, Edition 53, No. 2.
Gosden, et al., Amniotic Fluid Cell Types and Culture, British Medical Bulletin, 1983, pp. 348-354, vol. 39, No. 4.
Graham, et al., Characteristics of a Human Cell Line Transformed by DNA from Human Adenovirus Type 5, Journal General Virology, 1977, pp. 59-72, vol. 36.
Gregg Duester, Retionoic Acid Synthesis and Signaling During Early Organogenesis, Cell, 2008, pp. 921-931, vol. 134.
Guo, et al., Stem Cells to Pancreatic B-Cells: New Sources for Diabetes Cell Therapy, Endocrine Reviews, May 2009, pp. 214-227, vol. 30, No. 3, The Endocrine Society.
Hadley, et al., Extracellular Matrix Regulates Sertoli Cell Differentiation, Testicular Cord Formation, and Germ Cell Development in Vitro, The Journal of Cell Biology, Oct. 1985, pp. 1511-1522, vol. 101, Rockefeller University Press.
Hainsworth, et al., Retinal Capillar Basement Membrane Thickening in a Porcine Model of Diabetes Mellitus, Comp Med, 2002, pp. 523-529, vol. 52.
Hamann, et al., Phenotypic and Functional Separation of Memory and and Effector Human CD8+ T Cells, Journal of Experimental Medicine, Mar. 11, 1997, 1407-1418, 186-9, Rockefeller University Press, US.
Harb, et al., The Rho-Rock-Myosin Signaling Axis Determines Cell-Cell Integrity of Self-Renewing Pluripotent Stem Cells, Plos One, 2008, Article e3001, vol. 3, Issue 8.
Harmon, et al., GDF11 Modulates NGN3+ Islet Progenitor Cell Number and Promotes B-Cell Differentiation in Pancreas Development, Development, 2004, pp. 6163-6174, vol. 131.
Haruta, et al., In Vitro and in Vivo Characterization of Pigment Epithelieal Cells Differentiated from Primate Embryonic Stem

(56) References Cited

OTHER PUBLICATIONS

Cells, Investigative Ophthalmology & Visual Science, Mar. 2004, pp. 1020-1025, vol. 45, No. 3, Association for Research in Vision and Ophthalmology.
Hasegawa, et al., A Method for the Selection of Human Embryonic Stem Cell Sublines with High Replating Efficiency After Single-Cell Dissociation, Stem Cells, 2006, pp. 2649-2660, vol. 24.
Hashemi, et al., A Placebo Controlled, Dose-Ranging, Safety Study of Allogenic Mesenchymal Stem Cells Injected by Endomyocardial Delivery after an Acute Myocardial Infarction, European Heart Journal, Dec. 11, 2007, pp. 251-259, vol. 29.
Hay, et al., Highly Ethicient Differentiation of hESCs to Functional Hepatic Endoderm Requires ActivinA and Wnt3a Signaling, PNAS, 2008, pp. 12301-12306, vol. 105, No. 34.
Heinis, et al., HIF1a and Pancreatic Beta-Cell Development, The FASEB Journal, 2012, pp. 2734-2742, vol. 26.
Heinis, et al., Oxygen Tension Regulates Pancreatic Beta-Cell Differentiation Through Hypoxia-Inducible Factor 1x, Diabetes, 2010, pp. 662-669, vol. 59.
Heit, et al., Embryonic Stem Cells and Islet Replacement in Diabetes Mellitus, Pediatric Diabetes, 2004, pp. 5-15, vol. 5.
Held, et al, The Effect of Oxygen Tension on Colony Formation and Cell Proliferation of Amniotic Fluid Cells In-Vitro, Prenatal Diagnosis, 1984, pp. 171-180, vol. 4, No. 3.
Henderson, et al., Preimplantation Human Embryos and Embryonic Stem Cells Show Comparable Expression of Stage-Specific Embryonic Antigens, Stem Cells, 2002, pp. 329-337, vol. 20.
Heng, et al., Mechanical dissociation of human embryonic stem cell colonies by manual scraping after collagenase treatment is much more detrimental to cellular viability than is trypsinization with gentle pipetting, Biotechnol. Appl. Biochem., 2007, pp. 33-37, vol. 47, Portland Press Ltd., GB.
Heremans, et al., Recapitulation of Embryonic Neuroendocrine Differentiation in Adult Human Pancreatic Duct Cells Expressing Neurogenin 3, The Journal of Cell Biology, 2002, pp. 303-311, vol. 159.
Herrera, Adult-Insulin-and Glucagon-Producing Cells Differentiate from Two Independent Cell Lineages, Development, 2000, pp. 2317-2322, vol. 127, No. 11.
Herzenberg, et al., Fluorescence-activated Cell Sorting, Scientific American, 1976, pp. 108-117, vol. 234, Scientific American, US.
Hess, et al., Bone Marrow-Derived Stem Cells Initiate Pancreatic Regeneration, Nature Biotechnology, Jul. 2003, pp. 763-770, vol. 21, No. 7.
Ho, et al., Animal Cell Bioreactors, Animal Cell Bioreactors, 1991, 1-512, Hardcover, Butterworth-Heinemann.
Hoehn, et al., Morphological and Biochemical Heterogeneity of Amniotic Fluid Cells in Culture, Methods in Cell Biology, 1982, pp. 11-34, vol. 26, Academic Press, Inc.
Hoffman, et al., Characterization and Culture of Human Embryonic Stem Cells, Nature Biotechnology, 2005, pp. 699-708, vol. 23, No. 6.
Hori, et al., Growth inhibitors promote differentiation of insulin-producing tissue from embryonic stem cells, Proceedings of the National Academy of Sciences, Dec. 2002, pp. 16105-16110, vol. 99-25, National Academy of Sciences.
Hosoya, et al., Induction of Differentiation of Undifferentiated Cells into Pancreatic Beta-Cells in Vertebrates, Int. J. Dev. Biol., 2012, pp. 313-323, vol. 56.
Hussain, et al., Stem-Cell Therapy for Diabetes Mellitus, Lancet, 2004, pp. 203-205, vol. 364.
Ianus, et al., In Vivo Derivation of Glucose-Competent Pancreatic Endocrine Cells from Bone Marrow Without vidence of Cell Fusion, The Journal of Clinical Investigation, Mar. 2003, pp. 843-850, vol. 111, No. 6.
Inami, et al., Differentiation of Induced Pluripotent Stem Cells to Thymic Epithelial Cells by Phenotype, Immunology and Cell Biology, Jun. 24, 2010, pp. 1-8.
Inman, et al., SB-431542 is a Potent and Specific Inhibitor of Transforming Growth Factor-B Superfamily Type I Activing Receptor-Like Kinase (ALK) Receptors ALK4, ALK5, and ALK7, Molecular Pharmacology, 2002, pp. 65-74, vol. 62, No. 1.
Int' Anker, et al., Amniotic Fluid as a Novel Source of Mesenchymal Stem Cells for Therapeutic Transplantation, Blood, Aug. 15, 2003, pp. 1548-1549, vol. 102, No. 4.
Inzunza, et al., Derivation of Human Embryonic Stem Cell Lines in Serum Replacement Medium Using Postnatal Human Fibroblasts as Feeder Cells, Stem Cells, 2005, pp. 544-549, vol. 23, AlphaMed Press.
Itkin-Ansari, et al., Cell-Based Therapies for Diabetes: Progress Towards a Transplantable Human B Cell Line, Annals of the New York Academy of Sciences, 2003, pp. 138-147, vol. 1005, No. 1.
Jafary, et al., Differential effect of activin on mouse embryonic stem cell differentiation in insulin-secreting cells under nestin-positive selection and spontaneous differentiation protocols, Cell Biology International, 2008, pp. 278-286, vol. 32, Elsevier.
Johansson, et al., Temporal Control of Neurogenin3 Activity in Pancreas Progenitors Reveals Competence Nindows for the Generation of Different Endocrine Cell Types, Developmental Cell, Mar. 2007, pp. 457-465, vol. 12.
Kahan, Pancreatic Precursors and Differentiated Islet Cell Types from Murine Embryonic Stem Cells, Diabetes, Aug. 2003, pp. 2016-2042, vol. 52.
Karvonen, et al., Incidene of Childhood Type 1 Diabetes Worldwide, Diabetes Care, 2000, pp. 1516-1526, vol. 23, No. 10.
Kicic, et al., Differentiation of Marrow Stromal Cells into Photoreceptors in the Rat Eye, The Journal of Neuroscience, Aug. 27, 2003, pp. 7742-7749, vol. 23, Issue 21.
Kingsley, The TGF-B Superfamily: New Members, New Receptors, and New Genetic Tests of Function in Different Drganisms, Genes & Development, 1994, pp. 133-146, vol. 8, Cold Spring Harbor Laboratory Press.
Kinkel, et al., Cyp26 Enzymes Function in Endoderm to Regulate Pancreatic Field Size, Pnas, May 12, 2009, pp. 7864-7869, vol. 106, No. 19.
Kleinman et al., Basement Membrane Complexes with Biological Activity, Biochemistry, 1986, pp. 312-318, vol. 25, American Chemical Society.
Klimanskaya, et al., Human Embryonic Stem Cells Derived without Feeder Cells, Lancet, May 2005, pp. 1636-1641, vol. 365, No. 9471.
Koblas, et al., Differentiation of CD133-Positive Pancreatic Cells Into Insulin-Producing Islet-Like Cell Clusters, Transplantation Proceedings, 2008, pp. 415-418, vol. 40.
Kohen, et al, Characterization of Matrigel Interfaces During Defined Human Embryonic Stem Cell Culture, Characterization of Matrigel Interfaces During Defined Human Embryonic Stem Cell Culture, Sep. 3, 2010, pp. 6979, vol. 4.
Koller, et al., Effects of Synergistic Cytokine Combinations, Low Oxygen, and Irradiated Stroma on the Expansion of Human Cord Blood Progenitors, Blood, Jul. 15, 1992, pp. 403-411, vol. 80, No. 2.
Konstantinova_et_al_2007, EphA-Ephrin-A-Mediated Beta Cell Communication Regulates Insulin Secretion Tom Pancreatic Islets, Cell, Apr. 20, 2007, pp. 359-370, vol. 129.
Koyangi et al., Inhibitio not the Rho/ROCK Pathway Reduces Apoptosis During Transplantatation of Embryonic Stem Cell-Derived Neural Precursors, Journal of Neurosciene Research, Sep. 7, 2007, pp. 270-280, vol. 86, Wiley-Liss, Inc.
Kozikowski, et al., New Amide-Bearing Benzolactam-Based Protein Kinase C Modulators Induce Enhanced Secretion of the Amyloid Precuros Protein Metabolite sAPPa, J. Med. Chem., 2003, pp. 364-373, vol. 46, No. 3.
Krapcho et al., Synthesis and Antineoplastic Evaluations of 5,8-Bis[(aminoalkyl)amino]-1-azaanthracene-9,10-diones, Journal of Medical Chemistry, 1985, pp. 1124-1126, vol. 28, American Chemical Society.
Krawetz, et al., Human Embryonic Stem Cells: Caught Between a ROCK Inhibitor and a Hard Place, BioEssays: News and Reviews in Molecular Cellular and Developmental Biology, 2009, pp. 336-343, vol. 31.
Kron, et al., Expression of Human Activin C Protein in Insect Larvae Infected with a Recombinant Baculovirus, Journal of Virological Methods, 1998, pp. 9-14, vol. 72.

(56) References Cited

OTHER PUBLICATIONS

Krutzik, et al., Coordinate Analysis of Murine Immune Cell Surface Markers and Intracellular Phosphoproteins by Flow Cytometry, Journal of Immunology, May 30, 2005, pp. 2357-2365, vol. 175, American Association of Immunologists, Inc., US.
Ku et al., Committing Embryonic Stem Cells to Early Endocrine Pancreas in Vitro, Stem Cells, 2004, pp. 1205-1217, vol. 22, AlphaMed Press.
Kubo et al., Development of definitive endoderm from embryonic stem cells in culture, Development, 2004, pp. 1651-1662, vol. 131, The Company of Biologists.
Kurihara-Bergstrom, et al., Characterization of the Yucatan Miniature Pig Skin and Small Intestine for Pharmaceutical Applications, Laboratory Animal Science, 1986, pp. 396-399, vol. 36, No. 4.
Lanza, et al., Characteristics and Characterization of Human Pluripotent Stem Cells, Stem Cell Anthology, 2010, pp. 141, 142, 144 and 146, 1st Edition.
Laplante, et al., RhoA/ROCK and Cdc42 Regulate Cell-Cell Contact and N-Cadherin Protein Level During Neurodetermination of P19 Embryonal Stern Cells, Journal of Neurobiology, 2004, pp. 289-307, vol. 60, No. 3.
Larsen, et al., Evaluation of B-Cell Mass and Function in the Gottingen Minipig, Diabetes, Obesity and Metabolism, 2007, pp. 170-179, vol. 9, Supplement 2, Blackwell Publishing Ltd.
Larsen, et al., Use of the Gootingen Minipig as a Model of Diabetes, with Special Focus on Type 1 Diabetes Research, ILAR Journal, 2004, pp. 303-313, vol. 45, No. 3.
Lavon et al., The Effect of Overexpression of Pdx1 and Foxa2 on the Differentiation of Human Embryonic Stem Cells into Pancreatic Cells, Stem Cells, 2006, pp. 1923-1930, vol. 24, Alpha Med Press, IL.
Le Blanc, et al., Mesenchymal Stem Cells Inhibit and Stimulate Mixed Lymphocyte Cultures and Mitogenic Responses Independently of the Major Histocompatibility Complex, Scandinavian Journal of Immunology, 2003, pp. 11-20, vol. 57, Blackwell Publishing Ltd.
Lee et al., Establishment and Maintenance of Human Embryonic Stem Cell Lines on Human Feeder Cells Derived from Uterine Endometrium under Serum-Free Condition, Biology of Reproduction, Aug. 18, 2004, pp. 42-49, vol. 72.
Lee, et al., Human B-cell Precursors Mature into Functional Insulin-Producing Cells in an Immunoisolation Device: Implications for Diabetes Cell Thereapies, Transplantation, Apr. 15, 2009, pp. 983-991, vol. 87, No. 7.
Lee, et al., PKC-Inhibitors Sustain Self-Renewal of Mouse Embryonic Stem Cells Under Hypoxia in Vitro, Experimental and Molecular Medicine, Apr. 2010, pp. 294-301, vol. 43, No. 4.
Lee, et al., Protein Kinase A- and C-Induced Insulin Release from Ca2+-Insensitive Pools, Cellular Signalling, 2003, pp. 529-537, vol. 15.
Lee, et al., Retionic Acid-Induced Human Secretin Gene Expression in Neuronal Cells is Mediated by Cyclin-Dependent Kinase 1, Annals of the New York Academy of Sciences, 2006, pp. 393-398, vol. 1070.
Leeper, et al., Stem Cell Therapy for Vascular Regeneration Adult, Embryonic, and Induced Pluripotent Stem Cells, Circulation, Aug. 3, 2010, pp. 517-526, vol. 122, No. 5.
Leon-Quinto, et al., In Vitro Directed Differentiation of Mouse Embryonic Stem Cells into Insulin-Producing Cells, Diabetologia, 2004, pp. 1442-1451, vol. 47, No. 8.
Levenstein et al., Basic Fibroblast Growth Factor Support of Human Embryonic Stem Cell Self-Renewal, Stem Cells, Nov. 10, 2005, pp. 568-574, vol. 24, AlphaMed Press.
Li, et al., Generation of Rat and Human Induced Pluripotent Stem Cells by Combining Genetic Reprogramming and Chemical Inhibitors, Cell Stem Cell, Jan. 9, 2009, pp. 16-19, vol. 4.
Li, et al., Pluripotency Can be Rapidly and Efficiently Induced in Human Amniotic Fluid-Derived Cells, Human Molecular Genetics, 2009, pp. 4340-4349, vol. 18, No. 22.
Lilja et al., Cyclin-dependent Kinase 5 Promotes Insulin Exocytosis, Journal of Biological Chemistry, Jul. 6, 2001, pp. 34199-34205, vol. 36-7, JBC Papers in Press.
Lim, et al., Proteome Analysis of Conditioned Medium from Mouse Embryonic Fibroblast Feeder Layers which Support the Growth of Human Embryonic Stem Cells, Proteomics, 2002, pp. 1187-1203, vol. 2.
Liu, et al., A Novel Chemical-Defined Medium with bFGF and N2B27 Supplements Supports Undifferentiated Growth in Human Embryonic Stem Cells, Biochemical and Biophysical Research Communications, 2006, pp. 131-139, vol. 346.
Ludwig, et al., Defined Culture Media for Human Embryonic Stem Cells, Embryonic Stem Cells, 2007, pp. 1-16, Springer.
Ludwig, et al., Derivation of Human Embryonic Stem Cells in Defined Conditions, Nature Biotechnology, Feb. 2006, pp. 185-187, vol. 24 No. 2.
Lumelsky, et al., Differentiation of Embryonic Stem Cells to Insulin-Secreting Structures Similar to Pancreatic Islets, Science, 2001, pp. 1389-1394, vol. 292, HighWire Press.
Lund, et al., Cell Transplantation as a Treatment for Retinal Disease, Progress in Retinal and Eye Research, 2001, pp. 415-449, vol. 20, No. 4, Elsevier Science Ltd.
Lund, et al., Retinal Transplantation: Progress and Problems in Clinical Application, Journal of Leukocyte Biology, Aug. 2003, pp. 151-160, vol. 74.
Lyttle, et al., Transcription Factor Expression in the Developing Human Fetal Endocrine Pancreas, Diabetologica, 2008, pp. 1169-1180, vol. 51, Spring-Verlag.
Macfarlane, et al., Glucose Stimulates Translocation of the Homeodomain Transcription Factor PDX1 from the Cytoplasm to the Nucleus in Pancreatic B-Cells, The Journal of Biological Chemistry, 1999, pp. 1011-1016, vol. 274, No. 2.
Maherali, et al., Directly Reprogrammed Fibroblasts Show Global Epigenetic Remodeling and Widespread Tissue Contribution, Cell Stem Cell, Jul. 2007, pp. 55-70, vol. 1, Elsevier, Inc.
Mao, et al., The Reversal of Hyperglycaemia in Diabetic Mice Using PLGA Scaffolds Seeded with Islet-like Cells Derived from Human Embyonica Stem Cells, Biomaterials, 2009, pp. 1706-1714, vol. 30.
Marshall, et al., Early Micro-and Macro-Angiopathy in the Streptozotocin, Research in Experimental Medicine, 1980, pp. 145-158, vol. 177, Springer-Verlag.
Marshall, et al., Isolation and Maintenance of Primate Embryonic Stem Cells, Methods in Molecular Biology, 2001, pp. 11-18, vol. 158.
Martin, et al., Bioreactors for Tissue Mass Culture: Design, Characterization, and Recent Advances, Biomaterials, Jul. 14, 2005, pp. 7481-7503, vol. 26.
Marzo, et al., Pancreatic Islets from Cyclin-Dependent Kinase 4/R24C (Cdk4) Knockin Mice have Significantly Increased Beta Cell Mass and are Physiologically Functional, Indicating that Cdk4 is a Potential Target for Pancreatic . . . , Diabetologia, 2004, pp. 686-694, vol. 47.
Mathis, et al., B-Cell Death During Progression to Diabetes, Nature, 2001, pp. 792-798, vol. 414.
Matveyenko, et al., Inconsistent Formation and Nonfunction of Insulin-Positive Cells from Pancreatic Endoderm Derived from Human Embyonic Stem Cells in Athymic Nude Rats, American Journal of Physiol Endocrinol Metab, 2010, pp. E713-E720, vol. 299.
Mckiernan, et al., Directed Differentiation of Mouse Embryonic Stem Cells into Pancreatic-Like or Neuronal-and Glial-Like Phenotypes, Tissue Engineering, 2007, pp. 2419-2430, vol. 13, No. 10.
Mclean et al., Activin A Efficiently Specifies Definitive Endoderm from Human Embryonic Stem Cells Only When Phosphatidylinositol 3-Kinase Signaling is Suppressed, Stem Cells, 2007, pp. 29-38, vol. 25, AlphaMed Press.
Meijer, et al, Pharmacological Inhibitors of Glycogen Synthase Kinase 3, Trends in Pharmacological Sciences, Sep. 2004, pp. 471-480, vol. 25, No. 9.
Micallef et al., Retinoic Acid Induces Pdx1-Positive Endoderm in Differentiating Mouse Embryonic Stem Cells, Diabetes, Feb. 2005, pp. 301-305, vol. 54, American Diabetes Association.

(56) References Cited

OTHER PUBLICATIONS

Miller, et al, The Pig as a Model for Human Nutrition, Annual Review of Nutrition, 1987, pp. 361-382, vol. 7, Annual Reviews Inc.

Milunsky, et al., Genetic Disorders and the Fetus: Diagnosis Prevention and Treatment, Pediatric and Developmental Pathology, 2011, pp. 84, vol. 14, Society for Pediatric Pathology.

Minami, et al., A Small Molecule that Promotes Cardiac Differentiation of Human Pluripotent Stem Cells Under Defined, Cytokine- and Xeno-free Conditions, Cell Reports, 2012, pp. 1448-1460, vol. 2, No. 5.

Mitalipova, et al., Preserving the Genetic Integrity of Human Embryonic Stem Cells, Nature Biotechnology, 2005, pp. 19-20, vol. 23, No. 1.

Mitsui, et al., The Homeoprotein Nanog is Required for Maintenance of Pluripotency in Mouse Epiblast and ES Cells, Cell, May 30, 2003, pp. 631-642, vol. 113, Cell Press.

Miyamoto et al., Human Placenta Feeder Layers Support Undifferentiated Growth of Primate Embryonic Stem Cells, Stem Cells, 2004, pp. 433-440, vol. 22, AlphaMed Press.

Miyazaki et al., Regulated Expression of pdx-1 Promotes in Vitro Differentiation of Insulin-Producing Cells From Embryonic Stem Cells, Diabetes, Apr. 2004, pp. 1030-1037, vol. 53, American Diabetes Association.

Moore, et al., The Corneal Epithelial Stem Cell, DNA and Cell Biology, 2002, pp. 443-451, vol. 21, No. 5/6.

Moran, et al., Bidirectional-Barbed Sutured Knotless Running Anastomosis v Classic van Velthoven in a Model System, Journal of Endourology, 2007, pp. 1175-1177, vol. 21, No. 10.

Morrison, et al., Culture in Reduced Levels of Oxygen Promotes Clonogenic Sympathoadrenal Differentiation by Isolated Neural Crest Stem Cells, Journal of Neuroscience, Oct. 1, 2000, pp. 7370-7376, vol. 20, No. 19.

Movassat, et al., Keratinocyte Growth Factor and Beta-Cell Differentiation in Human Fetal Pancreatic Endocrine Precursor Cells, Diabetologia, 2003, pp. 822-829, vol. 46.

Muchamuel, et al., Preclinical Pharmacology and in Vitro Characterization of PR-047, An Oral Inhibitor of the 20s Proteasome, Blood, Nov. 16, 2008, p. 1257, vol. 112, No. 11.

Munoz et al, Conventional Pluripotency Markers are Unspecific for Bovine Embryonic-Derived Cell-Lines, Thierogenology, 2008, pp. 1159-1164, vol. 69.

Murtha, et al., Evaluation of a Novel Technique for Wound Closure Using a Barbed Suture, Cosmetic, Aug. 2, 2005, pp. 1769-1780, vol. 117, No. 6.

Nakagawa, et al., Generation of Induced Pluripotent Stem Cells without Myc from Mouse and Human Fibroblasts, Generation of Induced Pluripotent Stem Cells without Myc from Mouse and Human Fibroblasts, Jan. 2008, pp. 101-106, vol. 26, No. 1.

Nakamura, et al., Ocular Surface Reconstruction Using Cultivated Mucosal Epithelial Stem Cells, Cornea, Oct. 2003, S75-S80, vol. 22, Supplement 1.

Nelson, et al., The Transcription Factors Nkx6.1 and Nkx6.2 Possess Equivalent Activities in Promoting Beta-Cell Fate Specification in Pdx1+ Pancreatic Progenitor Cells, Development, 2007, pp. 2491-2500, vol. 134.

Nicholas et al., A Method for Single-Cell Sorting and Expansion of Genetically modified Human Embryonic Stem Cells, Stem Cells and Development, 2007, 109-117, 16, Mary Ann Liebert, Inc.

Nie, et al., Scalable Passaging of Adherent Human Pluripotent Stem Cells, PLOS One, 2014, pp. 1-9, vol. 9, Issue 1.

Nishimura, et al., Expression of MafA in Pancreatic Progenitors is Detrimental for Pancreatic Development, Developmental Biology, 2009, pp. 108-120, vol. 333.

Odom, et al., Control of Pancreas and Liver Gene Expression by HNF Transcription Factors, Science, 2004, pp. 1378-1381, vol. 303, No. 5662.

Oh, et al., Human Embryonic Stem Cells: Technological Challenges Towards Therapy, Clinical and Experimental Pharmacology and Physiology, 2006, pp. 489-495, vol. 33.

Okita, et al., Generation of Germline-Competent Induced Pluripotent Stem Cells, Nature, Jul. 19, 2007, pp. 313-317, vol. 448.

Orlowski, et al., Safety and Antitumor Efficacy of the Proteasome Inhibitor Carfilzomib (PR-171) Dosed for Five Consecutive Days in Hematologic Malignancies: Phase 1 Results, Blood, 2007, Part 1, vol. 110, No. 11.

Osborne, et al., Some Current Ideas on the Pathogenesis and the Role of Neuroprotection in Glaucomatous Optic Neuropathy, European Journal of Ophthalmology, 2003, pp. S19-S26, vol. 13, Supplement 3, Wichtig Editore.

Ostrom, et al., Retinoic Acid Promotes the Generation of Pancreatic Endocrine Progenitor Cells and Their Further Differentiation into B-Cells, PLOS One, Jul. 30, 2008, e2841, pp. 1-7, vol. 3, No. 7.

Ouziel-Yahalom, et al., Expansion and Redifferentiation of Adult Human Pancreatic islet Cells, Biochemical and Biophysical Research Communications, 2006, pp. 291-298, vol. 341.

Paling, et al., Regulation of Embryonic Stem Cell, Self-Renewal by Phosphoinositide 3-kinase-dependent Signaling, Journal of Biological Chemistry, 2004, pp. 48063-48070, vol. 279, No. 46.

Panchision, et al., Optimized Flow Cytometric Analysis of Central Nervous System Tissue Reveals Novel Functional Relationships Among Cells Expressing CD133, CD15, and CD24, Stem Cells, 2007, pp. 1560-1570, vol. 25.

Panepinto, et al., The Yucatan Miniature Pig: Characterization and Utilization in Biomedical Research, Laboratory Animal Science, Aug. 1986, pp. 344-347, vol. 36, No. 4, American Association for Laboratory Animal Science.

Pangas, et al., Production and Purification of Recombinant Human Inhibin and Activin, Journal of Endocrinology, 2002, pp. 199-210, vol. 172.

Pardo, et al, Corning CellBIND Surface: An Improved Surface for Enhanced Cell Attachment, Corning Technical Report, 2005, 8 page report.

Paris, et al., Equine Embryos and Embryonic Stem Cells: Defining Reliable Markers of Pluripotency, Theriogeneology, 2010, pp. 516-524, vol. 74.

Park, et al., Effects of Activin A on Pancreatic Ductal Cells in Streptozotocin-Inducted Diabetic Rats, Experimental Transplantation, 2007, pp. 925-930, vol. 83.

Peerani, et al., Niche-Mediated Control of Human Embryonic Stem Cell Self-Renewal and Differentiation, The EMBO Journal, 2007, pp. 4744-4755, vol. 26.

Perrier, et al., Derivation of Midbrain Dopamine Neurons from Human Embryonic Stem Cells, PNAS, Aug. 24, 2004, pp. 12543-12548, vol. 101, No. 34.

Phillips, et al., Attachment and Growth of Human Embryonic Stem Cells on Microcarriers, Journal of Biotechnology, 2008, pp. 24-32, vol. 138.

Phillips, et al., Directed Differentiation of Human Embryonic Stem Cells into the Pancreatic Endocrine Lineage, Stem Cells and Development, 2007, pp. 561-578, vol. 16, No. 4.

Pouton, et al., Embryonic Stem Cells as a Source of Models for Drug Discovery, Nature Reviews Drug Discovery, Aug. 2007, pp. 1474-1776, vol. 6, No. 8.

Prichard, et al., Adult Adipose Derived Stem Cell Attachment to Biomaterials, Biomaterials, 2006, pp. 936-946, vol. 28, No. 6.

Prowse, et al., A Proteome Analysis of Conditioned Media from Human Neonatal Fibroblasts Used in the Maintenance of Human Embryonic Stem Cells, Proteomics, 2005, pp. 978-989, vol. 5.

Prusa, et al., Oct-4-Expressing Cells in Human Amniotic Fluid: a New Source for Stem Cell Research?, Human Reproduction, 2003, pp. 1489-1493, vol. 18, No. 7.

Ptasznik, et al., Phosphatidylinositol 3-Kinase Is a Negative Regulator of Cellular Differentiation, The Journal of Cell Biology, 1997, pp. 1127-1136, vol. 137, No. 5.

R&D Systems, Embryonic & Induced Pluripotent Stem Cell Transcription Factors, Embryonic & Induced Pluripotent Stem Cell Transcription Factors, 2013, http://www.mdsystems.com/molecule_group.aspx?r=1&g-3041, 2 page web printout.

R&D Systems, Pancreatic Endoderm, Pancreatic Endoderm, Jun. 24, 2013, http://www.rndsystems.com/molecule_group.aspx?g=801 &r, 1 page web printout.

(56) References Cited

OTHER PUBLICATIONS

Rajagopal, et al., Insulin Staining of ES Cell Progeny from Insulin Uptake, Science, Jan. 17, 2003, pp. 363, vol. 299.
Rajala, et al., Testing of Nine Different Xeno-free Culture Media for Human Embryonic Stem Cell Cultures, Human Reproduction, Jan. 24, 2007, pp. 1231-1238, vol. 22, No. 5.
Ramiya, et al., Reversal of Insulin-Dependent Diabetes Using Islets Generated in vitro from Pancreatic Stem Cells, Nature Medicine, 2000, pp. 278-281, vol. 6.
Rao, Conserved and Divergent Paths that Regulate Self-Renewal in Mouse and Human Embryonic Stem Cells, Developmental Biology, Aug. 10, 2004, pp. 269-286, vol. 275, Elsevier, Inc.
Rebbapragada, et al., Myostatin Signals Through a Transforming Growth Factor B-Like Signaling Pathway to Block Adipogenesis, Molecular and Cellular Biology, 2003, pp. 7230-7242, vol. 23, No. 20.
Rebollar, et al., Proliferation of Aligned Mammalian Cells on Laser-Nanostructured Polystyrene, Biomaterials, 2008, pp. 1796-1806, vol. 29.
Reisner, Growing Organs for Transplantation form Embryonic Precursor Tissues, Immunol. Res., 2007, pp. 261-273, vol. 38.
Reubinoff et al., Embryonic stem cell lines from human blastocysts: somatic differentiation in vitro, Nature Biotech, Apr. 18, 2000, pp. 399-404, vol. 18, Nature America Inc.
Rezania, E al., Maturation of Human Embryonic Stem Cell-Derived Pancreatic Progenitors Into Functional Islets Capable of Treating Pre-Existing Diabetes in Mice, Diabetes, 2012, pp. 2016-2029, vol. 61.
Richards et al., Comparative Evaluation of Various Human Feeders for Prolonged Undifferentiated Growth of Human Embryonic Stem Cells, Stem Cells, 2003, pp. 546-556, vol. 21, AlphaMed Publlishing.
Richards, et al., Development of Defined Media for the Serum-Free Expansion of Primary Keratinocytes and Human Embryonic Stem Cells, Tissue Engineering, 2008, pp. 221-232, vol. 14, No. 3.
Richardson, et al., Bortezomid (PS-341): A Novel, First-in-Class Proteasome Inhibitor for the Treatement of Multiple Myeloma and Other Cancers, Cancer Control, 2003, pp. 361-369, vol. 10, No. 5.
Ricordi et al., Automated Method for Isolation of Human Pancreatic Islets, Diabetes, Apr. 1988, pp. 413-420, vol. 37, American Diabetes Association.
Ross, et al., Cytochrome P450s in the Regulation of Cellular Retinoic Acid Metabolism, Annu. Rev. Nutr., 2011, pp. 65-87, vol. 31.
Rowley, et al., Meeting Lot-Size Challenges of Manufacturing Adherent Cells for Therapy, Cell Therapies Manufacturing, 2012, pp. 16-22, vol. 10, No. 3.
Ryan, et al., Clinical Outcomes and Insulin Secretion After Islet Transplantation with the Edmonton Protocol, Diabetes, Apr. 2001, pp. 710-719, vol. 50.
Sakaguchi, et al., Integration of Adultmesenchymal Stem Cells in the CNS, Society for Neuroscience Abstract Viewer and Itineray Planner, 2002, Program 237.18.
Sander, et al., Homeobox Gene Nkk6.1 Lies Downstream of Nkx22 in the Major Pathway of Betta-Cell Formation in the Pancreats, Development, 2000, pp. 5533-5540, vol. 127.
Sato, et al., Maintenance of Pluripotency in Human and Mouse Embryonic Stem Cells Through Activation of Wnt Signaling by a Pharmacological GSK-3-specific Inhibitor, Nature Medicine, Jan. 2004, pp. 55-63, vol. 10, No. 1.
Sato, et al., Manipulation of Self-Renewal in Human Embryonic Stem Cells Through a Novel Pharmacological GSK-3 Inhibitor, Methods in Molecular Biology, 2006, pp. 115-128, vol. 331.
Sato, et al., Molecular Signature of Human Embryonic Stem Cells and its Comparison with the Mouse, Developmental Biology, Apr. 23, 2003, pp. 404-413, vol. 260.
Savino et al., Generation of Interleukin-6 Receptor Antagonists by Molecular-Modeling Guided Mutagenesis of Residues Important for gp130 Activation, EMBO Journal, 1994, pp. 1357-1367, vol. 13-6, IT.
Schisler, et al., The Nkx6.1 Homeodomain Transcription Factor Suppresses Glucagon Expression and Regulates Glucose-Stimulated Insulin Secretion in Islet Beta Cells, Proceedings of the National Academy of Sciences of the USA, 2005, pp. 7297-7302, vol. 102, No. 20.
Schnier, et al., G1 Arrest and Down-Regulation of Cyclin Elcyclin-dependent Kinase 2 by the Protein Kinase Inhibitor Staurosporine are Dependent on the Retinoblastoma Protein in the Bladder Carcinoma Cell Line 5637, Proceedings of the National Academy of Sciences, 1996, pp. 5941-5946, vol. 93.
Schraermeyer, et al., Subretinally Transplanted Embryonic Stem Cells Rescue Photoreceptor Cells From Degeneration in the RCS Rats, Cell Transplantation, 2001, pp. 673-680, vol. 10.
Schroeder, et al., Differentiation of Mouse Embryonic Stem Cells to Insulin-Producing Cells, Nature Protocols, 2005, pp. 495-507, vol. 1, No. 2.
Schuldiner, et al., Induced Neuronal Differentiation of Human Embryonic Stem Cells, Brain Research, 2001, pp. 201-205, vol. 913.
Schulz, et al., A Scalable System for Production of Functional Pancreatic Progenitors from Human Embryonic Stem Cells, PLOS One, 2012, pp. 1-17, vol. 7, Issue 5.
Scullica, et al., Diagnosis and Classification of Macular Degenerations: an Approach Based on Retinal Function Testing, Documenta Ophthalmologica, 2001, pp. 237-250, vol. 102.
Seaberg et al., Cfonal identification of multipotent precursors from adult ~ mouse pancreas that generate neural and pancreatic lineages, Nature Biotechnology, Sep. 2004, pp. 1115-1124, vol. 22, No. 9, Nature Publishing Group.
Segev, et al., Differentiation of Human Embryonic Stem Cells into Insulin-Producing Clusters, Stem Cells, Jan. 1, 2004, pp. 265-274.
Serafimidis, et al., Novel Effectors of Directed and Ngn3-Mediated Differentiation of Mouse Embryonic Stem Cells Into Endocrine Pancreas Progenitors, Stem Cells, 2008, pp. 3-16, vol. 26.
Shackleton, et al., Generation of a Functional Mammary Gland from a Single Stem Cell, Nature, Jan. 5, 2006, pp. 34-88, vol. 439.
Shamblott et al., Derivation of pluripotent stem cells from cultured human primordial germ cells, Developmental Biology, Nov. 1998, 13726-13731, 95, National Academy of Sciences.
Shapiro, et al., Islet Transplantation in Seven Patients with Type 1 Diabetes Mellitus Using a Glucocorticoid-Free Immunosuppressive Regimen, The New England Journal of Medicine, Jul. 27, 2000, pp. 230-238, vol. 343, No. 4, The Massachusetts Medical Society.
Shen, et al, The Effects of Surface Chemistry and Adsorbed Proteins on Monocyte/Macrophage Adhesion to chemically Modified Polystyrene Surfaces, Journal of Biomedical Matter Research, 2001, pp. 336-345, vol. 57.
Shim, et al., Directed Differentiation of Human Embryonic Stem Cells Towards a Pancreatic Cell Fate, Diabetologia, 2007, pp. 1228-1238, vol. 50.
Schindler et al., A synthetic nanofibrillar matrix promotes in vivo-like organization and morphogenesis for cells in culture, Biomaterials, Apr. 18, 2005, pp. 5624-5631, vol. 26, Elsevier.
Shiraki et al., TGF-B Signaling Potentiates Differentiation of Embryonic Stem Cells to Pdx-1 Expressing Endodermal Cells, Genes to Cells, 2005, pp. 503-516, vol. 10, Blackwell Publishing Limited.
Shiraki, et al., Guided Differentiation of Embryonic Stem Cells into Pdx1-Expressing Regional-Specific Definitive Endoderm, Stem Cells, 2008, pp. 874-885, vol. 26.
Sidhu et al., Derivation of Three Clones from Human Embryonic Stem Cell Lines by FACS Sorting and Their Characterization, Stem Cells and Development, 2006, pp. 61-69, vol. 15, Mary Ann Liebert, Inc.
Simandi, et al., Retinoid Signaling is a Context-Dependent Regulator of Embryonic Stern Cells, Embryonic Stem Cells—Differentiation and Pluripotent Alternatives, 2011, pp. 55-79, Chapter 3.
Simons, et al., Assembly of Protein Tertiary Structures from Fragments with Similar Local Sequences Using Simulated Annealing and Bayesian Scoring Functions, Journal of Molecular Biology, 1997, pp. 209-225, vol. 268.
Simons, et al., Improved Recognition of Native-Like Protein Structures Using a Combination of Sequence-Dependent and Sequence-

(56) References Cited

OTHER PUBLICATIONS

Independent Features of Proteins, Proteins: Structure, Function, and Genetics, 1999, pp. 82-95, vol. 34, Wiley-Liss, Inc.
Skoudy et al., Transforming growth factor (TGF)β, fibroblast growth factor (FGF) and retinoid signalling pathways promote pancreatic exocrine gene expression in mouse embryonic stem cells, Journal of Biochemistry, 2004, pp. 749-756, vol. 379, Biochemical Society, GB.
Smith et al., Anti-Interleukin-6 Monocolnal Antibody Induces Regression of Human Prostate Cancer Xenografts in Nude Mice, The Prostate, Mar. 2, 2001, 47-53, 48, Wiley-Liss, Inc.
Sneddon, et al., Self-Renewal of Embryonic-Stem-Cell-Derived Progenitors by Organ-Matched Mesenchyme, Nature, Nov. 29, 2012, pp. 765-770, vol. 491.
Soria et al., Insulin-Secreting Cells Derived From Embryonic Stem Cells Normalize Glycemia in Streptozotocin-Induced Diabetic Mice, Diabetes, Feb. 2000, 1-6, 49, American Diabetes Association.
Soria, et al, From Stem Cells to Beta Cells: New Strategies in Cell Therapy of Diabetes Mellitus, Diabetologia, 2001, pp. 407-415, vol. 44.
Spence, et al., Translation Embryology: Using Embryonic Principles to Generate Pancreatic Endocrine Cells from Embryonic Stem Cells, Developmental Dynamics, 2007, pp. 3218-3227, vol. 236.
Stacpoole, et al., Efficient Derivation of Neural Precuros Cells, Spinal Motor Neurons and Midbr, Nat Protoc, 2012, pp. 1-26, vol. 6, Issue 8.
Stadtfeld, et al., Defining Molecular Cornerstones During Fibroblast to iPS Cell Reprogramming in Mouse, Cell Stem Cell, Mar. 2008, pp. 230-240, vol. 2.
Stafford, et al., Retinoids Signal Directly to Zebrafish Endoderm to Specify Insuilin-Expressing B-cells, Development, 2005, pp. 949-956, vol. 133.
Stoffel, et al., Navigating the Pathway from Embryonic Stem Cells to Beta Cells, Seminars in Cell & Developmental Biology, 2004, pp. 327-336, vol. 15.
Stojkovic et al., An Autogeneic Feeder Cell System That Efficiently Supports Growth of Undifferentiated Human Embryonic Stem Cells, Stem Cells, 2005, pp. 306-314, vol. 23, AlphaMed Press.
Sugiyama, et al., Conserved Markers of Fetal Pancreatic Epithelium Permit Prospective Isolation of Islet Progenitor Cells by FACS, PNAS, Jan. 2, 2007, pp. 175-180, vol. 104, No. 1.
Sugiyama, et al., Fluorescence-Activated Cell Sorting Purification of Pancreatic Progenitor Cells, Diabetes, Obesity and Metabolism, 2008, pp. 179-185, vol. 10, Supplement 4.
Suh, et al., Characterization of His-X3-His Sites in a-Helices of Synthetic Metal-Binding Bovine Somatotropin, Protein Engineering, 1991, pp. 301-305, vol. 4, No. 3.
Sulzbacher, et al., Activin A-Induced Differentiation of Embryonic Stem Cells into Endoderm and Pancreatic Progenitors—The Influence of Differentiation Factors and Culture Conditions, Stem Cell Rev, 2009, pp. 159-173, vol. 5.
Sun, et al., Feeder-Free Derivation of Induced Pluripotent Stem Cells from Adult Human Adipose Stem Cells, Proceedings and the National Academy of Sciences, 2009, pp. 15720-15725, vol. 106, No. 37.
Suzuken, Differentiation of Multifunctional Stem Cells Using Human Feeder Cells, Research Papers of the Suzuken Memorial Foundation, 2007, pp. 193-197, vol. 24, JP.
Swindle, et al., Swine in Biomedical Research: Management and Models, ILAR News, 1994, pp. 1-5, vol. 36, No. 1.
Takahashi, et al., Homogenous Seeding of Mesenchymal Stem Cells into Nonwoven Fabric for Tissue Engineering, Tissue Engineering, 2003, pp. 931-938, vol. 9, No. 5.
Takahashi, et al., Induction of Pluripotent Stem Cells from Adult Human Fibroblasts by Defined Factors, Cell, 2007, pp. 861-872, vol. 131.
Takehara, et al., Rho-Associate Kinase Inhibitor Y-27632 Promotes Survival of Cynomolgus Monkey Embryonic Stem Cells, Molecular Human Reproduction, 2008, pp. 627-634, vol. 14, No. 11.
Tang, et al., Reprogramming Liver-Stem WB Cells into Functional Insulin-Producing Cells by Persistent Expression of Pdx1-and Pdx1-VP16 Mediated by Lentiviral Vectors, Laboratory Investigation, 2006, pp. 83-93, vol. 86.
Tannock, et al., Chemotherapy with Mitoxantrone Plus Prednisone or Prednisone Alone for Symptomatic Hormone-Resistant Prostate Cancer: A Canadian Randomized Trial With Palliative End Points, Journal of Clinical Oncology, 1996, pp. 1756-1764, vol. 14-6, American Society of Clinical Oncology, US.
Teare, et al., Cellular Attachment to Ultraviolet Ozone Modified Polystyrene Surfaces, Langmuir, 2000, pp. 2818-2824, vol. 16.
Tomita, et al., Bone Marrow-Derived Stem Cells Can Differentiate into Retinal Cells in Injured Rat Retina, Stem Cells, 2002, pp. 279-283, vol. 20.
Totonchi, et al., Feeder-and Serum-Free Establishment and Expansion of Human Induced Pluripotent Stem Cells, Int. J. Dev. Biol., 2010, pp. 8770886, vol. 54.
Tsai, et al., Isolation of Human Multipotent Mesenchymal Stem Cells from Second-Trimester Amniotic Fluid Using a Novel Two-Stage Culture Protocol, Human Reproduction, Apr. 22, 2004, pp. 1450-1456, vol. 19, No. 6.
Tsuchida, et al., Activin Isoforms Signal Through Type I Receptor Serine/Threonin Kinase ALK7, Molecular and Cellular Endocrinology, 2004, pp. 59-65, vol. 22.
Tulachan et al, TGF-β isoform signaling regulates secondary transition and mesenchymal-induced endocrine development in the embryonic mouse pancreas, Developmental Biology, 2007, pp. 508-521, vol. 305, Elsevier.
Ubeda et al., Inhibition of Cyclin-dependent Kinase 5 Activity Protects Pancreatic Beta Cells from Glucotoxicity, Journal of Biological Chemistry, Aug. 3, 2006, pp. 28858-28864, vol. 39, JBC Papers in Press.
Uludag, et al., Technology of Mammalian Cell Encapsulation, Advanced Drug Delivery Reviews, 2000, pp. 29-64, vol. 42.
Ungrin, et al., Reproducible, Ultra High-Throughput Formation of Multicellular Organization from Single Cell Suspension-Derived Human Embryonic Stem Cell Aggregates, Plos ONE, 2008, e1565, pp. 1-12, vol. 3, Issue 2.
Unknown, MeSH Descriptor Data, National Library of Medicine—Medical Subject Headings, Feb. 26, 1992, XP002553615.
Unknown, Preserve the Stability of Your Stem Cells, Stem Cells, 2006, Internet Citation, XP002496166.
Vacanti, et al., Selective Cell Transplantation Using Bioabsorbable Artificial Polymers as Matrices, Journal of Pediatric Surgery, Jan. 1988, 3-9, 23-1.
Valet, et al., Pretherapeutic Identification of High-Risk Acute Myeloid Leukemia (AML) Patients from . . . , Clinical Dytometry, Feb. 17, 2003, 4-10, 53B, Wiley-Liss, Inc., US.
Vallier, et al., Activin/Nodal and FGF Pathways Cooperate to Maintain Pluripotency of Human Embryonic Stem Dells, Journal of Cell Sciences, 2005, pp. 4495-4509, vol. 118.
Van Der Greef et al., Rescuing drug discovery: in vivo systems pathology and systems pharmacology, Nature, Dec. 31, 2005, pp. 961-967, vol. 4-1, Nature Reviews, US.
Van Der Windt, et al., The Chioce of Anatomical Site for Islet Transplantation, Cell Transplantation, 2008, pp. 1005-1014, vol. 17.
Van Kooten, et al., Plasma-Treated Polystyrene Surfaces: Model Surfaces for Studying Cell-Biomaterial Interactions, Biomaterials, 2004, pp. 1735-1747, vol. 25.
Van Wachem, et al., Method for the Fast Application of an Evenly Distributed Cell Layer on Porous Vascular Grafts, Biomaterials, 1990, pp. 602-606, vol. 11.
Vanderford et al., Multiple kinases regulate mafA expression in the pancreatic beta cell line MIN6, Biochemistry and Biophysics, 2008, pp. 138-142, vol. 480, Elsevier.
Verfaillie, et al., Stem Cells: Hype and Reality, Hematology, 2002, pp. 369-391.
Vieira, et al., Modulation of Neuronal Stem Cell Differentiation by Hypoxia and Reactive Oxygen Species, Progress in Neurobiology, 2011, pp. 444-455, vol. 93.
Vodicka, et al, The Miniature Pig as an Animal Model in Biomedical Research, Annals New York Academy of Sciences, 2005, pp. 161-171, vol. 1049.

(56) References Cited

OTHER PUBLICATIONS

Vunjak-Novakovic, et al., Dynamic Cell Seeding of Polymer Scaffolds for Cartilage Tissue Engineering, Biotechnology Program, 1998, pp. 193-202, vol. 14, Issue 2.

Wang et al., Derivation and Growing Human Embryonic Stem Cells on Feeders Derived from Themselves, Stem Cells, 2005, pp. 1221-1227, vol. 23, AlphaMed Press.

Wang et al., Relationship of Chemical Structurs of Anthraquinones with their Effects onthe Suppression of Immune Responses, International Journal of Immunopharmacology, 1987, pp. 733-739, vol. 9-6, International Society for Immunopharmacology, GB.

Wang, et al, Noggin and bFGF Cooperate to Maintain the Pluripotency of Human Embryonic Stem Cells in the Absence of Feeder Layers, Biochemical and Biophysical Research Communications, 2005, pp. 934-942, vol. 33, No. 3.

Want, et al., Large-Scale Expansion and Exploitation of Pluripotent Stem Cells for Regenerative Medicine Purposes: beyond the T Flask, Loughborough University Institutional Repository, 2012, pp. 71-84, vol. 7, Issue 1.

Watanabe, et al., A Rock Inhibitor Permits Survival of Dissociated Human Embryonic Stem Cells, Nature Biotechnology, 2007, pp. 681-686, vol. 25, No. 6.

Wei et al., Cdk5-dependent regulation of glucose-stimulated insulin secretion, Nature Medicine, Sep. 11, 2005, pp. 1104-1108, vol. 11-10, Nature Publishing Group.

Wei, et al., Human Amnion-Isolated Cells Normalize Blood Glucose in Strepozotocin Induced Diabetic Mice, Cell Transplantation, 2003, pp. 545-552, vol. 12, No. 5.

Wei, et al, Transcriptome Profiling of Human and Murine ESCs Identifies Divergent Paths Required to Maintain the Stem Cell State, Stem Cells, 2005, pp. 166-185, vol. 23.

Wernig, et al, c-Myc is Dispensable for Direct Reprogramming of Mouse Fibroblasts, Cell Stem Cell, Jan. 2008, pp. 10-12, vol. 2.

White, et al, Complex Regulation of cyp26a1 Creates a Robust Retinoic Acid Gradient in the Zebrafish Embryo, PLOS Biology, 2007, pp. 2522-2533, vol. 5, Issue 11.

Wiles et al., Embryonic Stem Cell Development in a Chemically Defined Medium, Experimental Cell Research, 1999, 241-248, 247, Academic Press.

Wong, et al., Directed Differentiation of Human Pluripotent Stem Cells into Mature Airway Epithelia Expressing Functional CFTR Protein, Nature Biotechnology, 2012, pp. 876-884, vol. 30, No. 9.

XP002553616_1989, RecName: Full=Inhibin beta B Chain; AltName: Full=Activin beta-B chain; Flags; Precursor, Database UniProt [Online], Jul. 1, 1989, Database Accession No. P09529, EBI Accession No. Uniprot: P09529.

Xu et al., Immortalized Fibroblast-Like Cells Derived from Human Embryonic Stem Cells Support Undifferentiated Cell Growth, Stem Cells, 2004, pp. 972-980, vol. 22, AlphaMed Press.

Xu, et al., Basic FGF and Suppression of BMP Signalling Sustain Undifferentiated Proliferation of Human ES Cells, Nature Methods, 2005, pp. 185-189, vol. 2, Issue 3.

Xu, et al., Feeder-free Growth of Undifferentiated Human Embryonic Stem Cells, Nature Biotechnology, 2001, pp. 971-974, vol. 19.

Xudong, et al., Research Progress in Inducing Stem Cels to Differentiate toward the B-like Cells of Pancreatic Islet, Chinese Bulletin of Life Sciences, 2007, pp. 526-530, vol. 19, No. 5 (English Abstract).

Yang et al., Novel cell immobilization method utilizing centrifugal force to achieve high-density hepatocyte culture in porous scaffold, Journal of Biomed Materials Research, Feb. 27, 2001, pp. 379-386, vol. 55, John Wiley & Sons, Inc.

Yang, et al., Evaluation of Humam MSCs Cell Cycle, Viability and Differentiation in Micromass Culture, Biorheology, 2006, p. 489-496, vol. 43 (Abstract Only).

Yang, et al., Survival of Pancreatic Islet Xenografts in NOD Mice with the Theracyte Device, Transplantation Proceedings, 2002, pp. 3349-3350, vol. 34.

Yasuda, et al., Development of Cystic Embryoid Bodies with Visceral Yolk-Sac-Like Structures from Mouse Embryonic Stem Cells Using Low-Adherence 96-Well Plate, Journal of Bioscience and Bioengineering, Apr. 4, 2009, pp. 442-446, vol. 107, No. 4.

Yoneda, et al., The Rho Kinases I and II Regulate Different Aspects of Myosin II Acitivity, The Journal of Cell Biology, 2005, pp. 443-445, vol. 170, No. 3.

Young, et al., Three-Dimensional Culture of Human Uterine Smooth Muscle Nyocytes on a Resorbably Scaffolding, Tissue Engineering, 2003, pp. 451-459, vol. 9, No. 3.

Yu, et al., Induced Pluripotent Stem Cell Lines Derived from Human Somatic Cells, Science, Dec. 21, 2007, pp. 1917-1920, vol. 318.

Yu, et al., Isolation of a Novel Population of Multipotent Adult Stem Cells from Human Hair Follicles, American Journal of Pathology, Jun. 6, 2006, pp. 1879-1888, vol. 168, No. 6.

Zalzman, et al., Differentiation of Human Liver-Derived, Insulin-Producing Cells Toward the B-Cell Phenotype, Diabetes, 2005, pp. 2568-2575, vol. 54.

Zembower, et al., Peptide Boronic Acids Versatile Synthetic Ligands for Affinity Chromatography of Serine Proteinases, International Journal Peptide Protein, 1996, pp. 405-413, vol. 47.

Zhang et al, MafA Is a Key Regulator of Glucose-Stimulated Insulin Secretion, Molecular and Cellular Biology, Jun. 2005, pp. 4969-4976, vol. 25-12, American Society for Microbiology.

Zhang, et al., Differentiation Potential of Bone Marrow Mesenchymal Stem Cells into Retina in Normal and Laser-Injured Rat Eye, Science in China Series, 2004, pp. 241-250, vol. 47, No. 3 (English Abstract).

Zhang, Jie, The Differentiation of Bone Marrow Mesenchymal Stem Cells into Retina in Rat Eye and the Therapeutical Effect on Severe Injured Retina, A Doctoral Thesis of Chinese PLA Acadamey of Military Medical Sciences, 2003, 1-127, 1-127 (English Abstract).

Zhao et al., The Islet B Cell-enriched MafA Activator is a Key Regulator of Insulin Gene Transcription, Journal of Biological Chemistry, Mar. 25, 2005, 11887-11894, 280-12, The Amerian Society for Biochemistry and molecular Biology, Inc.

Zhao et al., Derivation and Characterization of Hepatic Progenitor Cells from Human Embryonic Stem Cells, PLoS ONE Hepatic Progenitors from hESCs, Jul. 2009, e6468 pp. 1-10, vol. 4, Issue 7.

Zubaty, et al., Transplantation of Mesenchymal Stem Cells into RCS Rats for Retinal Repair, Investigative Ophthalmology and Visual Science, 2005, pp. 4160-13518, vol. 46, Supplement S.

Zuscik, et al., Regulation of Chondrogenesis and Chondrocyte Differentiation by Stress, J Clin Invest, 2008, pp. 129-438, vol. 118, Issue 2.

Cohick, et al., The Insulin-Like Growth Factors, Annual Reviews Physiol, 1993, pp. 131-153, vol. 55, Annual Reviews Inc.

Hebrok, et al., Notochord repression of endodermal Sonic hedgehog permits pancreas development, Genes & Development, Jun. 1, 1998, pp. 1705-1713, vol. 12 , Issue 11, Cold Spring Harbor Laboratory Press.

Jaenisch, et al., Stem Cells, the Molecular Circuitry of Pluripotency and Nuclear Reprogramming, cell, Feb. 22, 2008, pp. 567-582, vol. 132, Elsevier Inc.

Klajnert, et al., Fluorescence studies on PAMAM dendrimers interactions with bovine serum albumin, Bioelectrochemistry, 2002, pp. 33-35, vol. 55.

Kubota,et al., Growth factors essential for self-renewal and expansion of mouse spermatogonial stem cells, cell Biology, Nov. 23, 2004, pp. 16489-16494, vol. 101 , Issue 47.

Nostro, et al., Generation of Beta Cells from Human Pluripotent Stem Cells: Potential for Regenerative Medicine, Seminars in Cell & Developmental Biology, 2012, pp. 701-710, vol. 23.

Ratanasavanh,et al., Immunocytochemical Evidence for the Maintenance of Cytochrome P450 Isozymes, NADPH Cytochrome C Reductase, and Epoxide Hydrolase in Pure and Mixed Primary Cultures of Adult Human Hepatocytes1, The Journal of Histochemistry and Cytocheinistry, 1986, pp. 527-533, vol. 34 , Issue 4.

Rezania, et al., Reversal of Diabetes with Insulin-Producing Cells Derived in vitro from Human Pluripotent Stem Cells, Nature Biotechnology, 2014, pp. 1121-1133, vol. 32, No. 11.

Schaefer-Graf, et al., Patterns of congenital anomalies and relationship to initial maternal fasting glucose levels in pregnancies com-

(56) References Cited

OTHER PUBLICATIONS plicated by type 2 and gestational diabetes, Am J Obstet Gynecol, 2000, pp. 313-320, vol. 182, Issue 2.
Thermofisher Scientific, B-27 Serum-Free Supplement (50x) Liquid, Technical Resources, 2016, URL:https://www.thermofisher.com/nl/en/home/technical-resources/media-formulation.250.html, retrieved from the internet.
Wachs, et al., High Efficacy of Clonal Growth and Expansion of Adult Neural Stem Cells, Laboratory Investigation, 2003, pp. 949-962, vol. 83, No. 7.
Beers, et al., Passaging and Colony Expansion of Human Pluripotent Stem Cells by Enzyme-Free Dissociation in Chemically Defined Culture Conditions, Nature Protocols, 2012, pp. 2029-2040, vol. 7, No. 11.
Brimble, S., et al., The Cell Surface Glycosphingolipis SSEA-3 and SSEA-4 Are Not Essential for Human ESC Pluripotency, Stem Cells, Jan. 2007, pp. 54-62, vol. 25.
Buta, et al., Reconsidering pluripotency tests: Do we still need teratoma assays?, Stem Cell Research, Mar. 26, 2013, pp. 552-562, vol. 11.
Chen, et al., Retinoic acid signaling is essential for pancreas development and promotes endocrine at the expense of exocrine cell differentiation in Xenopus, Developmental Biology, May 4, 2004, pp. 144-160, vol. 271.
Chen, et al., Scalable GMP Compliant Suspension Culture System for Human ES Cells, Stem Cell Research, 2012, pp. 388-402, vol. 8.
Cirulli, et al., Netrins: beyond the brain, Molecular Cell Biology, Apr. 2007, pp. 296-306, vol. 8.
Furue, et al., Heparin propotes the growth of human embryonic stem cells in a defined serum-free medium, PNAS, Sep. 9, 2008, pp. 13409-13414, vol. 105, Issue 36.
Gibco, Insulin-Transferin-Selenium-X 100X, Invitrogen Cell Culture, Apr. 2005, pp. 1, Form No. 3032.
Gomez, et al., Derivation of cat embryonic stem-like cells from in vitro-produced blastocysts on homologous and heterologous feeder cells, Theriogenology, May 11, 2010, pp. 498-515, vol. 74.
Gordon Weir., Do stem cells hold the key to a future cure for diabetes?, DiabetesVoice, Jun. 2008, pp. 29-31, vol. 53, Issue 2.
Guo, et al., Efficient differentiation of insulin-producing cells from skin-derived stem cells, Cell Proliferation, 2009, pp. 49-62, vol. 42.
Hiemisch, H., et al., Transcriptional Regulation in Endoderm Development: Characterization of an Enhancer Dontrolling Hnf3g Expression by Transgenesis and Targeted Mutagenesis, The EMBO Journal, 1997, pp. 3995-4006, vol. 16(13).
Jean, et al., Pluripotent genes in avian stem cells, Development Growth & Differentitaion, 2013, pp. 41-51, vol. 55.
Kang, et al., Plasma treatment of textiles—Synthetic Polymer—Based Textiles, AATCC Review, 2004, pp. 29-33.
King, et al., Bioreactor development for stem cell expansion and controlled differentiation, Current Opinion in Chemical Biology, Jul. 25, 2007, pp. 394-398, vol. 11, Elsevier Ltd.
Kunisada, et al., Small molecules induce efficient differentiation into insulin-producing cells from human induced pluripotent stem cells, Stem Cell Research, Oct. 11, 2011, pp. 274-284, vol. 8.
Lavial, et al., Chicken Embryonic Stem Cells as a Non-Mammalian Ebryonic Stem Cell Model, Development Growth Differentiation, Jan. 2010, pp. 101-114, vol. 52(1).
Lin, C. et al., Coagulation Dysregulatin as a Barrier to Xenotransplantation in the Primate, Transplant Immunology, 2009, pp. 75-80, vol. 21.
Maria-Jesus Obregon, Thyroid hormone and adipocyte differentiation, Thyroid, 2008, pp. 185-195, vol. 18 Issue 2.
McMahon, et al., Noggin-mediated antagonsim of BMP signaling is required for growth and patterning of the neural tube and somite, Genes & Development, Mar. 16, 1998, pp. 1438-1452, vol. 12.
Nakase, et al., Myeliod Antigen, CD13, CD14, and/ or CD33 Expression Is Restricted to Certain Lymphiod Neoplasms, Hematopathology, Jun. 1996, pp. 761-768, vol. 105, Issue 6.
Narang, A., et al., Biological and Biomaterial Approaches for Improved Islet Transplantation, Pharmacological Review, Jun. 2006, pp. 194-243, vol. 58(2).
Olmer, et al., Long Term Expansion of Undifferentiated Human iPS and ES Cells in Suspension Culture Using Defined Medium, Stem Cell Research, 2010, pp. 51-64, vol. 5.
Ouziel-Yahalom, et al., Expansion and redifferentiation of adult human pancreatic islet cells, Biochemical and Biophysical Research Communications, Jan. 19, 2006, pp. 291-298, vol. 341.
Petitte, J., et al., Avian Pluripotent Stem Cells, Mechanisms of Development, 2004, pp. 1159-1168, vol. 121.
Ramiya, et al., Reversal of insulin-dependent diabetes using islets generated in vitro from pancreatic stem cells, Nature Medicine, Mar. 2000, pp. 278-282, vol. 6, Issue 3.
Rother, et al., Challenges facing islet transplantation for the treatment of type 1 diabetes mellitus, The Journal of Clinical Investigation, 2004, pp. 877-883, vol. 114, Issue 7.
Rowely, et al., Meeting Lot-size Challenges of Manufacturing Adherent Cells for Therapy, Bio Process International, Mar. 2012, pp. 16-22, vol. 10, Issue 3.
Sjögren-Jansson, et al., Large-Scale Propagation of Four Undifferentiated Human Embryonic Stem Cell Lines in a Feeder-Free Culture System, Developmental Dynamics, Jun. 17, 2005, pp. 1304-1314, vol. 233.
Strizzi, et al., Netrin-1 regulates invasion and migration of mouse mammary epithelial cells overexpressing Cripto-1 in vitro and in vivo, Journal of Cell Science, Jul. 7, 2005, pp. 4633-4643, vol. 118, Issue 20.
Suzuken., Differentiation of Multifunctional Stem Cells Using Human Feeder Cells, Research Papers of the Suzuken Memorial Foundation, 2007, pp. 193-197, vol. 2.
Thomson, Bioprocessing of Embryonic Stem Cells for Drug Discovery, Trends in Biotechnology, 2007, pp. 224-230, vol. 25, No. 5.
Yadlin, et al., Small-molecule inducers of insulin expression in pancreatic α-cells, PNAS, Aug. 24, 2010, pp. 15099-15104, vol. 107, Issue 34.
Yang JW, et al., Evaluation of human MSCs cell cycle, viability and differentiation in micromass culture, Biorheology, 2006, pp. 1-2, vol. 43, Issue (3-4).
Yim, et al., Proliferation and differentiation of human embryonic germ cell derivatives in bioactive polymeric fibrous scaffold, J.Biomater. Sci.Polymer Edn,, Jan. 19, 2005, pp. 1193-1217, vol. 16, Issue 10.
Zulewski, et al., Multipotentital Nestin-Positive Stem Cells lasolated From Adult Pancreatic Islets Differentiate Ex Vivo Into Pancreatic Endocrine, Exocrine, and Hepatic Phenotypes, Diabetes, 2001, pp. 521-533, vol. 50.
Blazhevich Kul'tivirovanie kletok. Kurs lektsij.—Mn.: BGU, (78 pages); pp. 56, 57, 59, with English translation (9 pages) (2004).
Cameron et al., "Improved development of human embryonic stem cell-derived embryoid bodies by stirred vessel cultivation," *Biotechnol Bioeng.* 94: 938-948 (2006).
Cimbaljuk et al. "Spinnoj mozg. Jelegija nadezhdy: monografija", *Novaja kniga.* 944 pages (p. 245) (2010). Relevance is based on English translation of Russian OA, No. 2018108851, dated Oct. 17, 2018.
Gerecht-Nir et al., "Bioreactor cultivation enhances the efficiency of human embryoid body (hEB) formation and differentiation," *Biotechnol Bioeng.* 86: 493-502 (2004).
Gilbert, "Developmental Biology," 3 volumes, the first volume: translation from English—M.: Mir, (228 pages): p. 187, with English translation (5 pages) (1993).
Kozhukharova I.V., "Novye linii ehmbrional'nykh stvolovykh kletok cheloveka S612 I S90," *Tsitologiya* 51: 551-558 (2009). (Relevance is based on the English translations of two Office Actions from Russian Application No. 2018108850 and Russian Application No. 2018108847, both attached).
Lian et al., "Directed cardiomyocyte differentiation from human pluripotent stem cells by modulating Wnt/β-catenin signaling under fully defined conditions," *Nat. Protoc.* 8: 162-175 (2013).
Menzorov "Embryonic Stem Cells of the Mouse and Human," *Vavilov J Genet Breed.* 17: 234-245(p. 237) with English translation (5 pages) (2013).

(56) References Cited

OTHER PUBLICATIONS

Nelson et al., "Therapeutic Potential of the Inhibition of the Retinoic Acid Hydroxylases CYP26A1 and CYP26B1 by Xenobiotics," *Curr Top Med Chem.* 13:1402-1428 (2013).

Serafimidis et al., "G Protein-Coupled Receptor Signaling and Sphingosine-1-Phosphate Play a Phylogenetically Conserved Role in Endocrine Pancreas Morphogenesis," *Mol Cell Biol.* 31:4442-4453 (2011).

Serafimidis et al., "Novel effectors of directed and Ngn3-mediated differentiation of mouse embryonic stem cells into endocrine pancreas progenitors," *Stem Cells* 26(1): 3-16 (e-PUB Oct. 11, 2007).

Stacpoole et al., "Efficient derivation of neural precursor cells, spinal motor neurons and midbrain dopaminergic neurons from human ES cells at 3% oxygen," *Nat Protoc.* 6: 1229-1240 (2012).

Stanford et al., "Sphingosine 1-phosphate S1P regulates glucose-stimulated insulin secretion in pancreatic beta cells," *J Biol. Chem.* 287: 13457-13464 (2012).

Balajthy, et al, Chapter 8. 8. Embryonic and adult stem cells in regenerative medicine I, Molecular therapies, 2011, pp. 1-6.

Condic, et al., Alternative Sources of Pluripotent Stem Cells: Ethical and Scientific Issues Revisited, Stem Cells and Development, 2010, pp. 1121-1129, vol. 19 Issue 8, Mary Ann Liebert, Inc.

Daheron, et al., LIF/STAT3 Signaling Fails to Maintain Self-Renewal of Human Embryonic Stem Cells, Stem Cells, 2004, pp. 770-778, vol. 22.

Findikli, et al., Establishment and characterization of new human embryonic stem cell lines, Reproductive BioMedicine Online, Mar. 3, 2005, pp. 617-627, vol. 10 Issue 5.

Foster, et al., Differentiation of Transplanted Microencapsulated Fetal Pancreatic Cells, Transplantation, Jun. 15, 2007, pp. 1440-1448, vol. 83 Issue 11.

Guillemain, et al., Glucose Is Necessary for Embryonic Pancreatic Endocrine Cell Differentiation*, The Journal of Biological Chemistry, May 18, 2007, pp. 15228-15237, vol. 282 Issue 20.

Kehoe, et al., Scalable Stirred-Suspension Bioreactor Culture of Human Pluripotent Stem Cells, Tissue Eng Part A, 2010, pp. 405-421, vol. 16 Issue 2.

Kim, et al., Reprogrammed Pluripotent Stem Cells from Somatic Cells, International Journal of Stem Cells, 2011, pp. 1-8, vol. 4 Issue 1.

Lee, et al., Available human feeder cells for the maintenance of human embryonic stem cells, Reproduction, 2004, pp. 727-735, vol. 128.

Ludwig, et al., Defined, Feeder-Independent Medium for human Embryonic Stem Cell Culture, Current Protocols in Stem Cell Biology, 2007, pp. 1C.2.1-1C.2.16, vol. 1, John Wiley & Sons, Inc.

Maimets, et al., Activation of p53 by nutlin leads to rapid differentiation of human embryonic stem cells, Oncogene, Jun. 2, 2008, pp. 5277-5287, vol. 27.

Micallef, et al., Pancreas Differentiation of Mouse ES Cells, Current Protocols in Stem Cell Biology, 2007, pp. 1G.1.1-1.2.8, John Wiley & Sons, Inc.

Misiti, et al., 3,5,30-Triiodo-L-Thyronine Enhances the Differentiation of a Human Pancreatic Duct Cell Line (hPANC-1) Towards a b-Cell-Like Phenotype, Journal of Cellular Physiology, 2005, pp. 286-296, vol. 204.

Nakanishi, et al., Pancreatic tissue formation from murine embryonic stem cells in vitro, Differentiation, 2007, pp. 1-11, vol. 75.

Nekrasov, et al., Induced pluripotent stem cells as a model for studying human diseases, Cellular Transplantology and Tissue Engineering, 2011, pp. 32-37, vol. 6 Issue 2.

Osafune, et al., Marked differences in differentiation propensity among human embryonic stem cell lines, Nature Biotechnology, Feb. 17, 2008, pp. 313-315, vol. 26 Issue 3.

Sigma-Aldrich, MCBD-131 product description, Sigma-Aldrich, 2007.

Verkhovskaya, et al., Effect of alkoxy-substituted of glycerin on the morphofunctional properties of continuous cell culture, Cryobiology, 1990, pp. 30-33, vol. 1 (English Abstract).

Wang, et al., Cultivation and identification of pancreatic endocrine progenitor cells, National Medical Journal of China, 2006, pp. 1850-1853, vol. 86 Issue 26 (English Abstract).

Wang, et al., Scalable expansion of human induced pluripotent stem cells in the defined xeno-free E8 medium under adherent and suspension culture conditions, Stem Cell Research, Nov. 2013, pp. 1103-1116, vol. 11 Issue 3.

Zhu et al., A Small Molecule Primes Embryonic Stem Cells for Differentiation, Cell Stem Cell, May 8, 2009, pp. 116-426, vol. 4.

Jorda et al., "How selective are pharmacological inhibitors of cell-cycle-regulating cyclin-dependent kinases?," *Journal of Medical Chemistry* 61(20): 9105-9120 (Sep. 20, 2018).

* cited by examiner

Isotype

Chromogranin

KI-67

NKX6.1

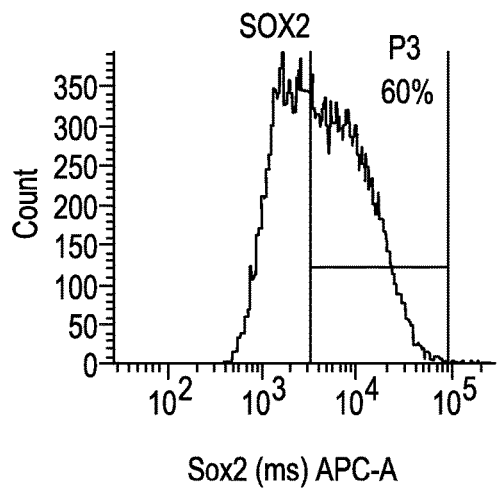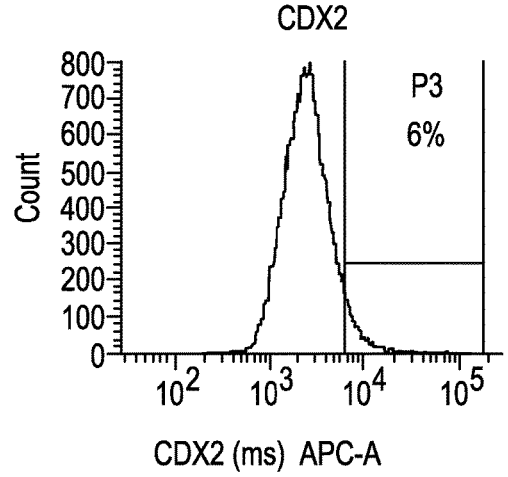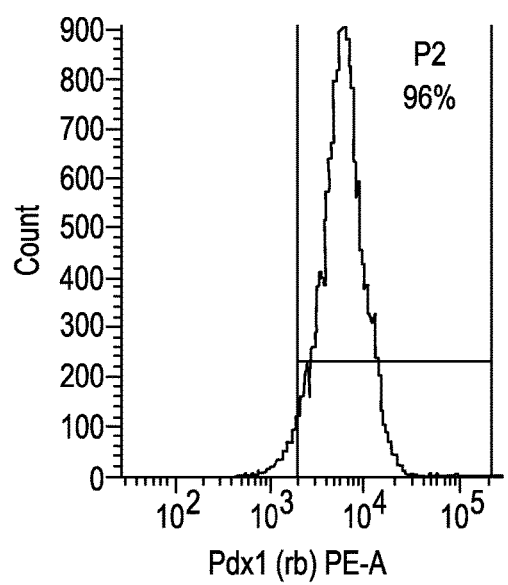

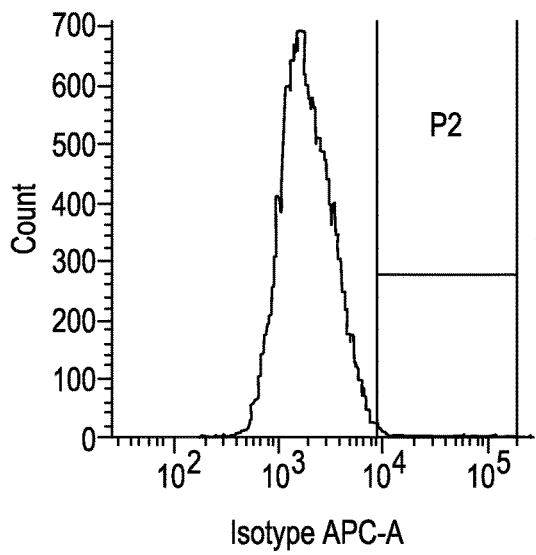
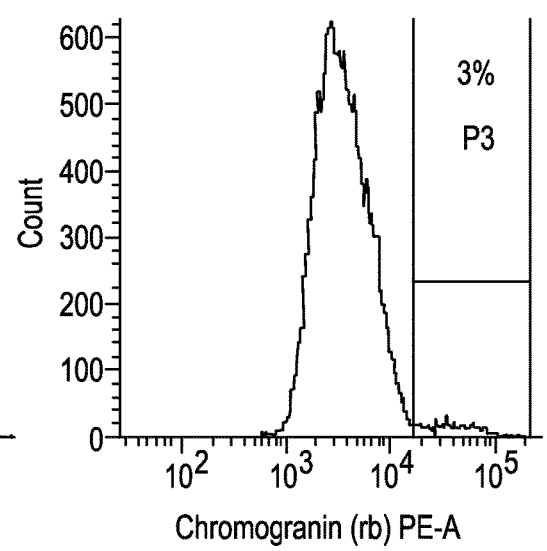
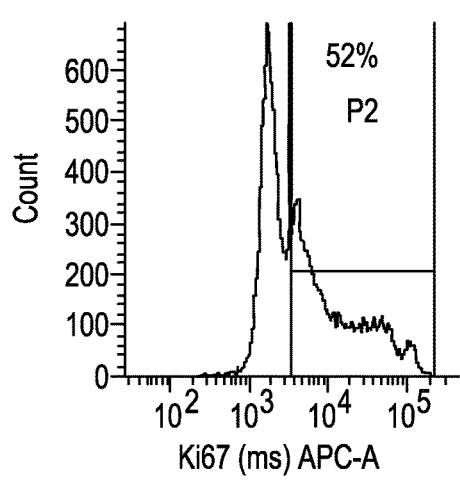
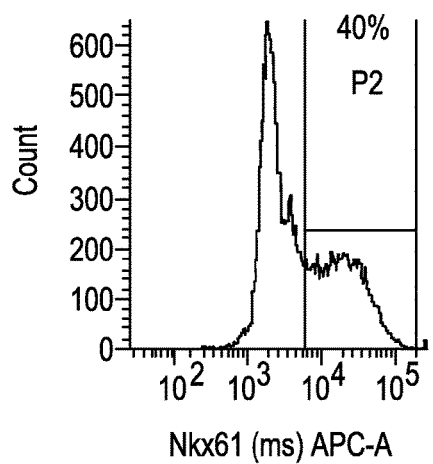

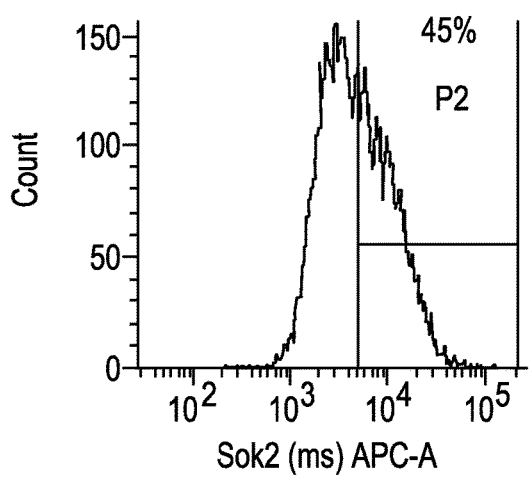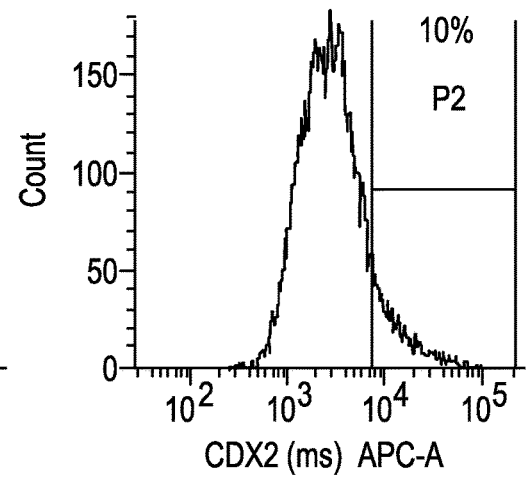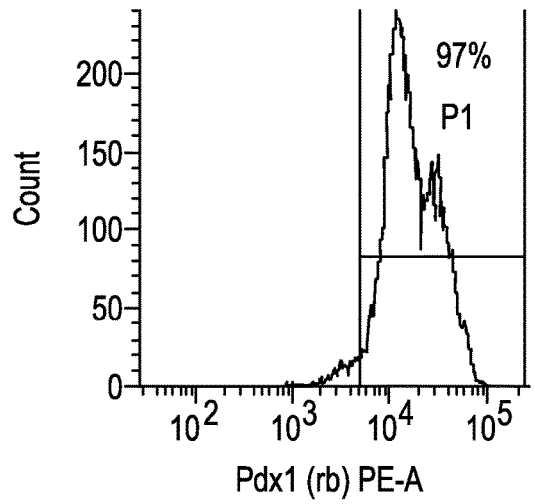

Isotype

Chromogranin

KI-67

NKX6.1

SOX2

CDX2

PDX-1

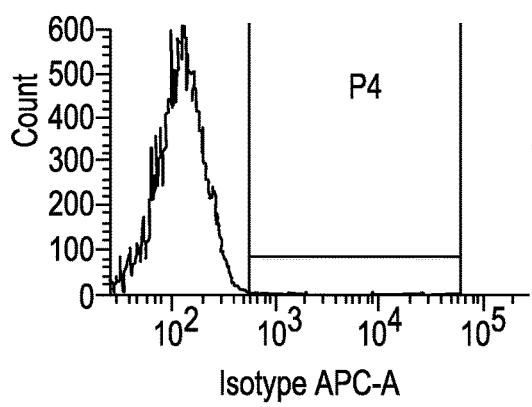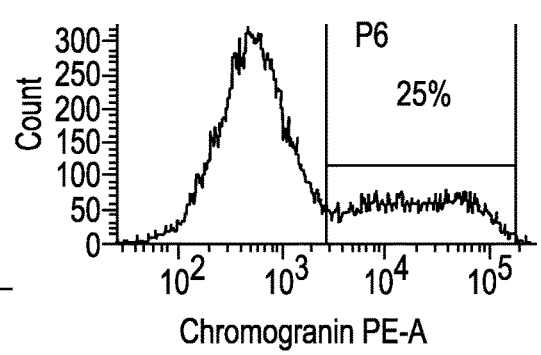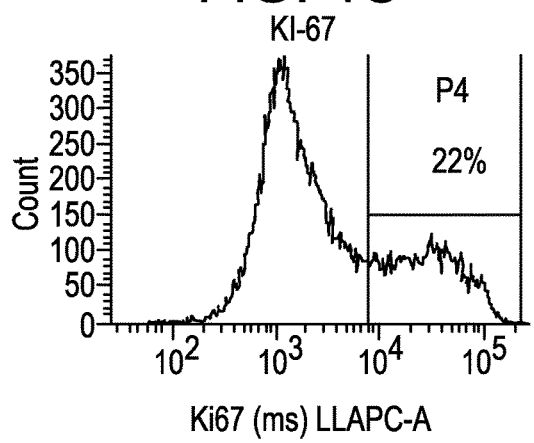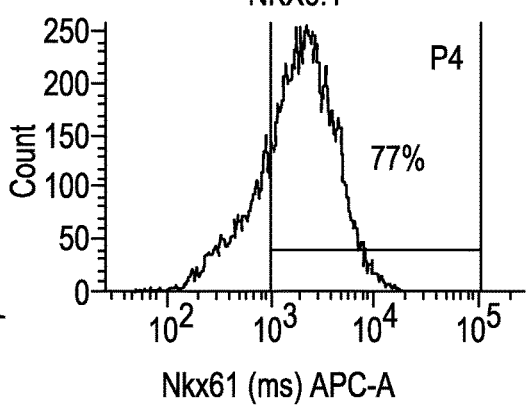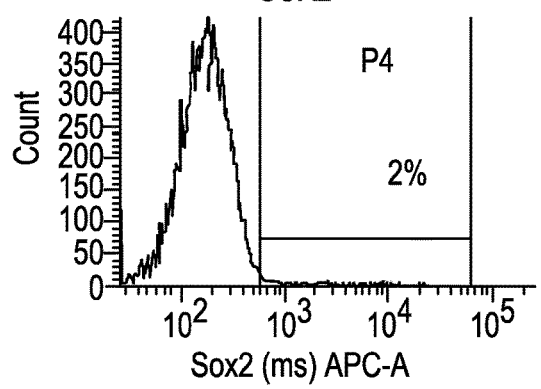

CDX2

PDX-1

HNF4a

NKX2.1

NKX2.2

NKX6.1

OSR1 (ODD1)

PDX1

NeuroD1

Somatostatin

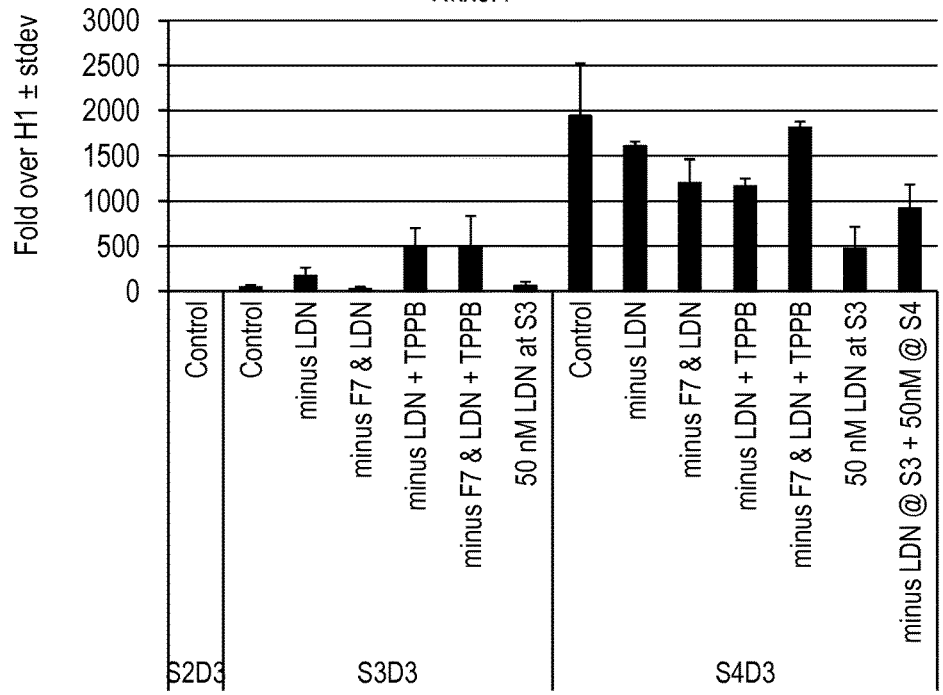
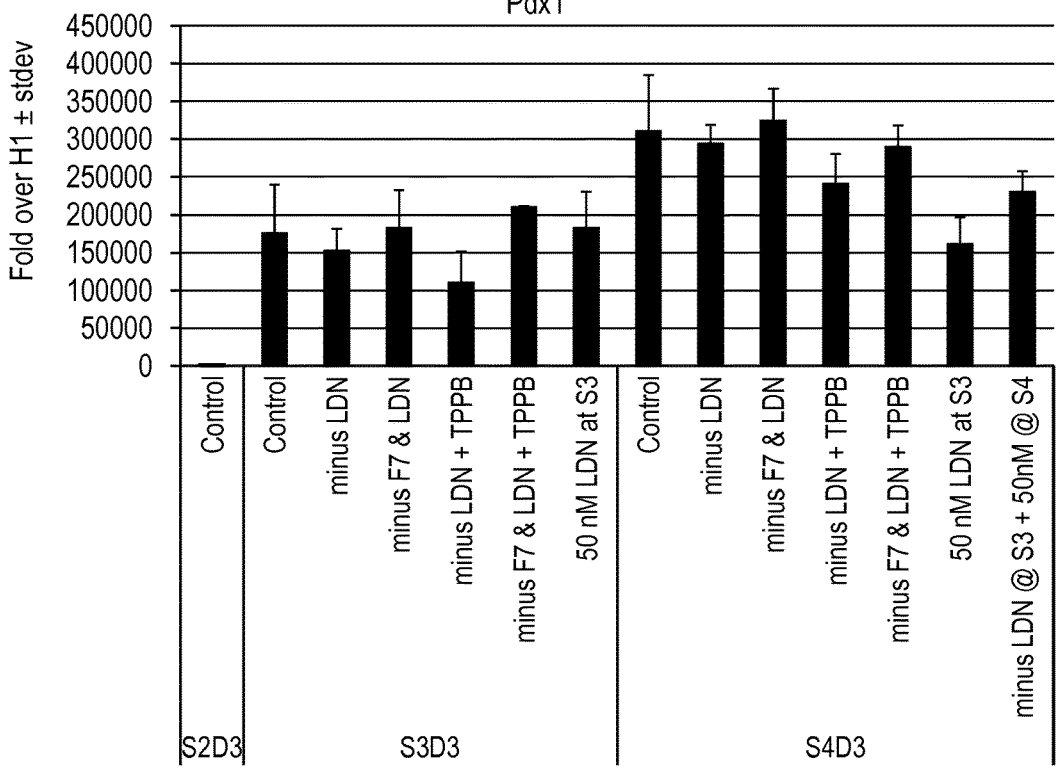

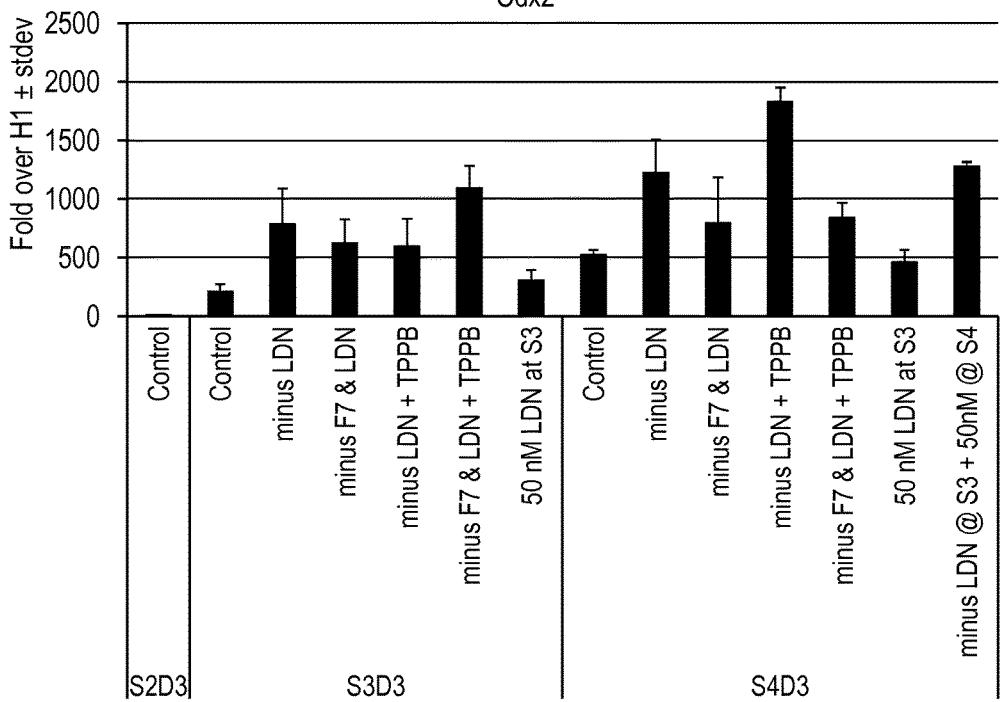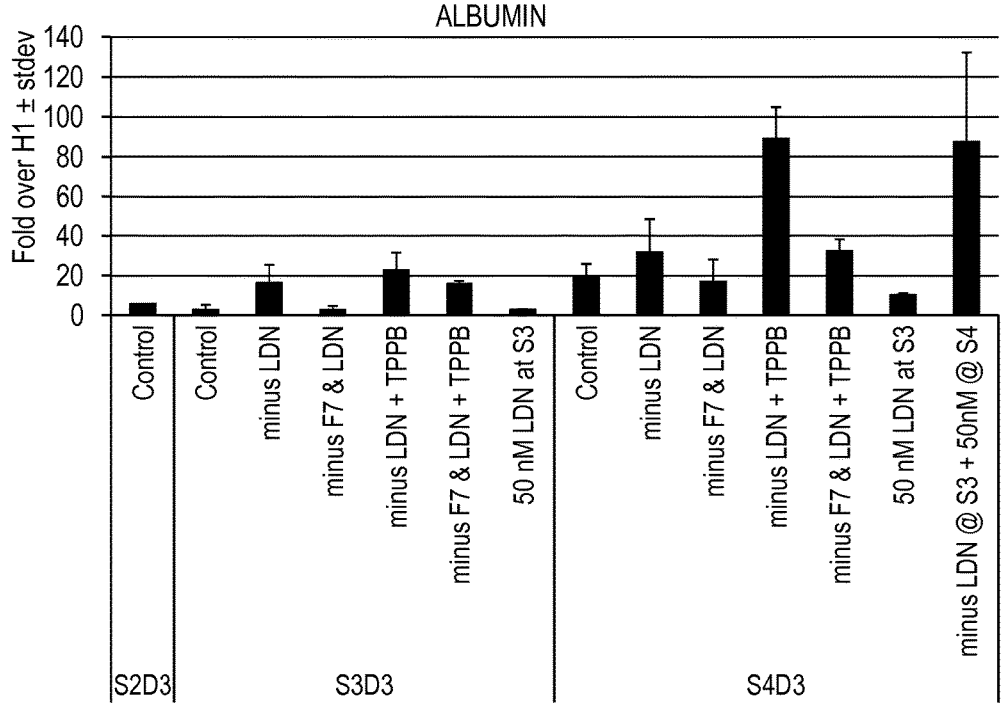

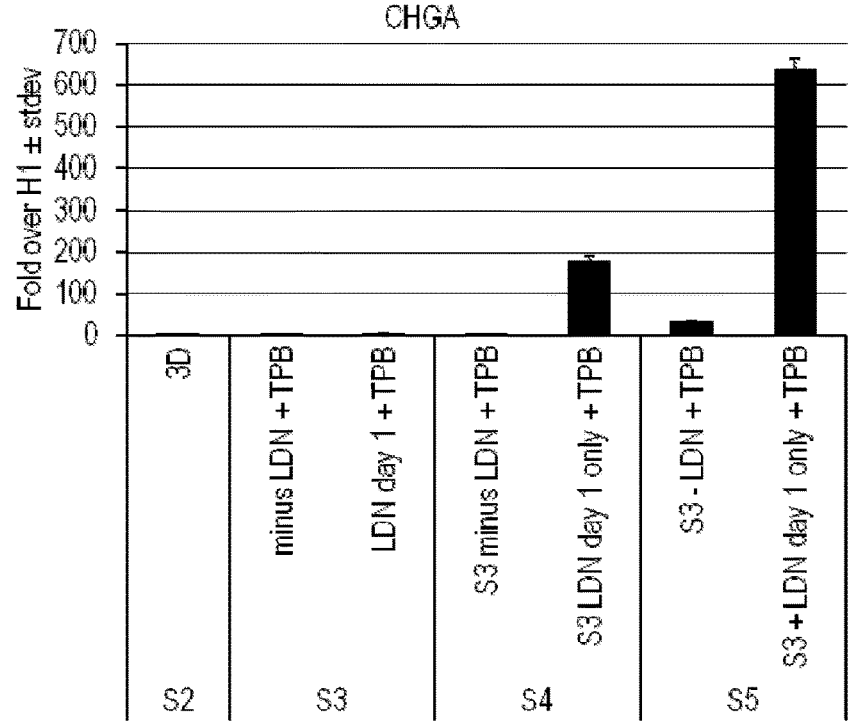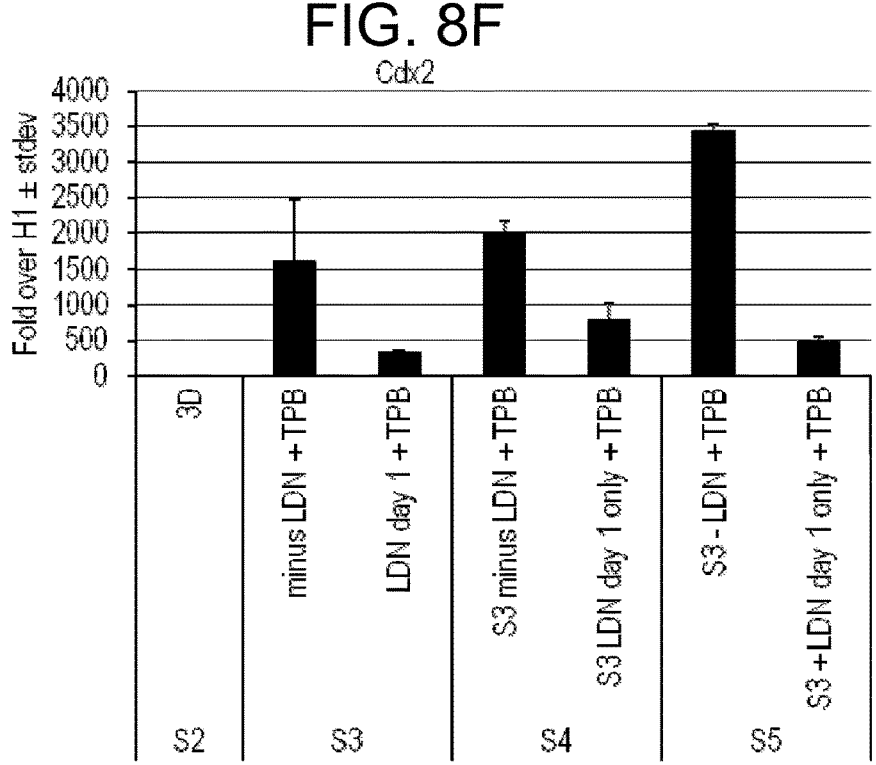

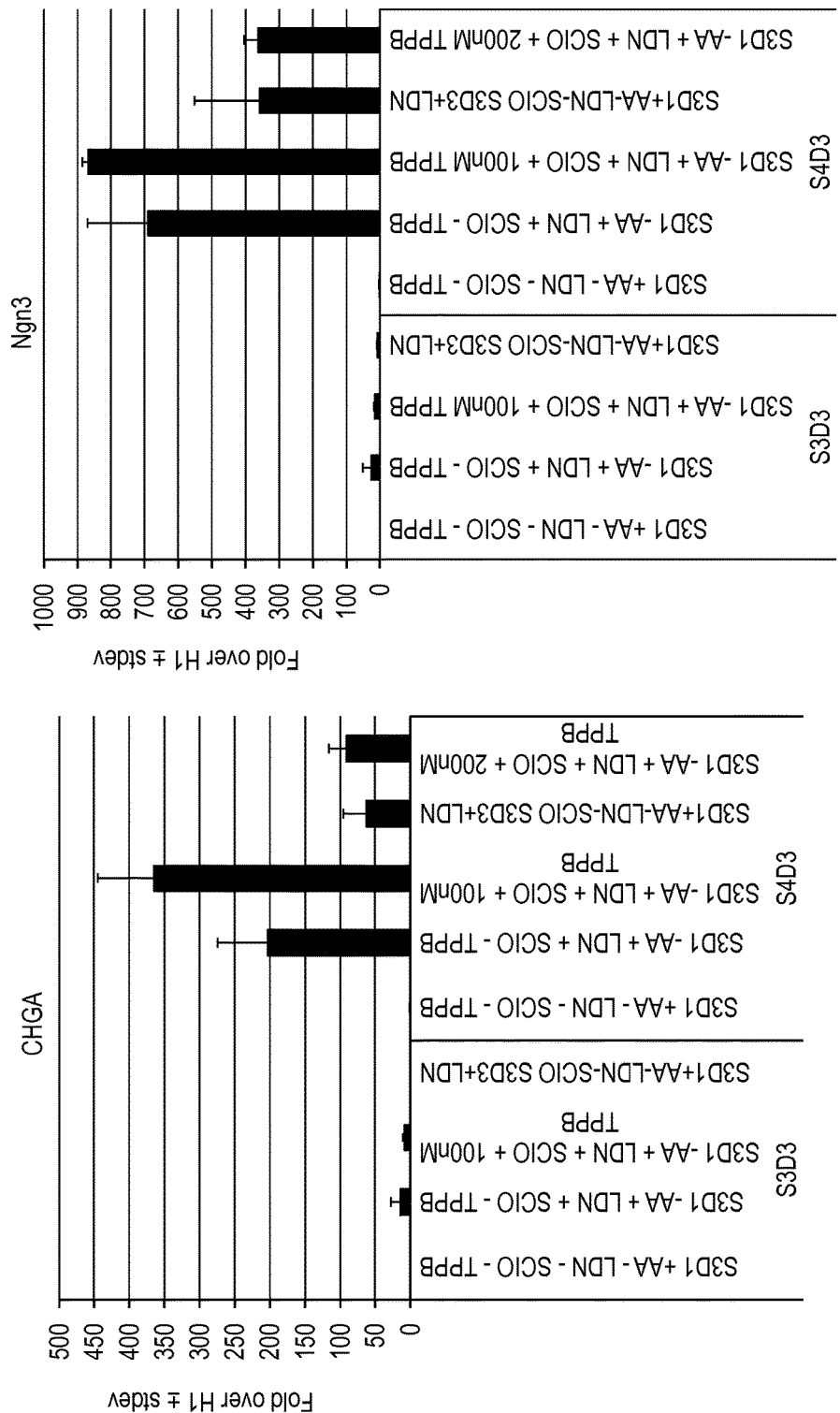

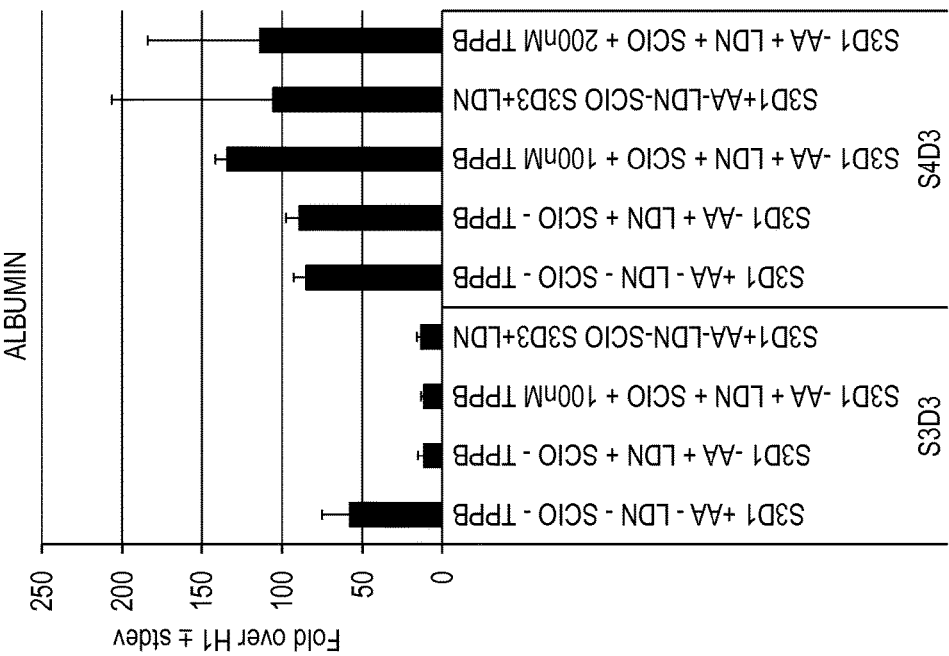
FIG. 9G ALBUMIN
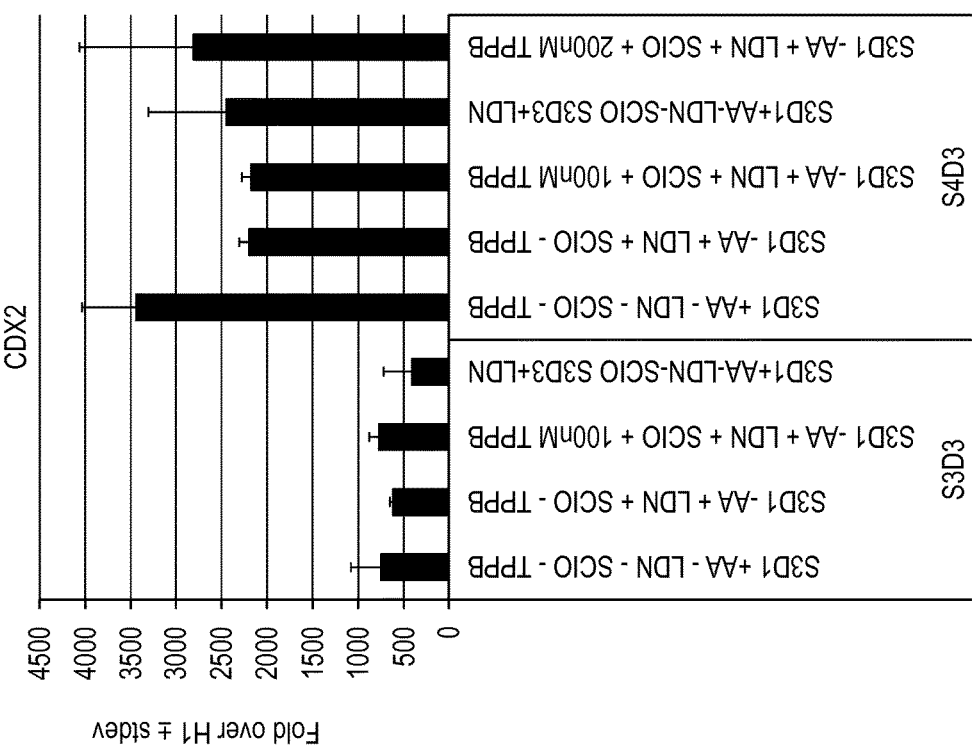
FIG. 9F CDX2

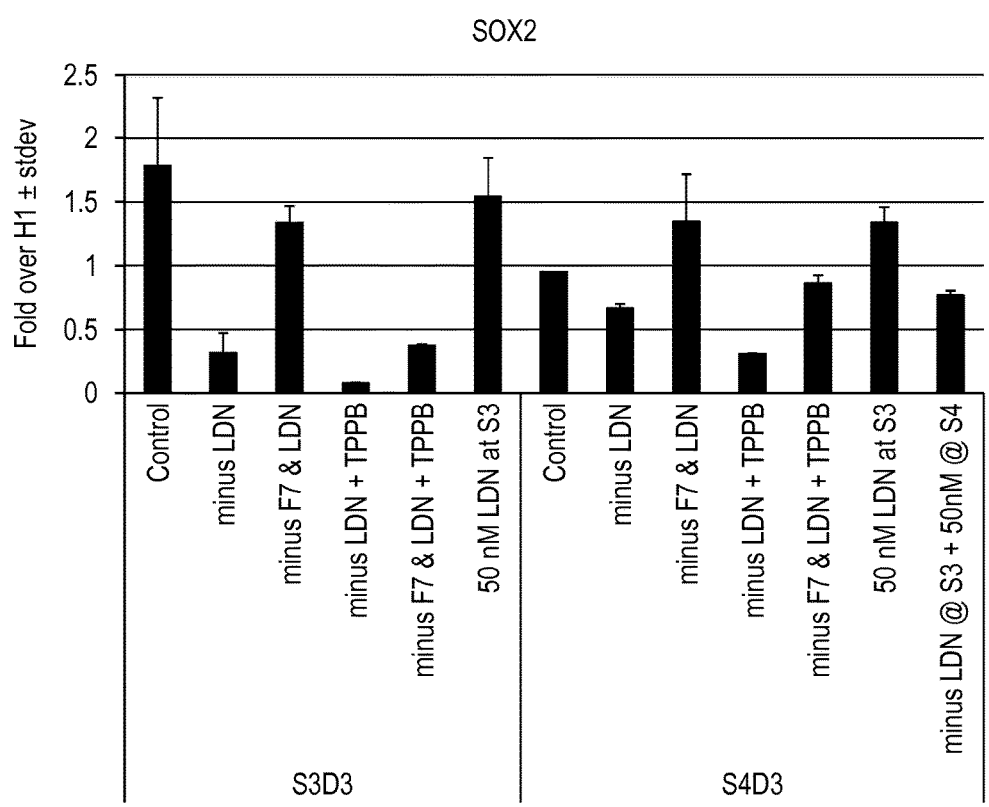

Cdx2

ALBUMIN

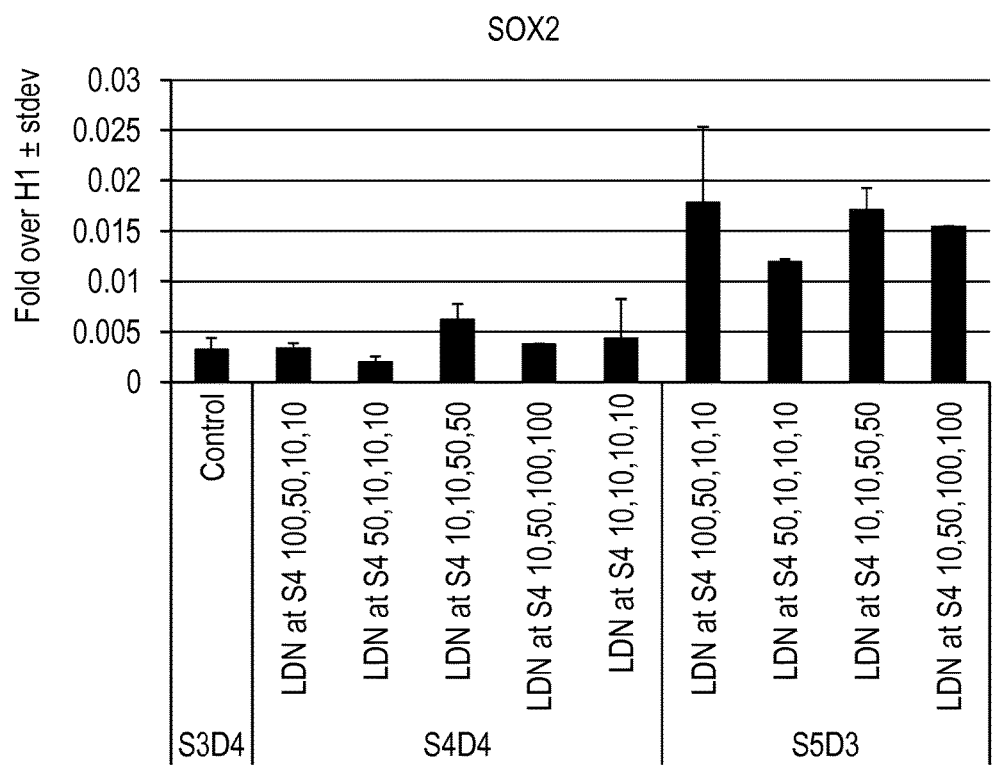

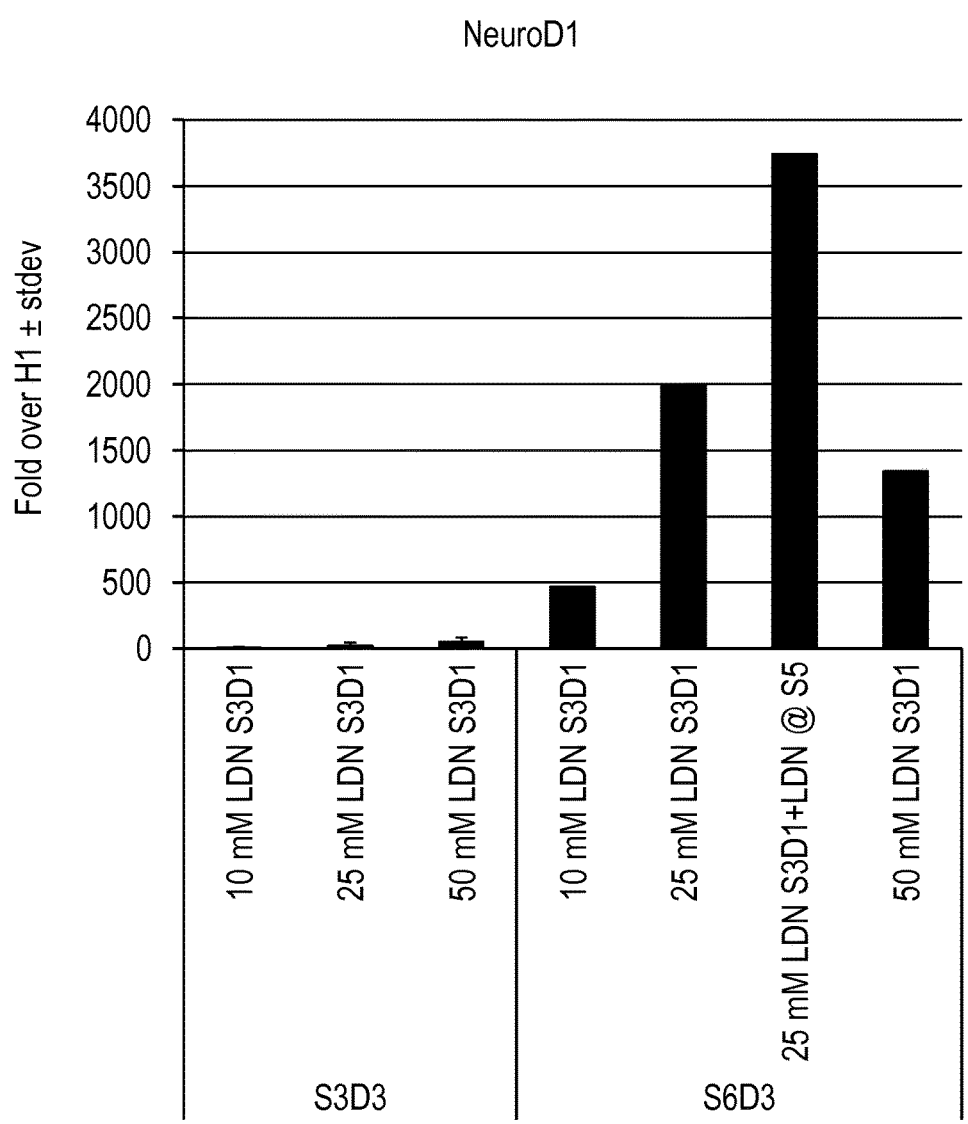

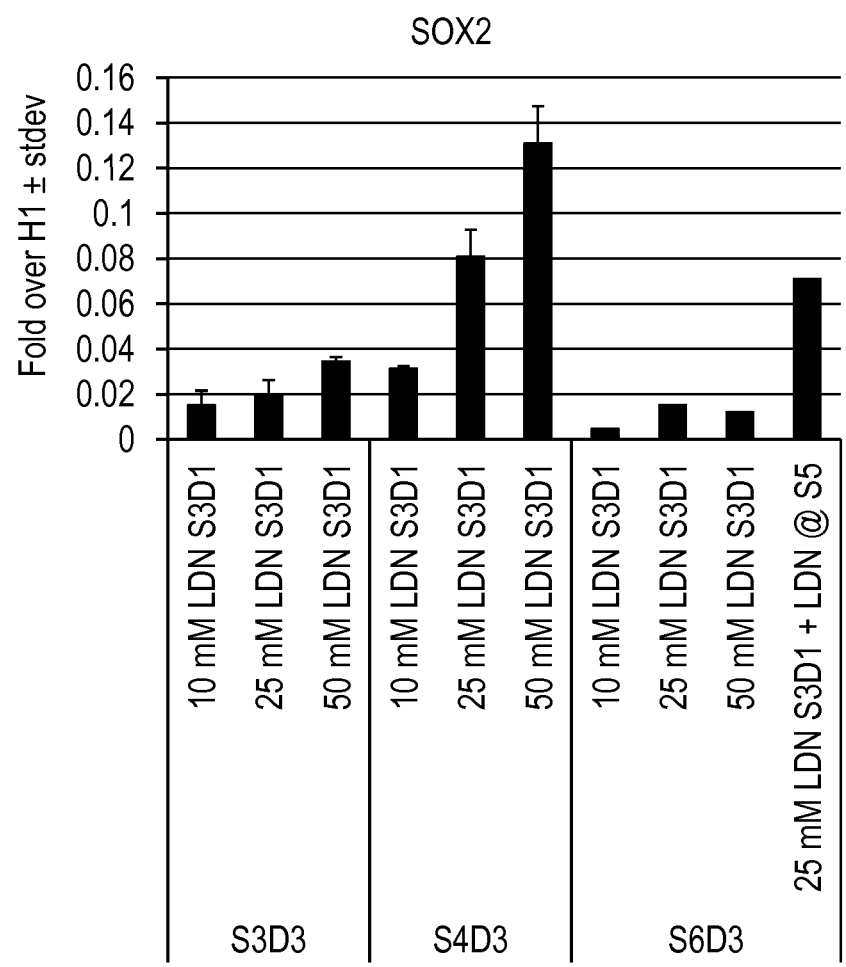

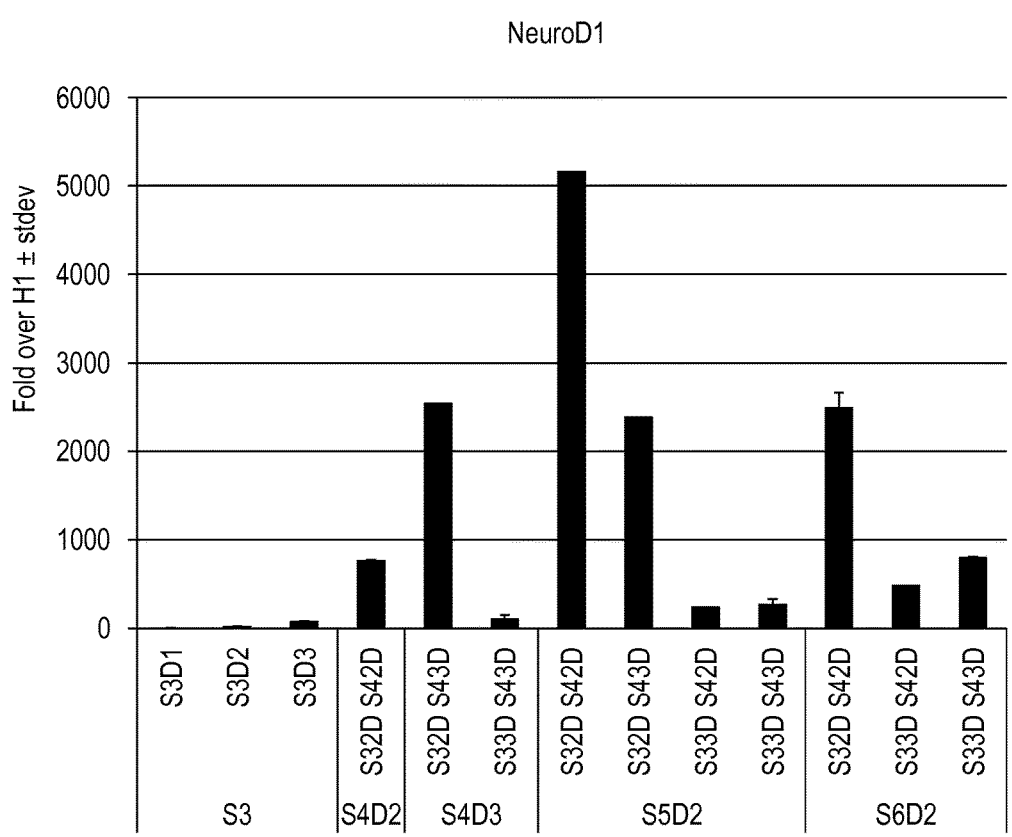

SOX2

HNF3B

CDX2

PDX-1

Isotype

NKX6.1

KI-67

Chromogranin

SOX2

CDX2

PDX-1

FIG. 16A
Isotype
FIG. 16B
NKX6.1
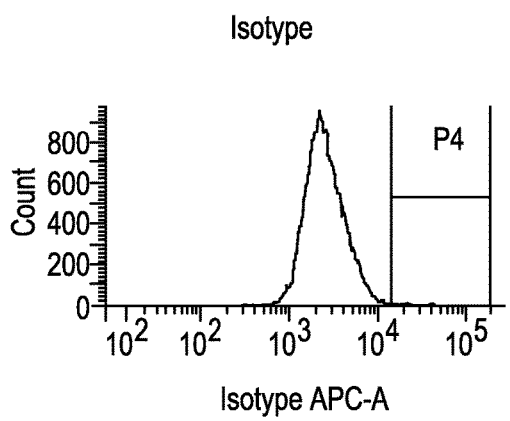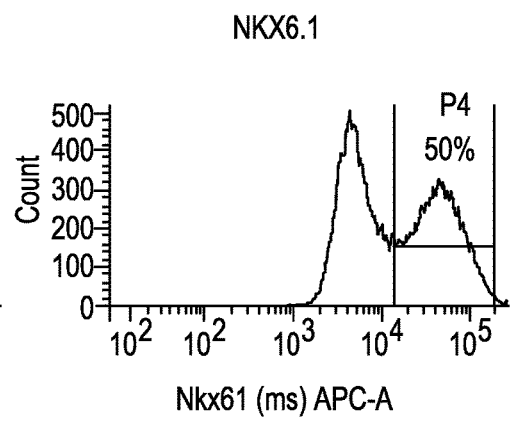
FIG. 16C
Chromogranin
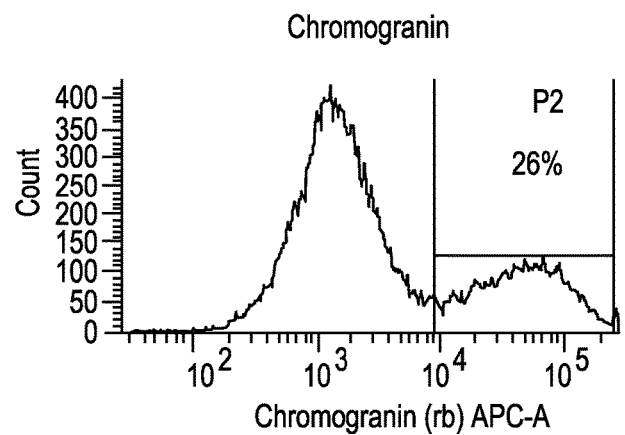
FIG. 16D
SOX2
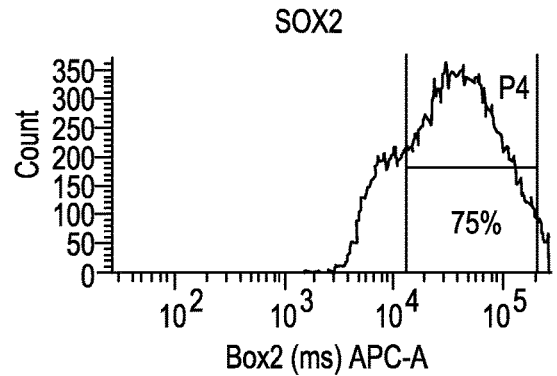

CDX2

PDX-1

FOXE1

IPF1

NKX6.1

PROX1

Isotype

NKX6.1

Chromogranin

SOX2

CDX2

KI-67

PDX-1

Isotype

NKX6.1

Chromogranin

SOX2

CDX2

KI-67

PDX-1

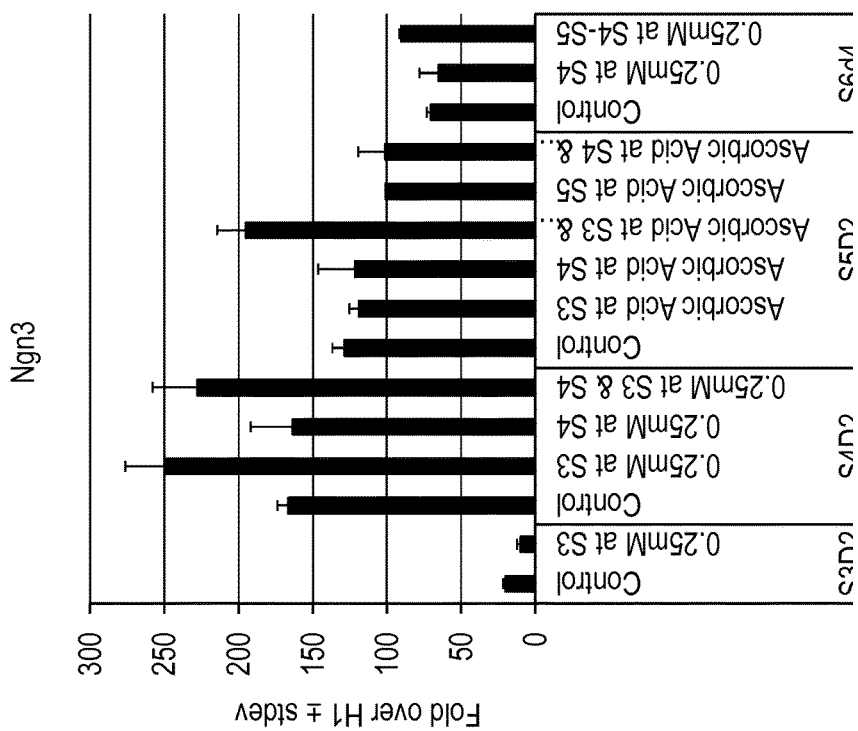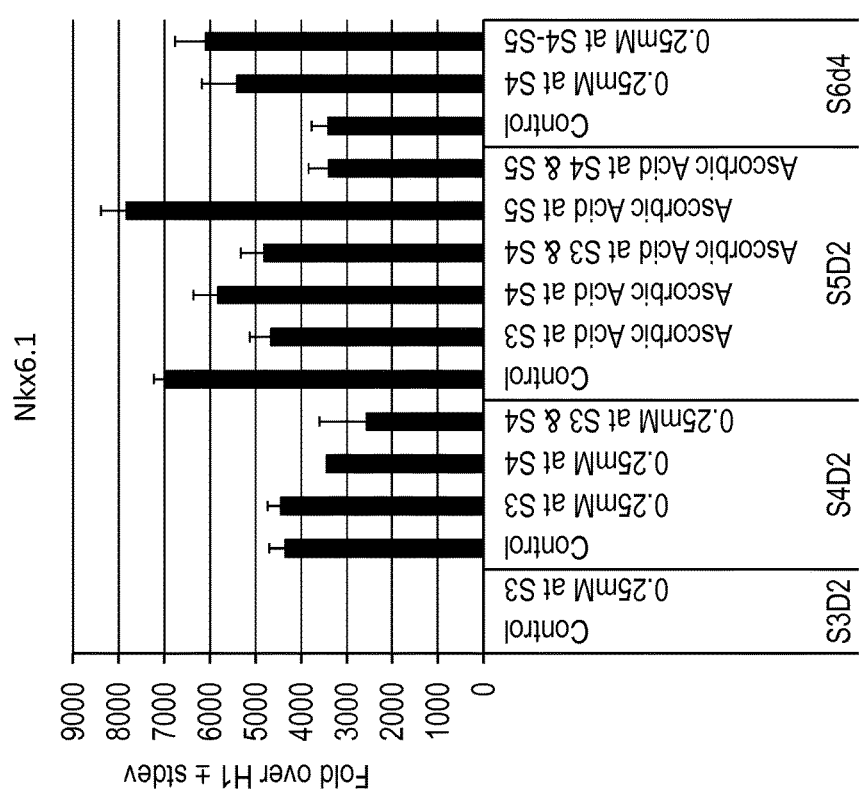

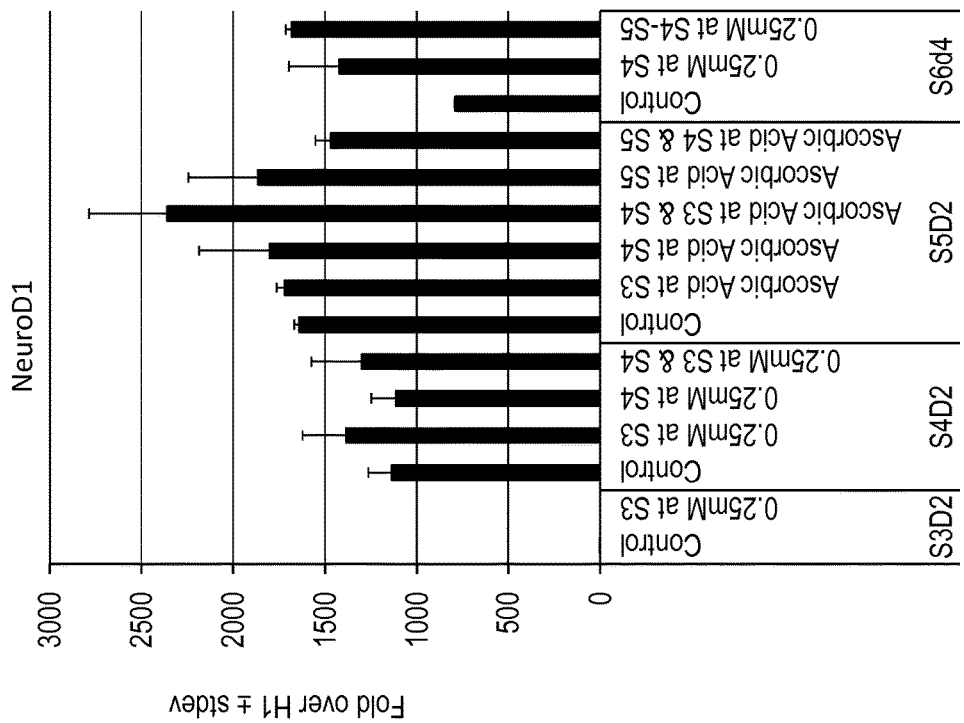
FIG. 20H NeuroD1
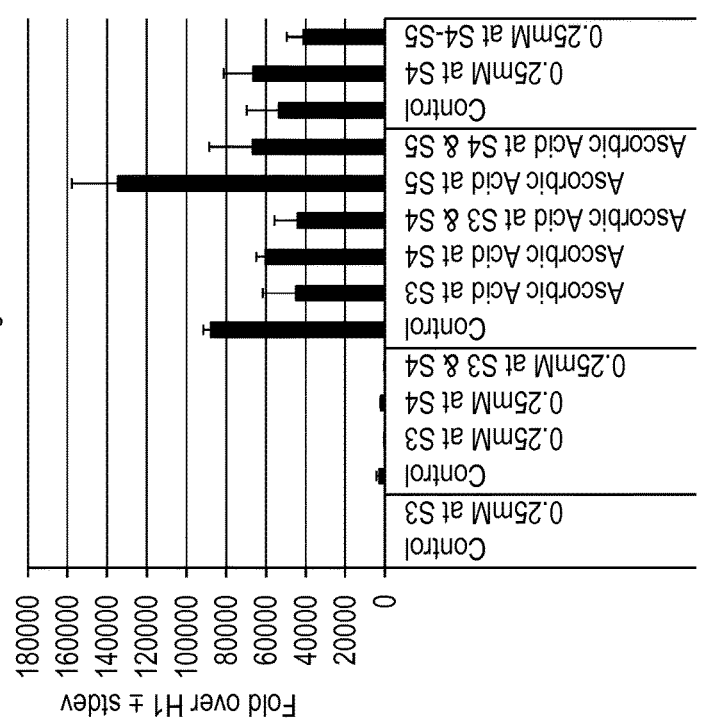
FIG. 20G Glucagon

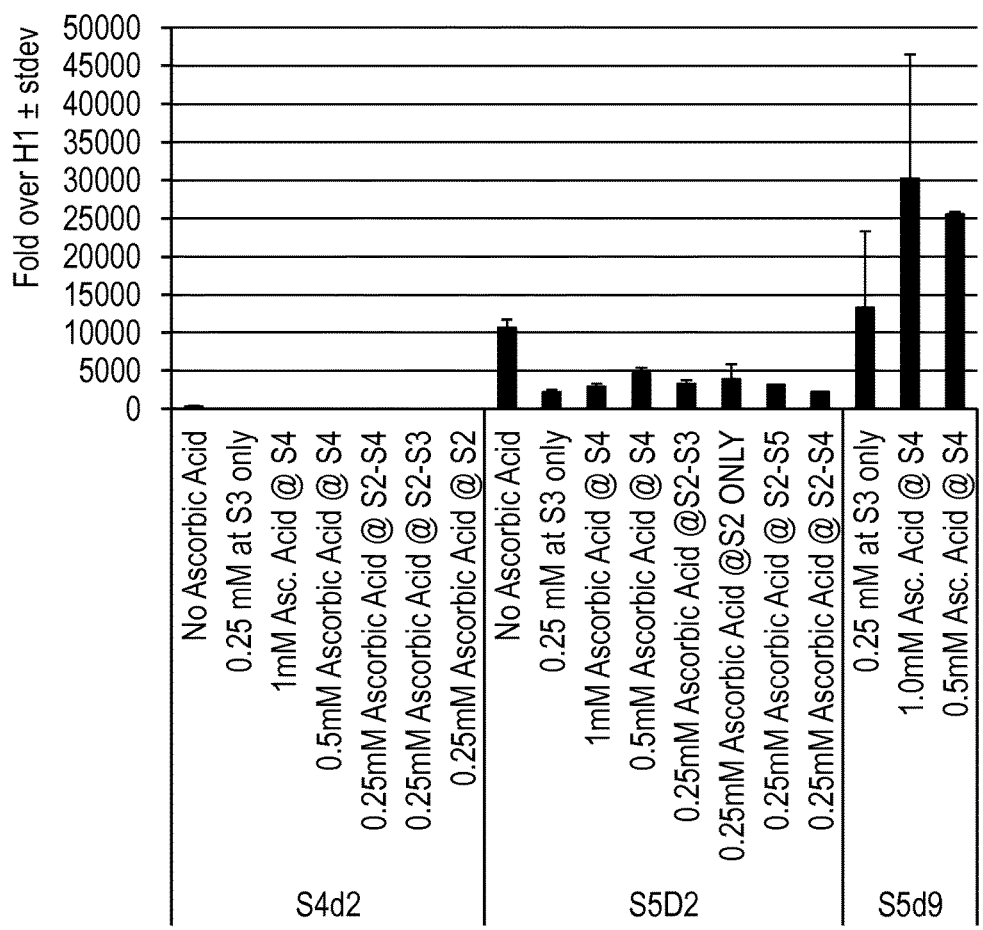

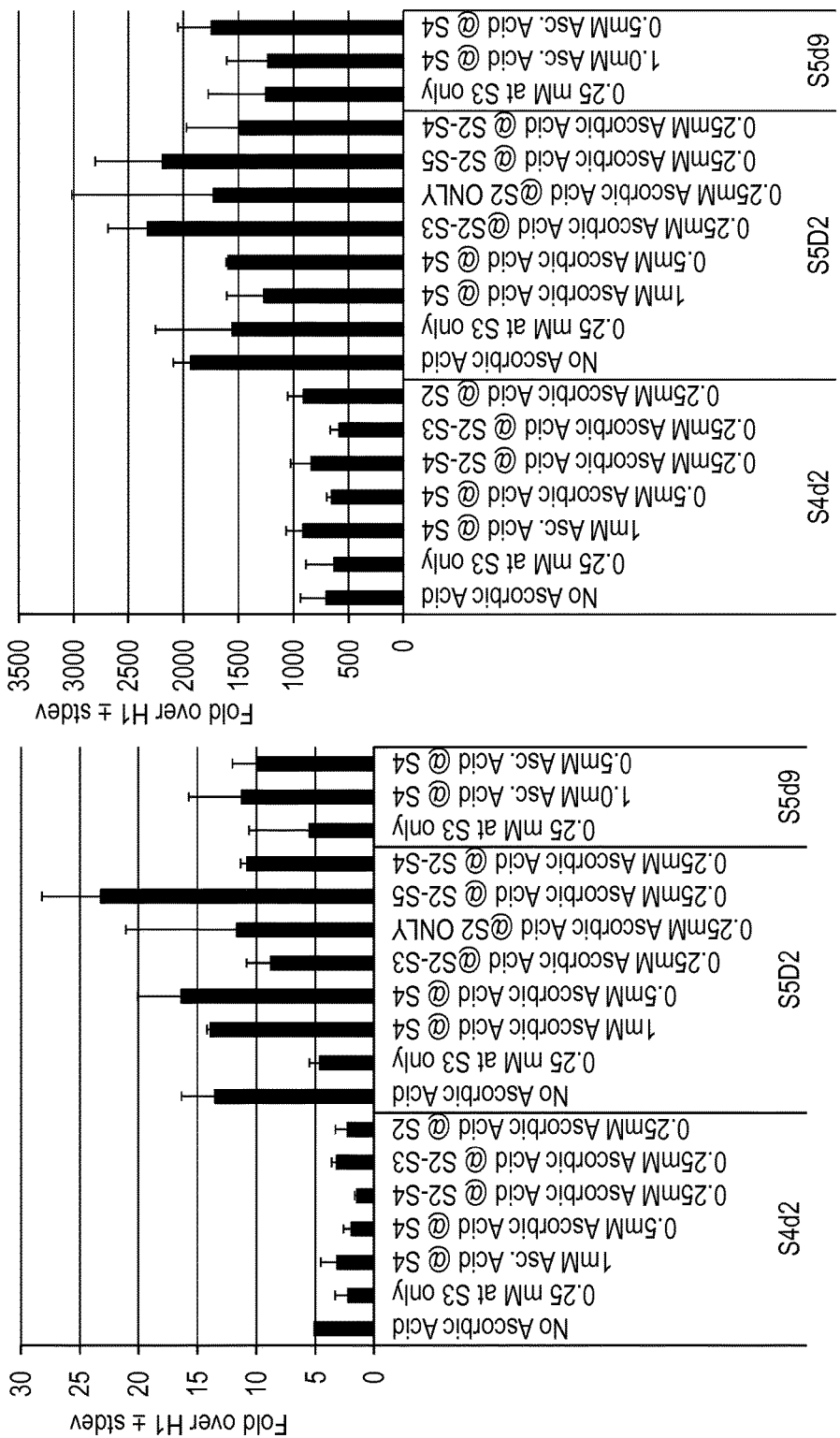

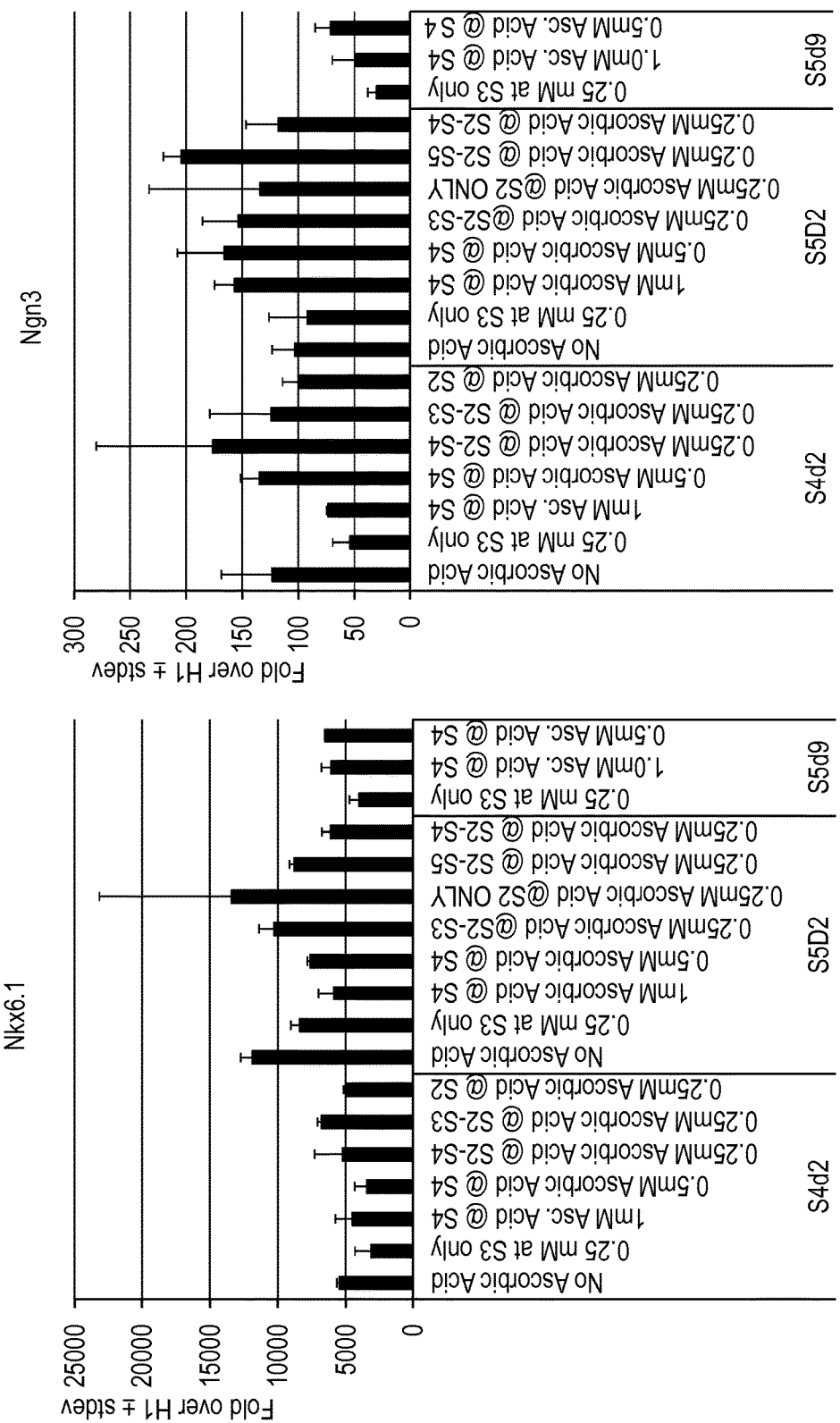

CHGA

Glucagon

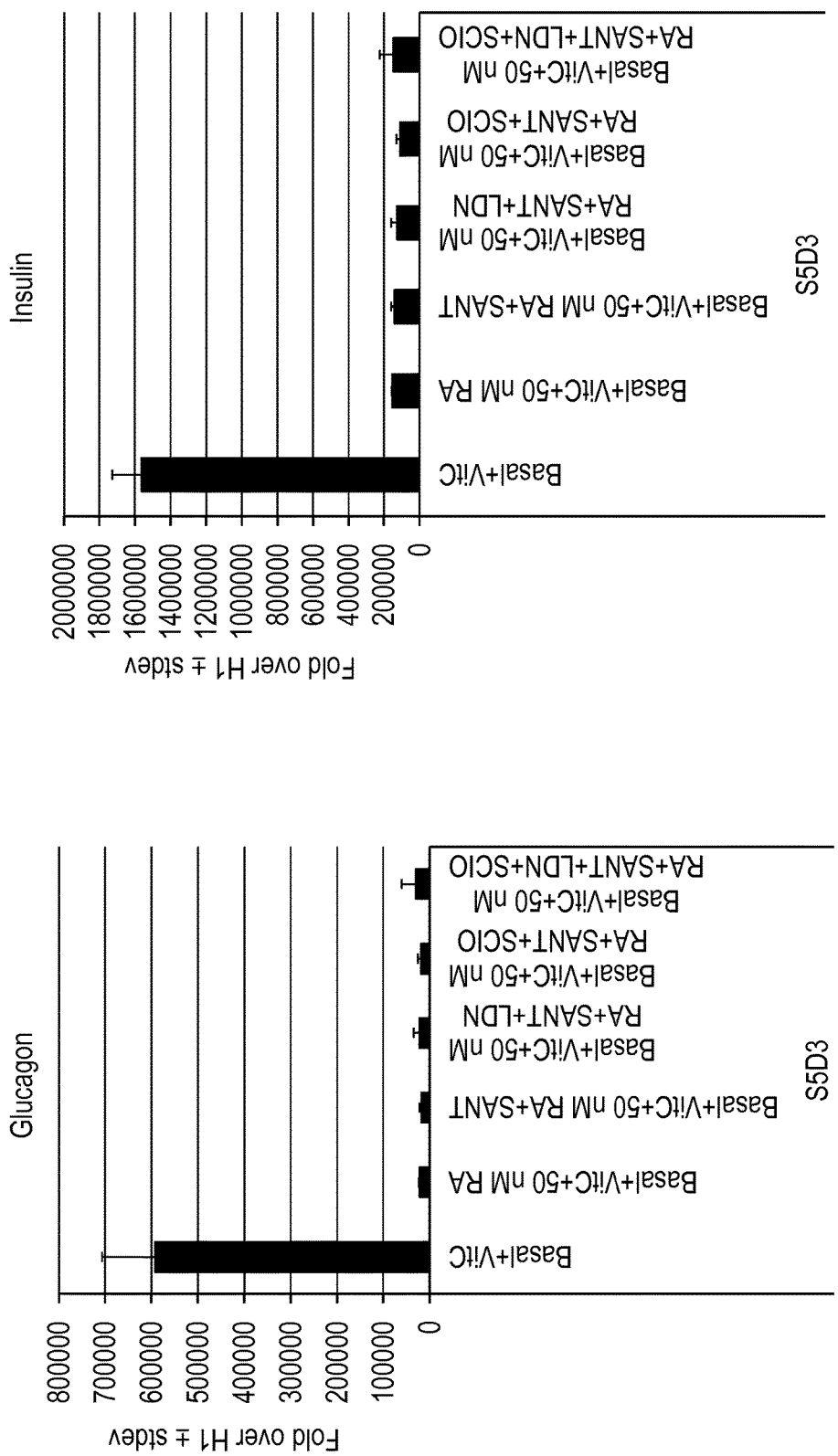

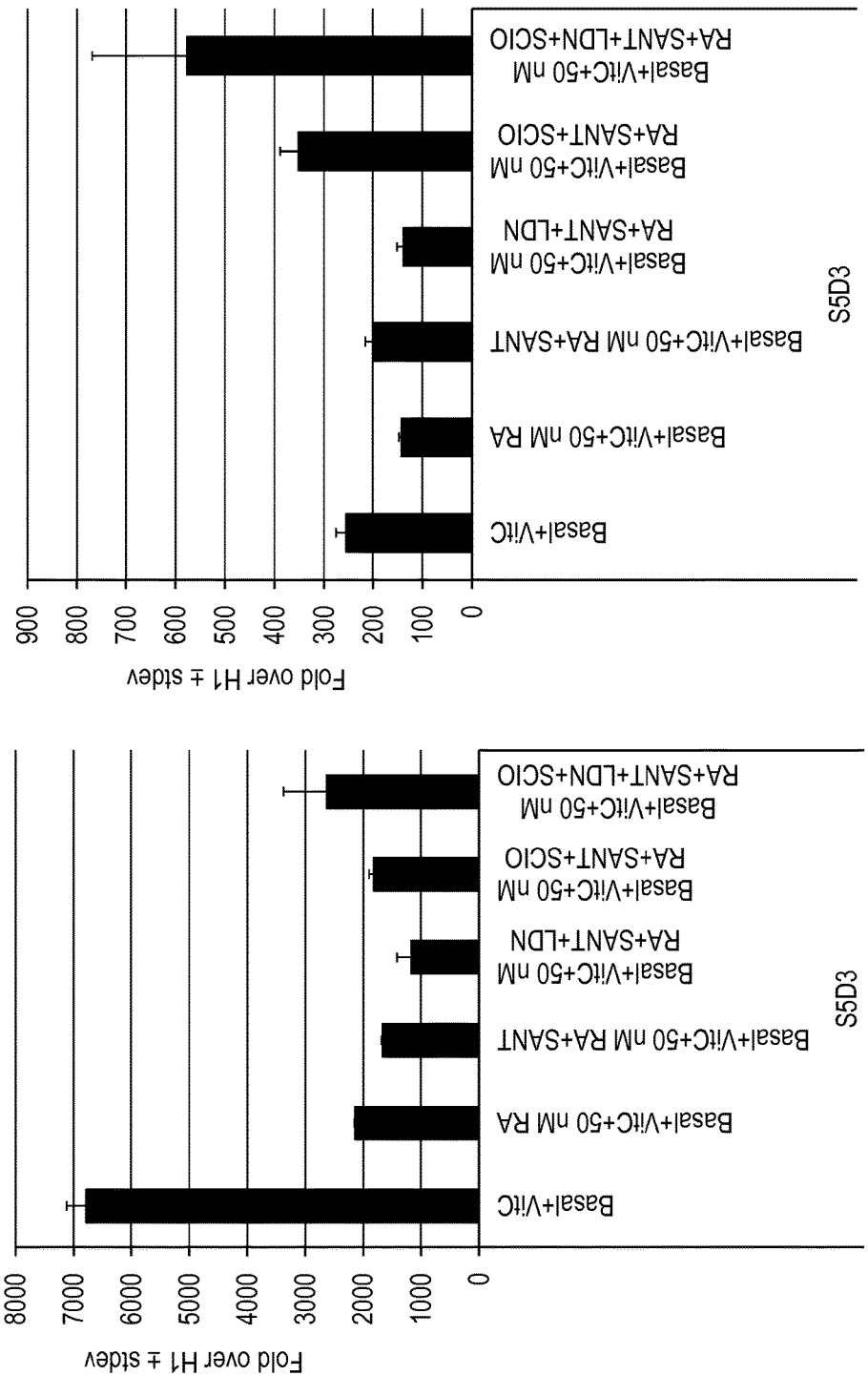
FIG. 22G NeuroD1
FIG. 22H Ngn3

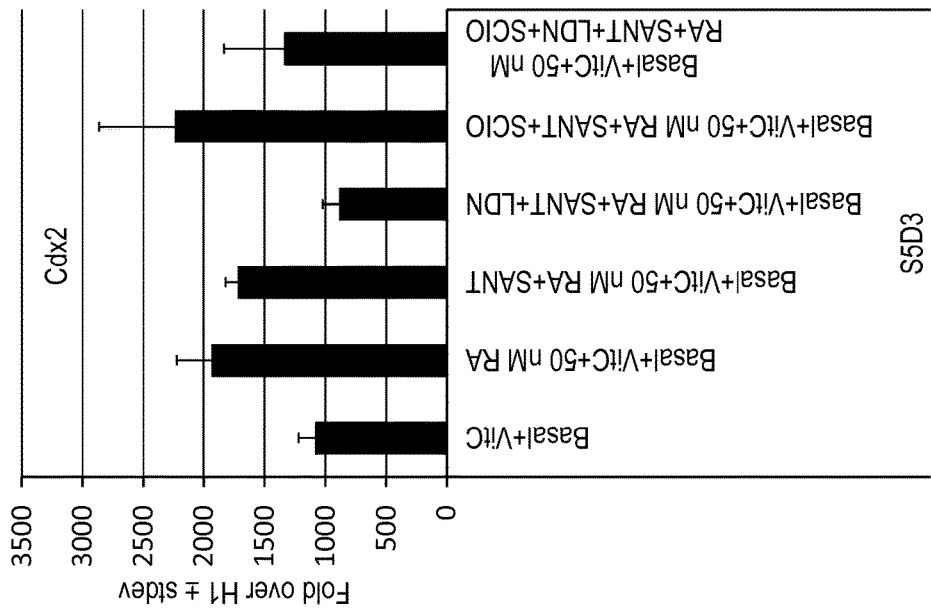
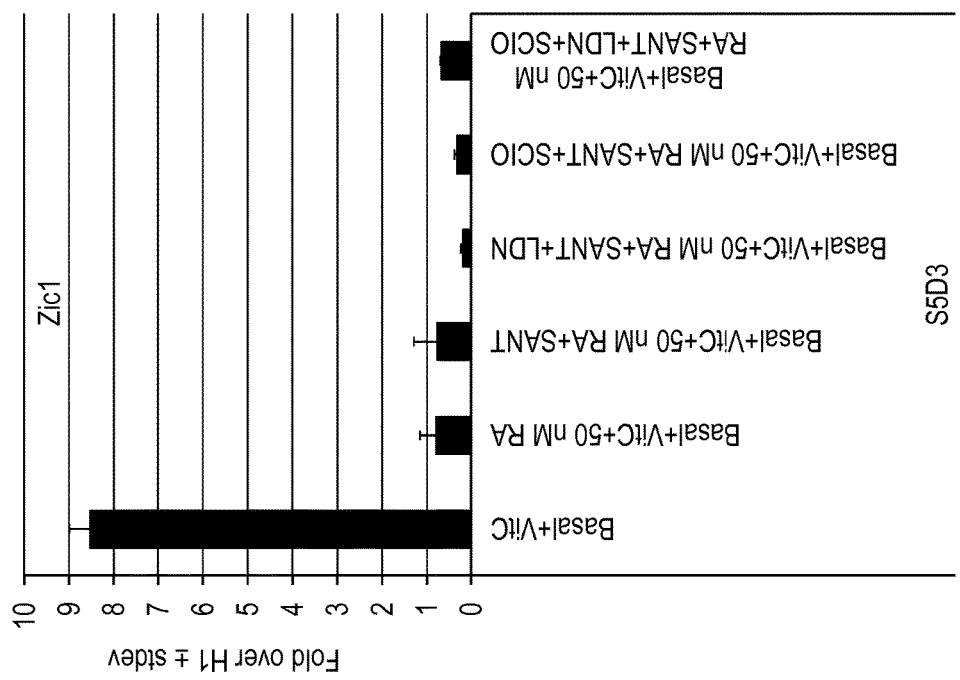

DIFFERENTIATION OF HUMAN EMBRYONIC STEM CELLS INTO SINGLE HORMONAL INSULIN POSITIVE CELLS

CROSS REFERENCE TO RELATED APPLICATIONS

This application is a divisional application of U.S. Ser. No. 13/708,369, filed Dec. 7, 2012, which application priority the benefit of U.S. Provisional Patent Application Ser. No. 61/579,351, filed Dec. 22, 2011, all of which are hereby incorporated by reference in their entirety.

FIELD OF THE INVENTION

The present invention is in the field of cell differentiation. More specifically, the invention provides single hormonal insulin producing cells differentiated from pluripotent stem cells using defined conditions at each step of a stepwise differentiation. Greater than 10% of the differentiated insulin producing cells in the population express markers characteristic of single hormonal pancreatic beta cells.

BACKGROUND

Advances in cell-replacement therapy for Type I diabetes mellitus and a shortage of transplantable islets of Langerhans have focused interest on developing sources of insulin-producing cells, or β cells, appropriate for engraftment. One approach is the generation of functional β cells from pluripotent stem cells, such as, for example, embryonic stem cells.

In vertebrate embryonic development, a pluripotent cell gives rise to a group of cells comprising three germ layers (ectoderm, mesoderm, and endoderm) in a process known as gastrulation. Tissues such as, thyroid, thymus, pancreas, gut, and liver, will develop from the endoderm, via an intermediate stage. An intermediate stage in this process is the formation of definitive endoderm. Definitive endoderm cells express a number of markers, such as, HNF3beta, GATA4, MIXL1, CXCR4 and SOX17.

By the end of gastrulation, the endoderm is partitioned into anterior-posterior domains that can be recognized by the expression of a panel of factors that uniquely mark anterior, mid, and posterior regions of the endoderm. For example, Hhex, and Sox2 identify the anterior region while Cdx1, 2, and 4 identify the posterior half of the endoderm.

Migration of endoderm tissue brings the endoderm into close proximity with different mesodermal tissues that help in regionalization of the gut tube. This is accomplished by a plethora of secreted factors, such as FGFs, Wnts, TGF-Bs, retinoic acid (RA), and BMP ligands and their antagonists. For example, FGF4 and BMP promote Cdx2 expression in the presumptive hindgut endoderm and repress expression of the anterior genes Hhex and SOX2 (Development 2000, 127:1563-1567). WNT signaling has also been shown to work in parallel to FGF signaling to promote hindgut development and inhibit foregut fate (Development 2007, 134:2207-2217). Lastly, secreted retinoic acid by mesenchyme regulates the foregut-hindgut boundary (Curr Biol 2002, 12:1215-1220).

The level of expression of specific transcription factors may be used to designate the identity of a tissue. During transformation of the definitive endoderm into a primitive gut tube, the gut tube becomes regionalized into broad domains that can be observed at the molecular level by restricted gene expression patterns. For example, the regionalized pancreas domain in the gut tube shows a very high expression of PDX-1 and very low expression of CDX2 and SOX2. Similarly, the presence of high levels of Foxe1 are indicative of esophagus tissue; highly expressed in the lung tissue is NKX2.1; SOX2/Odd1 (OSR1) are highly expressed in stomach tissue; expression of PROX1/Hhex/AFP is high in liver tissue; SOX17 is highly expressed in biliary structure tissues; PDX1, NKX6.1/PTf1a, and NKX2.2 are highly expressed in pancreatic tissue; and expression of CDX2 is high in intestine tissue. The summary above is adapted from Dev Dyn 2009, 238:29-42 and Annu Rev Cell Dev Biol 2009, 25:221-251.

Formation of the pancreas arises from the differentiation of definitive endoderm into pancreatic endoderm (Annu Rev Cell Dev Biol 2009, 25:221-251; Dev Dyn 2009, 238:29-42). Dorsal and ventral pancreatic domains arise from the foregut epithelium. Foregut also gives rise to the esophagus, trachea, lungs, thyroid, stomach, liver, pancreas, and bile duct system.

Cells of the pancreatic endoderm express the pancreatic-duodenal homeobox gene PDX1. In the absence of PDX1, the pancreas fails to develop beyond the formation of ventral and dorsal buds. Thus, PDX1 expression marks a critical step in pancreatic organogenesis. The mature pancreas contains, among other cell types, exocrine tissue and endocrine tissue. Exocrine and endocrine tissues arise from the differentiation of pancreatic endoderm.

D'Amour et al. describes the production of enriched cultures of human embryonic stem cell-derived definitive endoderm in the presence of a high concentration of activin and low serum (Nature Biotechnol 2005, 23:1534-1541; U.S. Pat. No. 7,704,738). Transplanting these cells under the kidney capsule of mice resulted in differentiation into more mature cells with characteristics of endodermal tissue (U.S. Pat. No. 7,704,738). Human embryonic stem cell-derived definitive endoderm cells can be further differentiated into PDX1 positive cells after addition of FGF-10 and retinoic acid (U.S. Patent Publication No. 2005/0266554A1). Subsequent transplantation of these pancreatic precursor cells under the kidney capsule of immune deficient mice resulted in formation of functional pancreatic endocrine cells following a 3-4 month maturation phase (U.S. Pat. Nos. 7,993,920 and 7,534,608).

Fisk et al. report a system for producing pancreatic islet cells from human embryonic stem cells (U.S. Pat. No. 7,033,831). In this case, the differentiation pathway was divided into three stages. Human embryonic stem cells were first differentiated to endoderm using a combination of sodium butyrate and activin A (U.S. Pat. No. 7,326,572). The cells were then cultured with BMP antagonists, such as Noggin, in combination with EGF or betacellulin to generate PDX1 positive cells. The terminal differentiation was induced by nicotinamide.

Small molecule inhibitors have also been used for induction of pancreatic endocrine precursor cells. For example, small molecule inhibitors of TGF-B receptor and BMP receptors (Development 2011, 138:861-871; Diabetes 2011, 60:239-247) have been used to significantly enhance number of pancreatic endocrine cells. In addition, small molecule activators have also been used to generate definitive endoderm cells or pancreatic precursor cells (Curr Opin Cell Biol 2009, 21:727-732; Nature Chem Biol 2009, 5:258-265).

Previous attempts at the induction of pancreatic precursor cells from human embryonic stem cells have highlighted the importance of co-expression of PDX-1 and NKX6.1 in correctly identifying pancreatic endoderm. However, while the art has identified the population of cells positive in expression of PDX-1 and NKX6.1 to be low or absent of CDX2 expression, previous reports have failed to test for presence of markers just anterior to the developing pancreas. SOX2, which marks the anterior endoderm, is not expressed in adult islets and is expressed at a very low level in developing pancreas (Diabetes 2005, 54:3402-4309). In contrast, some of the examples in this application disclose cell populations where at least 30% of the pancreatic endoderm cells generated from human embryonic stem cells are positive for the expression of PDX-1 and NKX6.1, and negative for the expression of CDX2 and SOX2.

All of the previous attempts to generate functional pancreatic beta cells have fallen short of attaining cells with characteristics of mature beta cells. Hallmarks of mature beta cells include expression of single hormonal insulin, correct processing of proinsulin into insulin and C-peptide, strong expression of PDX-1 and NKX6.1, appropriate insulin release in response to glucose, expression of glucose transporters, and high expression of glucokinase. All of the previous reports have resulted in endocrine cells that produce two or more of the pancreatic hormones. For example, D'Amour et al (Nature Biotech 2006, 24:1392-1401) report the generation of a cell population comprising ~10% insulin positive cells and ~20% endocrine cells as measured by synaptophysin. Similar reports by others (Cell Res 2009, 19:429-438; Stem Cells 2007, 25:1940-1953; Diabetes Obes Metab 2008, 10:186-194) have also shown differentiation of pluripotent cells to non-functional insulin positive cells. Indeed, recent studies have clearly established that transplantation of polyhormonal cells in Severe Combined ImmunoDeficiency (SCID) mice did not result in generation of functional beta cells (Diabetes 2011, 60:239-247; Nature Biotech 2011, 29:750-756). While in human fetal pancreas a fraction (~10-20%) of endocrine cells are polyhormonal cells; polyhormonal cells disappear in adult human pancreas (Histochem Cell Biol 1999, 112:147-153; J Histochem Cytochem 2009, 57:811-824).

As the burgeoning field of regenerative medicine continues to mature, a method for the formation of terminally differentiated, appropriately regulated pancreatic endocrine cells is highly desirable. It is demonstrated herein that with appropriate and defined manipulation of culture conditions, and precise timing of the addition of activators/inhibitors of various pathways, human embryonic stem cells can be differentiated in vitro into functional pancreatic beta cells. In particular, precise timing of BMP inhibition, using a gradient of retinoic acid along with the use of Vitamin C proved effective in generation of single hormonal pancreatic endocrine cells.

SUMMARY

The present invention provides a population of cells of the pancreatic endoderm lineage obtained in vitro by the stepwise differentiation of pluripotent cells. The medium used at each step of differentiation is supplemented with glucose. In some embodiments, at each step of differentiation the cells are cultured in medium comprising 5 mM to 20 mM glucose.

In some embodiments, differentiation of pluripotent stem cells generates a pancreatic endoderm cell population where greater than 10% of the cells in the differentiated population express markers characteristic of single hormonal pancreatic beta cells.

In some embodiments, differentiation of pluripotent stem cells generates a pancreatic endoderm cell population where greater than 30% of the differentiated population is positive for the expression of PDX-1 and NKX6.1 while being negative for the expression of CDX2 and SOX2.

In some embodiments, the stepwise differentiation comprises culturing undifferentiated human embryonic stem cells in medium further supplemented with a TGF-B ligand. In some embodiments, the stepwise differentiation comprises culturing undifferentiated human embryonic stem cells in medium further supplemented with a WNT activator. In some embodiments, the stepwise differentiation comprises culturing definitive endoderm cells in medium further supplemented with a FGF ligand. In some embodiments, the stepwise differentiation comprises culturing gut tube cells in medium further supplemented with a shh inhibitor, a FGF ligand, a PKC activator, a TGF-B ligand, a retinoid, and a gradient of a BMP inhibitor. In some embodiments, the stepwise differentiation comprises culturing posterior foregut cells in medium further supplemented with a PKC activator, a shh inhibitor, a retinoid, and a BMP inhibitor. In some embodiments, the stepwise differentiation comprises culturing cells in medium further supplemented with ascorbic acid.

In an embodiment, the invention provides an in vitro method for the stepwise differentiation of pluripotent cells into a population of cells of the pancreatic endoderm lineage, which comprises culturing the cells at each stage of differentiation in medium comprising 5 mM to 20 mM glucose. In some embodiments, the in vitro method for the stepwise differentiation of pluripotent cells further comprises differentiating the pluripotent cells into definitive endoderm (DE) cells by culturing the pluripotent cells in medium supplemented with a TGF-B ligand and a WNT activator. In some embodiments, the in vitro method for the stepwise differentiation of pluripotent cells further comprises differentiating the DE cells into gut tube cells by culturing the DE cells in medium supplemented with a FGF ligand. In some embodiments, the in vitro method for the stepwise differentiation of pluripotent cells further comprises differentiating the gut tube cells into posterior foregut endoderm cells by culturing the gut tube cells in medium supplemented with a shh inhibitor, a FGF ligand, a PKC activator, a TGF-B ligand, a retinoid, and a BMP inhibitor. In some embodiments, the in vitro method for the stepwise differentiation of pluripotent cells further comprises differentiating the gut tube cells into posterior foregut endoderm cells by culturing the gut tube cells in medium supplemented with a shh inhibitor, a FGF ligand, a PKC activator, a TGF-B ligand, a retinoid, and a BMP inhibitor. In some embodiments, the in vitro method for the stepwise differentiation of pluripotent cells further comprises differentiating the posterior foregut endoderm cells into pancreatic foregut cells by culturing the posterior foregut endoderm cells in medium supplemented with a PKC activator, a shh inhibitor, a retinoid, and a BMP inhibitor. In some embodiments, the in vitro method for the stepwise differentiation of pluripotent cells further comprises differentiating the pancreatic foregut cells into pancreatic endoderm cells by culturing the pancreatic foregut cells in medium supplemented with a shh inhibitor, a TGF-B inhibitor, and a retinoid. In some embodiments, the in vitro method for the stepwise differentiation of pluripotent cells further comprises differentiating the pancreatic endoderm cells into a pancreatic beta cell population.

In an embodiment, in at least one step of the in vitro method for the stepwise differentiation of pluripotent cells the medium is further supplemented with ascorbic acid. In some embodiments, greater than 10% of the cells in the differentiated population are single hormonal insulin positive cells. In some embodiments, greater than 30% of pancreatic endoderm cells in culture generated by the methods of the invention are PDX-1+, NKX6.1+, SOX2−, and CDX2−.

In an embodiment, the invention relates to an in vitro method for differentiating human embryonic stem cells into pancreatic beta cells comprising: a) culturing undifferentiated human embryonic stem cells in medium supplemented with glucose, a TGF-B ligand, and a WNT activator, to generate a population of definite endoderm (DE) cells; b) culturing the DE cells in medium supplemented with glucose, and a FGF ligand to generate a population of gut tube cells; c) culturing the gut tube cells in medium supplemented with glucose, a shh inhibitor, a FGF ligand, a PKC activator, a TGF-B ligand, a retinoid, and a gradient of a BMP inhibitor to generate a population of posterior foregut endoderm cells expressing PDX-1 and SOX2; d) culturing the posterior foregut cells in medium supplemented with glucose, a PKC activator, a shh inhibitor, a retinoid, and a BMP inhibitor to generate a population of pancreatic foregut cells expressing PDX-1 and NKX6.1, and expressing lower level of SOX2 as compared to the posterior foregut cells; e) culturing the pancreatic foregut cells in medium supplemented with glucose, a shh inhibitor, a TGF-B inhibitor, and a retinoid to obtain a population of pancreatic endoderm cells expressing PDX-1, a higher level of NKX6.1, and a lower level of SOX2 as compared to pancreatic foregut cells; and f) differentiating the pancreatic endoderm cells into a pancreatic beta cell population. In some embodiments, the pancreatic beta cell population generated by the methods of the invention is PDX-1+, NKX6.1+, SOX2−, and CDX2−. In some embodiments the medium in at least one step of the stepwise differentiation method is further supplemented with ascorbic acid. In some embodiments, the pancreatic beta cells obtained by the methods of the invention are single hormonal insulin-producing cells which are also NKX6.1+ and PDX-1+.

BRIEF DESCRIPTION OF THE DRAWINGS

FIG. 1A to FIG. 1G show the FACS histogram expression profiles of the following markers at S3 day 2 of cells differentiated according to Example 1. FIG. 1A: Isotype control; FIG. 1B: chromogranin; FIG. 1C: KI-67; FIG. 1D: NKX6.1; FIG. 1E: SOX2; FIG. 1F: CDX2; FIG. 1G: PDX-1. Percentage expression for each marker is shown on each histogram.

FIG. 2A to FIG. 2G show the FACS histogram expression profiles of the following markers in cells differentiated according to Example 1, and harvested at S4 day 2. FIG. 2A: Isotype control; FIG. 2B: chromogranin; FIG. 2C: KI-67; FIG. 2D: NKX6.1; FIG. 2E: SOX2; FIG. 2F: CDX2; FIG. 2G: PDX-1. Percentage expression for each marker is shown on each histogram.

FIG. 3A: Isotype control; FIG. 3B: chromogranin; FIG. 3C: KI-67; FIG. 3D: NKX6.1; FIG. 3E: SOX2; FIG. 3F: CDX2; FIG. 3G: PDX-1. Percentage expression for each marker is shown on each histogram.

FIG. 4A to FIG. 4G show FACS histogram expression profiles of the following markers of cells differentiated according to Example 1 and harvested at S5 day 7. FIG. 4A: Isotype control; FIG. 4B: chromogranin; FIG. 4C: KI-67; FIG. 4D: NKX6.1; FIG. 4E: SOX2; FIG. 4F: CDX2; FIG. 4G: PDX-1. Percentage expression for each marker is shown on each histogram.

FIG. 5A: chromogranin (y-axis) and CDX2 (x axis); FIG. 5B: chromogranin (y-axis) and SOX2 (x axis); FIG. 5C: chromogranin (y-axis) and NKX6.1 (x axis). Percentage co-expression for each plot is shown on each histogram.

FIG. 6A: CDX2; FIG. 6K: PTF1a; FIG. 6T: somatostatin.

FIG. 7A to FIG. 7G depict data from real-time PCR analyses of the expression of the following genes in cells of the H1 cell line differentiated according to Example 2 and harvested at day 3 of S2, S3, or S4. FIG. 7A: NKX6.1; FIG. 7B: PDX-1; FIG. 7C: chromogranin; FIG. 7D: NGN3; FIG. 7E: CDX2; FIG. 7F: albumin; FIG. 7G: SOX2.

FIG. 8A to FIG. 8G depict data from real-time PCR analyses of the expression of the following markers in H1 cells differentiated according to Example 3 and harvested at S2, S3, S4, or S5. FIG. 8A: NKX6.1; FIG. 8B: PDX-1; FIG. 8C: NGN3; FIG. 8D: NeuroD; FIG. 8E: chromogranin; FIG. 8F: CDX2; FIG. 8G: SOX2.

FIG. 9A to FIG. 9H depict data from real-time PCR analyses of the expression of the following markers in H1 cells differentiated according to Example 4 and harvested at day 4 of S3 and S4. FIG. 9A: NKX6.1; FIG. 9B: PDX-1; FIG. 9C: chromogranin; FIG. 9D: NGN3; FIG. 9E: NeuroD; FIG. 9F: CDX2; FIG. 9G: albumin; FIG. 9H: SOX2.

FIG. 10A to FIG. 10H depict data from real-time PCR analyses of the expression of the following genes in cells of the human embryonic stem cell line H1 differentiated according to the Example 5 and harvested at stage 4. FIG. 10A: NKX6.1; FIG. 10B: PDX-1; FIG. 10C: chromogranin; FIG. 10D: NGN3; FIG. 10E: NeuroD; FIG. 10F: CDX2; FIG. 10G: albumin; FIG. 10H: SOX2.

FIG. 11A to FIG. 11H show data from real-time PCR analysis of the expression of the following genes in cells of the human embryonic stem cell line H1 differentiated according to the Example 6 and harvested at day 3 of S3 or S6. FIG. 11A: NKX6.1; FIG. 11B: PDX-1; FIG. 11C: chromogranin; FIG. 11D: NGN3; FIG. 11E: NeuroD; FIG. 11F: CDX2; FIG. 11G: albumin; FIG. 11H: SOX2.

FIG. 12A: NKX6.1; FIG. 12B: PDX-1; FIG. 12C: chromogranin; FIG. 12D: NGN3; FIG. 12E: NeuroD; FIG. 12F: CDX2; FIG. 12G: SOX2.

FIG. 13A to FIG. 13G depict data from real-time PCR analyses of the expression of the following genes in cells of the human embryonic stem cell line H1 differentiated according to the Example 8 and harvested at S3, S4, S5, or S6. FIG. 13A: NKX6.1; FIG. 13B: PDX-1; FIG. 13C: chromogranin; FIG. 13D: NGN3; FIG. 13E: NeuroD; FIG. 13F: CDX2; FIG. 13G: SOX2.

FIG. 14A: Isotype control; FIG. 14B: chromogranin; FIG. 14C: KI-67; FIG. 14D: NKX6.1; FIG. 14E: SOX2; FIG. 14F: HNF3B; FIG. 14G: CDX2; FIG. 14H: PDX-1. Percentage expression for each marker is shown on each histogram.

FIG. 15A: Isotype control; FIG. 15B: NKX6.1; FIG. 15C: KI-67; FIG. 15D: chromogranin; FIG. 15E: SOX2; FIG. 15F CDX2; FIG. 15G: PDX-1. Percentage expression for each marker is shown on each histogram.

FIG. 16A to FIG. 16F show FACS histogram expression profiles of the following markers at S4 day 4 of cells differentiated according to Example 9. FIG. 16A: Isotype control; FIG. 16B: NKX6.1; FIG. 16C: chromogranin; FIG. 16D: SOX2; FIG. 16E: CDX2; FIG. 16F: PDX-1. Percentage expression for each marker is shown on each histogram.

FIG. 17A: CDX2; FIG. 17B: HHex; FIG. 17C: FOXE1; FIG. 17D: IPF1 (PDX-1); FIG. 17E: NKX2.1; FIG. 17F: NKX2.2; FIG. 17G: NKX6.1; FIG. 17H: PROX1; FIG. 17I: SOX2; FIG. 17J: SOX9.

FIG. 18A: Isotype control; FIG. 18B: NKX6.1; FIG. 18C: chromogranin; FIG. 18D: SOX2; FIG. 18E: CDX2; FIG. 18F: KI-67; FIG. 18G: PDX-1. Percentage expression for each marker is shown on each histogram.

FIG. 19A: Isotype control; FIG. 19B: NKX6.1; FIG. 19C: chromogranin; FIG. 19D: SOX2; FIG. 19E: CDX2; FIG. 19F: KI-67; FIG. 19G: PDX-1. Percentage expression for each marker is shown on each histogram.

FIG. 20A to FIG. 20J show real-time PCR analysis of the expression of the following genes in cells of the human embryonic stem cell line H1 differentiated according to the Example 11. FIG. 20A: somatostatin; FIG. 20B: PDX1; FIG. 20C: Pax6; FIG. 20D: Pax4; FIG. 20E: NKX6.1; FIG. 20F: NGN3; FIG. 20G: glucagon; FIG. 20H: NeuroD; FIG. 20I: insulin; FIG. 20J: chromogranin.

FIG. 21A to FIG. 21J show data from real-time PCR analysis of the expression of the following genes in cells of the human embryonic stem cell line H1 differentiated according to the Example 12 and harvested at S4 day 2, S5 day 2, and S5 day 9. FIG. 21A: somatostatin; FIG. 21B: PDX1; FIG. 21C: Pax6; FIG. 21D: Pax4; FIG. 21E: NKX6.1; FIG. 21F: NGN3; FIG. 21G: NeuroD; FIG. 21H: insulin; FIG. 21I: glucagon; FIG. 21J: chromogranin.

FIG. 22A to FIG. 22L show data from real-time PCR analyses of the expression of the following genes in cells of the embryonic stem cell line H1 differentiated according to example 13 and harvested at S5 day 3. FIG. 22A: Pax4; FIG. 22B: Pax6; FIG. 22C: PDX1; FIG. 22D: PTF1a; FIG. 22E: glucagon; FIG. 22F: insulin; FIG. 22G: NeuroD; FIG. 22H: ngn3; FIG. 22I: Zic1; FIG. 22J: CDX2; FIG. 22K: albumin; FIG. 22L: NKX6.1.

DETAILED DESCRIPTION

Figure 1A:
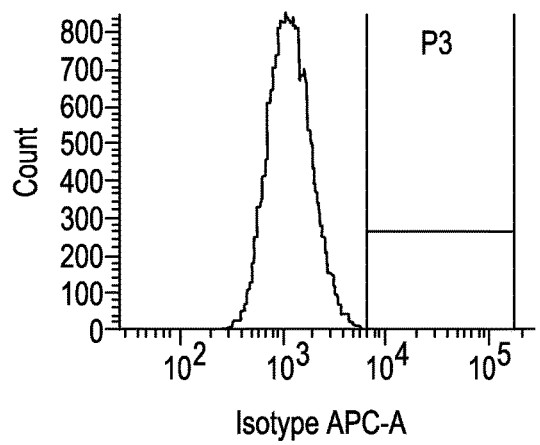

For clarity of disclosure, and not by way of limitation, the detailed description of the invention is divided into the following subsections that describe or illustrate certain features, embodiments or applications of the present invention.

Definitions

Stem cells are undifferentiated cells defined by their ability, at the single cell level, to both self-renew and differentiate. Stem cells may produce progeny cells, including self-renewing progenitors, non-renewing progenitors, and terminally differentiated cells. Stem cells are also characterized by their ability to differentiate in vitro into functional cells of various cell lineages from multiple germ layers (endoderm, mesoderm and ectoderm). Stem cells also give rise to tissues of multiple germ layers following transplantation and contribute substantially to most, if not all, tissues following injection into blastocysts.

Stem cells are classified by their developmental potential as: (1) totipotent, meaning able to give rise to all embryonic and extraembryonic cell types; (2) pluripotent, meaning able to give rise to all embryonic cell types; (3) multipotent, meaning able to give rise to a subset of cell lineages but all within a particular tissue, organ, or physiological system (for example, hematopoietic stem cells (HSC) can produce progeny that include HSC (self-renewal), blood cell restricted oligopotent progenitors, and all cell types and elements (e.g., platelets) that are normal components of the blood); (4) oligopotent, meaning able to give rise to a more restricted subset of cell lineages than multipotent stem cells; and (5) unipotent, meaning able to give rise to a single cell lineage (e.g., spermatogenic stem cells).

Differentiation is the process by which an unspecialized ("uncommitted") or less specialized cell acquires the features of a specialized cell such as, for example, a nerve cell or a muscle cell. A differentiated cell or a differentiation-induced cell is one that has taken on a more specialized ("committed") position within the lineage of a cell. The term "committed", when applied to the process of differentiation, refers to a cell that has proceeded in the differentiation pathway to a point where, under normal circumstances, it will continue to differentiate into a specific cell type or subset of cell types, and cannot, under normal circumstances, differentiate into a different cell type or revert to a less differentiated cell type. "De-differentiation" refers to the process by which a cell reverts to a less specialized (or committed) position within the lineage of a cell. As used herein, the lineage of a cell defines the heredity of the cell, i.e., which cells it came from and what cells it can give rise to. The lineage of a cell places the cell within a hereditary scheme of development and differentiation. A lineage-specific marker refers to a characteristic specifically associated with the phenotype of cells of a lineage of interest and can be used to assess the differentiation of an uncommitted cell to the lineage of interest.

"Markers", as used herein, are nucleic acid or polypeptide molecules that are differentially expressed in a cell of interest. In this context, differential expression means an increased level for a positive marker and a decreased level for a negative marker. The detectable level of the marker nucleic acid or polypeptide is sufficiently higher or lower in the cells of interest compared to other cells, such that the cell of interest can be identified and distinguished from other cells using any of a variety of methods known in the art.

As used herein, a cell is "positive for" a specific marker or "positive" when the specific marker is detected in the cell. Similarly, the cell is "negative for" a specific marker, or "negative" when the specific marker is not detected in the cell.

As used herein, "stage 1" and "S1" are used interchangeably to identify cells expressing markers characteristic of the definitive endoderm (DE).

"Definitive endoderm", as used herein, refers to cells which bear the characteristics of cells arising from the epiblast during gastrulation and which form the gastrointestinal tract and its derivatives. Definitive endoderm cells express at least one of the following markers: HNF3 beta, GATA4, SOX17, CXCR4, Cerberus, OTX2, goosecoid, C-Kit, CD99, and MIXL1.

"Gut tube", as used herein, refers to cells derived from definitive endoderm that express at least one of the following markers: HNF3-beta, HNF1-beta, or HNF4-alpha. Gut tube cells can give rise to all endodermal organs, such as lungs, liver, pancreas, stomach, and intestine.

Used herein interchangeably are "stage 2" and "S2" which identify cells expressing markers characteristic of the primitive gut tube.

"Foregut endoderm" refers to endoderm cells that give rise to esophagus, lungs, stomach, liver, pancreas, gall bladder, and a portion of the duodenum.

"Posterior foregut" refers to endoderm cells that can give rise to posterior stomach, pancreas, liver, and a portion of the duodenum.

"Mid-gut endoderm" refers to endoderm cells that can give rise to the intestines, portions of the duodenum, appendix, and ascending colon.

"Hind-gut endoderm" refers to endoderm cells that can give rise to the distal third of the transverse colon, the descending colon, sigmoid colon and rectum.

Both "stage 3" and "S3" are used interchangeably to identify cells expressing markers characteristic of the foregut endoderm. "Cells expressing markers characteristic of the foregut lineage", as used herein, refers to cells expressing at least one of the following markers: PDX-1, FOXA2, CDX2, SOX2, and HNF4 alpha.

Used interchangeably herein are "stage 4" and "S4" to identify cells expressing markers characteristic of the pancreatic foregut precursor. "Cells expressing markers characteristic of the pancreatic foregut precursor lineage", as used herein, refers to cells expressing at least one of the following markers: PDX-1, NKX6.1, HNF6, FOXA2, PTF1a, Prox1 and HNF4 alpha.

As used herein, "stage 5" and "S5" are used interchangeably to identify cells expressing markers characteristic of the pancreatic endoderm and pancreatic endocrine precursor cells. "Cells expressing markers characteristic of the pancreatic endoderm lineage", as used herein, refers to cells expressing at least one of the following markers: PDX1, NKX6.1, HNF1 beta, PTF1 alpha, HNF6, HNF4 alpha, SOX9, HB9 or PROX1. Cells expressing markers characteristic of the pancreatic endoderm lineage do not substantially express CDX2 or SOX2.

As used herein, "stage 6" and "S6" are used interchangeably to identify cells enriched in pancreatic endocrine cells.

"Pancreatic endocrine cell", or "Pancreatic hormone expressing cell", or "Cells expressing markers characteristic of the pancreatic endocrine lineage" as used herein, refers to a cell capable of expressing at least one of the following hormones: insulin, glucagon, somatostatin, ghrelin, and pancreatic polypeptide.

"Pancreatic endocrine precursor cell" or "Pancreatic endocrine progenitor cell" refers to pancreatic endoderm cells capable of becoming a pancreatic hormone expressing cell. Such a cell can express at least one of the following markers: NGN3, NKX2.2, NeuroD, ISL-1, Pax4, Pax6, or ARX.

"Functional pancreatic beta cell" as used herein, refers to a single hormonal insulin positive cell capable of being glucose responsive and positive for PDX-1 and NKX6.1.

Used interchangeably herein are "d1", "d 1", and "day 1"; "d2", "d 2", and "day 2"; "d3", "d 3", and "day 3", and so on. These number letter combinations specify the day of incubation in the different stages during the stepwise differentiation protocol of the instant application.

"Ascorbic acid" and "Vitamin C" are used interchangeably herein and relate to an essential nutrient for humans and other animal species.

"Glucose" and "D-Glucose" are used interchangeably herein and refer to dextrose, a sugar commonly found in nature.

A cell "positive" for a specific marker or which is marker "+" (i.e., PDX-1+) is a cell in which the particular marker may be detected. A cell "negative" for a specific marker or which is marker "−" (i.e., NKX6.1−) is a cell in which the marker is not detected by the methods taught in the instant specification.

In the instant application "chromogranin" and "CHGN" are used interchangeably to identify the gene encoding the acidic secretory glycoprotein chromogranin.

Used interchangeably herein are "NeuroD" and "NeuroD1" which identify a protein expressed in pancreatic endocrine progenitor cells and the gene encoding it.

Used interchangeably herein are "LDN" and "LDN-193189" to indicate a BMP receptor inhibitor available from Stemgent, Calif., USA.

Isolation, Expansion and Culture of Pluripotent Stem Cells

Pluripotent stem cells may express one or more of the stage-specific embryonic antigens (SSEA) 3 and 4, and markers detectable using antibodies designated Tra-1-60 and Tra-1-81 (Thomson et al., Science 282:1145, 1998). Differentiation of pluripotent stem cells in vitro results in the loss of SSEA-4, Tra-1-60, and Tra-1-81 expression. Undifferentiated pluripotent stem cells typically have alkaline phosphatase activity, which can be detected by fixing the cells with 4% paraformaldehyde, and then developing with Vector Red as a substrate, as described by the manufacturer (Vector Laboratories, CA, USA). Undifferentiated pluripotent stem cells also typically express OCT4 and TERT, as detected by RT-PCR.

Another desirable phenotype of propagated pluripotent stem cells is a potential to differentiate into cells of all three germinal layers: endoderm, mesoderm, and ectoderm tissues. Pluripotency of stem cells can be confirmed, for example, by injecting cells into SCID mice, fixing the teratomas that form using 4% paraformaldehyde, and then examining them histologically for evidence of cell types from the three germ layers. Alternatively, pluripotency may be determined by the creation of embryoid bodies and assessing the embryoid bodies for the presence of markers associated with the three germinal layers.

Propagated pluripotent stem cell lines may be karyotyped using a standard G-banding technique and compared to published karyotypes of the corresponding primate species. It is desirable to obtain cells that have a "normal karyotype," which means that the cells are euploid, wherein all human chromosomes are present and not noticeably altered. Pluripotent cells may be readily expanded in culture using various feeder layers or by using matrix protein coated vessels. Alternatively, chemically defined surfaces in combination with defined media such as mTesr™ 1 media (StemCell Technologies, Vancouver, Canada) may be used for routine expansion of the cells. Pluripotent cells may be readily removed from culture plates using enzymatic, mechanical or use of various calcium chelators such as EDTA (Ethylenediaminetetraacetic acid). Alternatively, pluripotent cells may be expanded in suspension in the absence of any matrix proteins or a feeder layer.

Sources of Pluripotent Stem Cells

The types of pluripotent stem cells that may be used include established lines of pluripotent cells derived from tissue formed after gestation, including pre-embryonic tissue (such as, for example, a blastocyst), embryonic tissue, or fetal tissue taken any time during gestation, typically but not necessarily, before approximately 10 to 12 weeks gestation. Non-limiting examples are established lines of human embryonic stem cells (hESCs) or human embryonic germ cells, such as, for example the human embryonic stem cell lines H1, H7, and H9 (WiCell Research Institute, Madison, Wis., USA). Also suitable are cells taken from a pluripotent stem cell population already cultured in the absence of feeder cells. Also suitable are inducible pluripotent cells (IPS) or reprogrammed pluripotent cells that can be derived from adult somatic cells using forced expression of a number of pluripotent related transcription factors, such as OCT4, Nanog, Sox2, KLF4, and ZFP42 (Annu Rev Genomics Hum Genet, 2011, 12:165-185). The human embryonic stem cells used in the methods of the invention may also be prepared as described by Thomson et al. (U.S. Pat. No. 5,843,780; Science, 1998, 282:1145; Curr. Top. Dev. Biol., 1998, 38:133; Proc. Natl. Acad. Sci. U.S.A., 1995: 92:7844).

Formation of Cells Expressing Markers Characteristic of the Pancreatic Endoderm Lineage from Pluripotent Stem Cells Characteristics of pluripotent stem cells are well known to those skilled in the art, and additional characteristics of pluripotent stem cells continue to be identified. Pluripotent stem cell markers include, for example, the expression of one or more of the following: ABCG2, cripto, FOXD3, CONNEXIN43, CONNEXIN45, OCT4, SOX2, NANOG, hTERT, UTF1, ZFP42, SSEA-3, SSEA-4, Tra 1-60, Tra 1-81.

Pluripotent stem cells suitable for use in the present invention include, for example, the human embryonic stem cell line H9 (NIH code: WA09), the human embryonic stem cell line H1 (NIH code: WA01), the human embryonic stem cell line H7 (NIH code: WA07), and the human embryonic stem cell line SA002 (Cellartis, Sweden). Also suitable for use in the present invention are cells that express at least one of the following markers characteristic of pluripotent cells: ABCG2, cripto, CD9, FOXD3, CONNEXIN43, CONNEXIN45, OCT4, SOX2, NANOG, hTERT, UTF1, ZFP42, SSEA-3, SSEA-4, Tra 1-60, and Tra 1-81.

Markers characteristic of the definitive endoderm lineage are selected from the group consisting of SOX17, GATA4, HNF3 beta, GSC, CERT, Nodal, FGF8, Brachyury, Mix-like homeobox protein, FGF4, CD48, eomesodermin (EOMES), DKK4, FGF17, GATA6, CXCR4, C-Kit, CD99, and OTX2. Suitable for use in the present invention is a cell that expresses at least one of the markers characteristic of the definitive endoderm lineage. In one aspect of the present invention, a cell expressing markers characteristic of the definitive endoderm lineage is a primitive streak precursor cell. In an alternate aspect, a cell expressing markers characteristic of the definitive endoderm lineage is a mesendoderm cell. In an alternate aspect, a cell expressing markers characteristic of the definitive endoderm lineage is a definitive endoderm cell.

Markers characteristic of the pancreatic endoderm lineage are selected from the group consisting of PDX1, NKX6.1, HNF1 beta, PTF1 alpha, HNF6, HNF4 alpha, SOX9, HB9 and PROX1. Suitable for use in the present invention is a cell that expresses at least one of the markers characteristic of the pancreatic endoderm lineage. In one aspect of the present invention, a cell expressing markers characteristic of the pancreatic endoderm lineage is a pancreatic endoderm cell wherein the expression of PDX-1 and NKX6.1 are substantially higher than the expression of CDX2 and SOX2.

Markers characteristic of the pancreatic endocrine lineage are selected from the group consisting of NGN3, NEUROD, ISL1, PDX1, NKX6.1, PAX4, ARX, NKX2.2, and PAX6. In one embodiment, a pancreatic endocrine cell is capable of expressing at least one of the following hormones: insulin, glucagon, somatostatin, and pancreatic polypeptide. Suitable for use in the present invention is a cell that expresses at least one of the markers characteristic of the pancreatic endocrine lineage. In one aspect of the present invention, a cell expressing markers characteristic of the pancreatic endocrine lineage is a pancreatic endocrine cell. The pancreatic endocrine cell may be a pancreatic hormone-expressing cell. Alternatively, the pancreatic endocrine cell may be a pancreatic hormone-secreting cell.

In one aspect of the present invention, the pancreatic endocrine cell is a cell expressing markers characteristic of the $\beta$ cell lineage. A cell expressing markers characteristic of the $\beta$ cell lineage expresses PDX1 and at least one of the following transcription factors: NKX2.2, NKX6.1, NEUROD, ISL1, HNF3 beta, MAFA, PAX4, and PAX6. In one aspect of the present invention, a cell expressing markers characteristic of the $\beta$ cell lineage is a $\beta$ cell.

This invention describes an in vitro method and a cell population that can generate single hormonal insulin positive cells which are also PDX-1 and NKX6.1 positive. The method used in this invention includes a series of stages that direct, in a stepwise manner, the differentiation of human pluripotent cells to single hormonal cells through the following intermediate stages:

a) generation of definite endoderm (DE) cells from undifferentiated human embryonic stem cells comprising culturing pluripotent cells in medium comprising glucose, a TGF-B ligand and a WNT activator;

b) differentiation of DE cells into gut tube cells comprising culturing DE cells in medium comprising glucose, Vitamin C, and a FGF ligand;

c) differentiation of gut tube cells into posterior foregut endoderm cells expressing PDX-1 and SOX2. This differentiation is accomplished by culturing the gut tube cells in the presence of a shh inhibitor, a BMP inhibitor, a TGF-B ligand, a FGF ligand, retinoic acid, vitamin C and a PKC activator;

d) differentiating the posterior foregut cells into pancreatic foregut cells expressing PDX-1 and NKX6.1, and expressing lower level of SOX2 as compared to posterior foregut cells. This differentiation is accomplished by culturing the posterior foregut cells in the presence of a shh inhibitor, a BMP inhibitor, low dose of retinoic acid, vitamin C and a PKC activator.

e) differentiating pancreatic foregut cells into pancreatic endoderm cells expressing PDX-1, a higher level of NKX6.1, and a lower level of SOX2 as compared to pancreatic foregut cells. The differentiation is accomplished by culturing the pancreatic foregut cells in medium supplemented with a shh inhibitor, a TGF-B inhibitor, low dose of retinoic acid, and vitamin C; and f) differentiating pancreatic endoderm cells into pancreatic endocrine precursor cells followed by single-hormonal pancreatic endocrine cells. The differentiation is accomplished by culturing the pancreatic endoderm cells in medium supplemented with a shh inhibitor, low dose of retinoic acid, and vitamin C.

In an embodiment, the cells in all stages of stepwise differentiation are cultured in a media formulation containing less than 25 mM glucose. In some embodiments, the glucose concentration is in the range of about 8 mM to about 20 mM glucose.

In some embodiments, media formulations used to generate gut tube stage cells and all subsequent steps contain ascorbic acid (also known as Vitamin C). In an embodiment, the concentration of ascorbic acid is about 0.01 mM to about 1 mM. In an embodiment, the concentration of ascorbic acid is from about 0.1 mM to about 0.5 mM.

The present invention is further illustrated, but not limited, by the following examples.

Example 1

Differentiation of Human Embryonic Stem Cells of the Cell Line H1 to Pancreatic Endocrine Precursor Cells in the Absence of Fetal Bovine Serum-Modulation of BMP/TGF-B Pathways Results in Improved Production of Pancreatic Endoderm Population and Reduced Percentage of SOX2+ Population This example was carried out to show that pancreatic endoderm cultures can be generated having very high expression levels of PDX-1 and NKX6.1 while having low level expression of CDX2 and SOX2.

Cells of the human embryonic stem cell line H1 (hESC H1) were harvested at various passages (passage 40 to passage 52) and were seeded as single cells at a density of 100,000 cells/cm$^2$ on MATRIGEL™ (1:30 dilution; BD Biosciences, NJ, USA) coated dishes in mTeSR® 1 media (StemCell Technologies, Vancouver, Canada) supplemented with 10 µM of Y27632 (Rock inhibitor, Catalog #Y0503, SigmaAldrich, MO, USA). Forty-eight hours post seeding, cultures were washed and incubated in incomplete PBS (phosphate buffered saline without Mg or Ca) for approximately 30 seconds. Cultures were differentiated into pancreatic endocrine lineage as follows:

a. Stage 1 (Definitive Endoderm (DE)—3 days): Cells were cultured for one day in stage 1 media: MCDB-131 medium (Catalog #10372-019, Invitrogen, CA, USA) supplemented with 0.1% fatty acid-free BSA (Catalog #68700, Proliant, Iowa, USA), 0.0012 g/ml sodium bicarbonate (Catalog #S3187, SigmaAldrich, MO, USA), 1× GlutaMax™ (Catalog #35050-079, Invitrogen), 5 mM D-Glucose (Catalog #G8769, SigmaAldrich, MO, USA), containing 100 ng/ml GDF8 (R&D Systems, MN, USA) and 1 µM MCX compound (a GSK3B inhibitor, 14-Prop-2-en-1-yl-3,5,7,14,17,23,27-heptaazatetracyclo[19.3.1.1~2,6~0.1~8,12~]heptacosa-1(25),2(27),3,5,8(26),9,11,21,23-nonaen-16-one, U.S. patent application Ser. No. 12/494,789; incorporated herein by reference in its entirety). Cells were then cultured for one day in MCDB-131 medium supplemented with 0.1% fatty acid-free BSA, 0.0012 g/ml sodium bicarbonate, 1× GlutaMax™, 5 mM D-Glucose, 100 ng/ml GDF8, and 100 nM MCX compound. Cells were then cultured for one day in MCDB-131 medium to which 0.1% fatty acid-free BSA, 0.0012 g/ml sodium bicarbonate, 1× GlutaMax™, 5 mM D-Glucose, and 100 ng/ml GDF8 had been added.

b. Stage 2 (Primitive gut tube—2 days): Stage 1 cells were treated for two days with MCDB-131 medium supplemented with 0.1% fatty acid-free BSA, 0.0012 g/ml sodium bicarbonate, 1× GlutaMax™, 5 mM D Glucose, and 25 ng/ml FGF7.

c. Stage 3 (Foregut-2 days): Stage 2 cells were cultured for one day in Stage 3 medium: MCDB-131 medium supplemented with 1:200 dilution of ITS-X (Invitrogen), 2.5 mM Glucose, 1× GlutaMax™, 0.0015 g/ml sodium bicarbonate, 2% fatty acid-free BSA, 25 ng/ml FGF7, 10 ng/ml activin-A (R & D systems), 0.25 µM SANT-1 (shh inhibitor, SigmaAldrich), 1 µM Retinoic acid (RA) (SigmaAldrich), and 200 nM TPB (PKC activator; Catalog #565740; EMD, NJ, USA), containing 100 nM LDN-193189 (BMP receptor inhibitor; Catalog #04-0019; Stemgent, Calif., USA). The cells were then cultured for an additional day in the Stage 3 medium supplement with 10 nM LDN-193189.

d. Stage 4 (Pancreatic foregut precursor-2 days): Stage 3 cells were cultured for two days in MCDB-131 medium supplemented with a 1:200 dilution of ITS-X, 2.5 mM Glucose, 1× GlutaMax™, 0.0015 g/ml sodium bicarbonate, 2% fatty acid-free BSA, 0.25 µM SANT-1, 50 nM RA, 200 nM TPB, and 50 nM LDN-193189.

e. Stage 5 (Pancreatic endoderm, 2-7 days): Stage 4 cells were cultured for 2-7 days in MCDB-131 medium supplemented with a 1:200 dilution of ITS-X, 2.5 mM Glucose, 1× GlutaMax™, 0.0015 g/ml sodium bicarbonate, 2% fatty acid-free BSA, 0.25 µM SANT-1, and 50 nM RA.

At specified stages, samples were collected and analyzed by real-time PCR, immune-histochemistry, or fluorescent activated cell sorting (FACS).

For FACS analyses, the hESC-derived cells were released into single-cell suspension by incubation in TrypLE Express (Catalog No. 12604, Invitrogen) at 37° C. for 3-5 minutes. Cells were then washed twice in staining buffer (PBS containing 0.2% fatty acid-free BSA) (Catalog No. 554657, BD Biosciences, NJ, USA). For intracellular antibody staining, cells were first incubated for 20 minutes at 4° C. with Green Fluorescent LIVE/DEAD cell dye (Invitrogen Catalog No. L23101), to allow for live/dead cell discrimination during analysis, followed by a single wash in cold PBS. Cells were fixed in 250 µl of Cytofix/Cytoperm Buffer (BD Biosciences Catalog No. 554722) for 20 minutes at 4° C. followed by two washes in BD Perm/Wash Buffer Solution (BD Biosciences Catalog No. 554723). Cells were resuspended in 100 µl staining/blocking solution consisting of Perm/Wash buffer supplemented with 2% normal serum (of the appropriate species of the secondary antibody). Cells were then incubated for 30 minutes at 4° C. with primary antibodies at empirically pre-determined dilutions followed by two washes in Perm/Wash buffer. Lastly, cells were incubated with the appropriate secondary antibodies for 30 minutes at 4° C. followed by two washes with Perm/Wash buffer prior to analyses on the BD FACS Canto II.

The following dilutions of primary antibodies were used: rabbit anti-insulin (1:100; Catalog No. C27C9; Cell Signaling, MA, USA), mouse anti-insulin (1:100; Catalog NO. ab6999, Abcam, MA, USA), mouse anti-glucagon (1:1250; Catalog No. G2654; Sigma-Aldrich), rabbit anti-synaptophysin (1:100; Catalog No. A0010, Dako, Calif., USA), rabbit anti-chromogranin A (1:800; Dako), mouse anti-NKX6.1 (1:50; DSHB, University of Iowa, IA, USA), mouse anti-CDX2 (1:250; Invitrogen), goat anti-NeuroD (1:500; R&D Systems), mouse anti-SOX2 (BD, CA, USA), mouse anti-NKX2.2 (DSHB), mouse anti-Pax6 (BD, CA, USA), mouse anti-PDX-1 (BD, CA, USA). Secondary antibodies were used at the following dilutions: goat anti-mouse Alexa 647 (1:500; Invitrogen), goat anti-rabbit PE (1:200; Invitrogen), donkey anti-goat (1:800; Invitrogen). Samples were incubated for 30 minutes at 4° C. after addition of secondary antibodies, followed by a final wash in Perm/Wash buffer. Cells were analyzed on a BD FACS Canto II using the BD FACS Diva Software with at least 30,000 events being acquired.

Figure 1B:
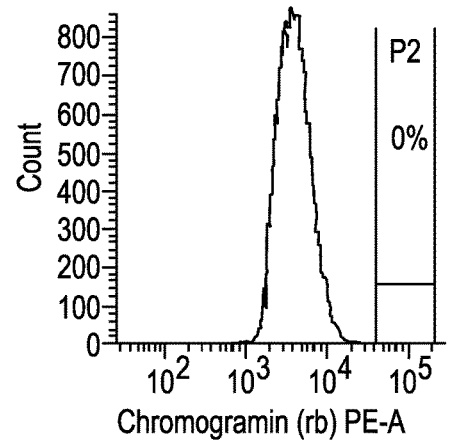
Figure 1C:
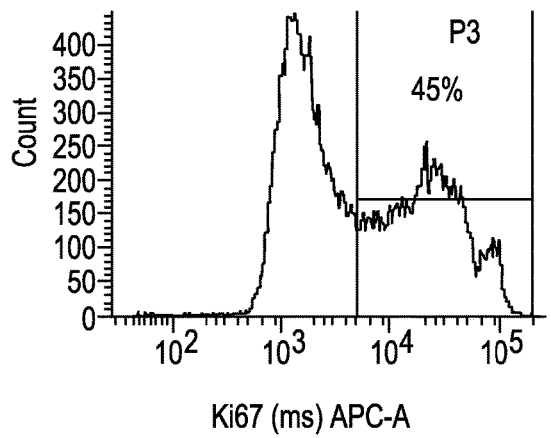
Figure 1D:
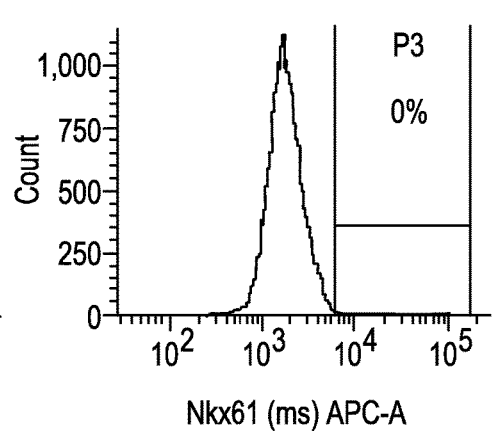

FIG. 1A to FIG. 1G depict FACS histogram expression profiles of Isotype control (FIG. 1A), chromogranin (FIG. 1B), KI-67 (FIG. 1C), NKX6.1 (FIG. 1D), SOX2 (FIG. 1E), CDX2 (FIG. 1F), PDX-1 (FIG. 1G) of cells differentiated according to Example 1 and analyzed at S3 day 2. Percentage expression for each marker is shown on each histogram. At day 2 of stage 3, over 95% of the cells were positive for expression of PDX-1 (FIG. 1G), and about 60% of the cells in the population were positive for expression of SOX2 (FIG. 1E), while less than 10% of the cells were positive for expression of CDX2 (FIG. 1F) or NKX6.1 (FIG. 1D), or chromogranin (FIG. 1B). A significant percentage of cells at stage 3 were in active cell cycle as shown by high percentage of KI-67 positive cells (FIG. 1C).

FIG. 2A to FIG. 2G depict the expression profiles of Isotype control (FIG. 2A), chromogranin (FIG. 2B), KI-67 (FIG. 2C), NKX6.1 (FIG. 2D), SOX2 (FIG. 2E), CDX2 (FIG. 2F), PDX-1 (FIG. 2G), as determined by FACS staining, of cells differentiated according to Example 1, and harvested at day 2 of S4. Percentage expression for each marker is shown on each histogram. Similar to stage 3, over 95% of the cells were positive for PDX-1 expression (FIG. 2G), while about 10% of the cells were positive for CDX2 expression (FIG. 2F), and about 40% of the cells were positive for NKX6.1 expression (FIG. 2D). About 45% of the cells were positive for SOX2 expression (FIG. 2E), a drop from 60% at S3. Chromogranin expression was approximately 3% (FIG. 2B). A significant percentage of cells at stage 4 were in active cell cycle as shown by high percentage of KI-67 positive cells (FIG. 2C).

Figure 3A:
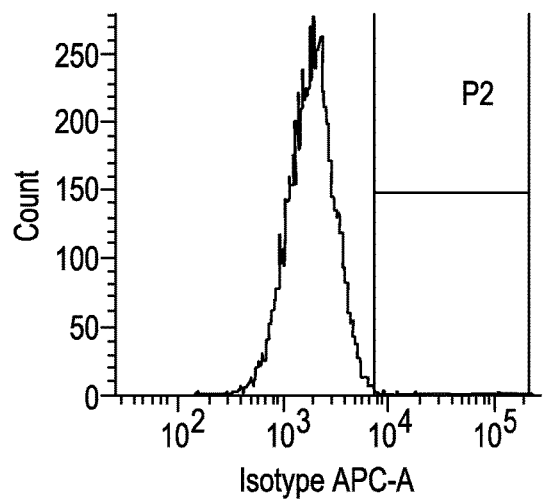
FIG. 3A to FIG. 3G show the FACS histogram expression profiles of the following markers in cells differentiated according to Example 1 and harvested at S5 day 2.
Figure 3B:
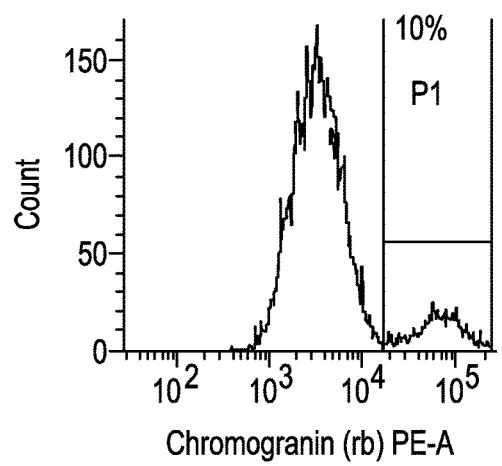
Figure 3C:
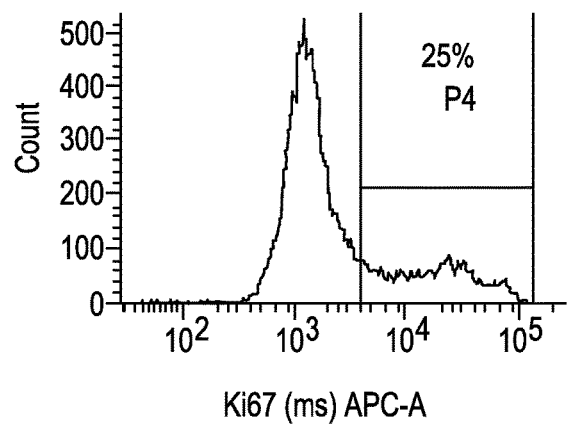
Figure 3D:
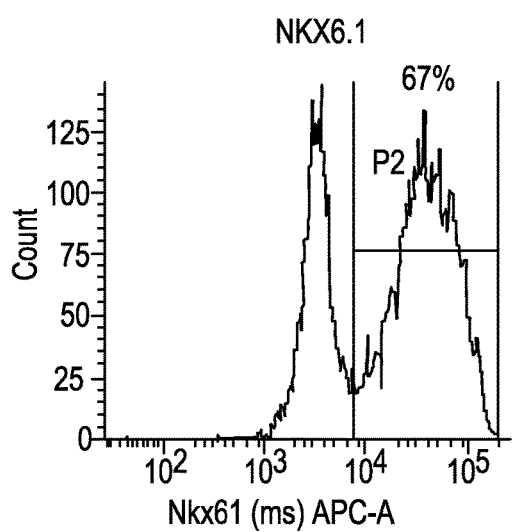
Figure 3E:
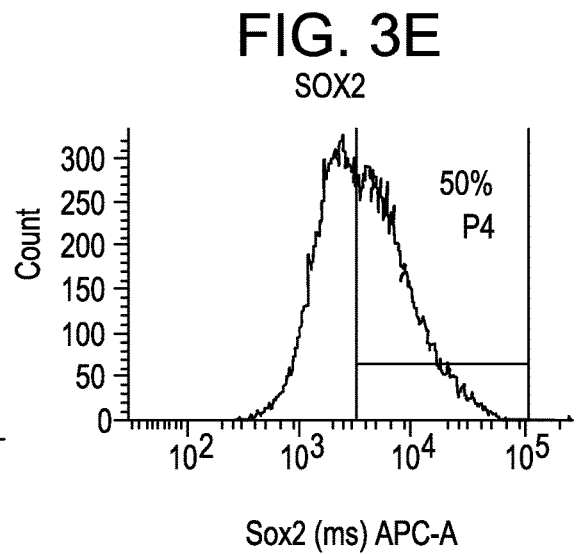
Figure 3F:
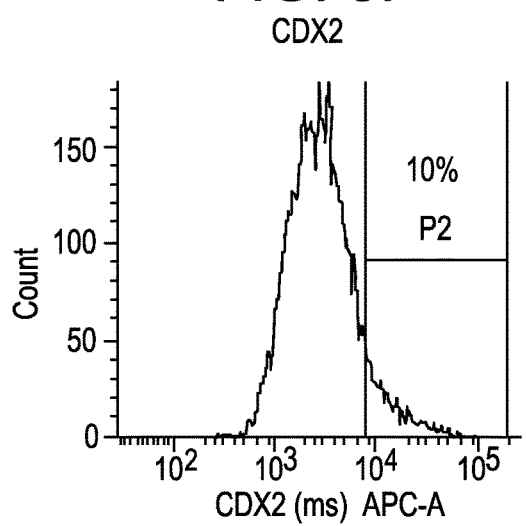
Figure 3G:
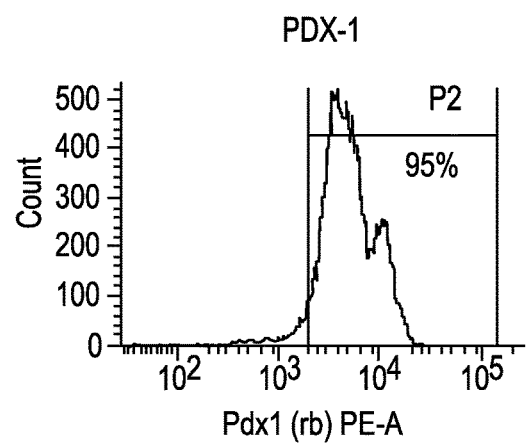

FIG. 3A to 3G depict the relative expression profiles, as determined by FACS analyses, of cells harvested at day 2 of stage 5 following the differentiation protocol outlined in this example. FIG. 3A: isotype control; FIG. 3B: chromogranin; FIG. 3C: KI-67; FIG. 3D: NKX6.1; FIG. 3E: SOX2; FIG. 3F: CDX2; FIG. 3G: PDX-1. Percentage expression for each marker is shown on each histogram. Similar to stages 3 and 4, over 95% of the cells were positive for expression of PDX-1, while approximately 10% of the cells were positive for CDX2 expression, and over 67% of the cells were positive for NKX6.1 expression. SOX2 expression, at approximately 50%, was lower when compared to stage 3, but similar to its expression at S4.

Figure 4F:
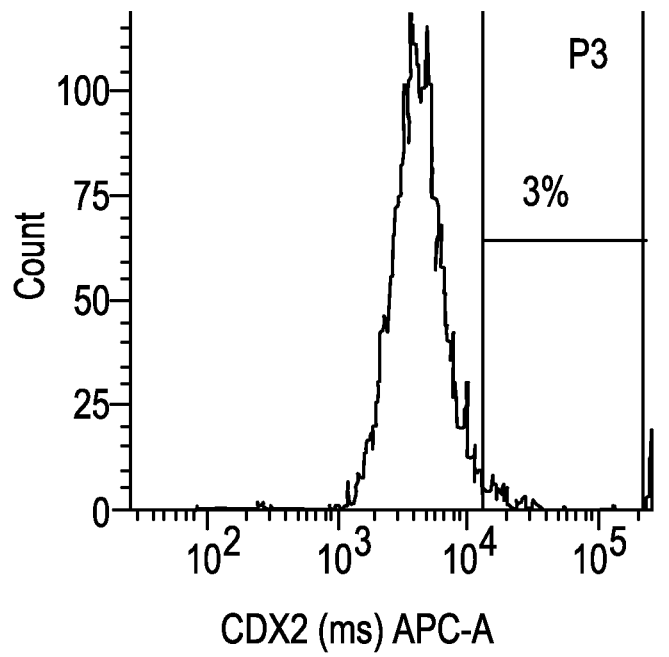
Figure 4G:
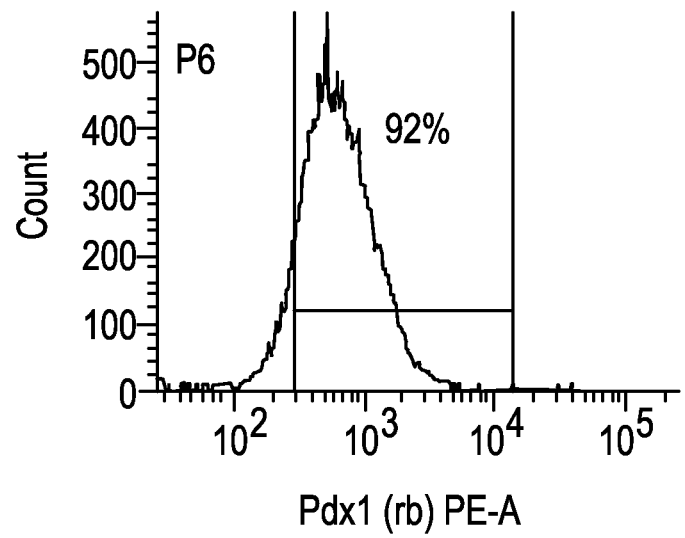

FIG. 4A to FIG. 4G depict the expression of PDX-1 (FIG. 4G), NKX6.1 (FIG. 4D), CDX2 (FIG. 4F), SOX2 (FIG. 4E), Ki-67 (proliferation marker; FIG. 4C) and chromogranin (pan endocrine marker; FIG. 4B) as measured by FACS staining of cells harvested and analyzed at day 7 of stage 5 of differentiation following the protocol outlined in this example. Similar to stages 3 and 4, >90% of the cells were positive for expression of PDX-1, while CDX2 expression was less than 10%, and NKX6.1 expression significantly increased to >70% and SOX2 expression dramatically decreased to about 2%.

Figure 5C:
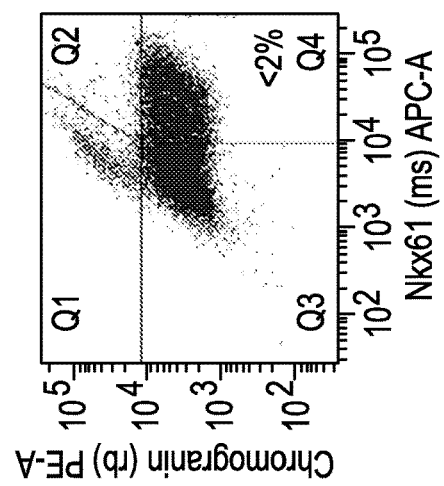
FIG. 5A to FIG. 5C depict FACS histogram expression profiles of the following markers in cells differentiated according to Example 1 and harvested at cells harvested at S5 day 2.
Figure 5B:
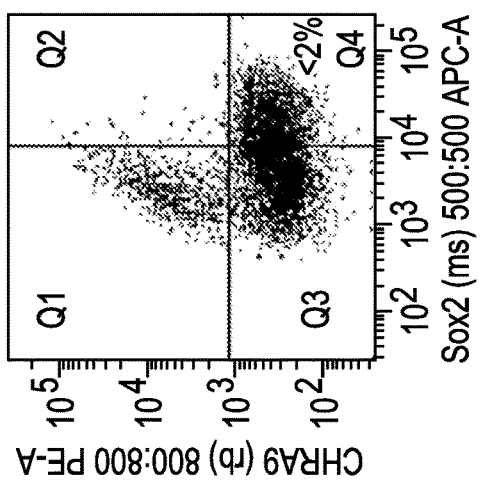
Figure 5A:
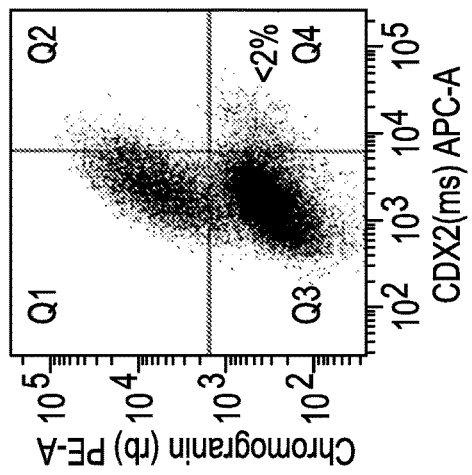

Furthermore, the majority of cells expressing SOX2, CDX2, and NKX6.1 were negative for the expression of chromogranin (see FIG. 5A to FIG. 5C). Thus, S5 cultures prepared following the protocol outlined in this example result in a population of cells where at least 50% of the cells express PDX-1 and NKX6.1 while being negative for CDX-2, SOX2, and chromogranin. Table I summarizes the percentage expression of various endoderm markers at S3-S5.

TABLE I

Average Expression of Endoderm Markers at S3 through S5

| | Total* | % PDX-1+ | % PDX-1+ and SOX2+ | % PDX-1+ NKX6.1+ and SOX2- | % PDX-1+ CDX2+ | % PDX-1+ NKX6.1+ SOX2+ |
|---|---|---|---|---|---|---|
| Stage 3 2 days | 7 | 96 | 60 | 0 | <5 | 0 |
| Stage 4 2 days | 9 | 97 | 45 | ~40 | <5 | <5 |
| Stage 5 2 days | 11 | 95 | 50 | ~42 | <10 | <25 |
| Stage 5 7 days | 16 | 92 | <2 | ~70 | <5 | <2 |

*Total number of days since start of differentiation.

Figure 6A:
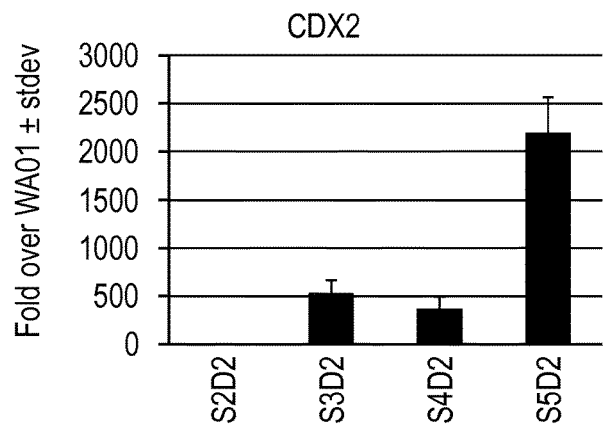
FIG. 6A to FIG. 6T show data from real-time PCR analyses of the expression of the following genes in cells of the human embryonic stem cell line H1 differentiated according to the Example 1 and harvested at S2, S3, S4, and S5.
Figure 6B:
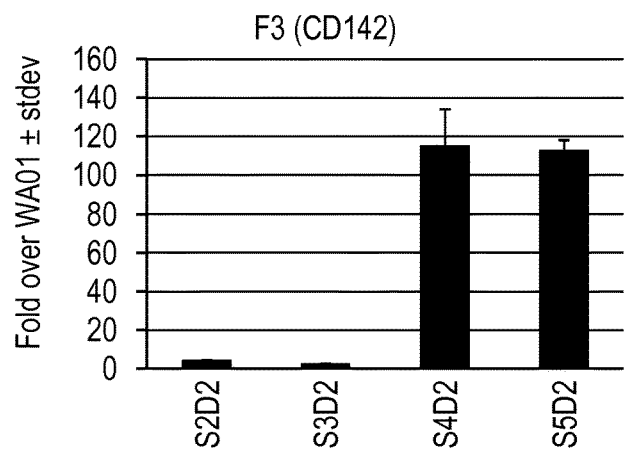
FIG. 6B: CD142.
Figure 6C:
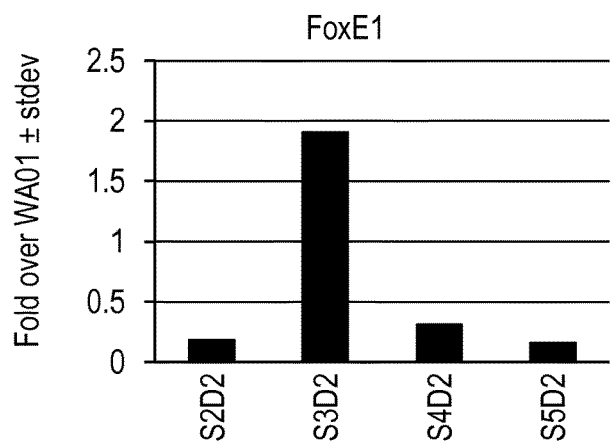
FIG. 6C: FOXE1.
Figure 6D:
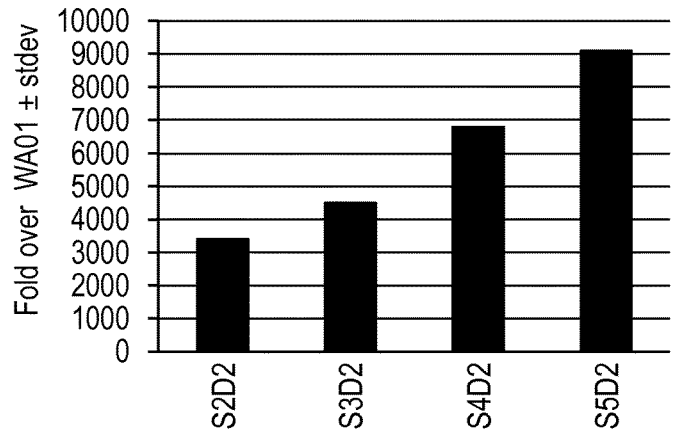
FIG. 6D: HNF4-alpha.
Figure 6E:
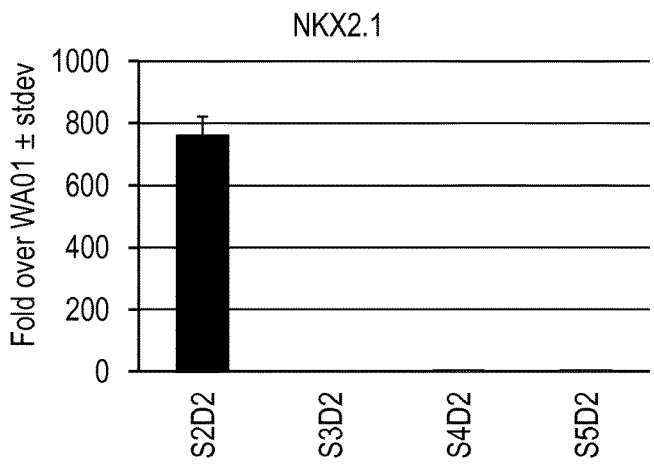
FIG. 6E: NKX2.1.
Figure 6F:
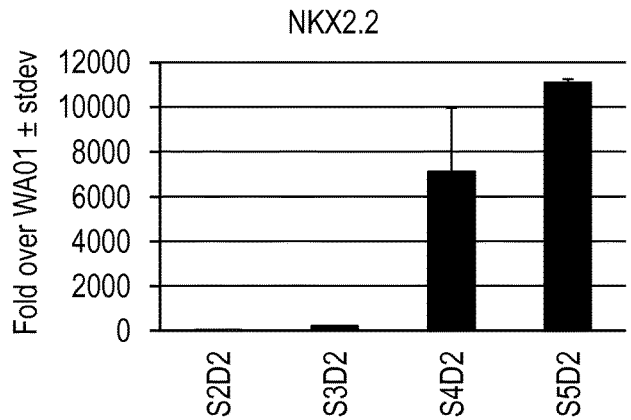
FIG. 6F: NKX2.2.
Figure 6G:
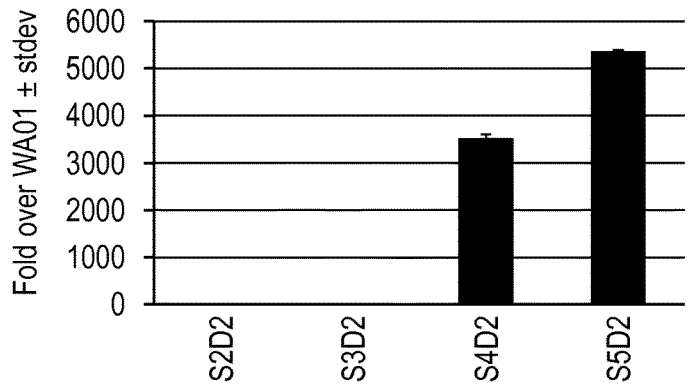
FIG. 6G: NKX6.1.
Figure 6H:
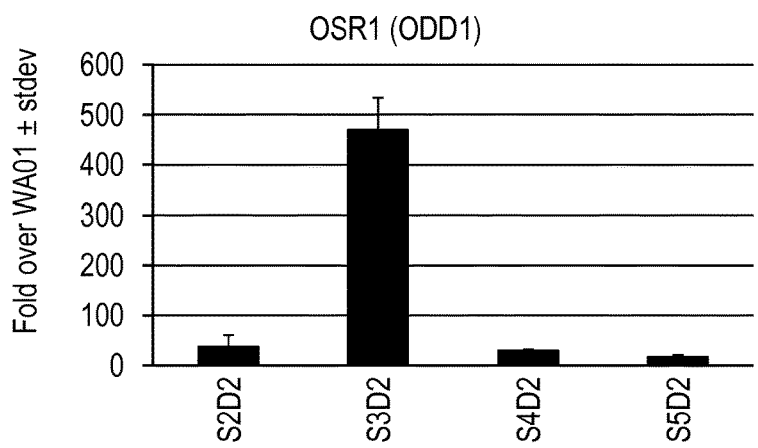
FIG. 6H: OSR1.
Figure 6I:
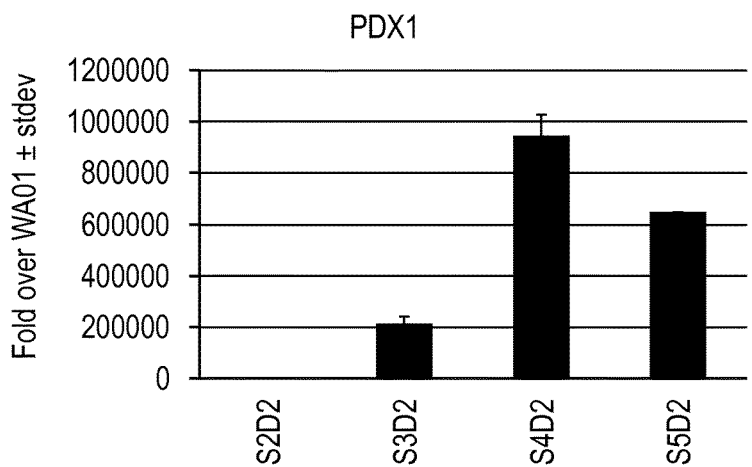
FIG. 6I: PDX-1.
Figure 6J:
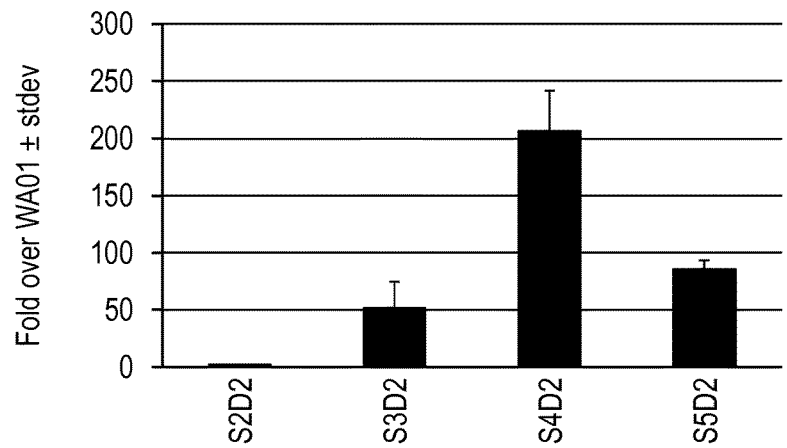
FIG. 6J: PROX1.
Figure 6K:
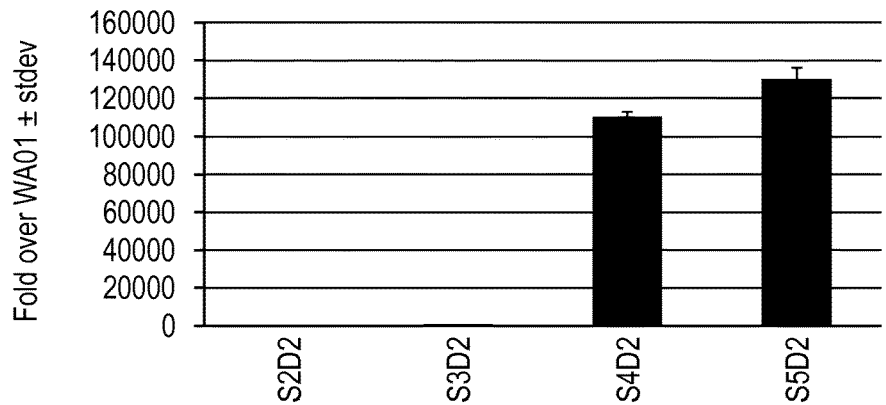
Figure 6L:
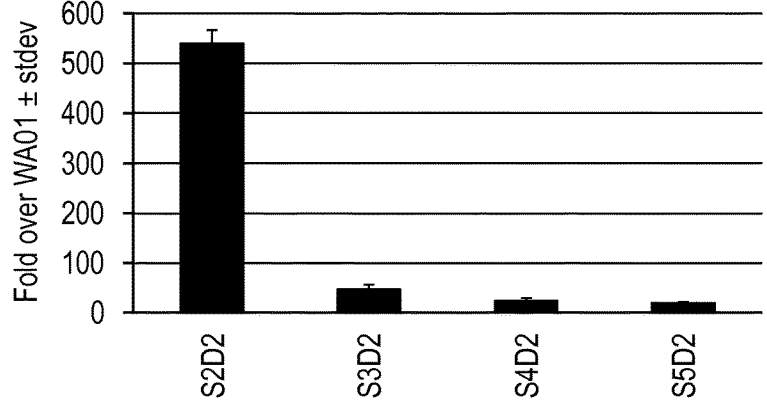
FIG. 6L: SOX17.
Figure 6M:
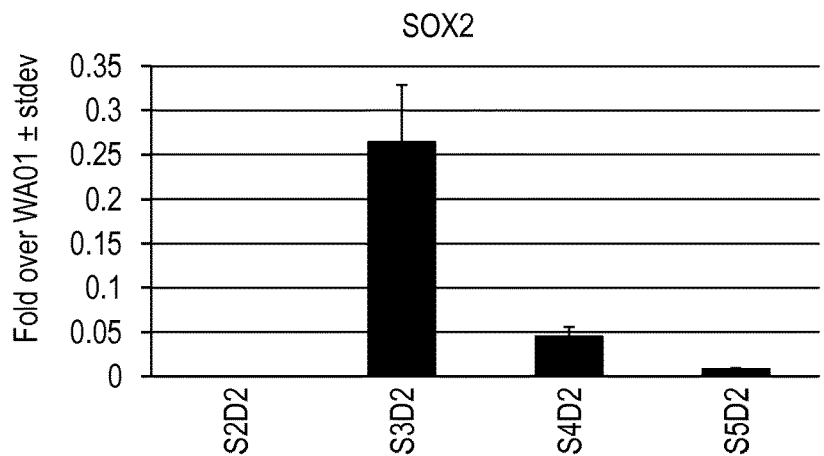
FIG. 6M: SOX2.
Figure 6N:
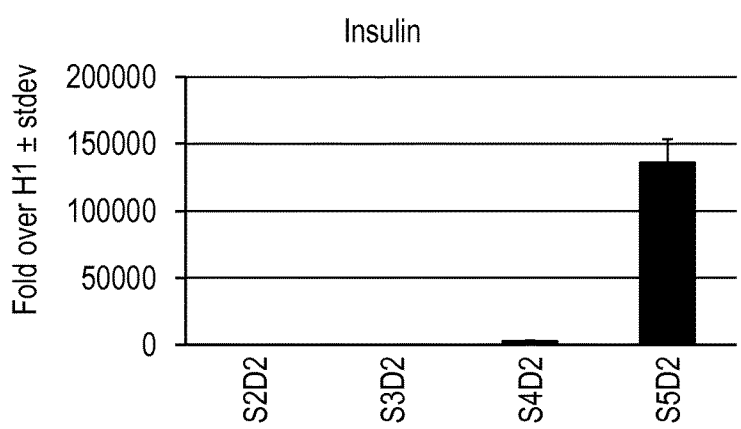
FIG. 6N: insulin.
Figure 6O:
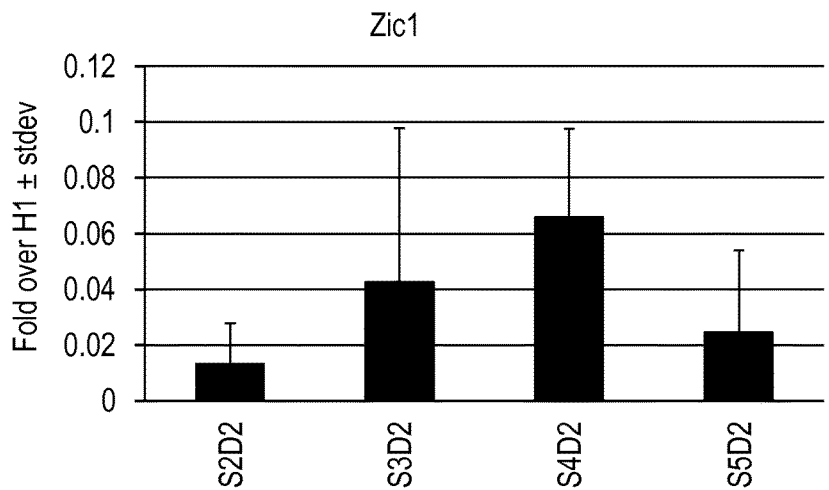
FIG. 6O: ZIC1.
Figure 6P:
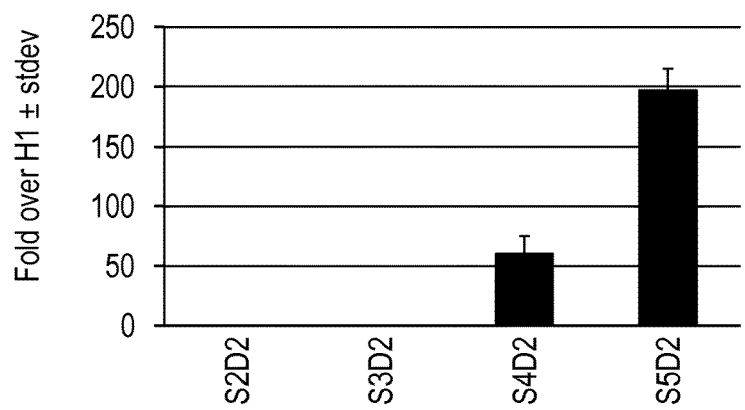
FIG. 6P: chromogranin.
Figure 6Q:
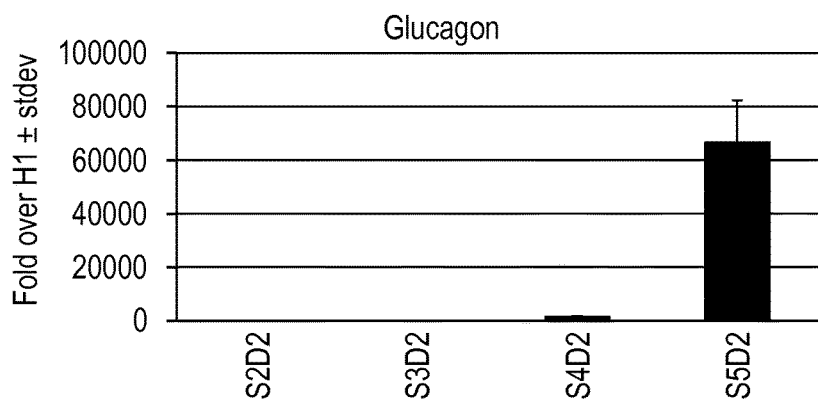
FIG. 6Q: glucagon.
Figure 6R:
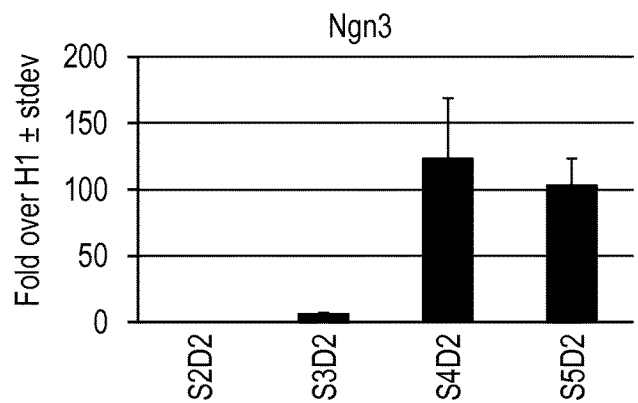
FIG. 6R: Ngn3.
Figure 6S:
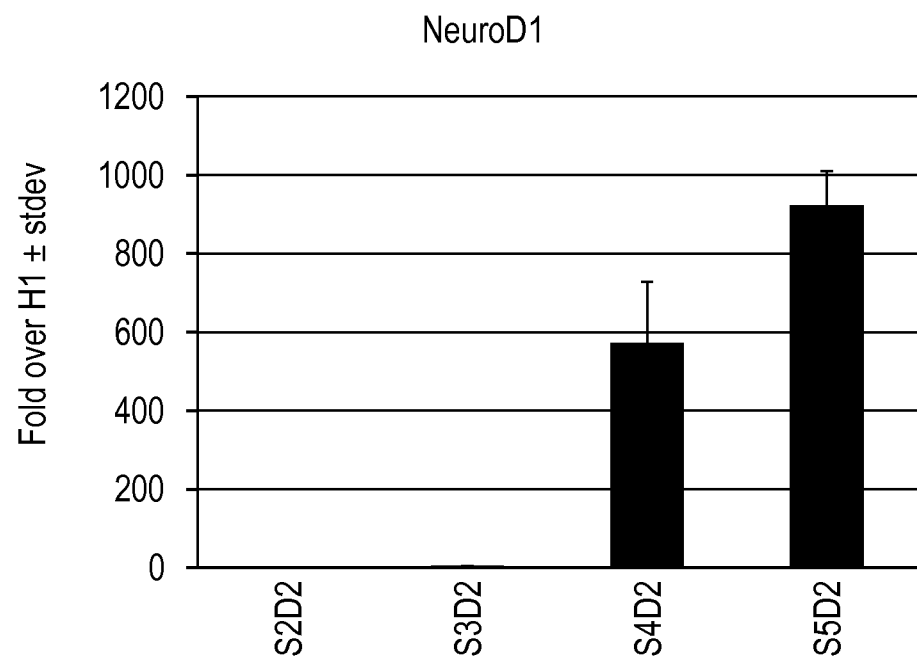
FIG. 6S: NeuroD.
Figure 6T:
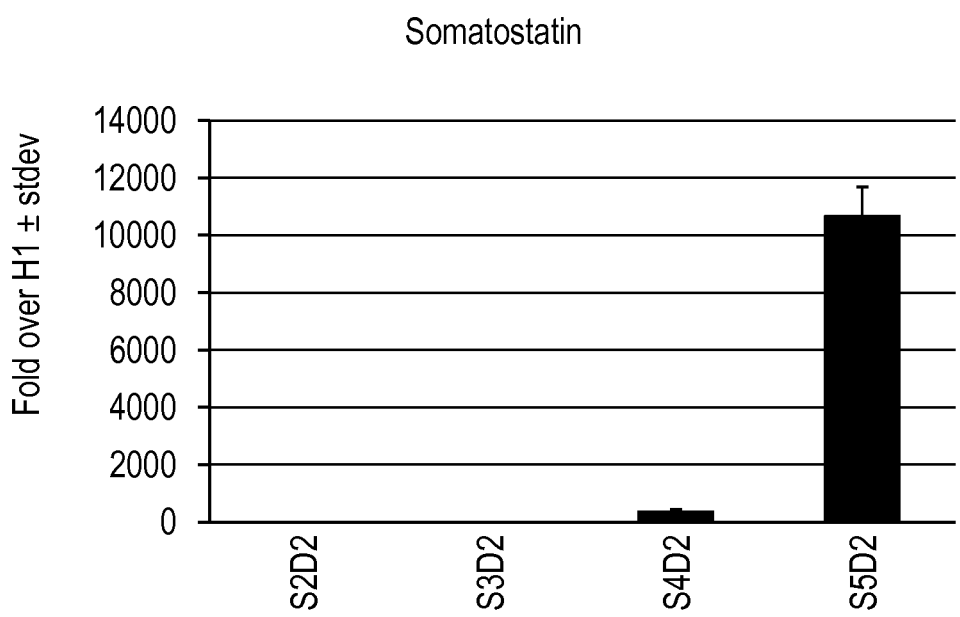

FIG. 6A to FIG. 6T depict mRNA expression profiles measured by real-time PCR of S2, S3, S4, and S5 cells differentiated following the protocol outlined in this example, and reported as fold change over the expression in undifferentiated H1 cells. At stage 3, there was a very low expression of anterior foregut markers such as FOXe1 (FIG. 6C) and NKX2.1 (FIG. 6E). However, at stage 3, SOX2 (FIG. 6M) and OSR1 (FIG. 6H), which mark the stomach region of the gut tube, were significantly upregulated and their expression declined at S4-S5. Pancreatic endoderm markers, such as PTF1a (FIG. 6K), NKX6.1 (FIG. 6G), and PDX-1 (FIG. 6I) reached maximal expression levels at S5 day 2 of culture. The PCR data indicate that at stage 3, the cells transition through a PDX-1+SOX2+ population before becoming PDX-1+NKX6.1+SOX2− CDX2− at S4-S5. (See FIG. 6I, FIG. 6G, FIG. 6M, and FIG. 6A.) Expression of endocrine markers (chromogranin, insulin, glucagon, and somatostatin) reached a maximal expression level at end of S5. Expression of pancreatic endocrine precursor markers, NKX2.2, NeuroD, and NGN3 reached a maximal expression level at S4-S5. Expression of other lineage markers, such as ZIC1 and SOX17 remained low at S4-S5.

In conclusion, cells at stage 5 day 2 which were differentiated following the protocol outlined in this example express low levels of CDX2 and SOX2 while maintaining a high expression level of NKX6.1 and PDX-1. It is believed that the unique combination of timely BMP inhibition, use of low dose RA at S4-S5, use of high glucose at S1-S2 results in the population of cells described in Example 1.

Example 2

Effect of BMP Inhibition and PKC Activation on the Expression of SOX2 at S3-S4

The protocol outlined in this example was performed to shed light on the effects of BMP inhibition, addition of FGF7 along with PKC activation on SOX2 expression at S3-S4.

Cells of the human embryonic stem cell line H1 were harvested at various passages (passage 40 to passage 52) and were seeded as single cells at a density of 100,000 cells/cm² on MATRIGEL™ (1:30 dilution) coated dishes in mTesr™ 1 media supplemented with 10 µM of Y27632. Forty eight hours post-seeding, cultures were differentiated into cells of the pancreatic endocrine lineage as follows:

a. Stage 1 (Definitive Endoderm (DE)—3 days): Prior to start of DE, the cultures were washed and incubated with incomplete PBS (no Mg or Ca) for 30 seconds followed by addition of the stage 1 media. Human embryonic stem cells cultured as single cells on MATRIGEL™-coated dishes were treated with MCDB-131 medium supplemented with 0.1% fatty acid-free BSA, 0.0012 g/ml sodium bicarbonate, 1× GlutaMax™, and 2.5 mM D-Glucose, 100 ng/ml GDF8, and 1.5 µM MCX compound (GSK3B inhibitor) for one day. Cells were then treated with MCDB-131 medium supplemented with 0.1% fatty acid-free BSA, 0.0012 g/ml sodium bicarbonate, 1× GlutaMax™, 2.5 mM glucose, and 100 ng/ml GDF8 for days 2-3.

b. Stage 2 (Primitive gut tube—3 days): Stage 1 cells were treated with MCDB-131 medium supplemented with 0.1% fatty acid-free BSA, 0.0012 g/ml sodium bicarbonate, 1× GlutaMax™, 2.5 mM D-Glucose, and 50 ng/ml FGF7 and for three days.

c. Stage 3 (Foregut—3 days): Stage 2 cells were treated with MCDB131 medium supplemented with a 1:200 dilution of ITS-X, 2.5 mM Glucose, 1× GlutaMax™, 0.0015 g/ml sodium bicarbonate, 2% fatty acid-free BSA, 0.25 µM SANT-1, 20 ng/ml of activin-A, 2 µM RA, in the presence or absence of 50 ng/ml FGF7, 50 nM or 200 nM LDN-193189, and/or 200 nM TPB. Cells were incubated for three days in medium using the combinations listed in Table II, below:

TABLE II

Figure 7C:
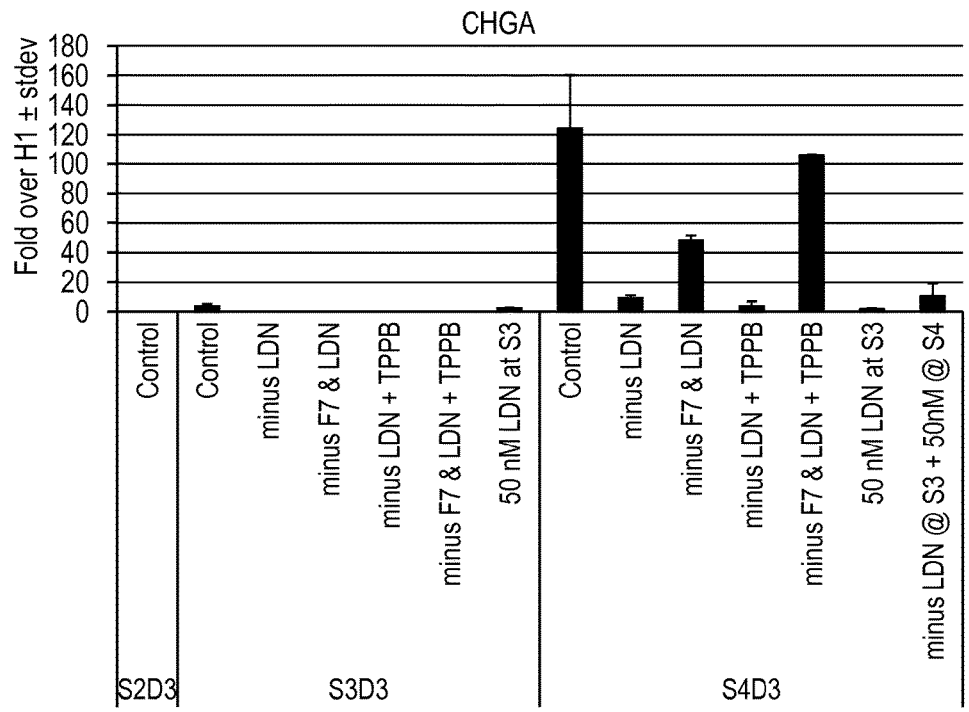
Figure 7D:
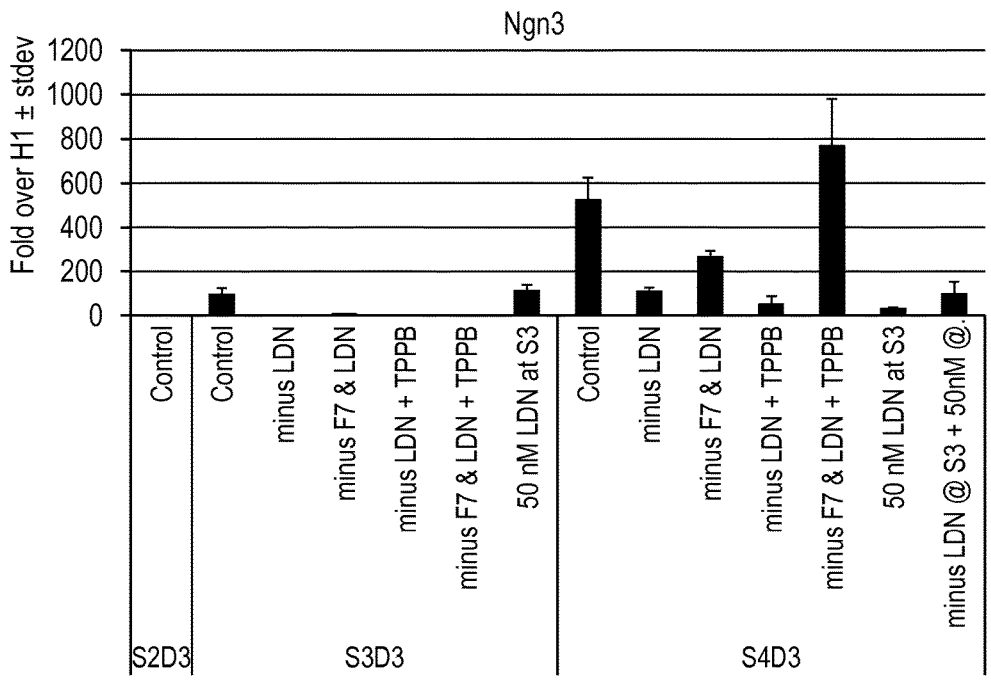
Figure 7G:
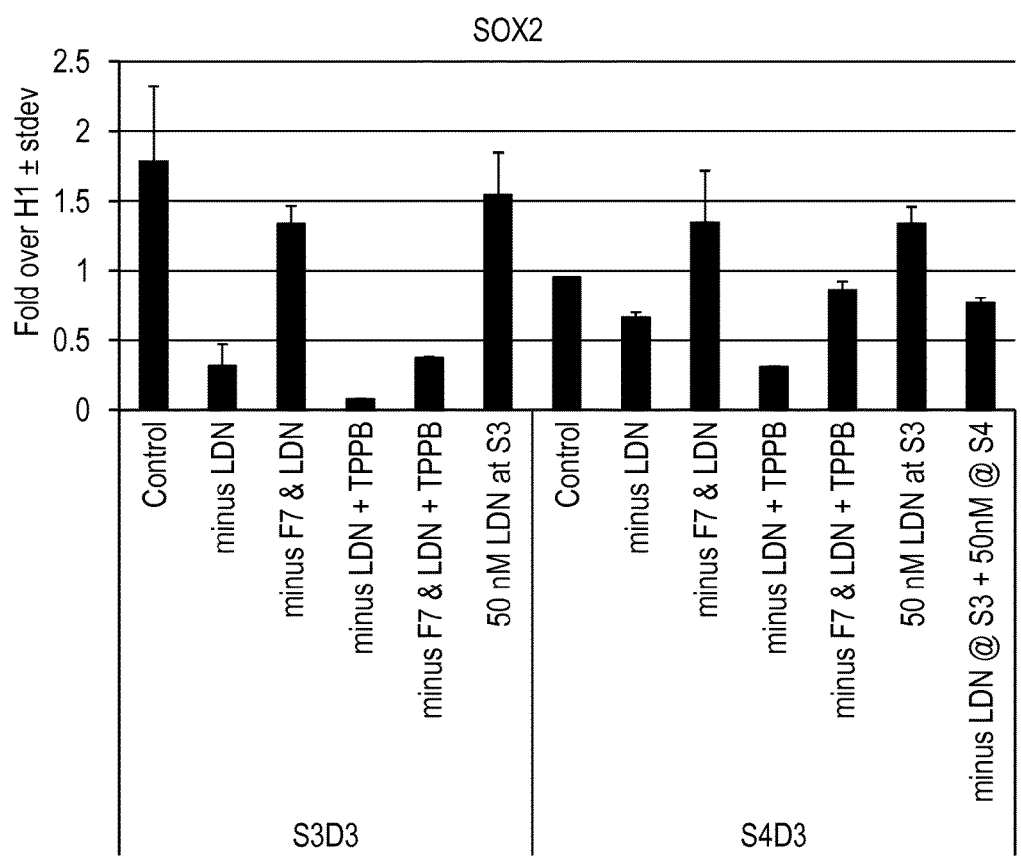

| | | | Stage 3 Treatments | | | |
|---|---|---|---|---|---|---|
| Treatment | AA | FGF7 | LDN-193189 | SANT | RA | TPB |
| 1 | + | + | 200 nM+ | + | + | − |
| 2 | + | + | − | + | + | − |
| 3 | + | − | − | + | + | − |
| 4 | + | + | − | + | + | + |
| 5 | + | − | − | + | + | + |
| 6 | + | + | 50 nM | + | + | − | d. Stage 4 (Pancreatic foregut precursor—3 days): Stage 3 cells were treated with MCDB131 medium supplemented with 1:200 dilution of ITS-X, 2.5 mM Glucose, 1× GlutaMax™, 0.0015 g/ml sodium bicarbonate, 2% fatty acid-free BSA, 0.25 µM SANT-1, 200 nM TPB, 400 nM LDN-193189, 2 µM ALk5 inhibitor (SD-208, disclosed in Molecular Pharmacology 2007, 72:152-161), and 100 nM CYP26A inhibitor (N-{4-[2-Ethyl-1-(1H-1,2,4-triazol-1-yl)butyl]phenyl}-1,3-benzothiazol-2-amine, Janssen, Belgium) for three days.

mRNA was collected at S2-S4 for all the conditions listed above and analyzed using real-time PCR. Control conditions, at S3, refer to cultures where FGF7, AA, SANT, RA, and 200 nM LDN-193189 were used at the concentrations listed at step c, above. As evident by PCR data shown in FIGS. 7A to 7G, removal of LDN-193189 at S3 resulted in a significant decrease in endocrine markers, such as NGN3 (FIG. 7D), and pan-endocrine marker such as chromogranin (see FIG. 7C). Addition of the PKC activator and removal of LDN-193189 at S3 further decreased endocrine markers while enhancing expression of NKX6.1 (see FIG. 7A to FIG. 7G). Furthermore, addition of 50 nM LDN-193189 was as effective as 200 nM LDN-193189 in induction of endocrine markers (chromogranin and NGN3). Removal of LDN-193189 and addition of TPB at S3 enhanced expression of CDX2 (FIG. 7E) and albumin (FIG. 7F) while suppressing SOX2 (FIG. 7G) expression. Moreover, removal of both FGF7 and LDN-193189 significantly enhanced expression of SOX2 (FIG. 7G) and reduced expression of Albumin (FIG. 7F) as compared to cultures were LDN-193189 was removed and FGF7 was retained. These data demonstrate that precise modulation of the BMP inhibition, FGF activation, and PKC activation can result in an endoderm domain that is rich in PDX-1 and NKX6.1 while being low for CDX2, SOX2, and albumin. Lastly, sustained inhibition of BMP at S3-S4 enhanced expression of proendocrine genes plus upregulation of SOX2 expression. This highlights that BMP inhibition needs to be precisely tuned to increase pancreatic endocrine genes while not upregulating SOX2 expression which is absent or low in pancreas development but present in anterior foregut endoderm organs, such as stomach.

Example 3

Early Inhibition of BMP at Foregut Stage is Required for Subsequent Induction of Endocrine Markers This example shows that early inhibition of BMP signaling at S3 is required for subsequent induction of endocrine markers. However, sustained inhibition of BMP at stage 3 also results in strong expression of SOX2. In order to obtain both a high expression of endocrine markers along with low expression of SOX2 expression, a gradient of BMP inhibition was required to induce pro-pancreatic endocrine markers while having a low expression of SXO2 and CDX2.

Cells of the human embryonic stem cell line H1 at various passages (passage 40 to passage 52) were seeded as single cells at a density of 100,000 cells/cm² on MATRIGEL™ (1:30 dilution) coated dishes in mTesr™ 1 media supplemented with 10 µM of Y27632. Forty eight hours post seeding, cultures were differentiated into cells of the pancreatic endocrine lineage as follows:

a. Stage 1 (Definitive Endoderm (DE)—4 days): Prior to start of DE, the cells were washed and incubated with incomplete PBS (no Mg or Ca) for 30 seconds followed by incubation in S1 media. Human embryonic stem cells cultured as single cells on MATRIGEL™-coated dishes were treated for one day with MCDB-131 medium supplemented with 0.1% fatty acid-free BSA, 0.0012 g/ml sodium bicarbonate, 1× GlutaMax™, 2.5 mM D-Glucose, 100 ng/ml GDF8, 1.5 µM MCX compound (GSK3B inhibitor). Cells were then treated for two days (days 2-4) with MCDB-131 medium supplemented with 0.1% fatty acid-free BSA, 0.0012 g/ml sodium bicarbonate, 1× GlutaMax™, 2.5 mM glucose, and 100 ng/ml GDF8.

b. Stage 2 (Primitive gut tube—3 days): Stage 1 cells were treated for three days with MCDB-131 medium supplemented with 0.1% fatty acid-free BSA, 0.0012 g/ml sodium bicarbonate, 1× GlutaMax™, 2.5 mM D-Glucose, and 50 ng/ml FGF7.

c. Stage 3 (Foregut—3 days): Stage 2 cells were treated with MCDB-131 medium supplemented with a 1:200 dilution of ITS-X, 2.5 mM Glucose, 1× GlutaMax™, 0.0015 g/ml sodium bicarbonate, 2% fatty acid-free BSA, 0.25 µM SANT-1, 20 ng/ml of Activin-A, 2 µM RA, 50 ng/ml FGF7, 100 nM LDN-193189 (on day 1 only or for the duration of stage 3), and 200 nM TPB. In some cultures, LDN-193189 was removed from stage 3.

d. Stage 4 (Pancreatic foregut precursor—3 days): Stage 3 cells were treated with MCDB-131 medium supplemented with a 1:200 dilution of ITS-X, 2.5 mM Glucose, 1× GlutaMax™, 0.0015 g/ml sodium bicarbonate, 2% fatty acid-free BSA, 0.25 µM SANT-1, 100 nM TPB, 200 nM LDN-193189, 2 µM ALk5 inhibitor, and 100 nM CYP26A inhibitor for three days.

e. Stage 5 (Pancreatic endoderm/endocrine –4 days): Stage 4 cells were treated with MCDB-131 medium supplemented with a 1:200 dilution of ITS-X, 2.5 mM Glucose, 1× GlutaMax™, 0.0015 g/ml sodium bicarbonate, 2% fatty acid-free BSA, 200 nM LDN-193189, and 2 µM ALk5 for four days.

Figure 8A:
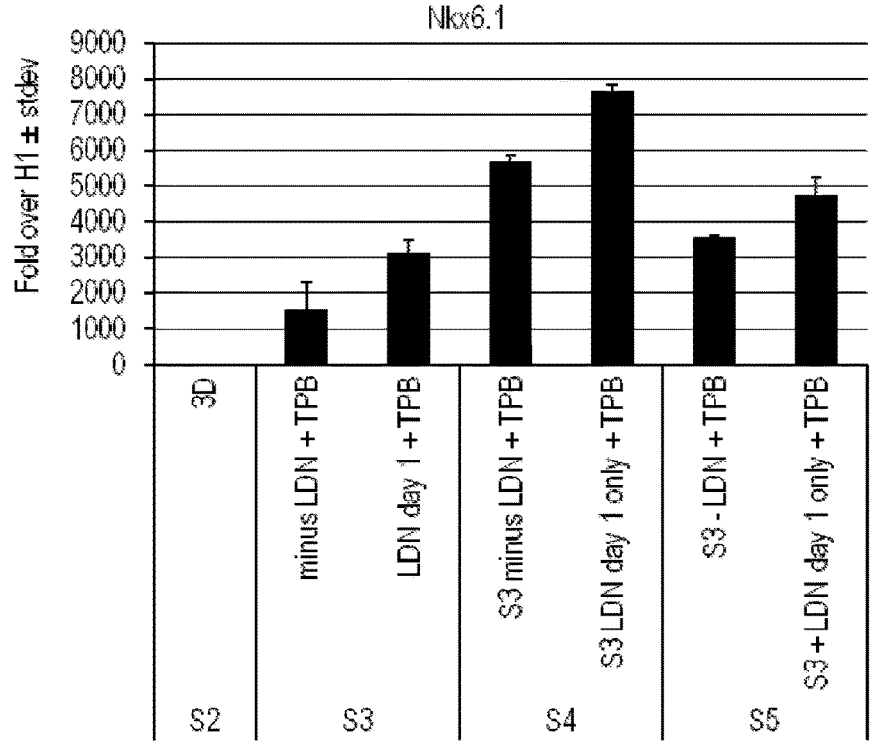
Figure 8B:
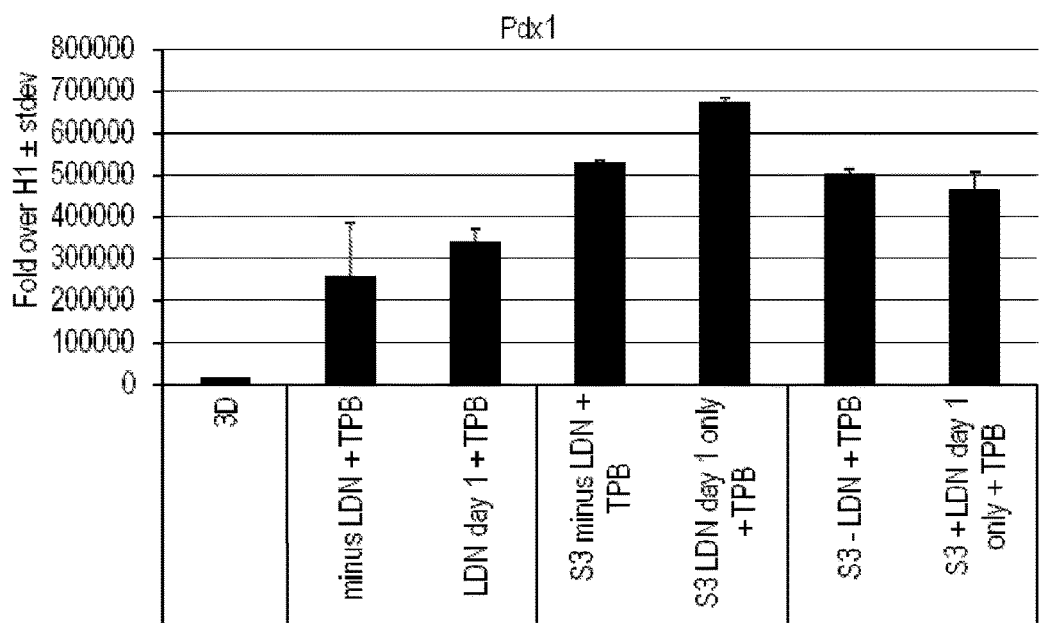
Figure 8C:
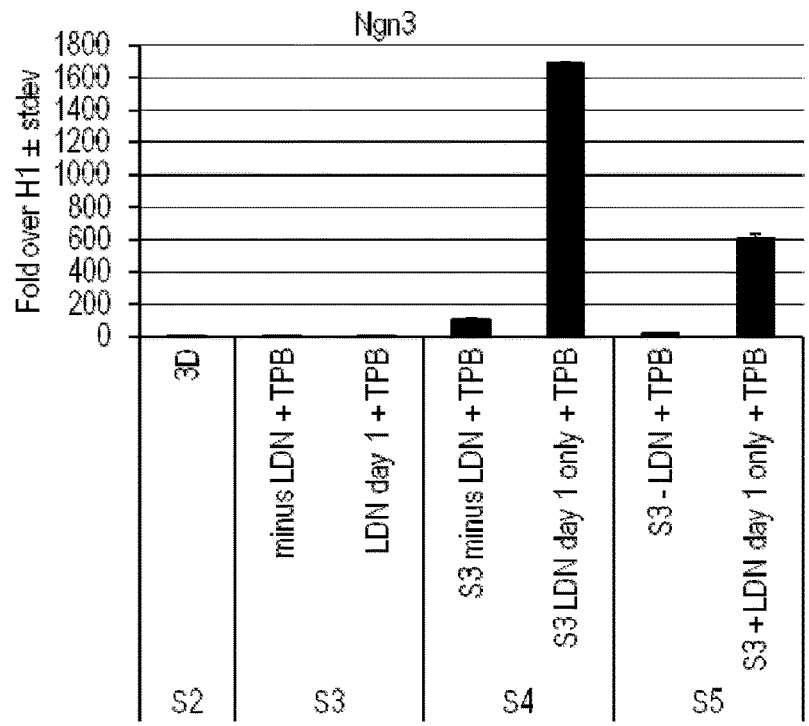
Figure 8D:
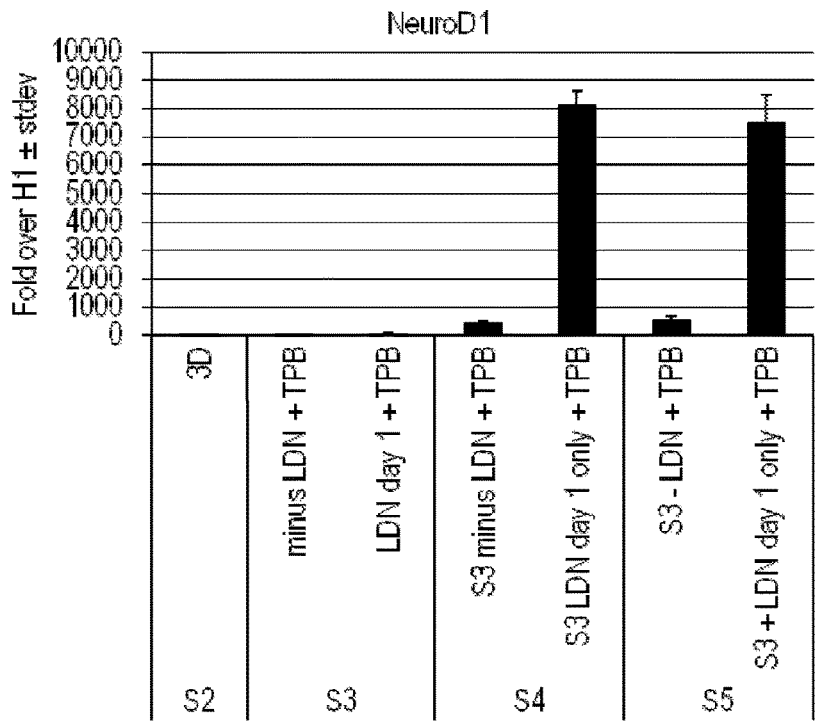
Figure 8G:
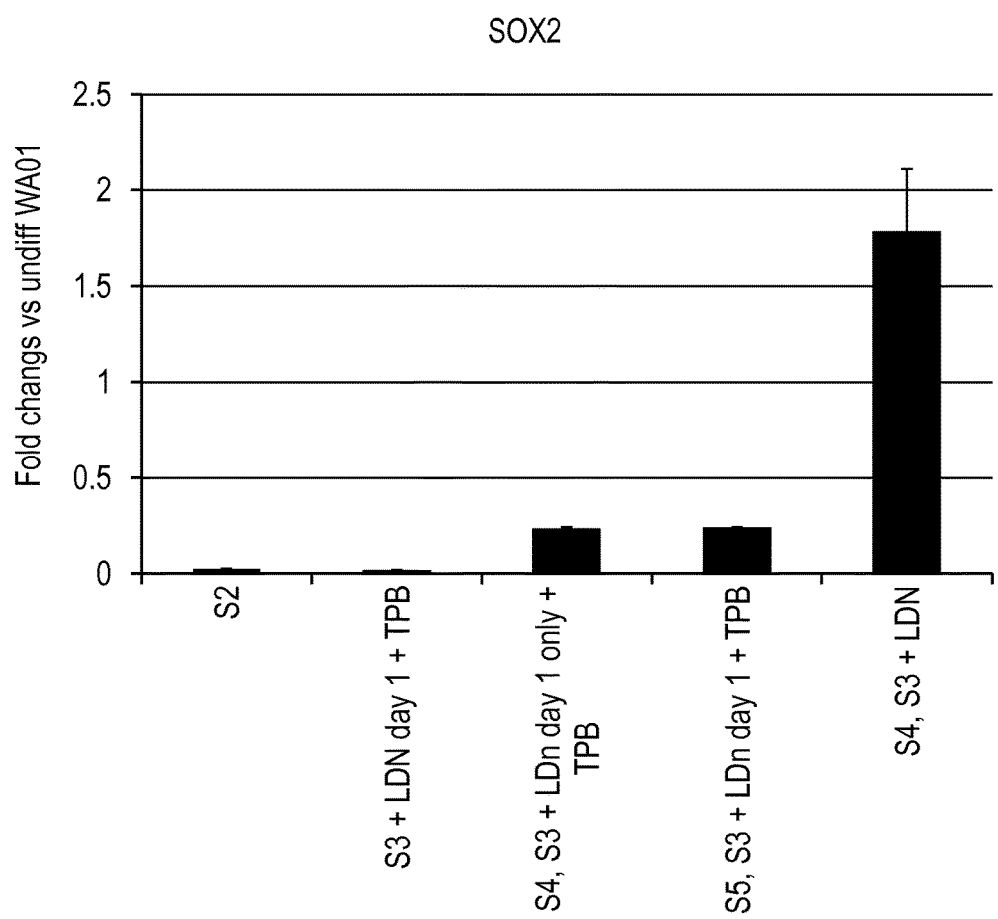

As evidenced by the PCR results shown in FIG. 8A to FIG. 8G, removal of LDN-193189 (BMP inhibitor) from stage 3 abolishes expression of pro-endocrine genes NGN3 (FIG. 8C); NeuroD (FIG. 8D); chromogranin (FIG. 8E) at stage 4 and stage 5. However, expression of PDX-1 (FIG. 8B) and NKX6.1 (FIG. 8A) are not significantly downregulated as compared to NGN3 and NeuroD at stages 4-5. Furthermore, complete removal of LDN-193189 at stage 3 results in a significant increase in CDX2 expression (FIG. 7F). Addition of LDN-193189 for the first day of stage 3 followed by its removal at days 2-3 of stage 3 significantly boosted expression of NGN3 and NeuroD while decreasing CDX2 and SOX2 expression at stage 4. Cultures where LDN-193189 was retained for the duration of stage 3 showed a very high expression of SOX2 (FIG. 8G) at S3-S4. This data shows that BMP inhibition on day 1 of stage 3 is sufficient to trigger pancreatic endocrine markers while suppressing SOX2 and CDX2 expression.

In summary, BMP inhibition is required at day 1 of stage 3 to induce formation of endocrine precursor cells at stages 4-5 and to maintain expression of PDX-1 and NKX6.1 while suppressing SOX2 expression. Furthermore, addition of a PKC activator at stages 3 further enhanced expression of PDX-1 and NKX6.1.

Example 4

Inhibition of BMP Signaling at Day 1 of Stage 3 is Sufficient to Generate Pancreatic Precursor Cells at Stage 4, while Inhibition of BMP Signaling on Last Day of Stage 3 Results in Significantly Lower Expression of Endocrine Markers This example shows that early inhibition of BMP signaling at stage 3 allows for induction of pancreatic endocrine precursor markers while inhibition of BMP signaling late at stage 3 significantly lowers expression level of endocrine precursor markers at stage 4.

Cells of the human embryonic stem cells line H1 at various passages (passage 40 to passage 52) were seeded as single cells at a density of 100,000 cells/cm$^2$ on MATRIGEL™ (1:30 dilution) coated dishes in mTesr™ 1 media supplemented with 10 µM of Y27632. Forty eight hours post seeding, cultures were differentiated into cells of the pancreatic endocrine lineage as follows:

a. Stage 1 (Definitive Endoderm (DE)—4 days): Prior to start of DE, the cultures were washed and incubated with incomplete PBS (no Mg or Ca) for 30 seconds followed by addition of the stage 1 media. Human embryonic stem cells cultured as single cells on MATRIGEL™-coated dishes were treated for one day with MCDB-131 medium supplemented with 0.1% fatty acid-free BSA, 0.0012 g/ml sodium bicarbonate, 1× GlutaMax™, 2.5 mM D-Glucose, 100 ng/ml GDF8 and 1.5 µM MCX compound (GSK3B inhibitor). Cells were then treated for three days with MCDB-131 medium supplemented with 0.1% fatty acid-free BSA, 0.0012 g/ml sodium bicarbonate, 1× GlutaMax™, 2.5 mM glucose, and 100 ng/ml GDF8.

b. Stage 2 (Primitive gut tube—3 days): Stage 1 cells were treated for three days with MCDB-131 supplemented with 0.1% fatty acid-free BSA, 0.0012 g/ml sodium bicarbonate, 1× GlutaMax™, 2.5 mM D-Glucose, and 50 ng/ml FGF7.

c. Stage 3 (Foregut—3 days): Stage 2 cells were treated with MCDB-131 medium supplemented with a 1:200 dilution of ITS-X, 2.5 mM Glucose, 1× GlutaMax™, 0.0015 g/ml sodium bicarbonate, 2% fatty acid-free BSA, 0.25 µM SANT-1, 50 ng/ml FGF7, 2 µM RA and the combinations listed in Table III, below for three days.

TABLE III

Stage 3 Treatments

| | | 20 ng/ml AA | LDN-193189 | 1 µM Alk5 inhibitor (SCIO compound) | TPB |
|---|---|---|---|---|---|
| A | S3D1 | + | — | — | +200 nM |
|   | D2-3 | + | — | — | +200 nM |
| B | D1 | — | +100 nM | +1 µM | — |
|   | D2-3 | + | — | — | +200 nM |
| C | D1 | — | +100 nM | +1 µM | +100 nM |
|   | D2-3 | + | — | — | +200 nM |
| D | D1 | — | +100 nM | +1 µM | +200 nM |
|   | D2-3 | + | — | — | +200 nM |
| E | D1 | + | — | — | +100 nM |
|   | D2-3 | + | +100 nM (on day 3 only) | — | +100 nM | d. Stage 4 (Pancreatic foregut precursor—3 days): Stage 3 cells were treated with MCDB-131 medium supplemented with a 1:200 dilution of ITS-X, 2.5 mM Glucose, 1× GlutaMax™, 0.0015 g/ml sodium bicarbonate, 2% fatty acid-free BSA, 0.25 µM SANT-1, 100 nM TPB, 200 nM LDN-193189, 2 µM ALk5 inhibitor, and 100 nM CYP26A inhibitor for three days.

Figure 9A:
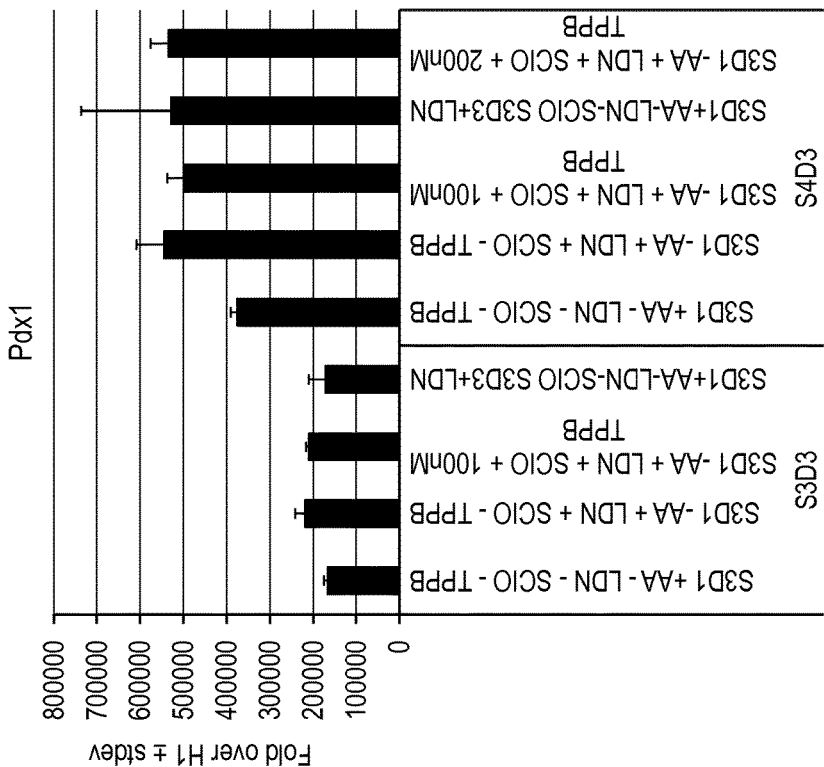
Figure 9B:
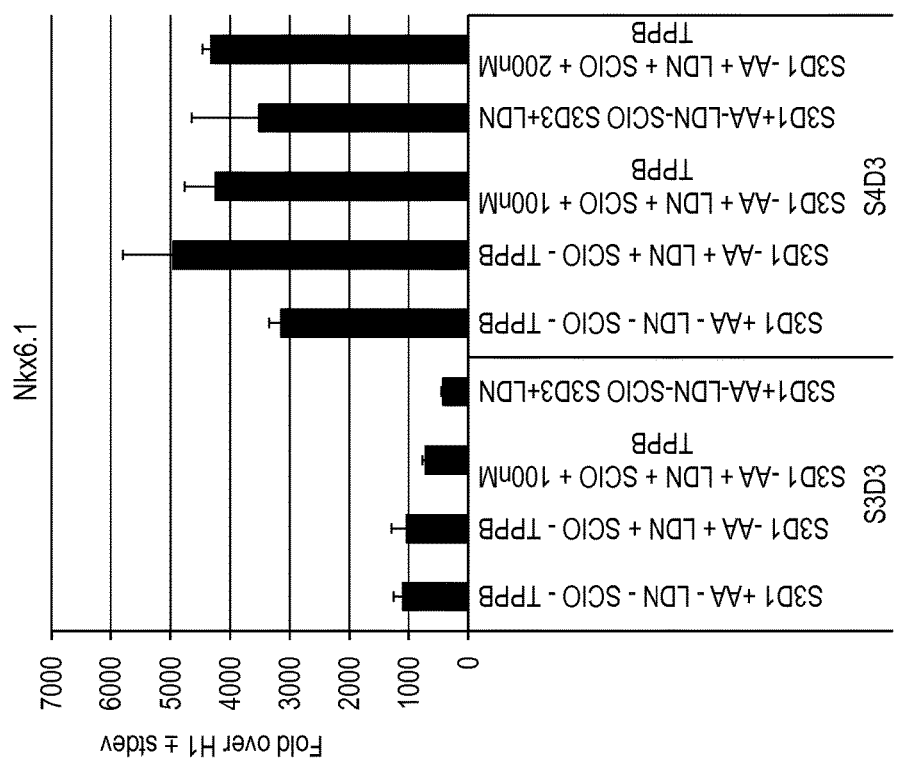
Figure 9E:
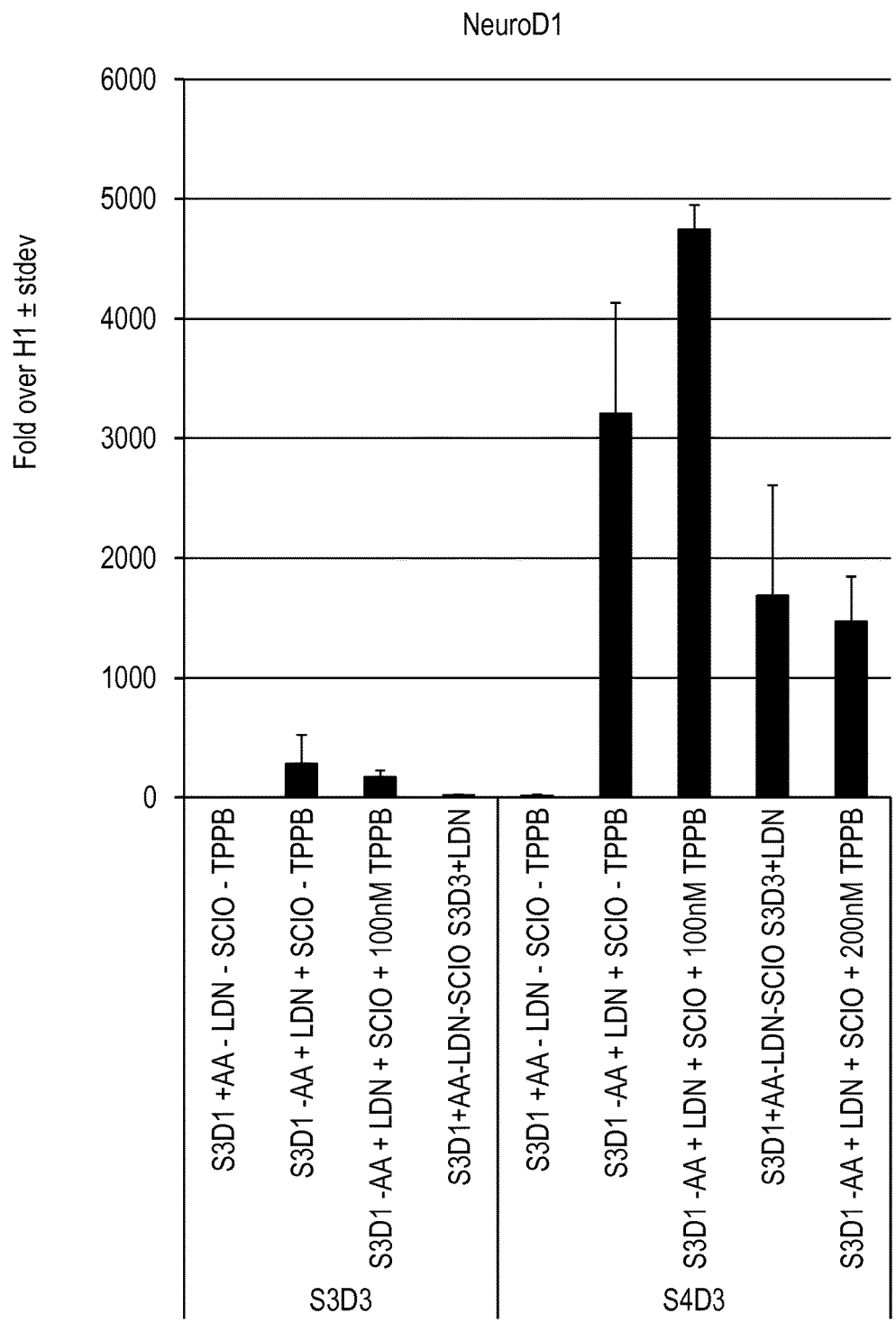
Figure 10B:
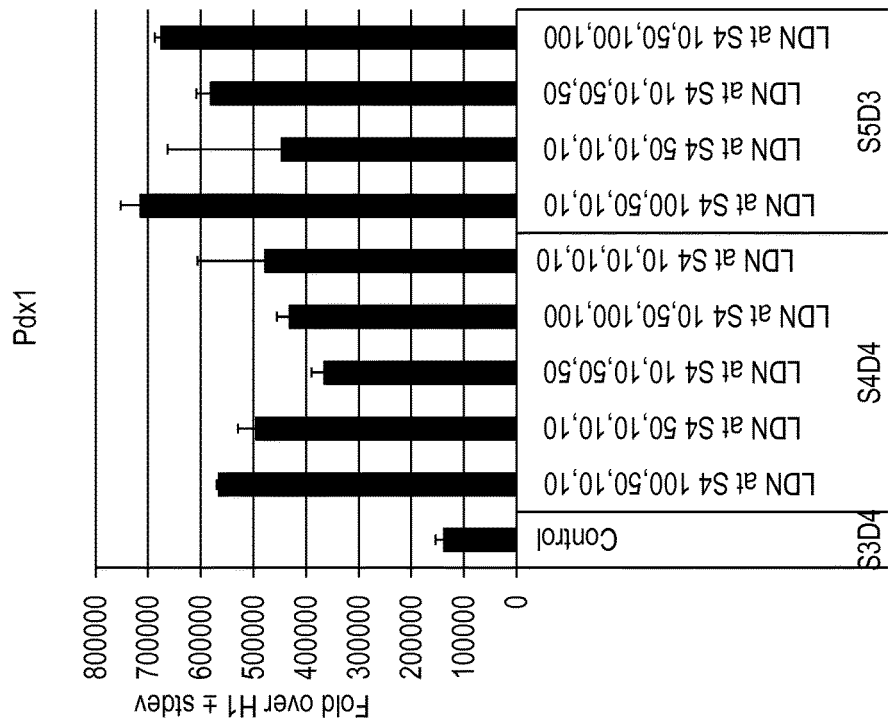
Figure 10A:
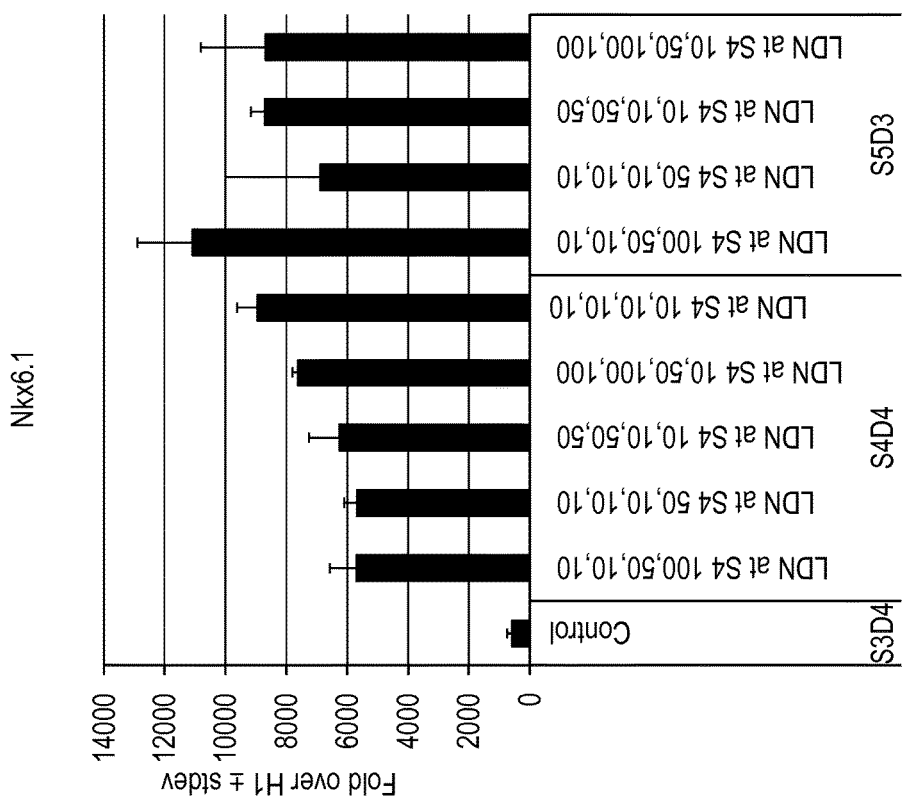
Figure 10C:
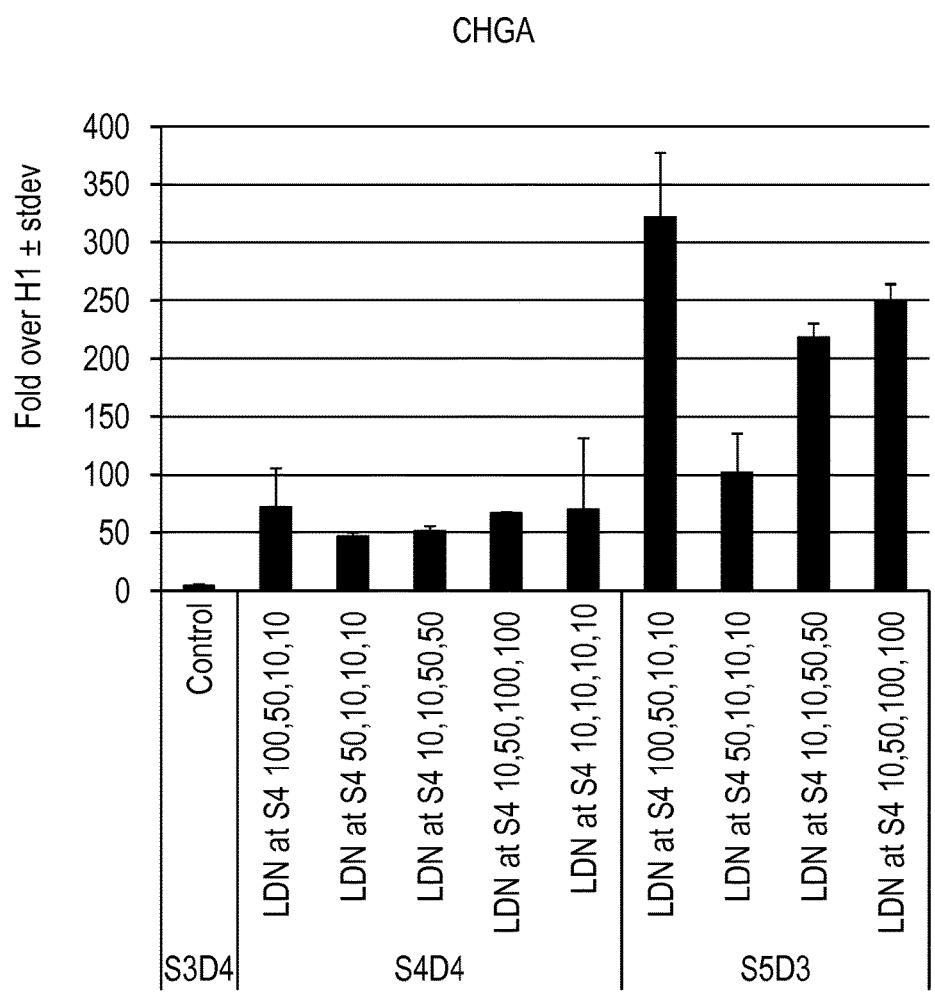
Figure 10D:
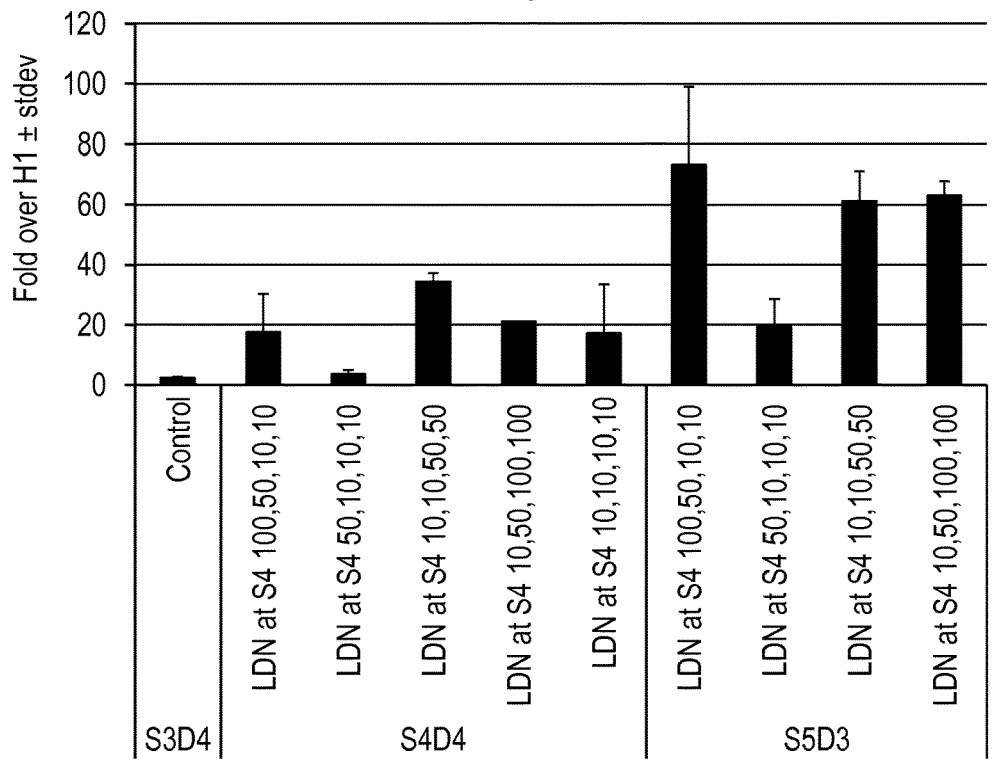
Figure 10E:
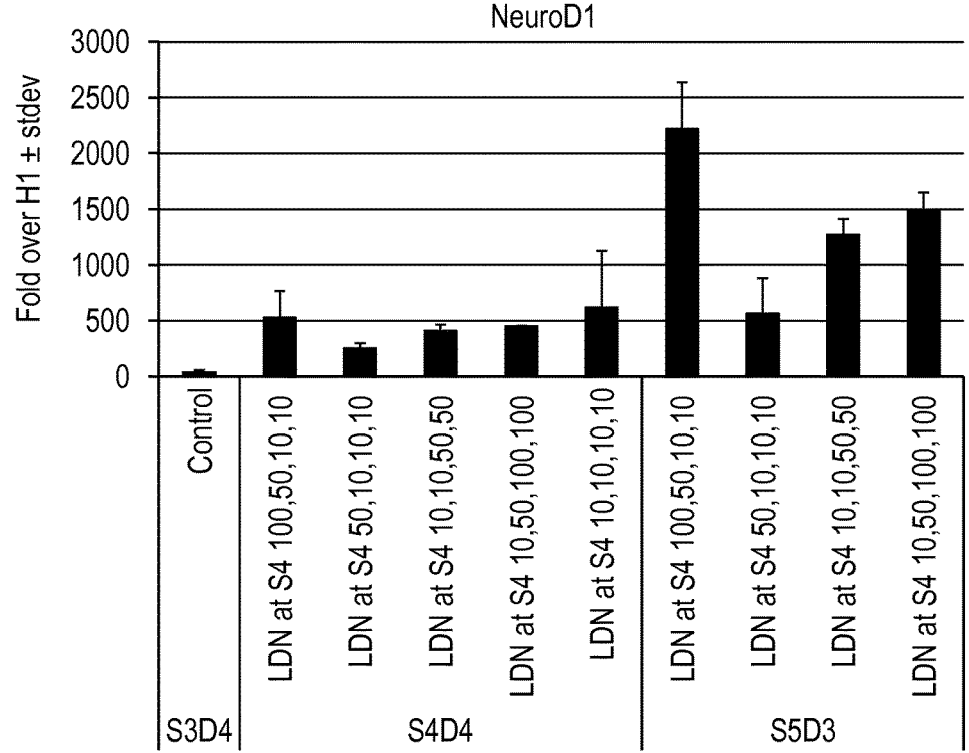
Figure 10F:
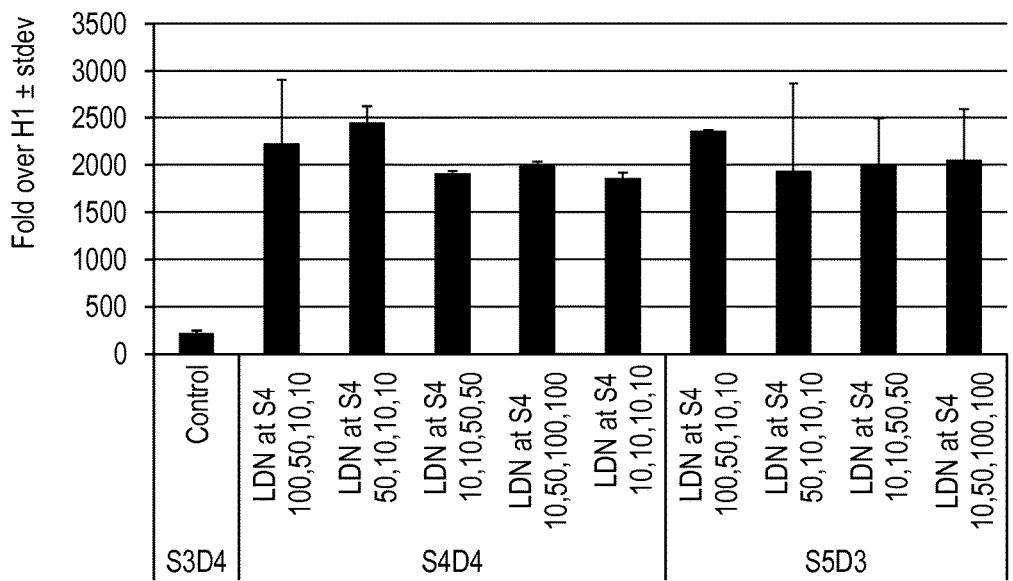
Figure 10G:
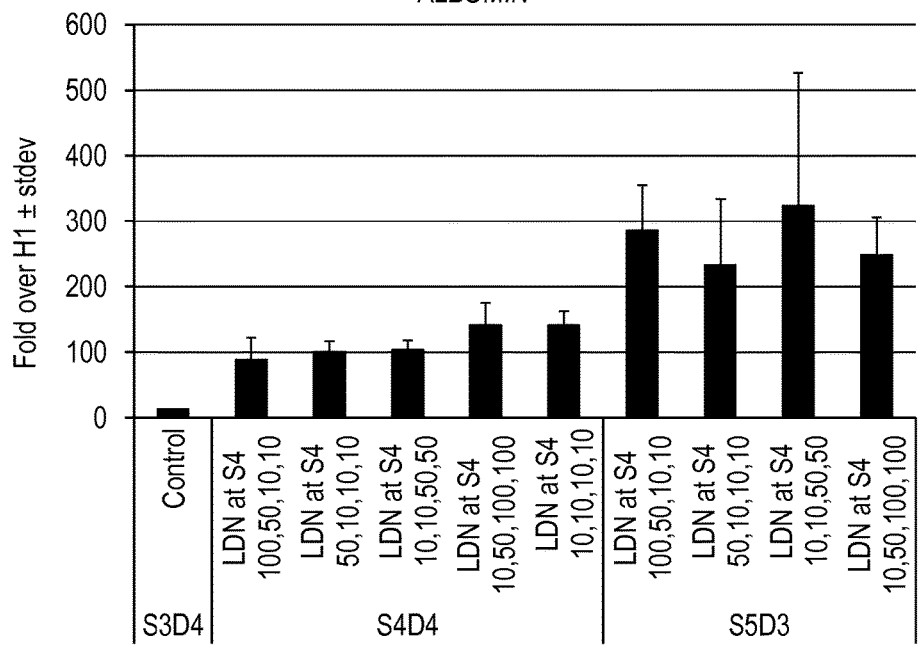
Figure 11A:
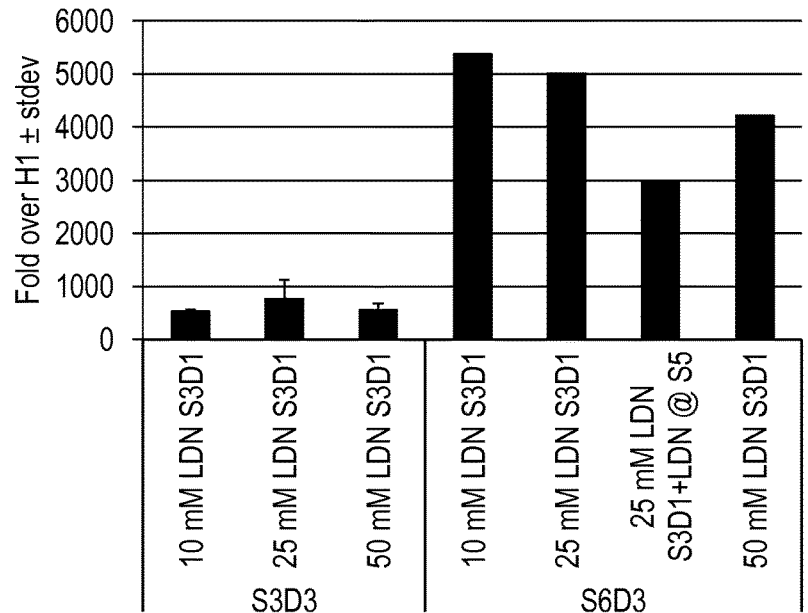
Figure 11B:
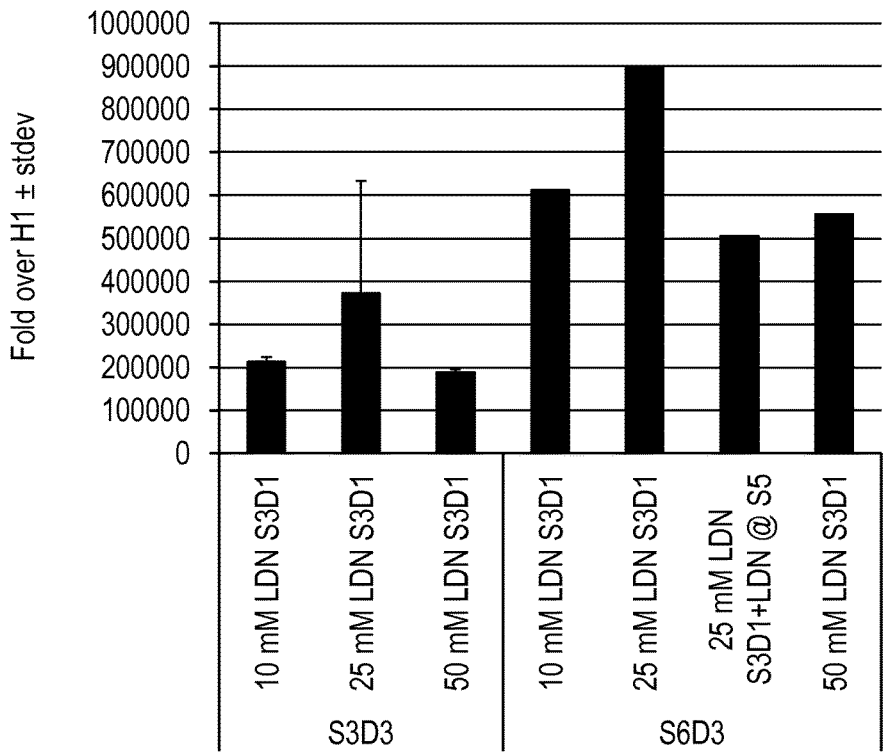
Figure 11C:
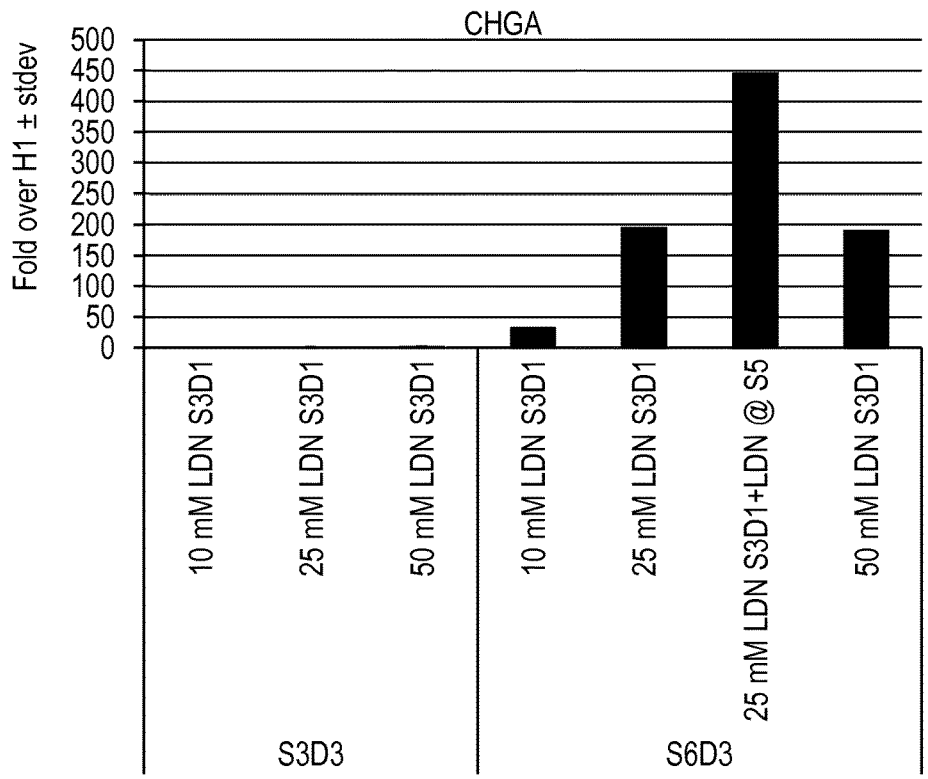
Figure 11D:
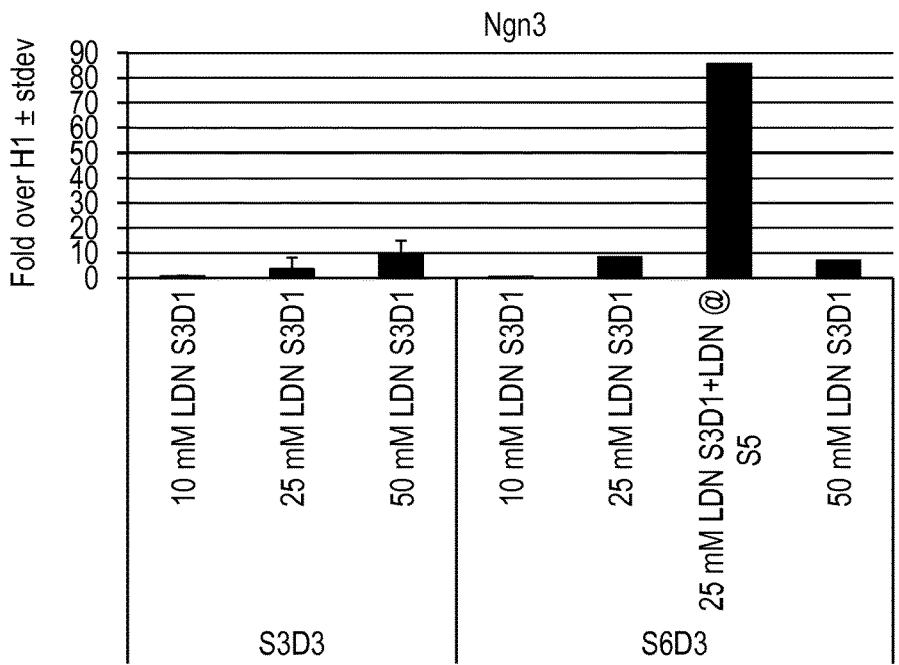
Figure 11F:
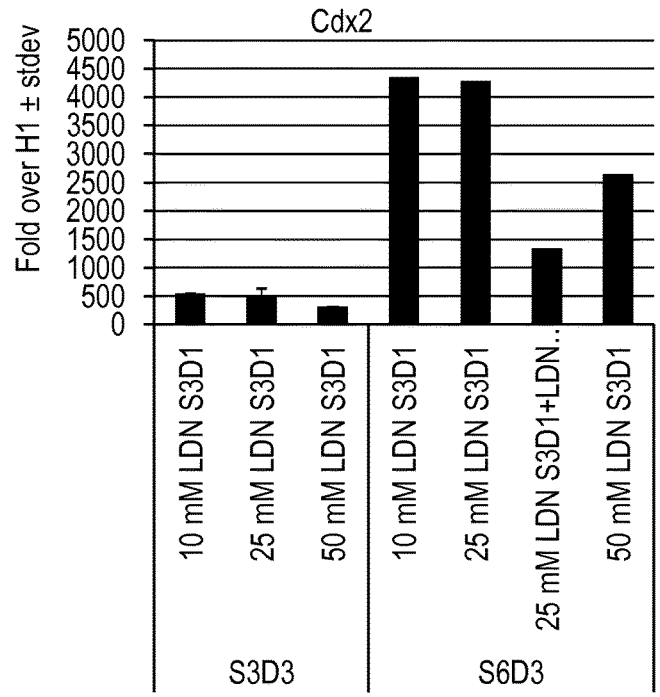
Figure 11G:
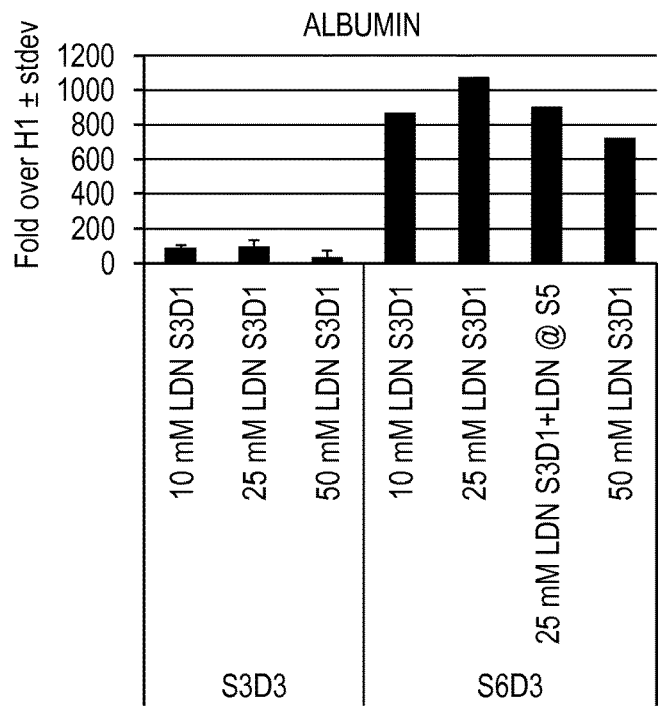

FIG. 9A to FIG. 9H depict the gene expression profile of pancreatic endoderm, endocrine precursor, and foregut endoderm markers for the combinations of culture conditions listed above. Consistent with previous example, blocking of BMP pathway on the first day of stage 3 is critical for the subsequent induction of the endocrine program as measured by expression of the pan-endocrine marker, chromogranin. (See FIG. 9C.) However, addition of the BMP inhibitor at day one of stage 3 triggers expression of endocrine markers at subsequent stages. Furthermore, addition of the BMP inhibitor at day one of stage 3 also decreased expression of foregut marker, SOX2, at stages 3-4 (FIG. 9H). However, addition of BMP inhibitor only at last day of stage 3 shows significantly higher expression of SOX2 at end of stage 3 as compared to cells treated with the BMP inhibitor only on the first day of stage 3. The expression levels shown in FIG. 9A to FIG. 9H are relative to the expression levels in undifferentiated H1 cells which have a very high expression level of SOX2. Besides being a marker of anterior foregut, SOX2 is a well-known transcription factor important in maintenance of pluripotency of ES cells. This example further supports previous results highlighting the sensitivity of stage 3 cultures to the duration and kinetics of BMP signaling and subsequent impact on pancreatic endocrine induction and expression of SOX2.

Example 5

Optimal Dose of BMP Inhibition at Pancreatic Foregut Stage (Stage 4)

Previous examples described the optimal duration of BMP inhibition at stage 3. This example identifies the optimal dose of BMP inhibitor at S4 media.

Cells of the human embryonic stem cell line H1 at various passages (passage 40 to passage 52) were seeded as single cells at a density of 100,000 cells/cm$^2$ on MATRIGEL™ (1:30 dilution) coated dishes in mTesr™ 1 media and 10 µM of Y27632. Forty eight hours post seeding, cultures were differentiated into pancreatic endocrine lineage as follows:

a. Stage 1 (Definitive Endoderm (DE)—4 days): Prior to start of DE, the cultures were washed and incubated with incomplete PBS (no Mg or Ca) for 30 seconds followed by addition of the stage 1 media. Human embryonic stem cells cultured as single cells on MATRIGEL™-coated dishes were treated with MCDB-131 medium supplemented with 0.1% fatty acid-free BSA, 0.0012 g/ml sodium bicarbonate, 1× GlutaMax™, 2.5 mM D-Glucose, 100 ng/ml GDF8, and 1 µM MCX compound (GSK3B inhibitor) for one day. Cells were then treated with MCDB-131 medium supplemented with 0.1% fatty acid-free BSA, 0.0012 g/ml sodium bicarbonate, 1× GlutaMax™, 2.5 mM glucose, and 100 ng/ml GDF8 for days 2-4.

b. Stage 2 (Primitive gut tube—3 days): Stage 1 cells were treated with MCDB-131 medium supplemented with 0.1% fatty acid-free BSA, 0.0012 g/ml sodium bicarbonate, 1× GlutaMax™, 2.5 mM D-Glucose, and 50 ng/ml FGF7 for three days.

c. Stage 3 (Foregut—4 days): Stage 2 cells were treated with MCDB-131 medium supplemented with a 1:200 dilution of ITS-X, 2.5 mM, Glucose, 1× GlutaMax™, 0.0015 g/ml sodium bicarbonate, 2% fatty acid-free BSA, 0.25 µM SANT-1, 50 ng/ml FGF7, 2 µM RA, 20 ng/ml of Activin-A, 100 nM LDN-193189, and 100 nM TPB for one day. Cells were then cultured in MCDB-131 medium supplemented with a 1:200 dilution of ITS-X, 2.5 mM, Glucose, 1× GlutaMax™, 0.0015 g/ml sodium bicarbonate, 2% fatty acid-free BSA, 0.25 µM SANT-1, 50 ng/ml FGF7, 2 µM RA, 20 ng/ml of Activin-A, and 100 nM TPB for three days.

d. Stage 4 (Pancreatic foregut precursor—4 days): Stage 3 cells were treated with MCDB-131 medium supplemented with a 1:200 dilution of ITS-X, 2.5 mM Glucose, 1× GlutaMax™, 0.0015 g/ml sodium bicarbonate, 2% fatty acid-free BSA, 200 nM LDN-193189-193189, 2 µM ALk5 inhibitor, 100 nM CYP26A inhibitor, and the concentrations of LDN-193189 listed on Table IV (below) for days 1-4 of stage 4:

TABLE IV

Concentrations of LDN-193189 Used at S4

|      | Condition A | Condition B | Condition C | Condition D | Condition E |
|------|-------------|-------------|-------------|-------------|-------------|
| S4D1 | 100 nM      | 50 nM       | 10 nM       | 10 nM       | 10 nM       |
| S4D2 | 50 nM       | 10 nM       | 50 nM       | 10 nM       | 10 nM       |
| S4D3 | 10 nM       | 10 nM       | 100 nM      | 50 nM       | 10 nM       |
| S4D4 | 10 nM       | 10 nM       | 100 nM      | 50 nM       | 10 nM       | d. Stage 5 (Pancreatic endoderm/endocrine precursor-3 days): Stage 4 cells were treated with MCDB-131 medium supplemented with a 1:200 dilution of ITS-X, 2.5 mM Glucose, 1× GlutaMax™, 0.0015 g/ml sodium bicarbonate, 2% fatty acid-free BSA, 50 nM LDN-193189, and 1 µM ALk5 inhibitor for three days.

The results of real-time PCR analyses of cells harvested after the treatments above are shown in FIG. 10A to FIG. 10H. This figure shows that addition of 50 nM or 100 nM of LDN-193189 at days 1, 2, 3, or 4 of S4 can prolong the expression of endocrine markers while maintaining a low expression of SOX2 at S4-S5. (See FIG. 10A to FIG. 10H.)

Example 6

Optimal Dose of BMP Inhibition at Foregut Stage (Stage 3)

This example identifies the optimal dose of BMP inhibition at stage 3 and subsequent effects on endocrine markers at stage 6.

Cells of the human embryonic stem cell line H1 at various passages (passage 40 to passage 52) were seeded as single cells at a density of 100,000 cells/cm$^2$ on MATRIGEL™ (1:30 dilution) coated dishes in mTesr™ 1 media supplemented with 10 µM of Y27632. Forty eight hours post seeding, cultures were differentiated into cells of the pancreatic endocrine lineage as follows:

a. Stage 1 (Definitive Endoderm (DE)—4 days): Prior to start of DE, the cultures were washed and incubated with incomplete PBS (no Mg or Ca) for 30 seconds followed by addition of the stage 1 media. Human embryonic stem cells cultured as single cells on MATRIGEL™-coated dishes were treated with MCDB-131 medium supplemented with 0.1% fatty acid-free BSA, 0.0012 g/ml sodium bicarbonate, 1× GlutaMax™, 2.5 mM D-Glucose, 100 ng/ml GDF8, and 1.5 µM MCX compound (GSK3B inhibitor) for one day. Cells were then treated with MCDB-131 medium supplemented with 0.1% fatty acid-free BSA, 0.0012 g/ml sodium bicarbonate, 1× GlutaMax™, 2.5 mM glucose, and 100 ng/ml GDF8 for days 2-4.

b. Stage 2 (Primitive gut tube—3 days): Stage 1 cells were treated with MCDB-131 medium supplemented with 0.1% fatty acid-free BSA, 0.0012 g/ml sodium bicarbonate, 1× GlutaMax™, 2.5 mM D-Glucose, and 50 ng/ml FGF7 for three days.

c. Stage 3 (Foregut—3 days): Stage 3 cells were treated with MCDB-131 medium supplemented with a 1:200 dilution of ITS-X, 2.5 mM Glucose, 1× GlutaMax™, 0.0015 g/ml sodium bicarbonate, 2% fatty acid-free BSA, 0.25 µM SANT-1, 50 ng/ml FGF7, 2 µM RA, 20 ng/ml Activin-A, 100 nM TPB, and 10-50 nM LDN-193189 for one day. Cells were then treated with MCDB-131 medium supplemented with a 1:200 dilution of ITS-X, 2.5 mM Glucose, 1× GlutaMax™, 0.0015 g/ml sodium bicarbonate, 2% fatty acid-free BSA, 0.25 µM SANT-1, 50 ng/ml FGF7, 2 µM RA, 20 ng/ml Activin-A, and 100 nM TPB for two days.
d. Stage 4 (Pancreatic foregut precursor—3 days): Stage 3 cells were treated with MCDB-131 medium supplemented with a 1:200 dilution of ITS-X, 2.5 mM Glucose, 1× GlutaMax™, 0.0015 g/ml sodium bicarbonate, 2% fatty acid-free BSA, 20 nM LDN-193189; 2 µM ALk5 inhibitor; 100 nM CYP26 A inhibitor, and 100 nM TPB for three days.
e. Stage 5 (Pancreatic endoderm/endocrine precursor-3 days): Stage 4 cells were treated with MCDB-131 medium supplemented with a 1:200 dilution of ITS-X; 2.5 mM Glucose; 1× GlutaMax™; 0.0015 g/ml sodium bicarbonate; 2% fatty acid-free BSA; +/−25 nM LDN-193189 and/or 2 µM ALk5 inhibitor for three days.
f. Stage 6 (Pancreatic endocrine hormone producing-3 days): Stage 5 cells were treated with MCDB-131 medium supplemented with a 1:200 dilution of ITS-X; 2.5 mM Glucose; 1× GlutaMax™; 0.0015 g/ml sodium bicarbonate; and 2% fatty acid-free BSA for three days.

FIG. 11A to FIG. 11H show that a low to moderate inhibition of BMP on the first day of stage 3 is required to trigger expression of endocrine markers while maintaining a low expression of SOX2. Furthermore, BMP inhibition at stage 5 while enhancing endocrine markers also led to upregulation of SOX2 expression.

The data in this Example further confirms the results presented in the previous examples. The data confirms that a precise modulation of the BMP pathway at stages 3-5 is required to trigger induction of pancreatic endocrine markers while suppressing SOX2 expression.

Example 7

Optimal Window for BMP Inhibition at S3 (Foregut Stage)

This example identifies the optimal window of time at stage 3 for inhibition of BMP signaling while preserving endocrine induction at later stages and lowering expression for SOX2.

Cells of the human embryonic stem cells line H1 at various passages (Passage 40 to passage 52) were seeded as single cells at a density of 100,000 cells/cm² on MATRIGEL™ (1:30 dilution) coated dishes in mTesr™ 1 media and 10 µM Y27632. Forty eight hours post seeding, cultures were differentiated into pancreatic endocrine lineage as follows:
a. Stage 1 (Definitive Endoderm (DE)—4 days): Prior to start of DE, the cultures were washed and incubated with incomplete PBS (no Mg or Ca) for 30 seconds followed by addition of the stage 1 media. Human embryonic stem cells cultured as single cells on MATRIGEL™-coated dishes were treated with MCDB-131 medium supplemented with 0.1% fatty acid-free BSA, 0.0012 g/ml sodium bicarbonate, 1× GlutaMax™, 2.5 mM D-Glucose, 100 ng/ml GDF8 and 1.5 µM MCX compound for one day. Cells were then treated with MCDB-131 medium supplemented with 0.1% fatty acid-free BSA, 0.0012 g/ml sodium bicarbonate, 1× GlutaMax™, 2.5 mM glucose, and 100 ng/ml GDF8 for days 2-4.
b. Stage 2 (Primitive gut tube—3 days): Stage 1 cells were treated with MCDB-131 medium supplemented with 0.1% fatty acid-free BSA, 0.0012 g/ml sodium bicarbonate, 1× GlutaMax™, 2.5 mM D-Glucose, and 50 ng/ml FGF7 for three days.
c. Stage 3 (Foregut—3 days): Stage 2 cells were treated with MCDB-131 medium supplemented with a 1:200 dilution of ITS-X, 2.5 mM Glucose, 1× GlutaMax™, 0.0015 g/ml sodium bicarbonate, 2% fatty acid-free BSA, 0.25 µM SANT-1, 50 ng/ml FGF7, 2 µM RA, 20 ng/ml Activin-A, and 100 nM TPB, containing 100 nM LDN-193189 for only the first 2 hours, 6 hours, or 24 hours of stage 3.
d. Stage 4 (Pancreatic foregut precursor—3 days): Stage 3 cells were treated with MCDB-131 medium supplemented with a 1:200 dilution of ITS-X, 2.5 mM Glucose, 1× GlutaMax™, 0.0015 g/ml sodium bicarbonate, 2% fatty acid-free BSA, 25 nM LDN-193189, 2 µM ALk5 inhibitor, 100 nM CYP26 A inhibitor, and 100 nM TPB for three days.
e. Stage 5 (Pancreatic endoderm/endocrine precursor-3 days): Stage 4 cells were treated with MCDB-131 medium supplemented with a 1:200 dilution of ITS-X, 2.5 mM Glucose, 1× GlutaMax™, 0.0015 g/ml sodium bicarbonate, 2% fatty acid-free BSA, and 2 µM ALk5 inhibitor for three days.

Figure 12A:
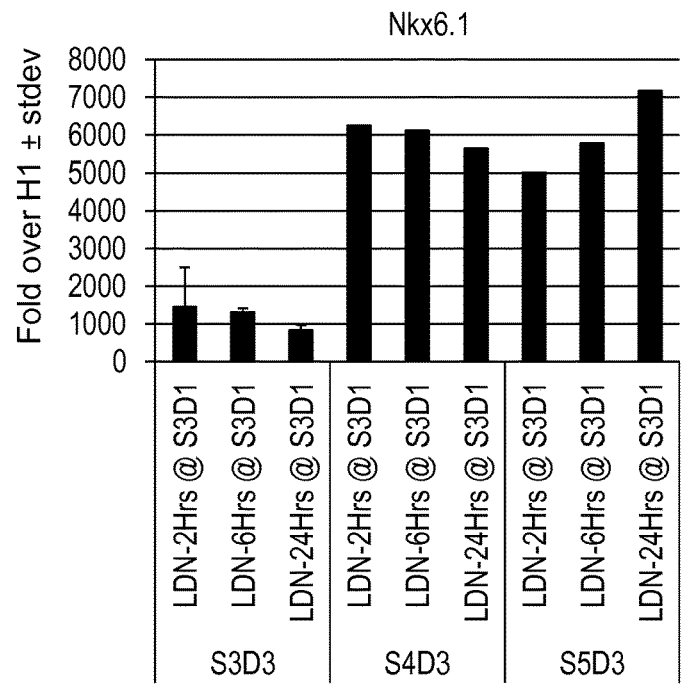
FIG. 12A to FIG. 12G depict data from real-time PCR analysis of the expression of the following genes in cells of the human embryonic stem cell line H1 differentiated according to the Example 7 and harvested at day 3 of S3, S4, or S5.
Figure 12B:
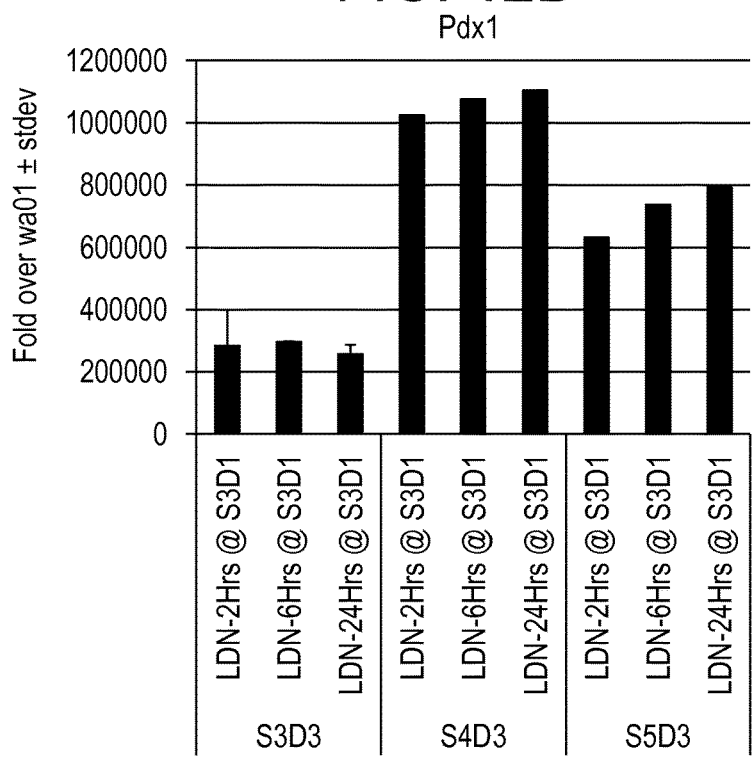
Figure 12C:
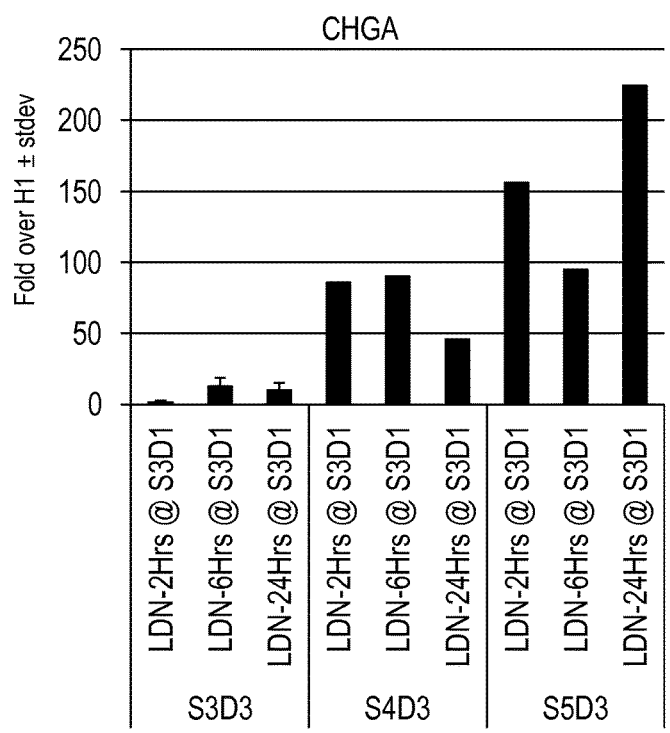
Figure 12D:
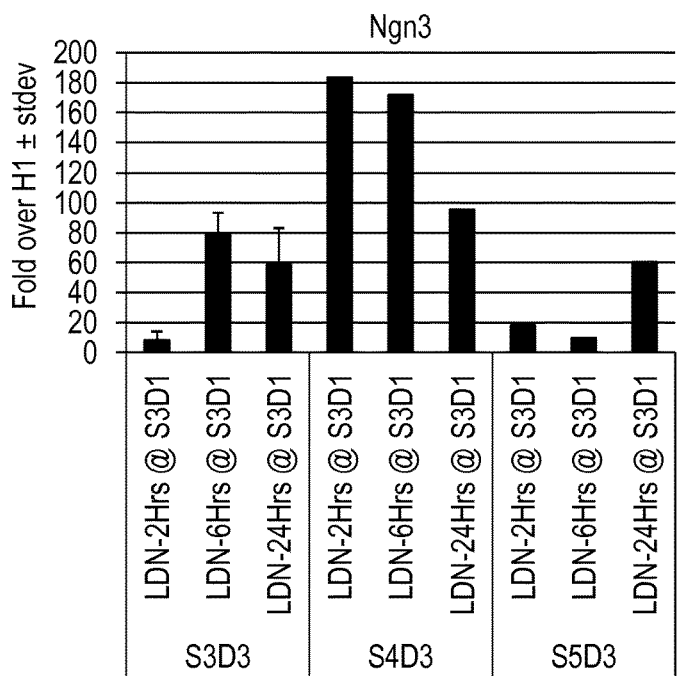
Figure 12E:
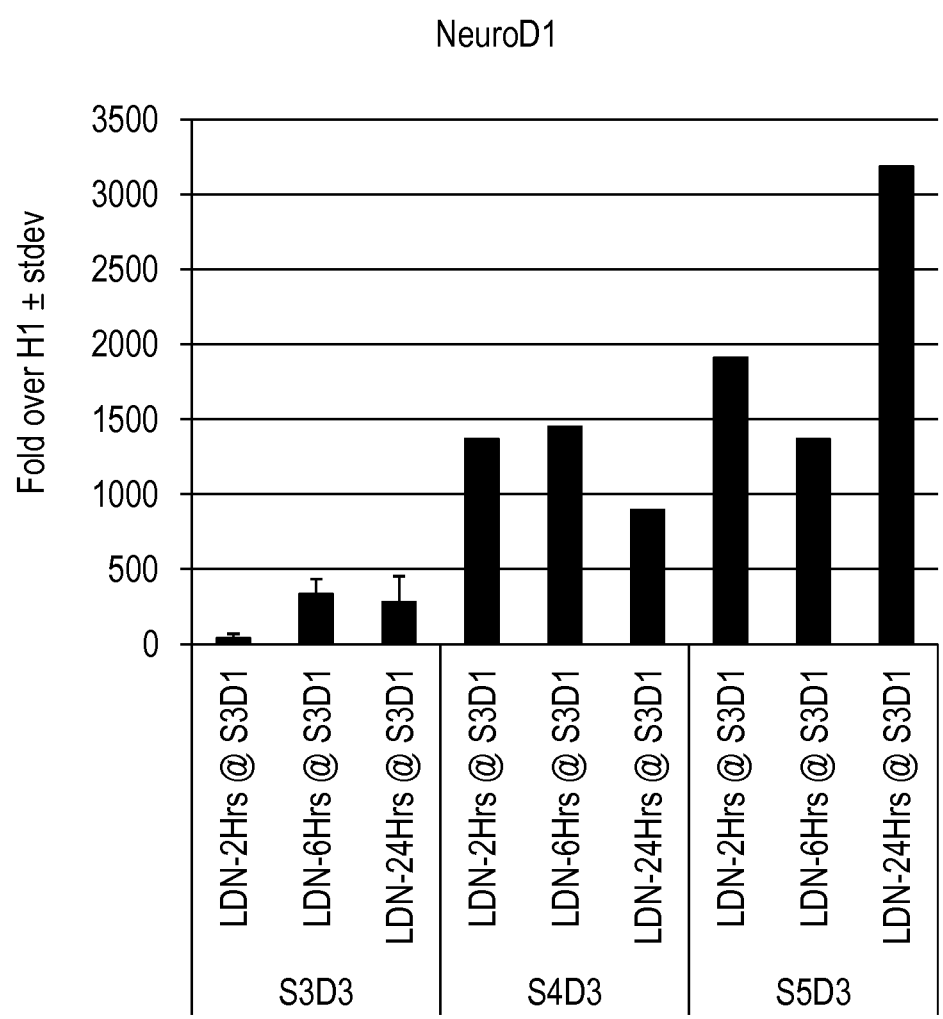
Figure 12F:
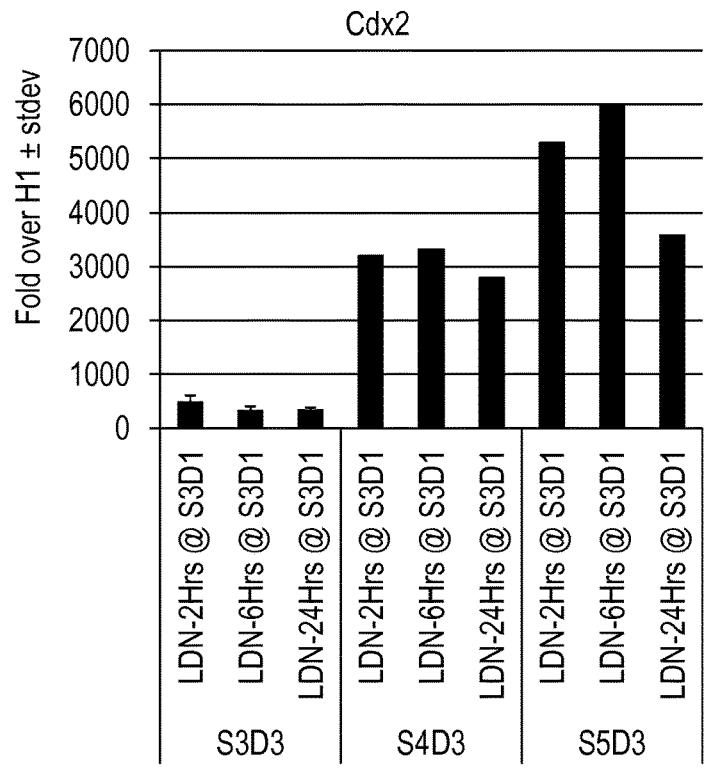
Figure 12G:
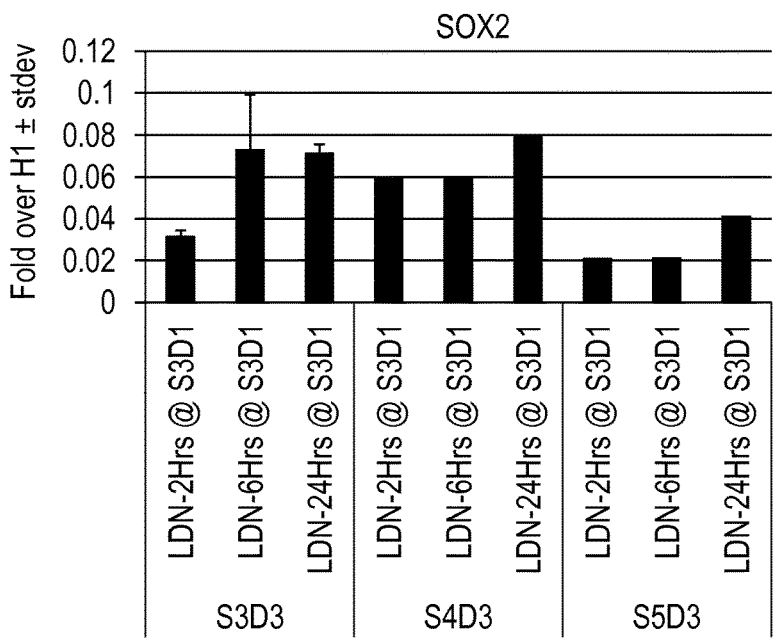

FIG. 12A to FIG. 12G show the real time PCR analyses for data gathered in this example. Treatment at stage 3 for at least 2 hours with a BMP inhibitor can trigger expression of pro-endocrine transcription factors such as Ngn3 (FIG. 12D) and NeuroD (FIG. 12E) while maintaining a very low expression of SOX2 (FIG. 12G) and significantly increases expression of NKX6.1 (FIG. 12A) and PDX-1 (FIG. 12B) at S4-S5. However, at stage 5 day 3 CDX2 expression was higher in cells treated for 2 or 6 hours with BMP inhibitor than in cells treated for 24 hours with the inhibitor (FIG. 12F).

The data from this Example suggests that a 24 hour inhibition of the BMP pathway is optimal for maintaining a low level of CDX2 expression and SOX2 expression, and to initiate endocrine differentiation while maintaining a high expression of pancreatic endoderm markers.

Example 8

Optimal Duration of Stages 3 (Foregut Stage) and Stage 4 (Pancreatic Foregut Precursor Stage)

This example was carried out to determine the optimal duration of S3 and S4 in the stepwise differentiation of pluripotent cells to a population of cells of pancreatic endocrine lineage.

Cells of the human embryonic stem cells line H1 at various passages (passage 40 to passage 52) were seeded as single cells at a density of 100,000 cells/cm² on MATRIGEL™ (1:30 dilution)-coated dishes in mTesr™ 1 media supplemented with 10 µM Y27632. Forty eight hours post seeding, cultures were differentiated into pancreatic endocrine lineage as follows:
a. Stage 1 (Definitive Endoderm (DE)—4 days): Prior to start of DE, the cultures were washed and incubated with incomplete PBS (no Mg or Ca) for 30 seconds followed by addition of the stage 1 media. Human embryonic stem cells cultured as single cells on MATRIGEL™-coated dishes were treated with MCDB-131 medium supplemented with 0.1% fatty acid-free BSA, 0.0012 g/ml sodium bicarbonate, 1× GlutaMax™; 2.5 mM D-Glucose; 100 ng/ml GDF8 and 1.5 µM MCX compound (GSK3B inhibitor) for one day. Cells were then treated with MCDB-131 medium supplemented with 0.1% fatty acid-free BSA; 0.0012 g/ml sodium bicarbonate; 1× GlutaMax™; 2.5 mM glucose, and 100 ng/ml GDF8 for days 2-4; then b. Stage 2 (Primitive gut tube—2 days): Stage 1 cells were treated with MCDB-131 medium supplemented with 0.1% fatty acid-free BSA, 0.0012 g/ml sodium bicarbonate, 1× GlutaMax™, 2.5 mM D-Glucose, and 50 ng/ml FGF7 for two days.

c. Stage 3 (Foregut—2-3 days): Stage 2 cells were treated with MCDB-131 medium supplemented with a 1:200 dilution of ITS-X, 2.5 mM Glucose, 1× GlutaMax™, 0.0015 g/ml sodium bicarbonate, 2% fatty acid-free BSA, 0.25 µM SANT-1, 50 ng/ml FGF7, 2 µM RA, 20 ng/ml Activin-A, and 100 nM TPB, containing 100 nM LDN-193189 for one day. Cells were then treated with MCDB-131 medium supplemented with a 1:200 dilution of ITS-X, 2.5 mM Glucose, 1× GlutaMax™, 0.0015 g/ml sodium bicarbonate, 2% fatty acid-free BSA, 0.25 µM SANT-1, 50 ng/ml FGF7, 2 µM RA, 20 ng/ml Activin-A, and 100 nM TPB.

d. Stage 4 (Pancreatic foregut precursor—2-3 days): Stage 3 cells were treated with MCDB-131 medium supplemented with a 1:200 dilution of ITS-X, 2.5 mM Glucose, 1× GlutaMax™, 0.0015 g/ml sodium bicarbonate, 2% fatty acid-free BSA, 25 nM LDN-193189, 100 nM CYP26 A inhibitor, and 100 nM TPB for two or three days.

e. Stage 5 (Pancreatic endoderm/endocrine precursor-2 days): Stage 4 cells were treated with MCDB-131 medium supplemented with a 1:200 dilution of ITS-X, 2.5 mM Glucose, 1× GlutaMax™, 0.0015 g/ml sodium bicarbonate, 2% fatty acid-free BSA, and 1 µM ALk5 inhibitor for two days.

f. Stage 6 (Pancreatic endocrine precursor/hormone-2 days): Stage 5 cells were treated with MCDB-131 medium supplemented with a 1:200 dilution of ITS-X, 2.5 mM Glucose, 1× GlutaMax™, 0.0015 g/ml sodium bicarbonate, and 2% fatty acid-free BSA for two days.

Figure 13A:
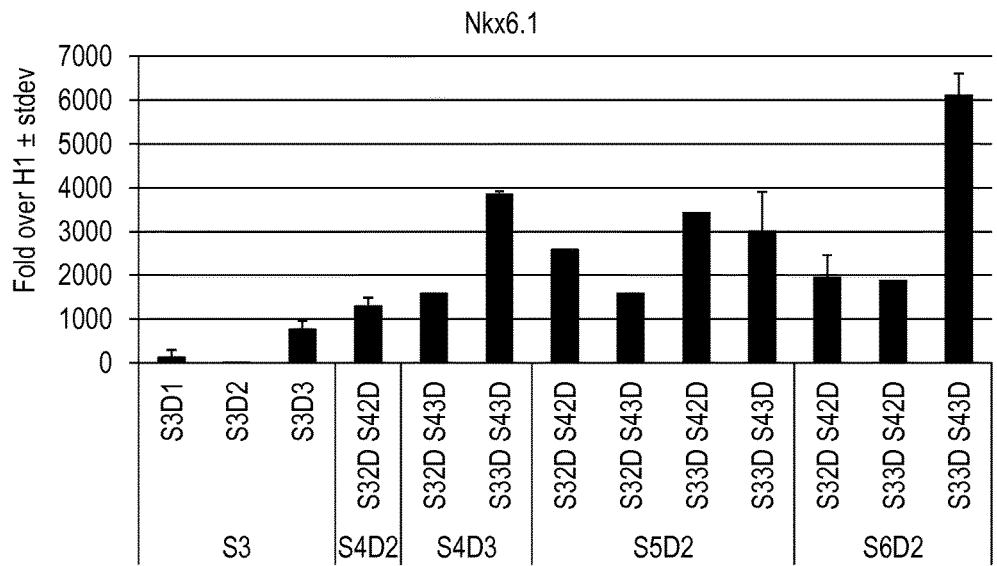
Figure 13B:
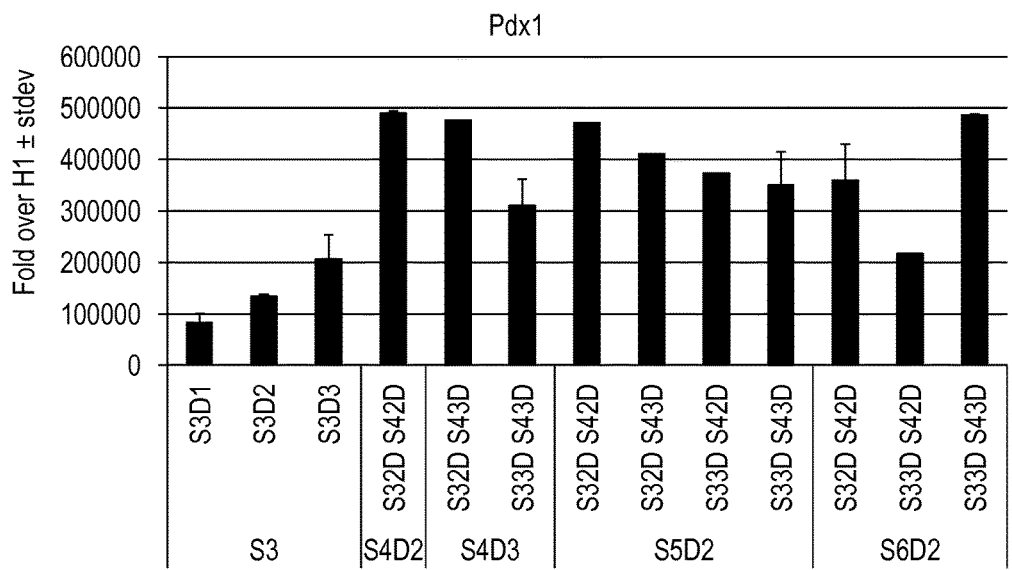
Figure 13C:
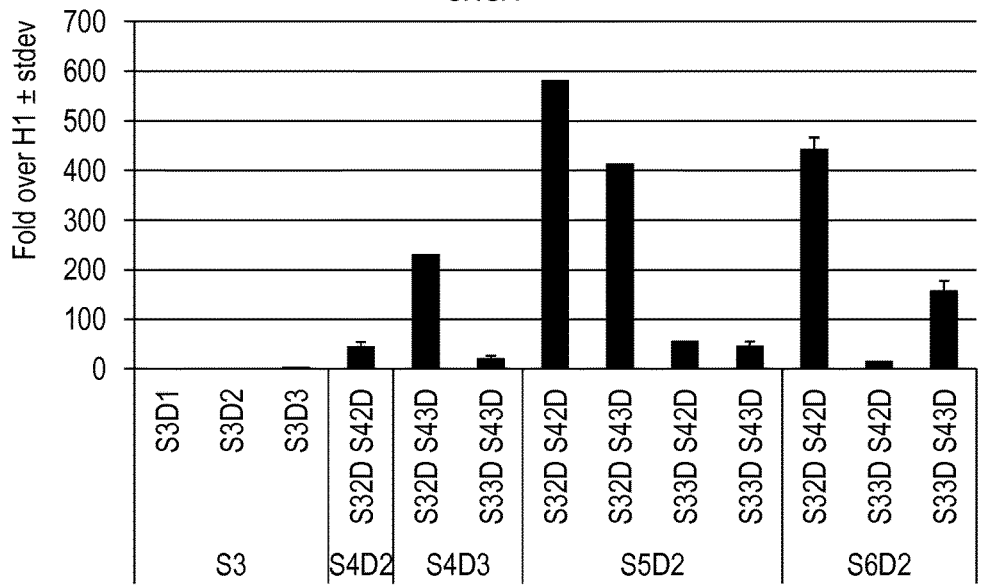
Figure 13D:
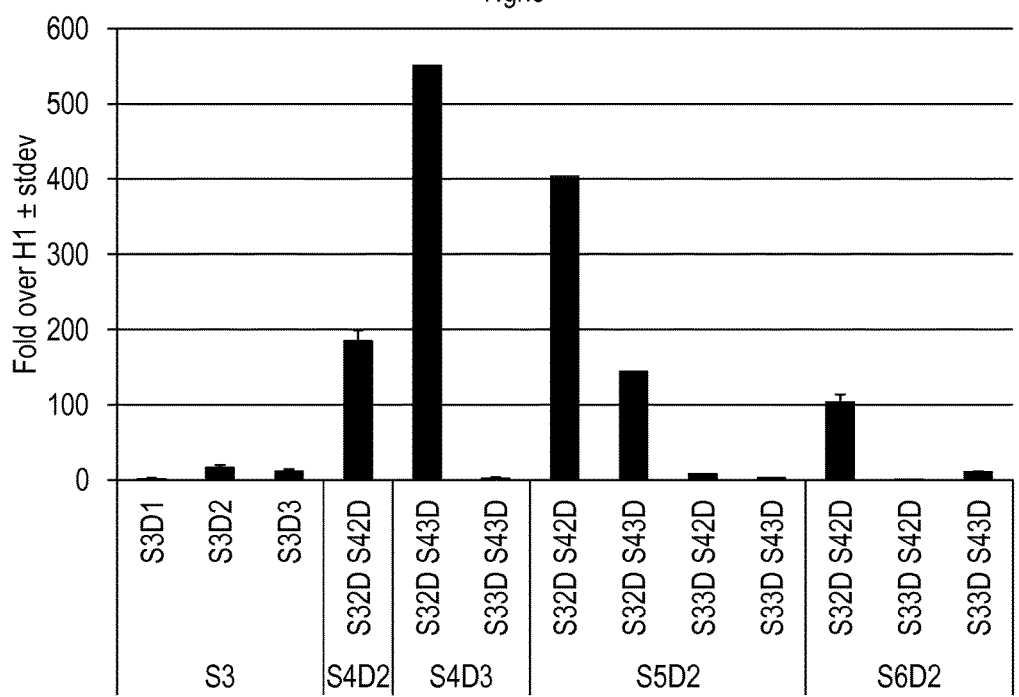
Figure 13F:
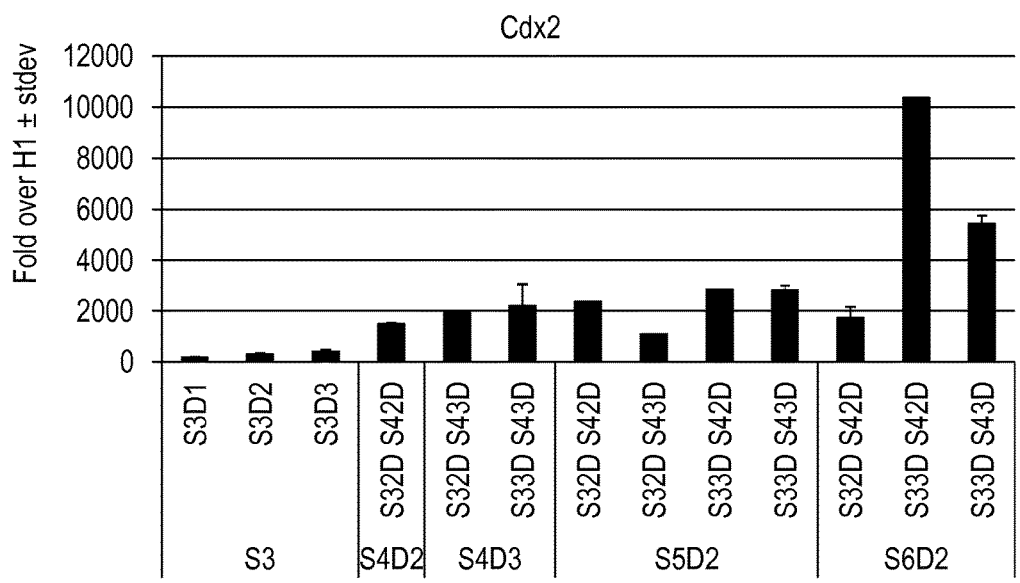
Figure 13G:
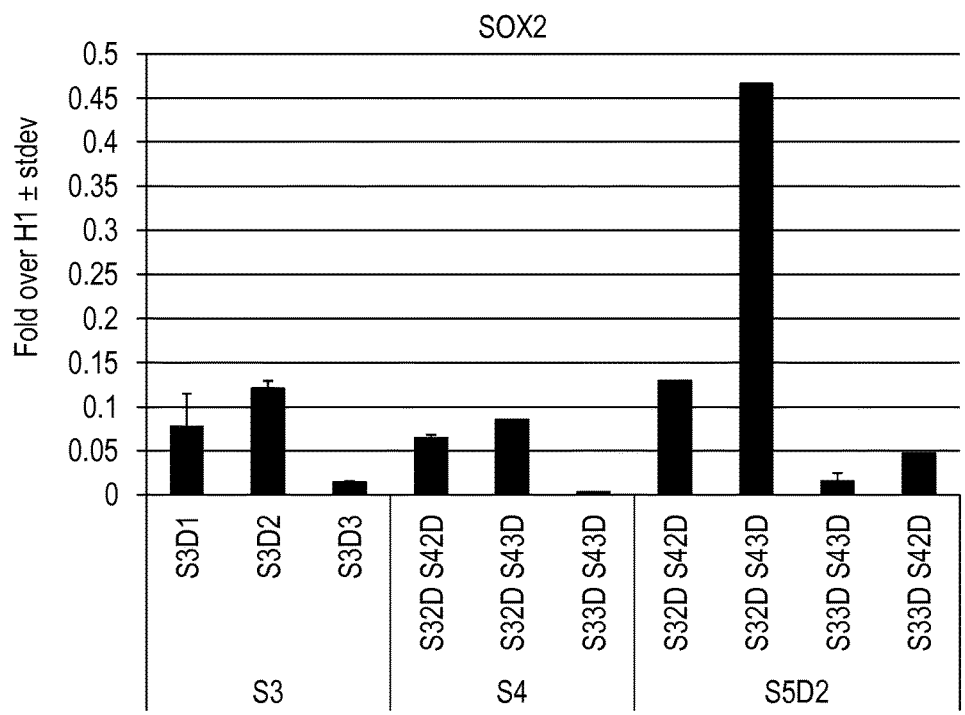

Data from real time PCR analyses of samples harvested at stage 3, stage 4, stage 5, or stage 6 is shown in FIG. 13A to FIG. 13G. This data shows that extending S3 and S4 to three days enhances expression of NKX6.1, when compared with cultures having a two day S3 and S4 (FIG. 13A). Cells treated for three days at stage 3 show down-regulation of the expression of pro-endocrine markers when compared to cultures where duration of S3 and S4 were only two days (FIG. 13D and FIG. 13E). Furthermore, prolonging stage 4 to three days did significantly enhance expression of SOX2 (FIG. 13G).

The data obtained in this Example is consistent with data generated in the previous examples in showing that prolonged BMP inhibition biases the foregut towards a population high in SOX2. Based on the data from this example and the previous examples, one may conclude that the optimal duration of stage 3 and stage 4 is two days. The ideal protocol will result in differentiated cells with high levels of expression of pro-endocrine markers, high NKX6.1, low CDX2 and low SOX2 expression.

Example 9

Prolonged Exposure to BMP Inhibition in the Presence of High Glucose and B27 Supplement Significantly Increases SOX2 Expression at S3 and S4

This protocol was performed to determine the factors that affect SOX2 expression at S3 and S4 during the stepwise differentiation of pluripotent cells into hormone producing cells.

Cells of the human embryonic stem cells line H1 were cultured on MATRIGEL™ (1:30 dilution)-coated dishes and cultured in mTesr™ 1 media until ~70% confluence and differentiated as follows:

a. Undifferentiated cells were cultured in RPMI medium (Invitrogen) supplemented with 0.2% FBS; 100 ng/ml activin A; 20 ng/ml WNT-3a for one day. Cells were then treated with RPMI medium supplemented with 0.5% FBS; 100 ng/ml activin A for an additional two days (Stage 1).

b. Stage 1 cells were treated with DMEM/F12 medium supplemented with 2% FBS; 50 ng/ml FGF7 for three days (Stage 2).

c. Stage 2 cells were cultured in DMEM-High glucose medium supplemented with 1% B27; 0.25 µM SANT-1; 2 µM RA; 100 ng/ml Noggin (R & D systems, MN, USA) for four days (Stage 3).

d. Stage 3 cells were treated with DMEM-High glucose medium supplemented with 1% B27; 100 ng/ml Noggin; 1 µM ALK5 inhibitor II (Axxora, Calif., USA); and 50 nM TPB for four days (Stage 4).

Figure 14A:
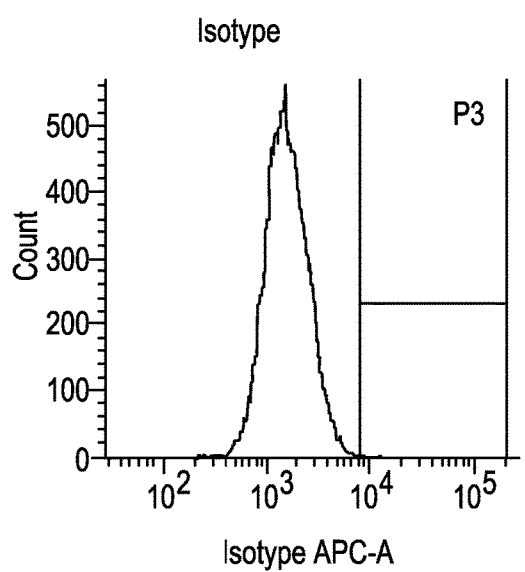
FIG. 14A to FIG. 14H show FACS histogram expression profiles of the following markers at S3 day 4 of cells differentiated according to Example 9.
Figure 14B:
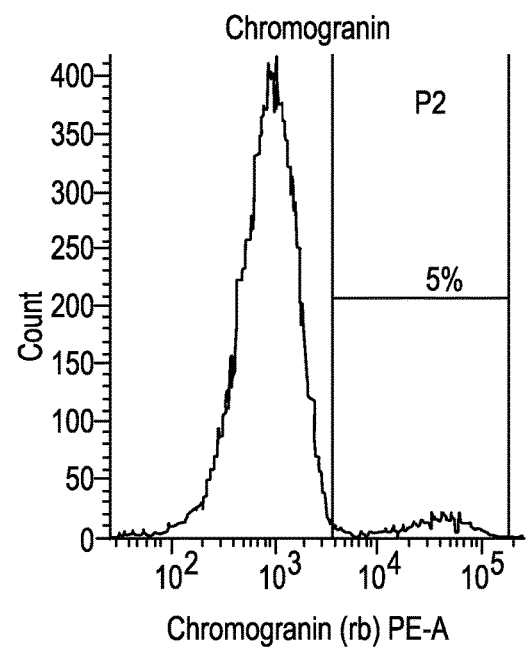
Figure 14C:
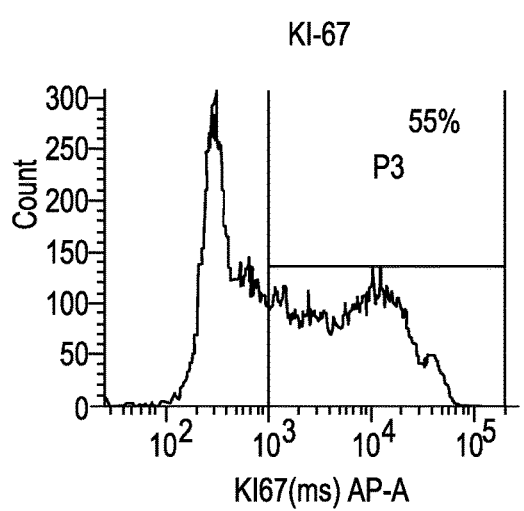
Figure 14D:
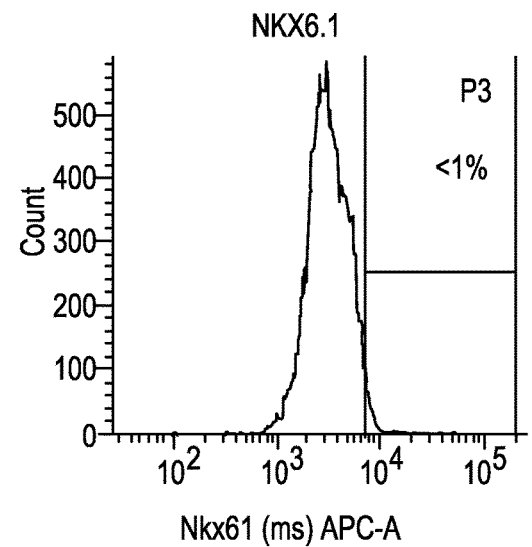
Figure 14E:
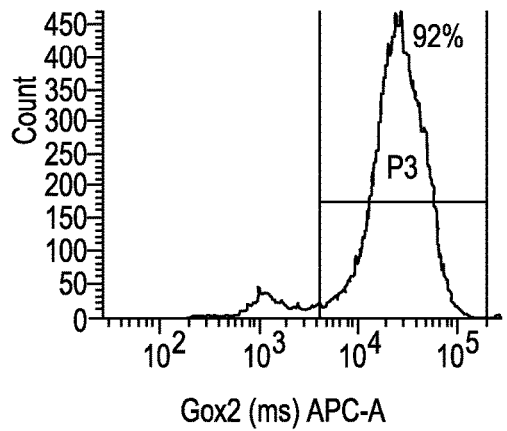
Figure 14F:
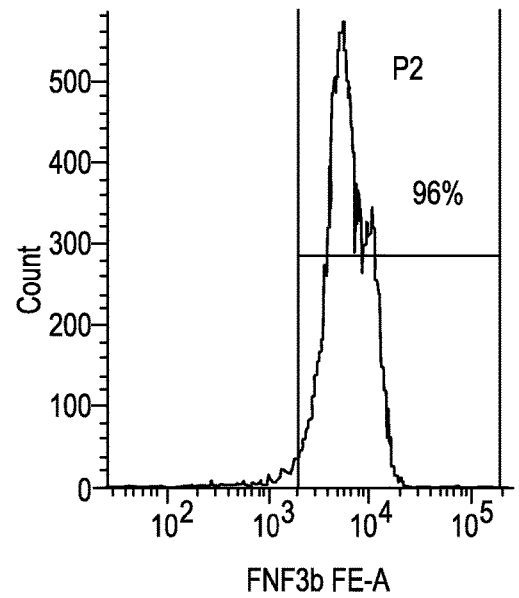
Figure 14G:
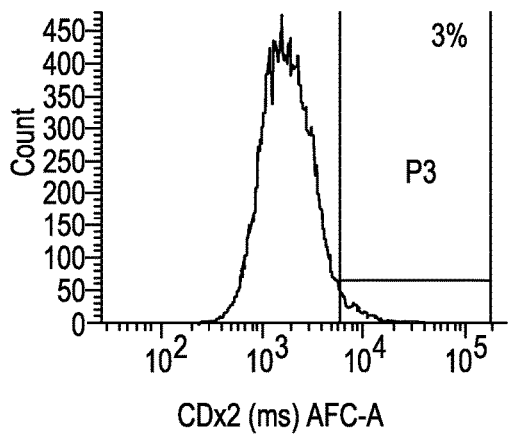
Figure 14H:
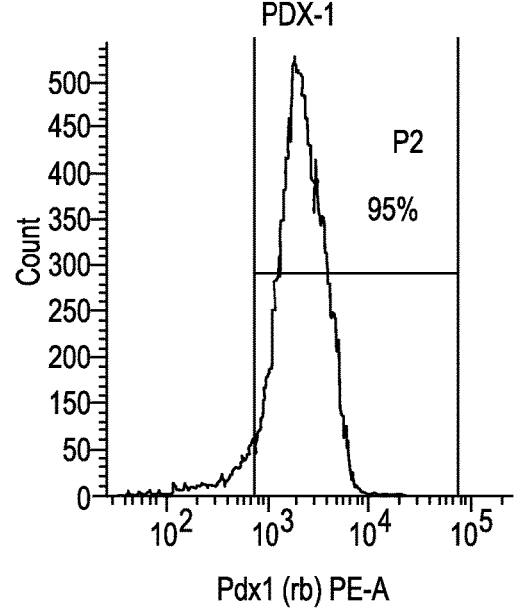

FIG. 14A to FIG. 14H depict FACS histograms for cells harvested at stage 3 day 4 obtained for the following markers: Isotype control (FIG. 14A), chromogranin (FIG. 14B), KI-67 (FIG. 14C), NKX6.1 (FIG. 14D), SOX2 (FIG. 14E), HNF3B (FIG. 14F), CDX2 (FIG. 14G), PDX-1 (FIG. 14H). Percentage expression for each marker is shown on each histogram. The majority of the cells at stage 3 were positive for expression of PDX-1 (FIG. 14H), and HNF3B (FIG. 14F), negative for expression of NKX6.1 (FIG. 14D), and showed low expression of chromogranin (FIG. 14B), and CDX2 (FIG. 14G). However, over 90% of the cells were also strongly positive for SOX2 (FIG. 14E). This indicates that at stage 3, the majority of cells were positive for PDX-1 and SOX2 and negative for NKX6.1 suggesting establishment of an endoderm population consistent with a foregut population anterior to the PDX-1 domain of pancreas.

Furthermore, the percentage of cells which were SOX2+ at stage 3, in the population of cells generated using the protocol outlined in this example, was significantly higher than the percentage of cells that were SOX2+ in the population of cells generated using the protocol outlined in Example 1. This difference can be attributed to the prolonged exposure to the BMP antagonist Noggin, lack of FGF7 and PKC activator in the culture medium at stage 3 of this example.

Figure 15A:
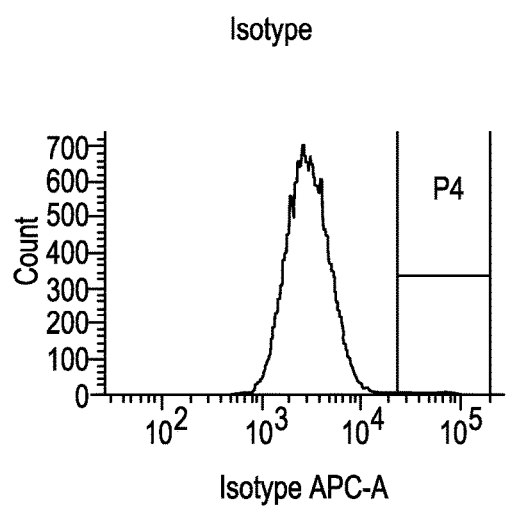
FIG. 15A to FIG. 15G show FACS histogram expression profiles of the following markers at S4 day 2 of cells differentiated according to Example 9.
Figure 15B:
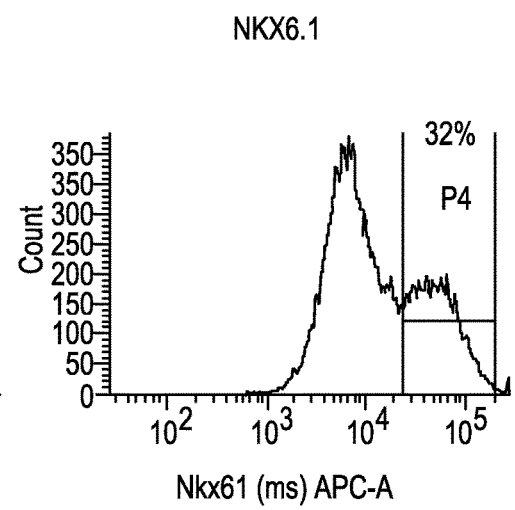
Figure 15C:
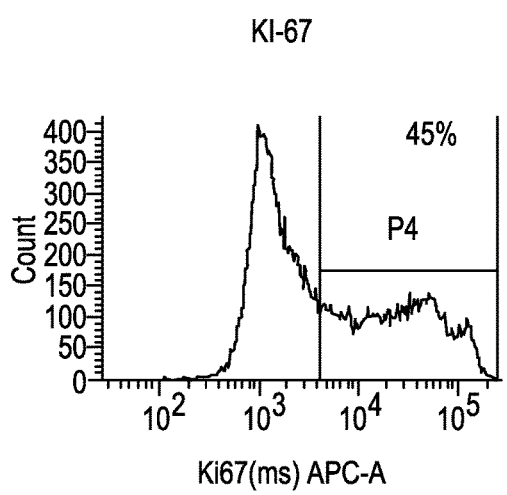
Figure 15D:
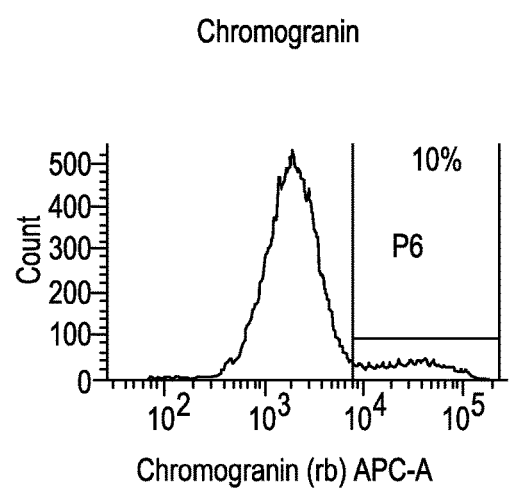
Figure 15E:
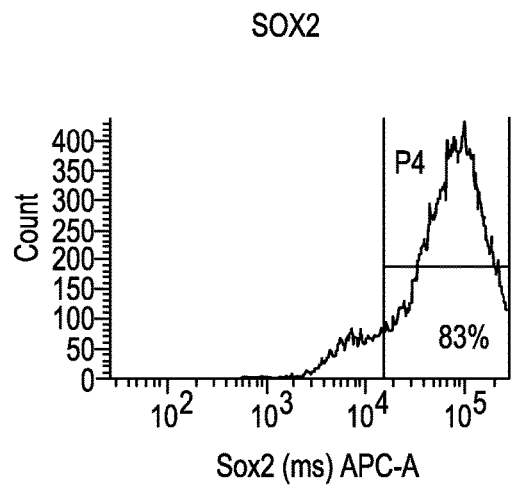
Figure 15F:
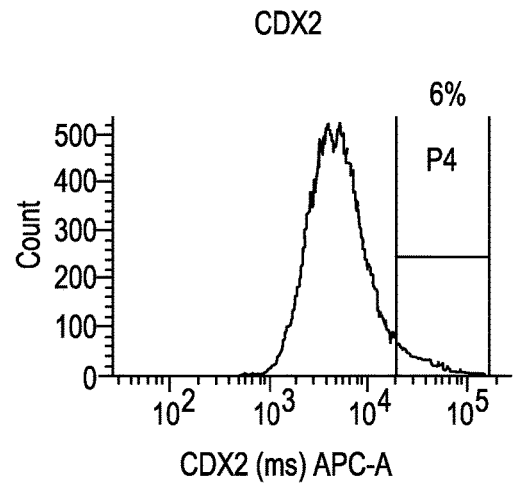
Figure 15G:
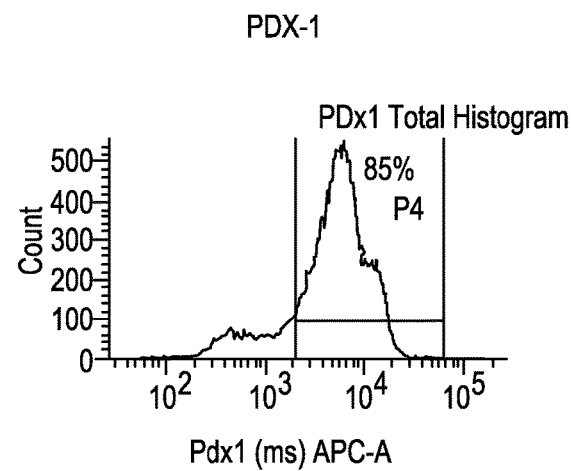

FIG. 15A through FIG. 15G show FACS histogram expression profiles of the following markers at S4 day 2 of cells differentiated according to Example 9: FIG. 15A: Isotype control, FIG. 15B: NKX6.1, FIG. 15C: KI-67, FIG. 15D: chromogranin, FIG. 15E: SOX2, FIG. 15F: CDX2, FIG. 15G: PDX-1. Percentage expression for each marker is shown on each histogram.

Figure 16E:
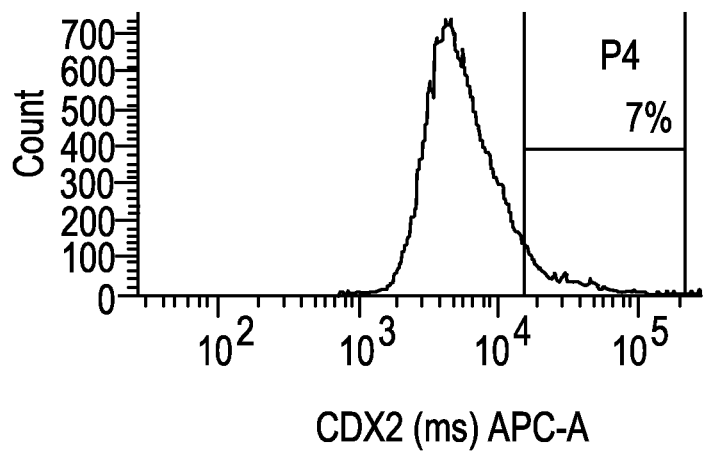
Figure 16F:
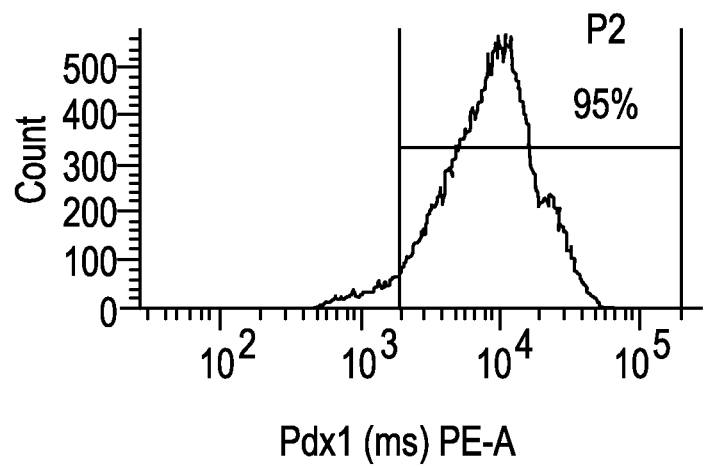

FIG. 16A to FIG. 16F show FACS histogram expression profiles of the following markers at S4 day 4 of cells differentiated according to Example 9. FIG. 16A: Isotype control, FIG. 16B: NKX6.1, FIG. 16C: chromogranin, FIG. 16D: SOX2, FIG. 16E: CDX2, FIG. 16F: PDX-1. Percentage expression for each marker is shown on each histogram.

Table V, below, summarizes the data obtained for the % expression of endoderm markers at S3 and S4 for cells differentiated according to the protocol outlined in this example.

TABLE V

% Expression of Endoderm Markers at S3-S4

| Stage (Days) | Total number of days since start of differentiation | % PDX-1+ | % PDX-1+ SOX2+ | % PDX-1+ NKX6.1+ SOX2− | % PDX-1+ CDX2+ | % PDX-1+ NKX6.1+ SOX2+ |
|---|---|---|---|---|---|---|
| Stage 3 4 days | 10 days | 95 | 92 | <1 | <5 | <1 |
| Stage 4 2 days | 12 days | 85 | 83 | <1 | ~6 | ~30 |
| Stage 4 4 days | 14 days | 95 | 75 | <5 | ~7 | ~50 |

Figure 17A:
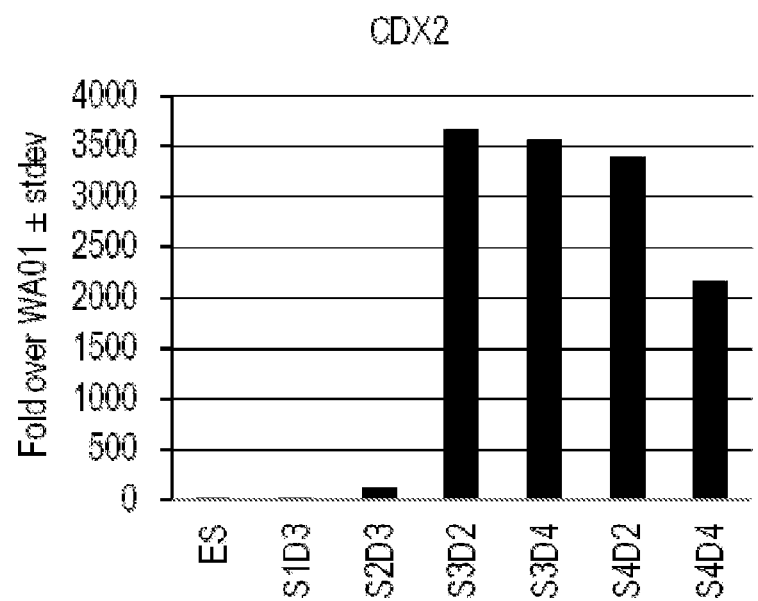
FIG. 17A to FIG. 17J show data from real-time PCR analysis of the expression of the following genes in cells of the human embryonic stem cell line H1 differentiated according to the Example 9 and harvested at S1D3, S2D3, S3D4, S4D2, and S4D4.
Figure 17B:
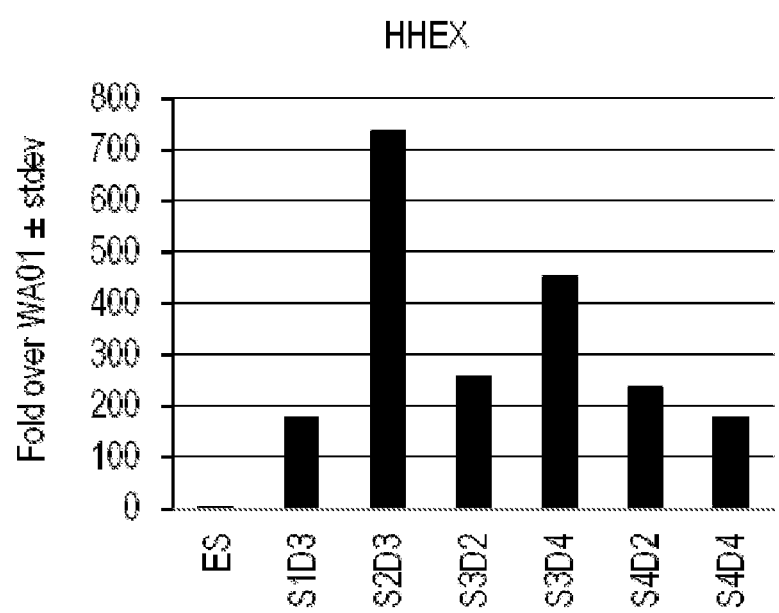
Figure 17C:
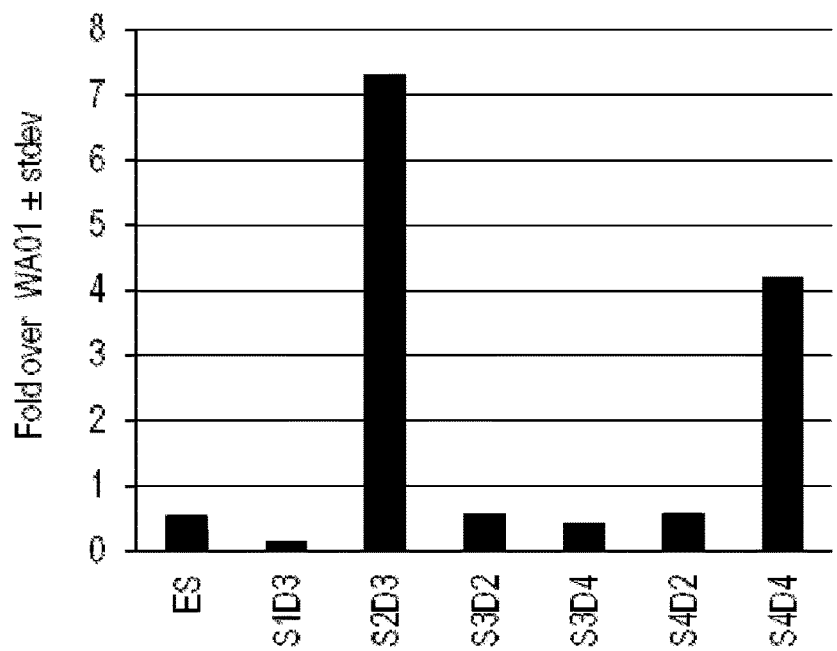
Figure 17D:
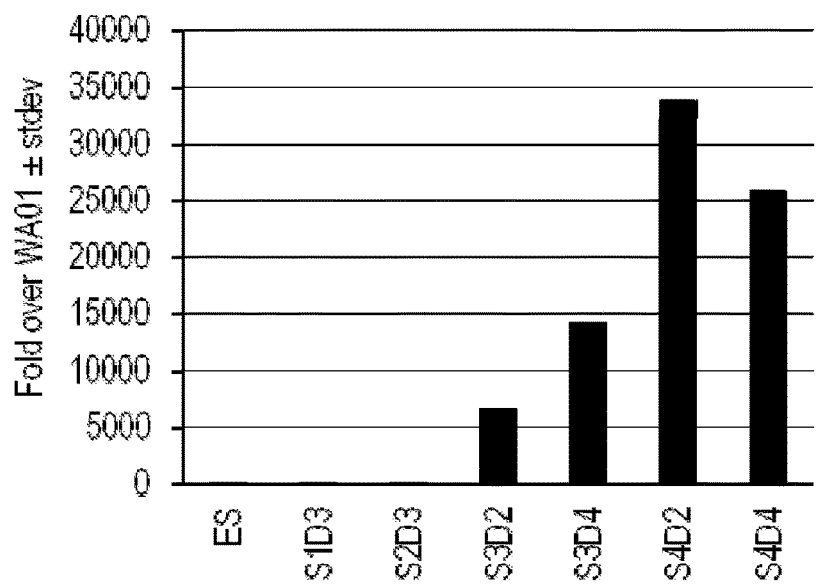
Figure 17E:
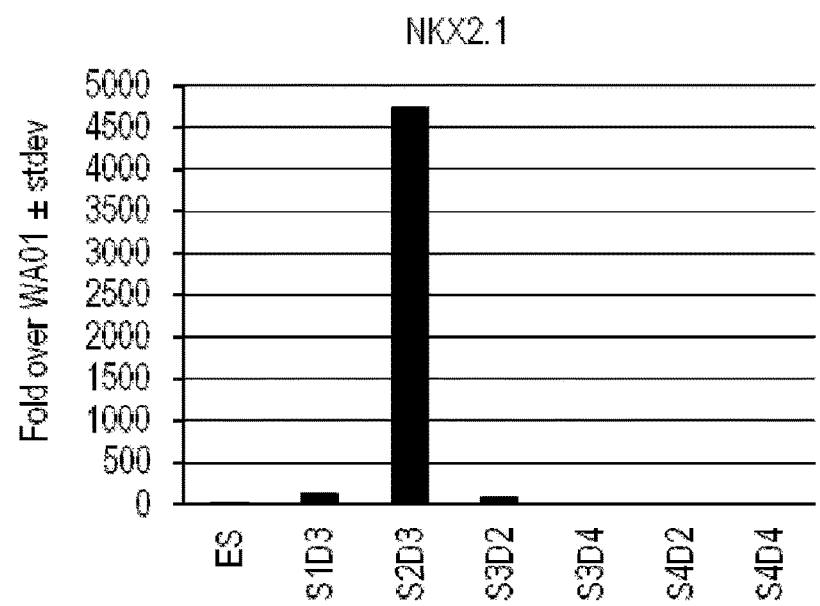
Figure 17F:
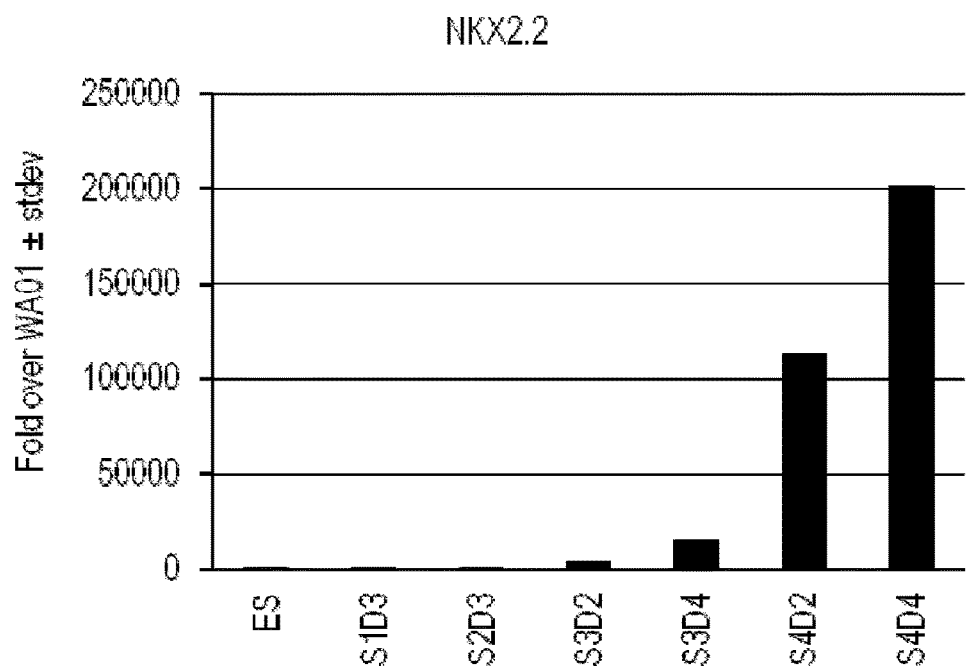
Figure 17G:
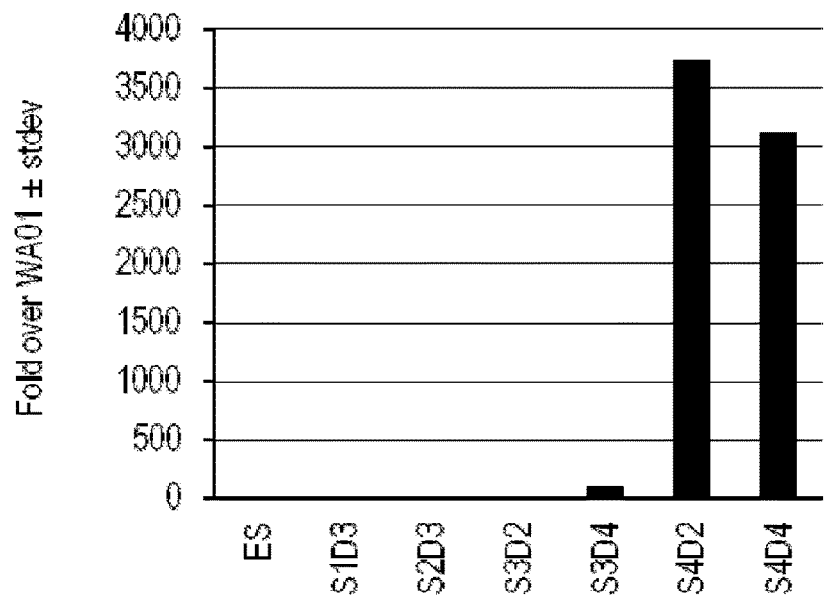
Figure 17H:
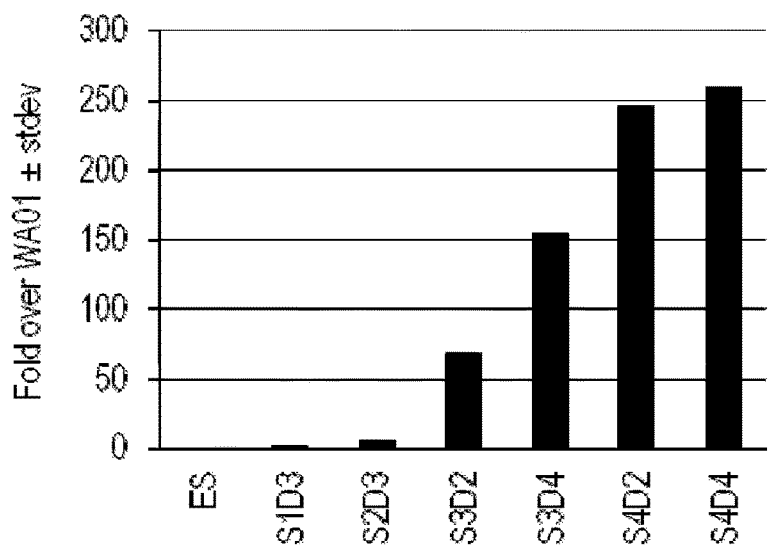
Figure 17I:
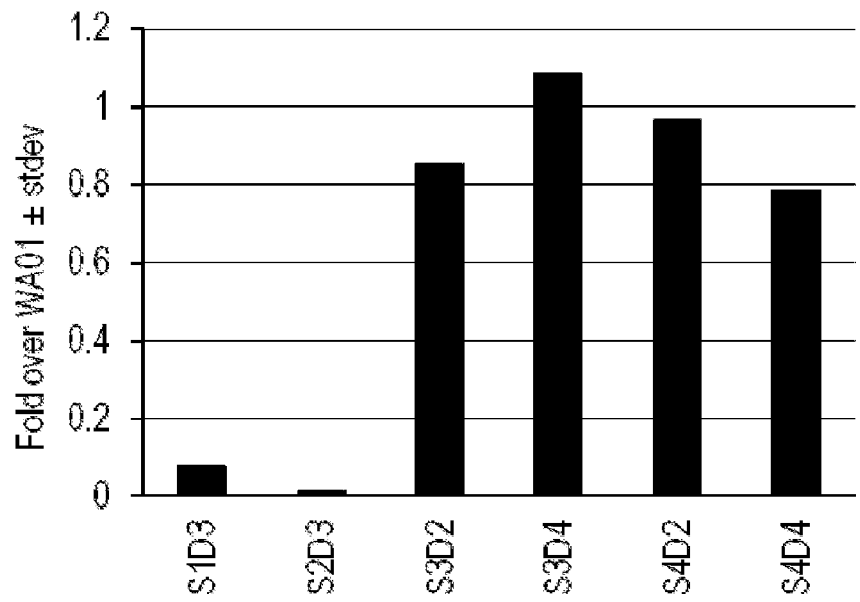
Figure 17J:
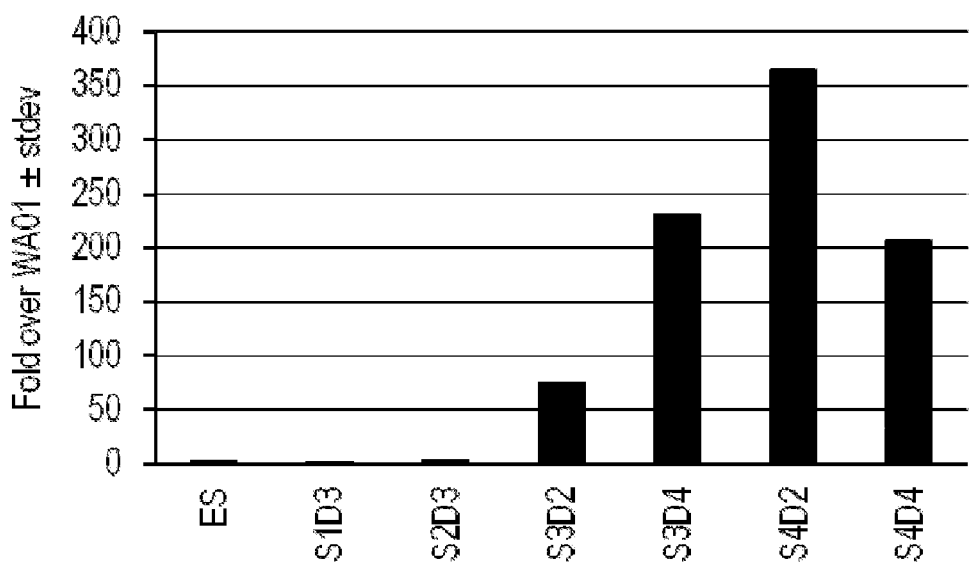

FIG. 17A to FIG. 17J depict the results of real-time PCR analyses of the expression of the following genes in cells of the human embryonic stem cell line H1 differentiated according to the Example 9. FIG. 17A: CDX2, FIG. 17B: HHex, FIG. 17C: FOXE1, FIG. 17D: IPF1 (PDX-1), FIG. 17E: NKX2.1, FIG. 17F: NKX2.2, FIG. 17G: NKX6.1, FIG. 17H: PROX1, FIG. 17I: SOX2, FIG. 17J: SOX9.

As seen in FIGS. 14 to 17 and in Table V, at days 2-4 of stage 4, there was a significant increase in expression of NKX6.1 while maintaining a high expression of PDX-1. Although, expression of SOX2 dropped from stage 3 to stage 4, ~75% of cells were still SOX2+. Same as in FIG. 5, CDX2+ cells, SOX2+ cells, and NKX6.1+ cells were mutually exclusive from chromogranin population. This implies that the population of stage 4 day 4 cells generated using the protocol outlined in Example 9 has ~50% NKX6.1+SOX2+ PDX-1+CDX2-chromogranin negative fraction. This is in contrast to the cell population generated in Example 1 which had 40-70% PDX-1+NKX6.1+SOX2−, CDX2−, chromogranin negative fraction and 2-25% PDX-1+NKX6.1+ SOX2+ at S4-S5. Clearly, cells generated using the protocol in Example 1 had far higher percentage of pancreatic endoderm, as defined as a population that is PDX-1+ and NXK6.1+ while being low or negative for SOX2 and CDX2, as compared to cells generated in Example 9.

The data obtained in this Example provides support that prolonged exposure to BMP inhibition in the presence of high glucose and B27 supplement significantly increases expression of SOX2 at stages 3 and 4 of differentiation.

Example 10

Previously Published Protocol Results in Formation of Significant Number of SOX2+ Population at the Stages 3-4

Kroon et al. have published a protocol for preparing cells of the pancreatic endoderm lineage from human embryonic stem cells (Nature Biotech 2008, 26: 443-452; hereinafter "Kroon"). In the Example provided here, human embryonic stem cells were differentiated following the Kroon protocol and assayed for expression of markers characteristic of the different stages of differentiation.

Cells of the human embryonic stem cells line H1 were plated on MATRIGEL™ (1:30 dilution)-coated dishes and cultured in mTesr™ 1 media until ~70% confluence and differentiated using the protocol previously published by Kroon as follows:

a) Undifferentiated cells were exposed to RPMI medium supplemented with 0.2% FBS, 100 ng/ml activin A, 20 ng/ml WNT-3a for one day followed by treatment with RPMI medium supplemented with 0.5% FBS, 100 ng/ml activin A for an additional two days (Stage 1).

b) Stage 1 cells were exposed to RPMI medium supplemented with 2% FBS, 50 ng/ml FGF7 for three days (Stage 2).

c) Stage 2 cells were treated with DMEM-High glucose medium supplemented with 1% B27, 0.25 µM SANT-1, 2 µM RA, 50 ng/ml of Noggin (R & D systems, MN) for three days (Stage 3).

d) Stage 3 cells were cultured in DMEM-High glucose medium supplemented with 1% B27 for three days (Stage 4).

e) Stage 4 cells were scraped from the wells and resuspended as clusters in DMEM-High glucose medium supplemented with 1% B27 for two days.

Figure 18A:
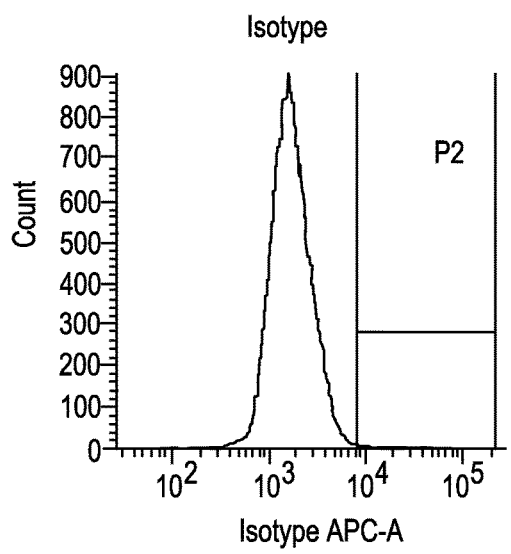
FIG. 18A to FIG. 18G show FACS histogram expression profiles of the following markers at S3 day 3 of cells differentiated according to Example 10.
Figure 18B:
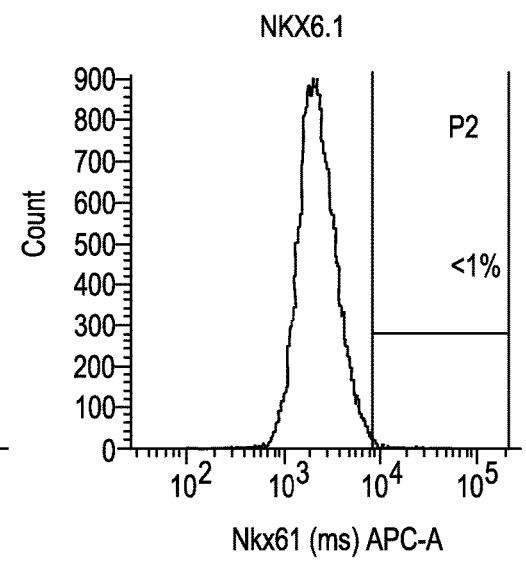
Figure 18C:
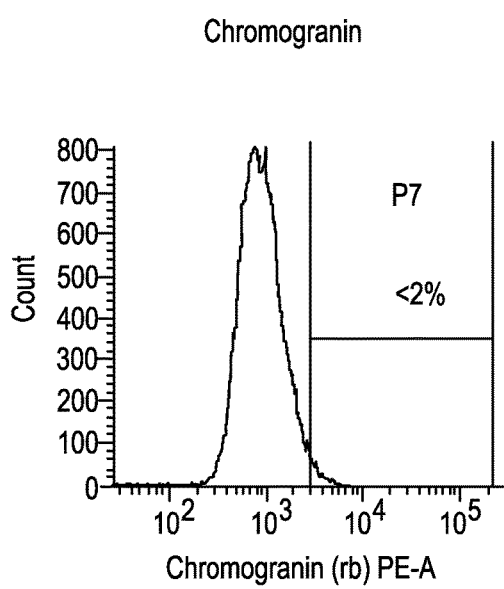
Figure 18D:
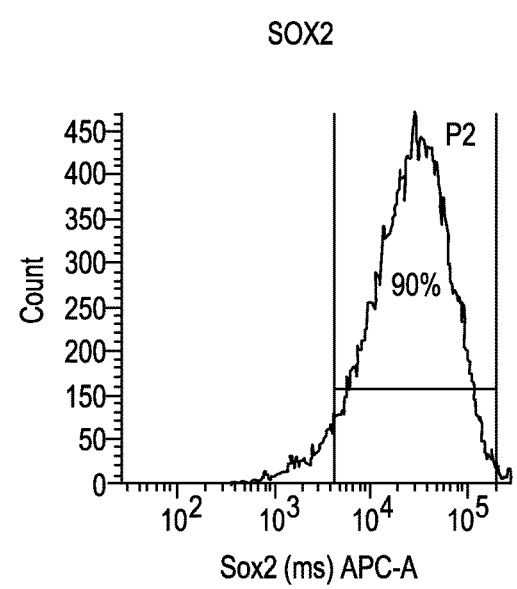
Figure 18E:
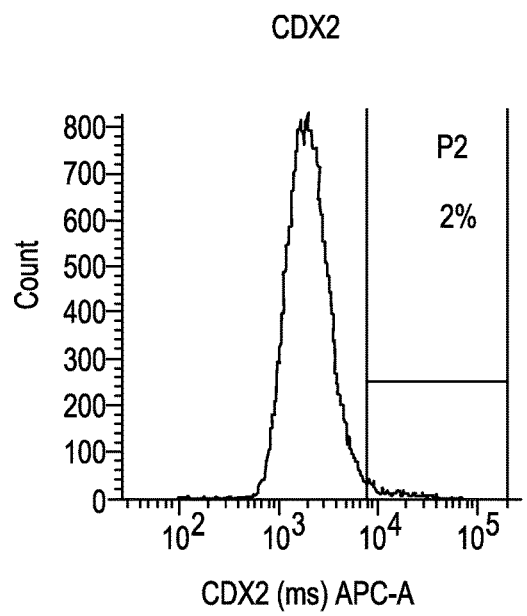
Figure 18F:
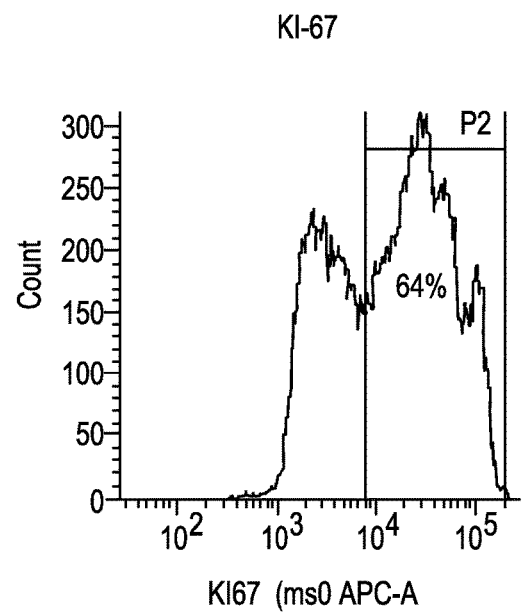
Figure 18G:
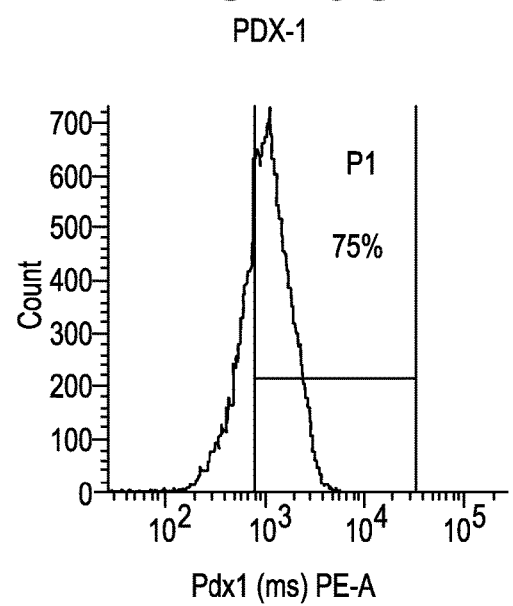

FIG. 18A to FIG. 18G show FACS histogram expression profiles of the following markers at S3 day 3 of cells differentiated according to Example 10: Isotype control (FIG. 18A), NKX6.1 (FIG. 18B), chromogranin (FIG. 18C), SOX2 (FIG. 18D), CDX2 (FIG. 18E), KI-67 (FIG. 18F), PDX-1 (FIG. 18G). Percentage expression for each marker is shown on each histogram.

Figure 19A:
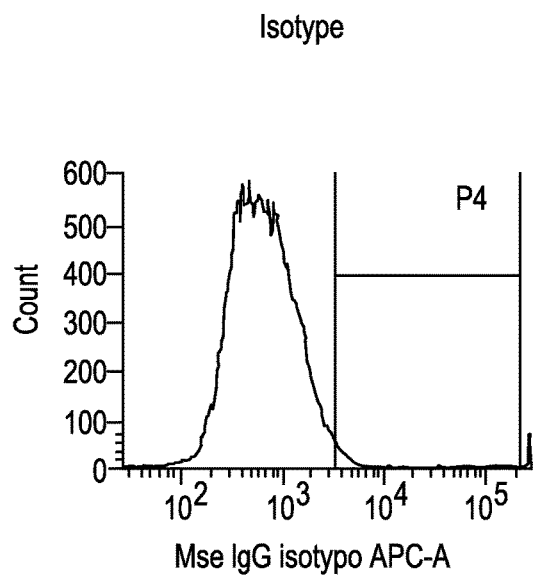
FIG. 19A to FIG. 19G show FACS histogram expression profiles of the following markers at S4 day 5 of cells differentiated according to Example 10.
Figure 19B:
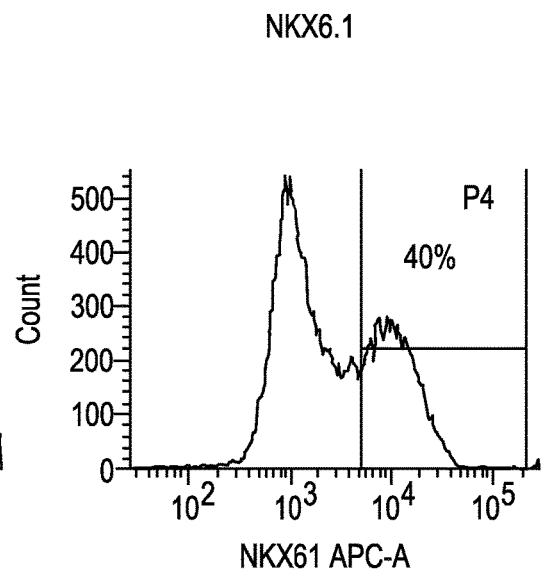
Figure 19C:
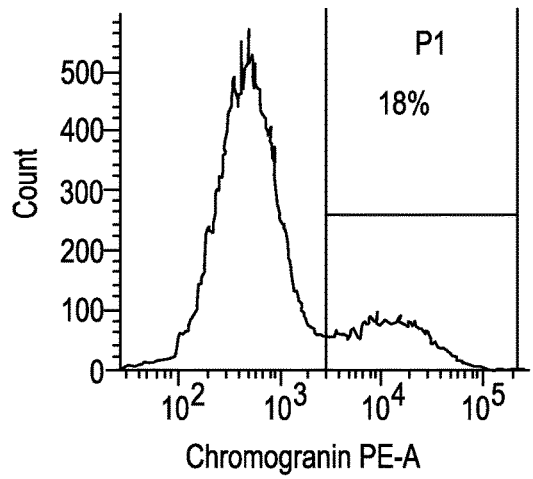
Figure 19D:
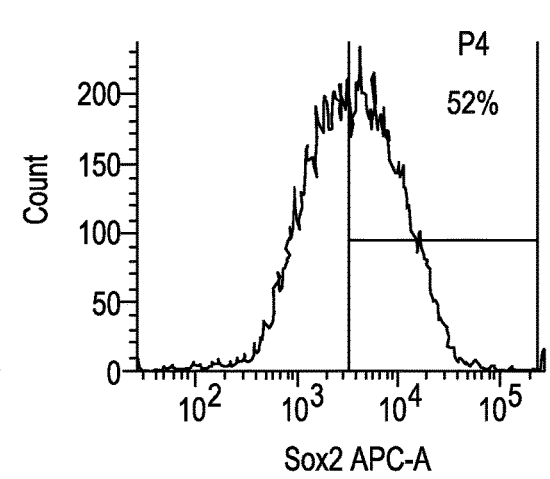
Figure 19E:
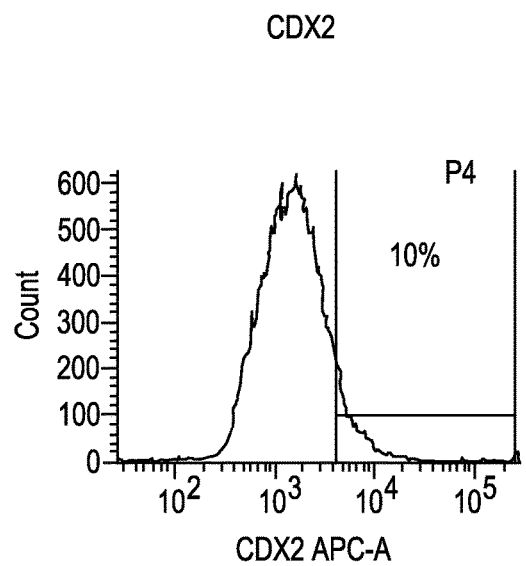
Figure 19F:
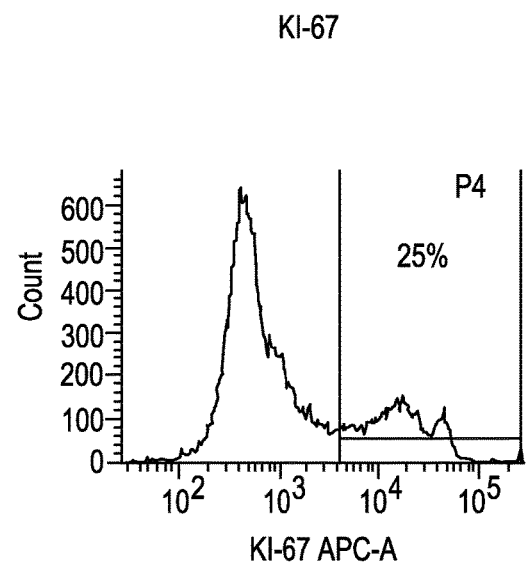
Figure 19G:
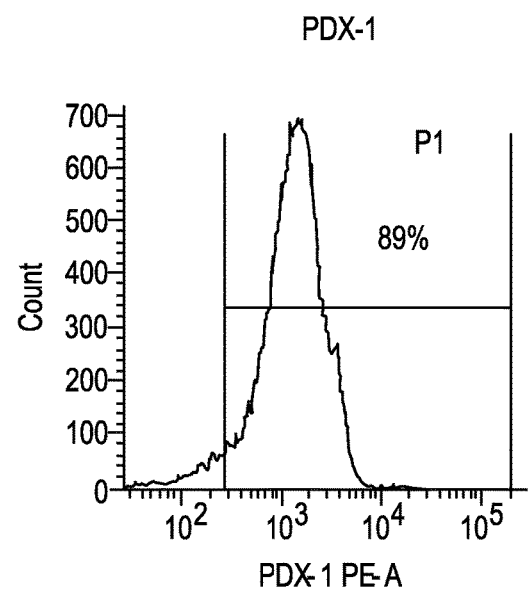

FIG. 19A to FIG. 19G show FACS histogram expression profiles of the following markers at S4 day 5 of cells differentiated according to Example 10: Isotype control (FIG. 19A), NKX6.1 (FIG. 19B), chromogranin (FIG. 19C), SOX2 (FIG. 19D), CDX2 (FIG. 19E), KI-67 (FIG. 19F), PDX-1 (FIG. 19G). Percentage expression for each marker is shown on each histogram As shown in FIGS. 18 and 19, by the end of stage 4 (day 5) the clusters of cells in suspension were ~20% NKX6.1+ PDX-1+SOX2− and ~20% PDX-1+NKX6.1+SOX2+. These results indicate that a significant fraction of the population of cells at stage 4 generated according to Example 10 that were NKX6.1+ were also SOX2+.

Table VI, shown below, summarizes the percentages of endoderm markers at S3-S4 of cells generated in this example.

TABLE VI

Expression of Endoderm Markers at S3-S4 in Cells Differentiated According to Kroon

| Stage (days) | Total number of days since start of differentiation | % PDX-1+ | % PDX-1+ SOX2+ | % PDX-1+ NKX6.1+ SOX2− | % PDX-1+ CDX2+ | % PDX-1+ NKX6.1+ SOX2+ |
|---|---|---|---|---|---|---|
| Stage 3 3 days | 9 days | 75 | 75 | <1 | <2 | <1 |
| Stage 4 5 days* | 14 days | 89 | 52 | ~20 | ~10 | ~20 |

*Last two days in suspension culture.

Example 11

Addition of Ascorbic Acid Results in Significant Decrease in the Number of Polyhormonal Cells and a Concomitant Increase in the Number of Single Hormonal Insulin Positive Cells The effect of ascorbic acid on the expression of markers during differentiation of pluripotent cells to hormone producing cells was tested. Cells were cultured in medium supplemented with glucose at every step of differentiation and supplemented with ascorbic acid at the formation of stages 3, 4, and 5 as follows:

Cells of the human embryonic stem cell line H1 at various passages (passage 40 to passage 52) were seeded as single cells at a density of 100,000 cells/cm$^2$ on MATRIGEL™ (1:30 dilution) coated dishes in mTesr™ 1 media and 10 µM of Y27632. Forty eight hours post seeding, cultures were differentiated into pancreatic endocrine lineage as follows:

a. Stage 1 (Definitive Endoderm (DE)—3 days): Prior to start of DE, the cultures were washed and incubated with incomplete PBS (no Mg or Ca) for 30 seconds followed by addition of the stage 1 media. Human embryonic stem cells cultured as single cells on MATRIGEL™-coated dishes were treated with MCDB-131 medium supplemented with 0.1% fatty acid-free BSA, 0.0012 g/ml sodium bicarbonate, 1× GlutaMax™, 5 mM D-Glucose, 100 ng/ml GDF8, and 1 µM MCX compound (GSK3B inhibitor) for one day. Cells were then treated with MCDB-131 medium supplemented with 0.1% fatty acid-free BSA, 0.0012 g/ml sodium bicarbonate, 1× GlutaMax™, 5 mM glucose, 100 ng/ml GDF8, and 100 nM MCX compound for day two, followed by an additional day in MCDB-131 medium supplemented with 0.1% fatty acid-free BSA, 0.0012 g/ml sodium bicarbonate, 1× GlutaMax™, 5 mM Glucose, and 100 ng/ml GDF8.

b. Stage 2 (Primitive gut tube—2 days): Stage 1 cells were treated with MCDB-131 medium supplemented with 0.1% fatty acid-free BSA, 0.0012 g/ml sodium bicarbonate, 1× GlutaMax™, 5 mM D-Glucose, and 25 ng/ml FGF7 for two days.

c. Stage 3 (Foregut-2 days): Stage 2 cells were treated with MCDB-131 medium supplemented with 1:200 dilution of ITS-X, 2.5 mM Glucose, 1× GlutaMax™, 0.0015 g/ml sodium bicarbonate, 2% fatty acid-free BSA, 10 ng/ml Activin A, 25 ng/ml FGF7, 0.25 µM SANT-1, 1 µM RA, 200 nM TPB (PKC activator), 100 nM LDN-193189 (BMP receptor inhibitor) for one day. Cells were then treated with MCDB-131 medium supplemented with 1:200 dilution of ITS-X, 2.5 mM Glucose, 1× GlutaMax™, 0.0015 g/ml sodium bicarbonate, 2% fatty acid-free BSA, 10 ng/ml Activin A, 25 ng/ml FGF7, 0.25 µM SANT-1, 1 µM RA, 200 nM TPB (PKC activator), 10 nM LDN-193189 for an additional day. Some cultures were treated with 0.25 mM ascorbic acid (Catalog #A4544, Sigma, MO, USA) for the duration of stage 3.

d. Stage 4 (Pancreatic foregut precursor-2 days): Stage 3 cells were treated with MCDB-131 medium supplemented with 1:200 dilution of ITS-X, 2.5 mM Glucose, 1× GlutaMax™, 0.0015 g/ml sodium bicarbonate, 2% fatty acid-free BSA, 0.25 µM SANT-1, 50 nM RA, 200 nM TPB, 50 nM LDN-193189, with or without 0.25 mM ascorbic acid for two days.

e. Stage 5 (Pancreatic endoderm, 2-7 days): Stage 4 cells were treated with MCDB-131 medium supplemented with a 1:200 dilution of ITS-X, 2.5 mM Glucose, 1× GlutaMax™, 0.0015 g/ml sodium bicarbonate, 2% fatty acid-free BSA, 0.25 µM SANT-1, 50 nM RA, with or without 0.25 mM ascorbic acid for 2-7 days.

Figure 20A:
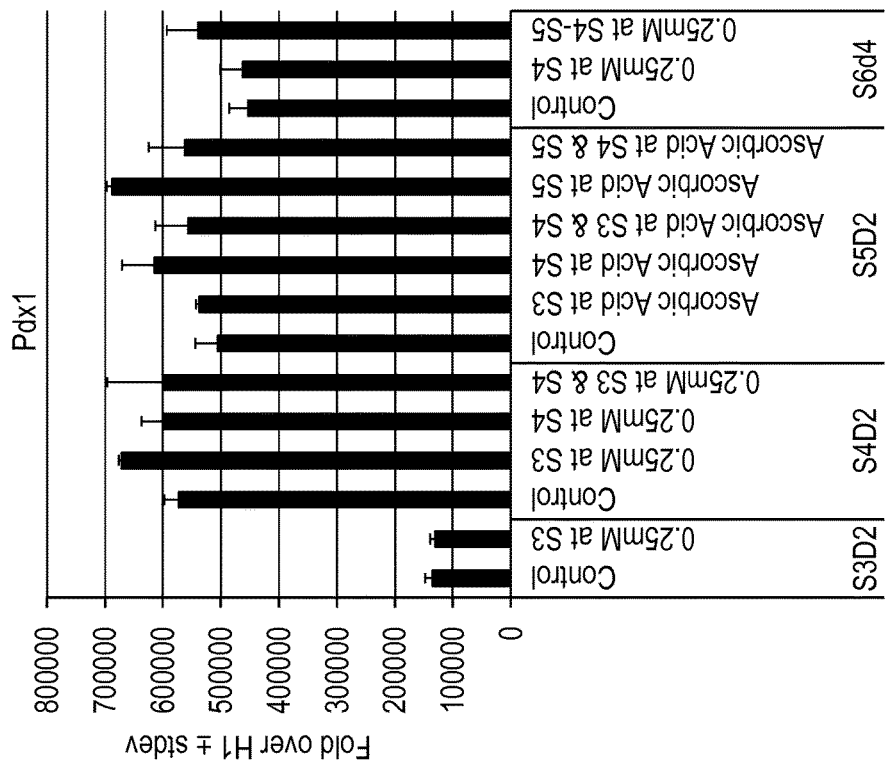
Figure 20B:
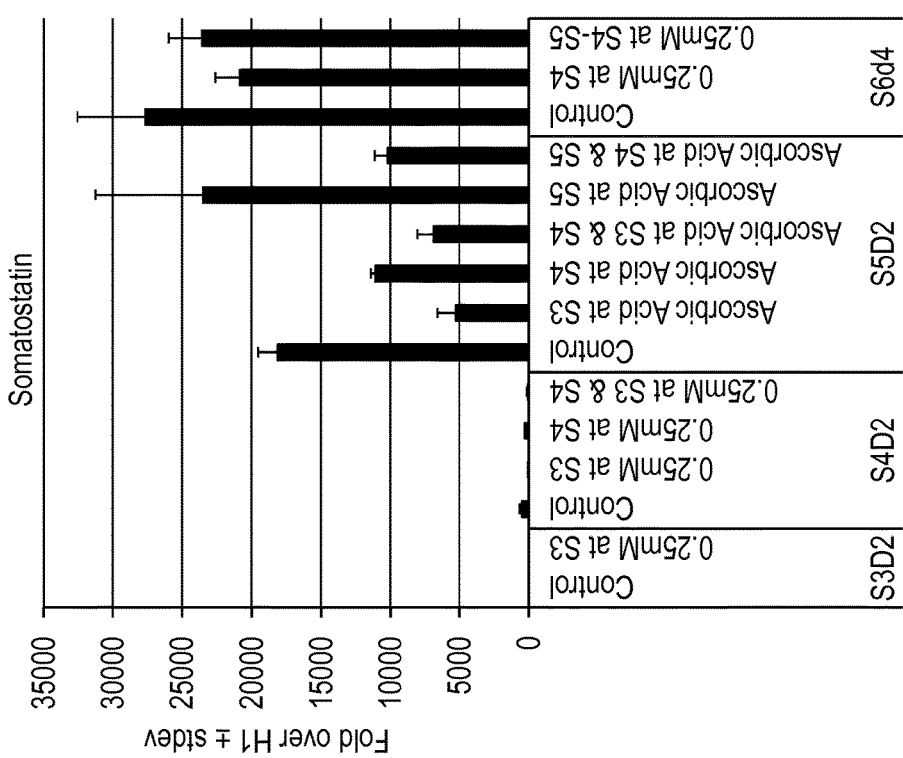
Figure 20C:
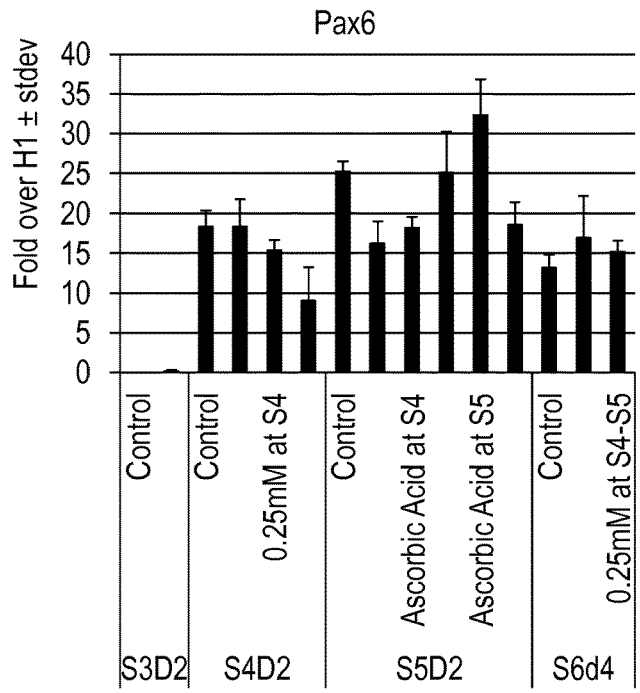
Figure 20D:
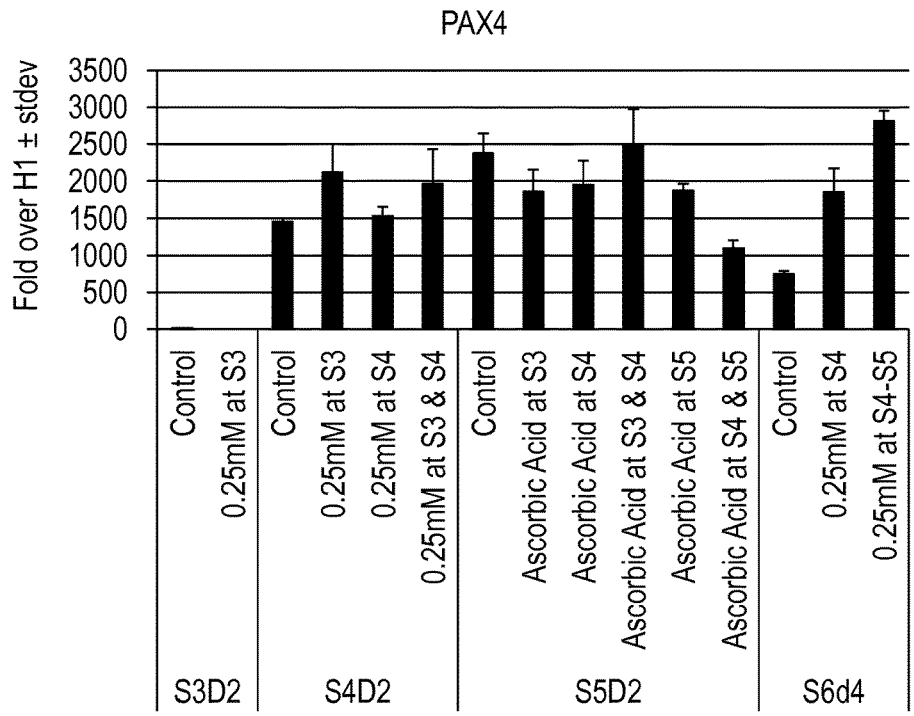
Figure 20J:
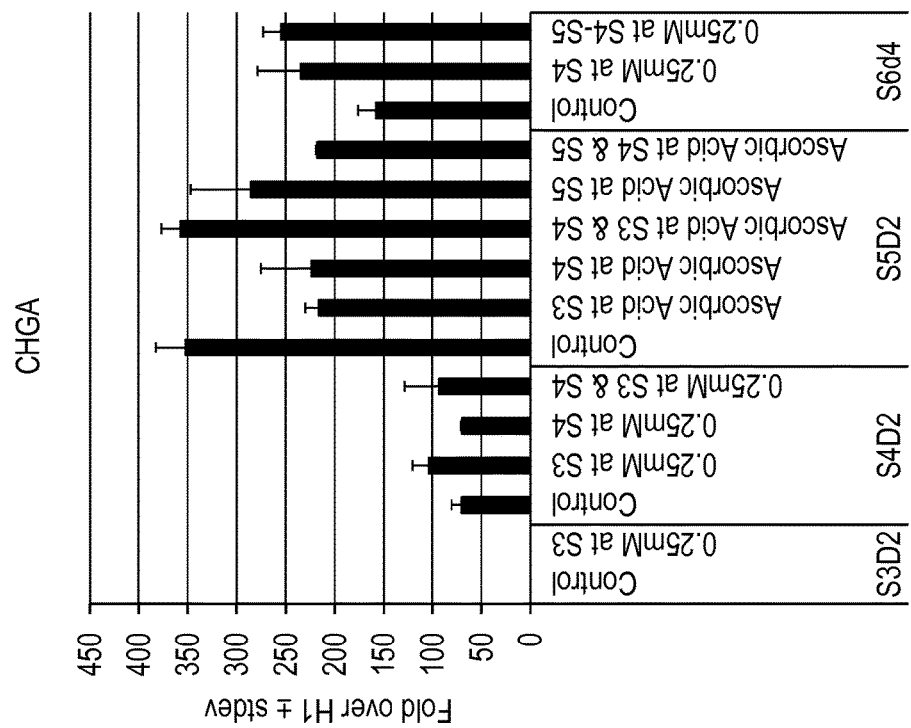
Figure 20I:
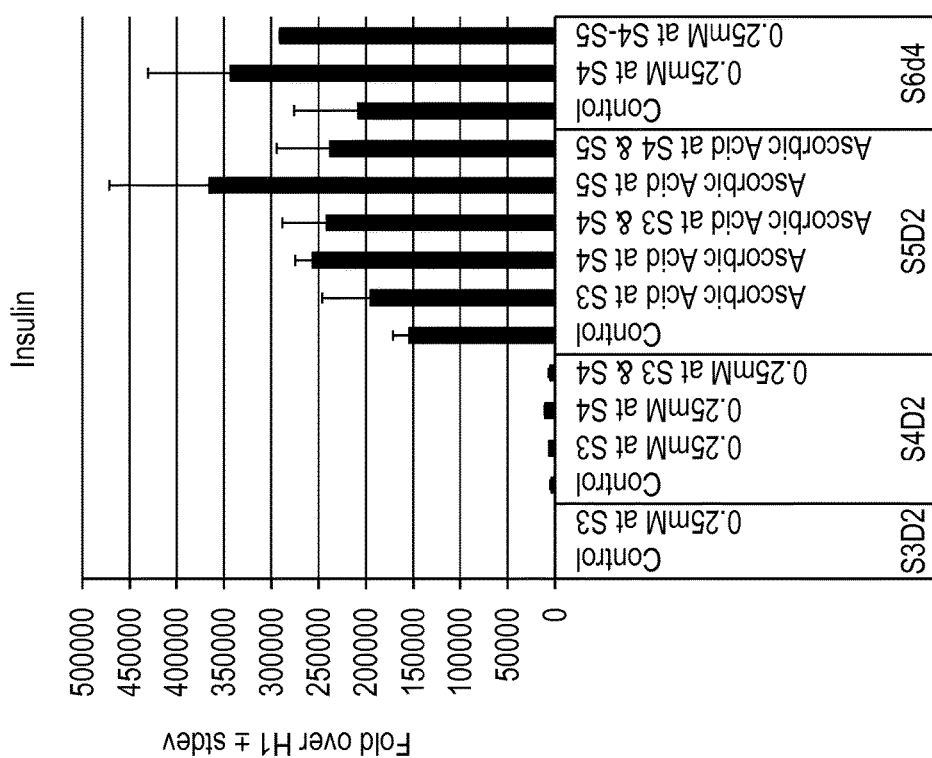

FIG. 20A to FIG. 20J depict real-time PCR analyses of the expression of the following genes in cells of the human embryonic stem cell line H1 differentiated according to the Example 11. FIG. 20A: somatostatin, FIG. 20B: PDX1, FIG. 20C: Pax6, FIG. 20D: Pax4, FIG. 20E: NKX6.1, FIG. 20F: NGN3, FIG. 20G: glucagon, FIG. 20H: NeuroD, FIG. 20I: insulin, FIG. 20J: chromogranin. This Figure shows that addition of ascorbic acid at stage 3 or at stages 3 and 4 significantly decreased expression of somatostatin and glucagon at stages 4-5 while increasing expression of insulin (see FIG. 20A, FIG. 20G, and FIG. 20I). Furthermore, at stages 4-5 expression of pancreatic endoderm markers, such as PDX-1 and NKX6.1 was not significantly altered by addition of 0.25 mM ascorbic acid (see FIG. 20B and FIG. 20D). At stages 4-5, Pax6 expression was down regulated and Pax4 expression was maintained (see FIG. 20C and FIG. 20D). At end of stage 5, cultures treated +/− ascorbic acid at S3-S5 were immune stained for insulin, glucagon, and somatostatin hormones. Table VII summarizes average percentage of insulin positive cells, glucagon and somatostatin positive cells, and polyhormonal cells (two more hormone expression in one cell).

TABLE VII

Expression of hormones as a percentage of the entire hormone count

| Treatment | % single hormonal Insulin+ | % glucagon + plus % somatostatin+ | % Polyhormonal |
|---|---|---|---|
| Control | 16 | 83 | 50 |
| +ascorbic acid at S3-S4 | 55 | 44 | 36 |

Example 12

Optimal Dose of Ascorbic Acid at Stage 3

This Example was carried out to determine the optimal dose of ascorbic acid to be used to generate insulin positive cells that are single hormonal, PDX-1 positive, and NKX6.1 positive.

Cells of the human embryonic stem cell line H1 at various passages (passage 40 to passage 52) were seeded as single cells at a density of 100,000 cells/cm$^2$ on MATRIGEL™ (1:30 dilution) coated dishes in mTesr™ 1 media and 10 µM of Y27632. Forty eight hours post seeding, cultures were differentiated into pancreatic endocrine lineage as follows:

a. Stage 1 (Definitive Endoderm (DE)—3 days): Prior to start of DE, the cultures were washed and incubated with incomplete PBS (no Mg or Ca) for 30 seconds followed by addition of the stage 1 media. Human embryonic stem cells cultured as single cells on MATRIGEL™-coated dishes were treated with MCDB-131 medium supplemented with 0.1% fatty acid-free BSA, 0.0012 g/ml sodium bicarbonate, 1× GlutaMax™, 5 mM D-Glucose, and 100 ng/ml GDF8 plus 1 µM MCX compound (GSK3B inhibitor) for one day. Cells were then treated with MCDB-131 medium supplemented with 0.1% fatty acid-free BSA, 0.0012 g/ml sodium bicarbonate, 1× GlutaMax™, 5 mM glucose, and 100 ng/ml GDF8 plus 100 nM MCX compound for day two, followed by an additional day in MCDB-131 medium supplemented with 0.1% fatty acid-free BSA, 0.0012 g/ml sodium bicarbonate, 1× GlutaMax™, 5 mM Glucose, and 100 ng/ml GDF8.

b. Stage 2 (Primitive gut tube—2 days): Stage 1 cells were treated with MCDB-131 medium supplemented with 0.1% fatty acid-free BSA, 0.0012 g/ml sodium bicarbonate, 1× GlutaMax™, 5 mM D-Glucose, with or without the addition of 0.25 mM ascorbic acid and 25 ng/ml FGF7 for two days.

c. Stage 3 (Foregut-2 days): Stage 2 cells were treated with MCDB131 medium supplemented with 1:200 dilution of ITS-X, 2.5 mM Glucose, 1× GlutaMax™, 0.0015 g/ml sodium bicarbonate, 2% fatty acid-free BSA, 10 ng/ml Activin A, 25 ng/ml FGF7, 0.25 µM SANT-1, +/−0.25 mM ascorbic acid, 1 µM RA, 200 nM TPB, 100 nM LDN-193189 for day 1, followed by treatment with MCDB131 medium supplemented with 1:200 dilution of ITS-X, 2.5 mM Glucose, 1× GlutaMax™, 0.0015 g/ml sodium bicarbonate, 2% fatty acid-free BSA, 10 ng/ml Activin A, 25 ng/ml FGF7, 0.25 µM SANT-1, +/−0.25 mM ascorbic acid, 1 µM RA, 200 nM TPB, 10 nM LDN-193189 for an additional day.

d. Stage 4 (Pancreatic foregut precursor-2 days): Stage 3 cells were treated with MCDB131 medium supplemented with 1:200 dilution of ITS-X, 2.5 mM Glucose, 1× GlutaMax™, 0.0015 g/ml sodium bicarbonate, 2% fatty acid-free BSA, 0.25 µM SANT-1, 50 nM RA, 200 nM TPB, 50 nM LDN-193189, with or without the addition of 0.25 mM to 1 mM ascorbic acid for two days.

e. Stage 5 (Pancreatic endoderm, 2-9 days): Stage 4 cells were treated with MCDB131 medium supplemented with a 1:200 dilution of ITS-X, 2.5 mM Glucose, 1× GlutaMax™, 0.0015 g/ml sodium bicarbonate, 2% fatty acid-free BSA, 0.25 µM SANT-1, 50 nM RA, with or without the addition of 0.25 mM ascorbic acid for 2-9 days.

Figure 21B:
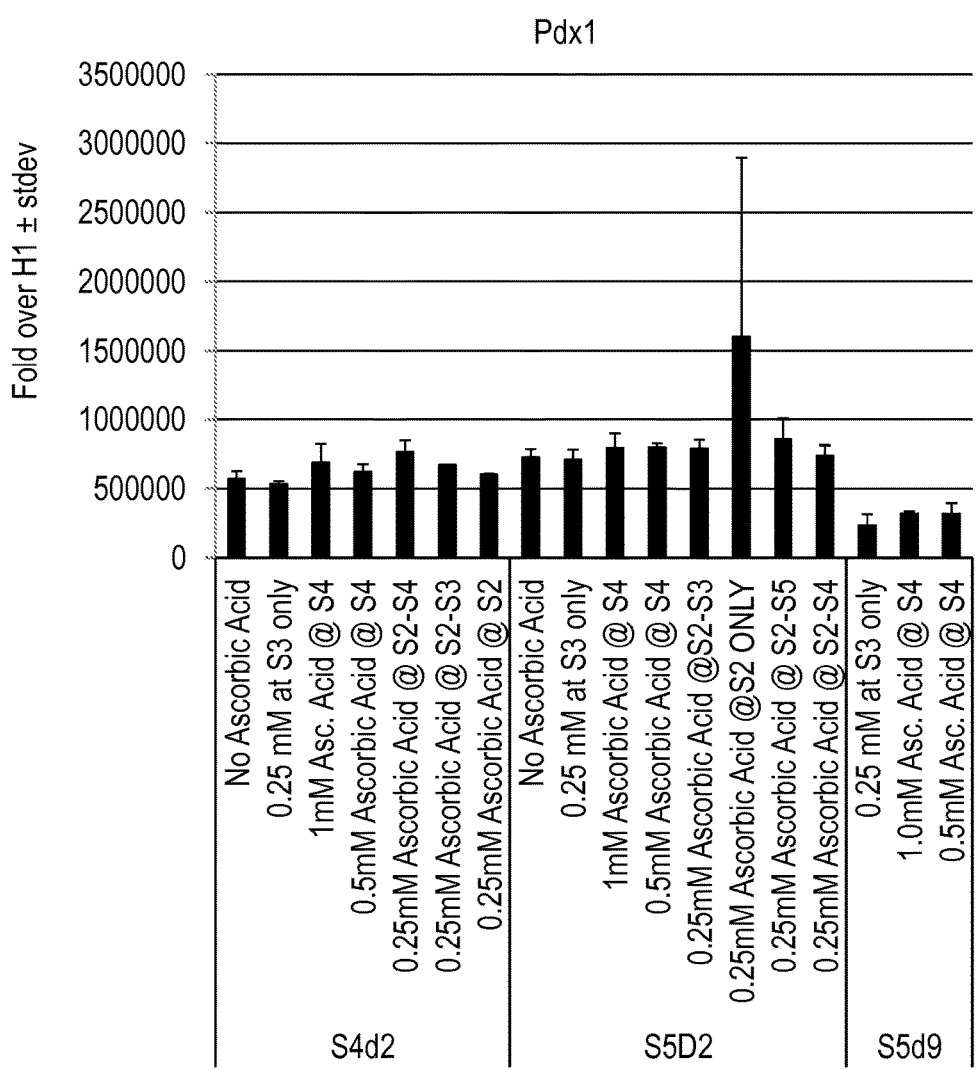
Figure 21H:
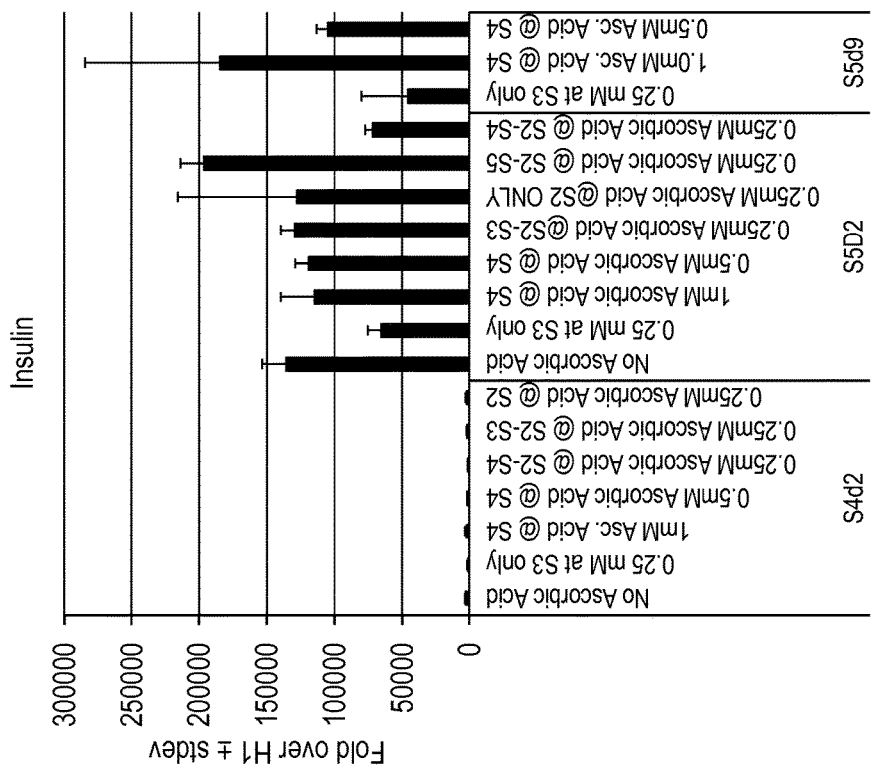
Figure 21G:
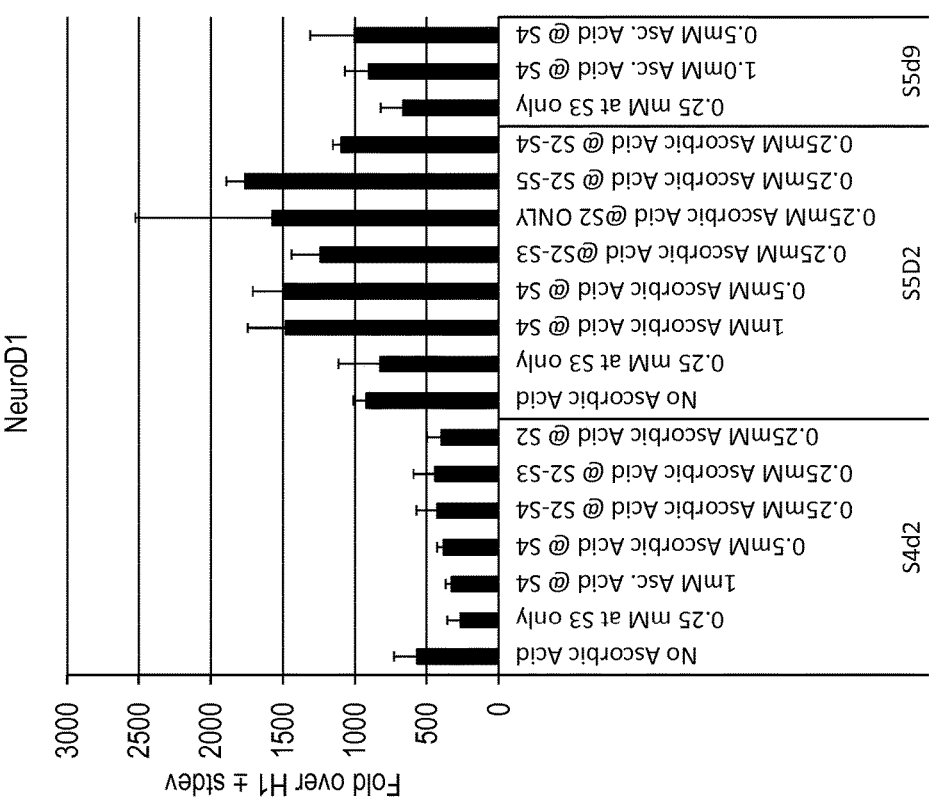
Figure 21J:
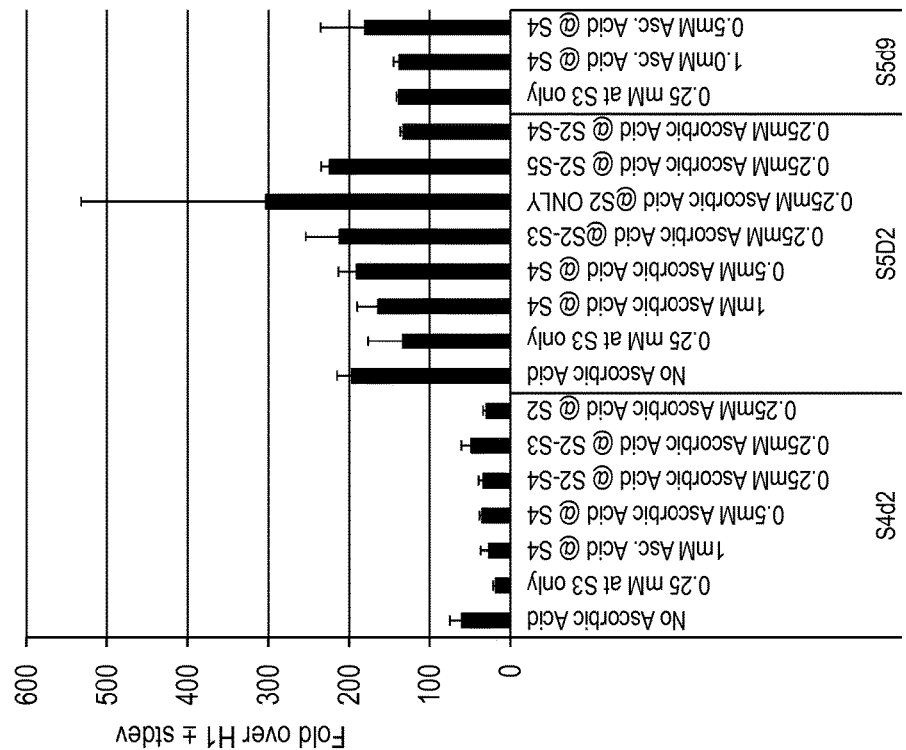
Figure 21I:
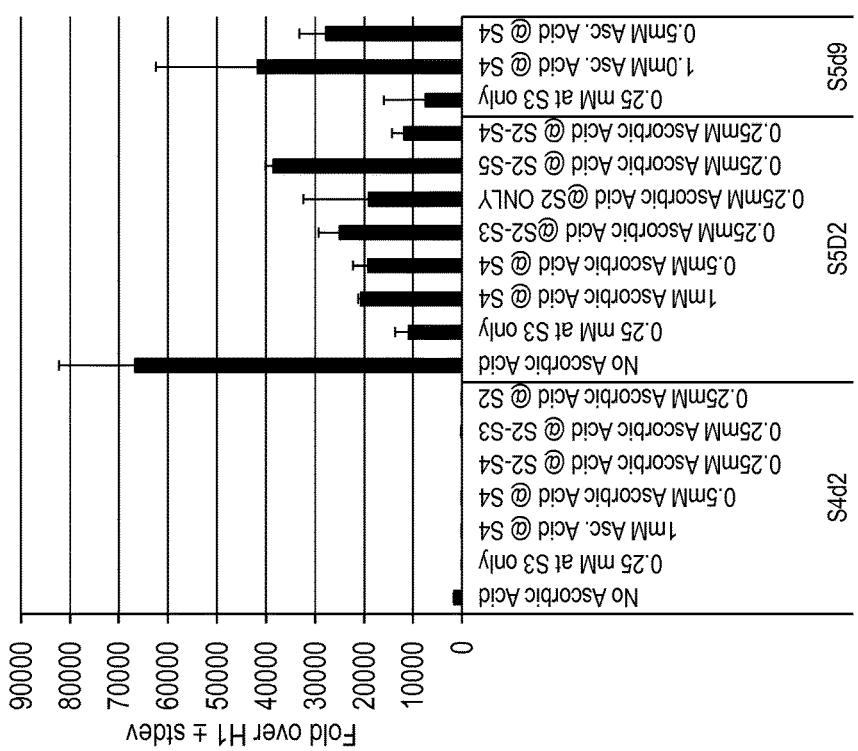

FIG. 21A to FIG. 21J depict data from real-time PCR analyses of the expression of the following genes in cells of the human embryonic stem cell line H1 differentiated according to the Example 12. FIG. 21A: somatostatin, FIG. 21B: PDX1, FIG. 21C: Pax6, FIG. 21D: Pax4, FIG. 21E: NKX6.1, FIG. 21F: NGN3, g FIG. 21G: NeuroD, FIG. 21H: insulin, FIG. 21I: glucagon, FIG. 21J: chromogranin. Consistent with the data from Example 10, addition of ascorbic acid at stages 2-4 significantly reduced expression of somatostatin, glucagon, and Pax6 while maintaining expression of insulin and Pax4 at stage 5. Furthermore, there was no significant benefit in using, at S4, 0.5-1 mM ascorbic acid as compared to 0.25 mM ascorbic acid. Lastly, addition of ascorbic acid at stage 2 also proved effective in lowering expression of glucagon and somatostatin at stage S3-5 while maintaining expression of insulin. Thus, ascorbic acid acts in a stage-specific fashion to regulate expression of single hormonal cells. Addition of ascorbic acid is important in early stages of the differentiation protocol, whereas at later stages it did not prove as effective in reducing numbers of polyhormonal cells.

Example 13

Combination of Retinoic Acid and Ascorbic Acid is Required to Generate Single Hormonal Insulin Positive Cells This Example was carried out to shed light on requirements to generate single hormonal insulin positive cells during differentiation of pluripotent cells.

Cells of the human embryonic stem cell line H1 at various passages (passage 40 to passage 52) were seeded as single cells at a density of 100,000 cells/cm$^2$ on MATRIGEL™ (1:30 dilution) coated dishes in mTesr™ 1 media and 10 µM of Y27632. Forty eight hours post seeding, cultures were differentiated into pancreatic endocrine lineage as follows:

a. Stage 1 (Definitive Endoderm (DE)—3 days): Prior to start of DE, the cultures were washed and incubated with incomplete PBS (no Mg or Ca) for 30 seconds followed by addition of the stage 1 media. Human embryonic stem cells cultured as single cells on MATRIGEL™-coated dishes were treated with MCDB-131 medium supplemented with 0.1% fatty acid-free BSA, 0.0012 g/ml sodium bicarbonate, 1× GlutaMax™, 5 mM D-Glucose, 100 ng/ml GDF8, 1 µM MCX compound (GSK3B inhibitor) for one day. Cells were then treated with MCDB-131 medium supplemented with 0.1% fatty acid-free BSA, sodium bicarbonate, GlutaMax™, extra 5 mM glucose, 100 ng/ml GDF8, and 100 nM MCX compound for day two followed by an additional day in MCDB-131 medium supplemented with 0.1% fatty acid-free BSA, 0.0012 g/ml sodium bicarbonate, 1× GlutaMax™, 5 mM Glucose, and 100 ng/ml GDF8.

b. Stage 2 (Primitive gut tube—2 days): Cells were treated with MCDB-131 medium supplemented with 0.1% fatty acid-free BSA, 0.0012 g/ml sodium bicarbonate, 1× GlutaMax™, 5 mM D-Glucose, 0.25 mM ascorbic acid, and 25 ng/ml FGF7 and for two days, then c. Stage 3 (Foregut-2 days): Cells were treated with MCDB131 supplemented with 1:200 dilution of ITS-X, 2.5 mM Glucose, 1× GlutaMax™, 0.0015 g/ml sodium bicarbonate, 2% fatty acid-free BSA, 10 ng/ml Activin A, 25 ng/ml FGF7, 0.25 mM ascorbic acid, 0.25 µM SANT-1, 1 µM RA, 200 nM TPB, 100 nM LDN-193189 for day 1, followed by treatment with tMCDB131 supplemented with 1:200 dilution of ITS-X, 2.5 mM Glucose, 1× GlutaMax™, 0.0015 g/ml sodium bicarbonate, 2% fatty acid-free BSA, 10 ng/ml Activin A, 25 ng/ml FGF7, 0.25 mM ascorbic acid, 0.25 µM SANT-1, 1 µM RA, 200 nM TPB, 10 nM LDN-193189 for an additional day.

d. Stage 4 (Pancreatic foregut precursor-2 days): Cells were treated with MCDB-131 medium supplemented with 1:200 dilution of ITS-X, 2.5 mM Glucose, 1× GlutaMax™, 0.0015 g/ml sodium bicarbonate, 2% fatty acid-free BSA, 0.25 µM SANT-1, 50 nM RA, 200 nM TPB, 50 nM LDN-193189, 0.1 mM ascorbic acid for two days, then e. Stage 5 (Pancreatic endoderm, 3 days): Cells were treated with MCDB-131 medium supplemented with 1:200 dilution of ITS-X, 2.5 mM Glucose, 1× Gluta-Max™, 0.0015 g/ml sodium bicarbonate, 2% fatty acid-free BSA and the following culture conditions for 3 days:
+0.1 mM ascorbic acid
0.1 mM ascorbic acid+50 nM RA
0.1 mM ascorbic acid+50 nM RA+0.25 µM SANT-1
0.1 mM ascorbic acid+50 nM RA+0.25 µM SANT-1+ 50 nM LDN-193189
0.1 mM ascorbic acid+50 nM RA+0.25 µM SANT-1+1 µM Alk5 inh
0.1 mM ascorbic acid+50 nM RA+0.25 µM SANT-1+1 µM Alk5 inh+50 nM LDN-193189.

Figure 22A:
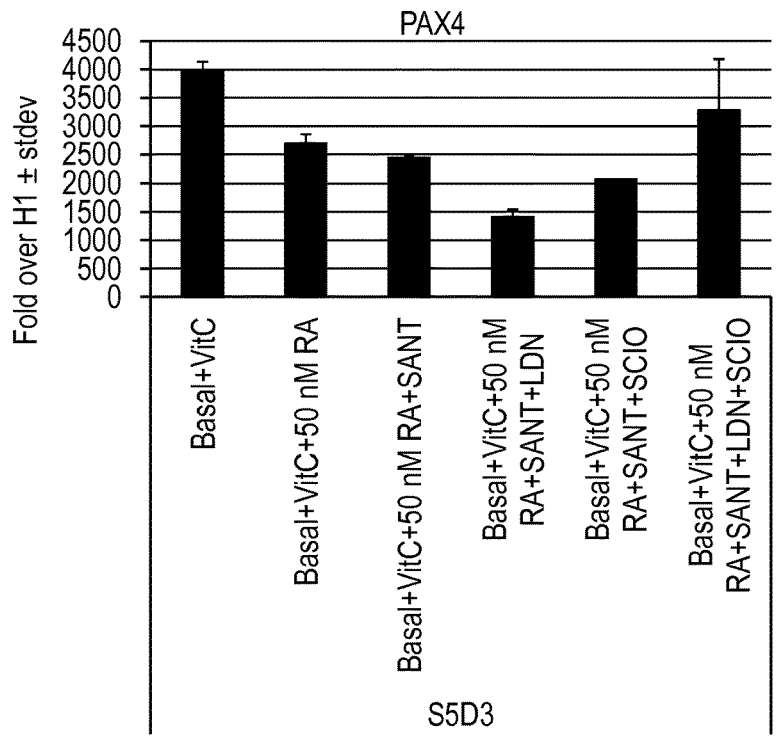
Figure 22B:
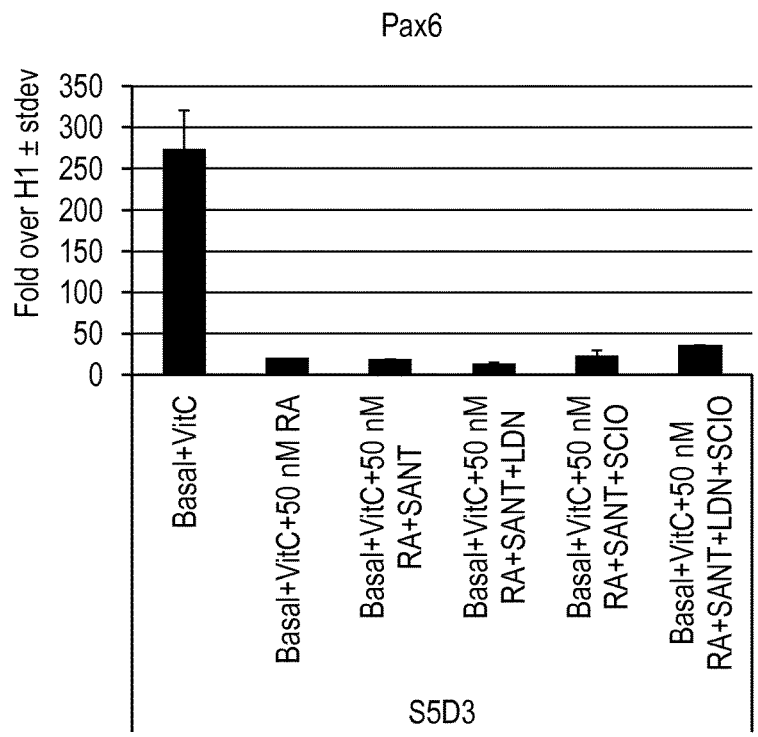
Figure 22C:
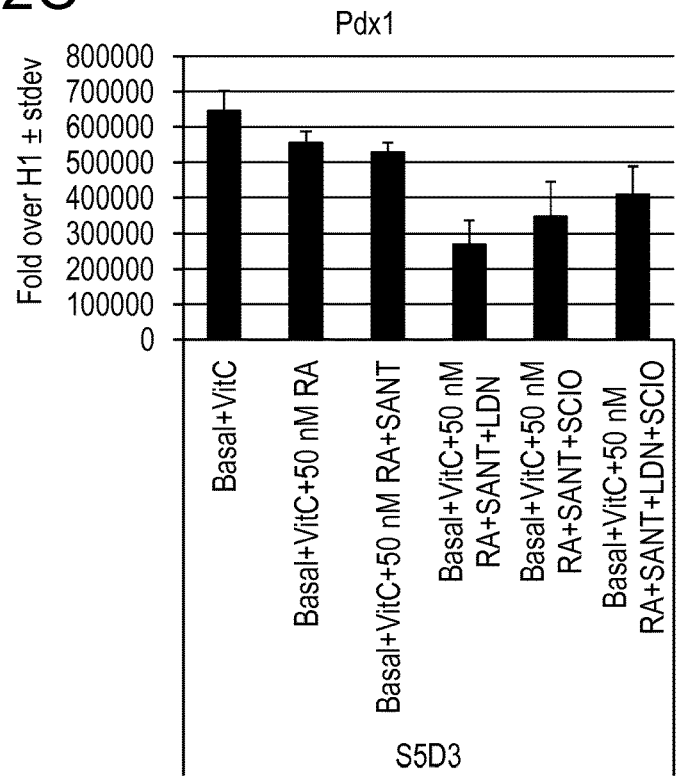
Figure 22D:
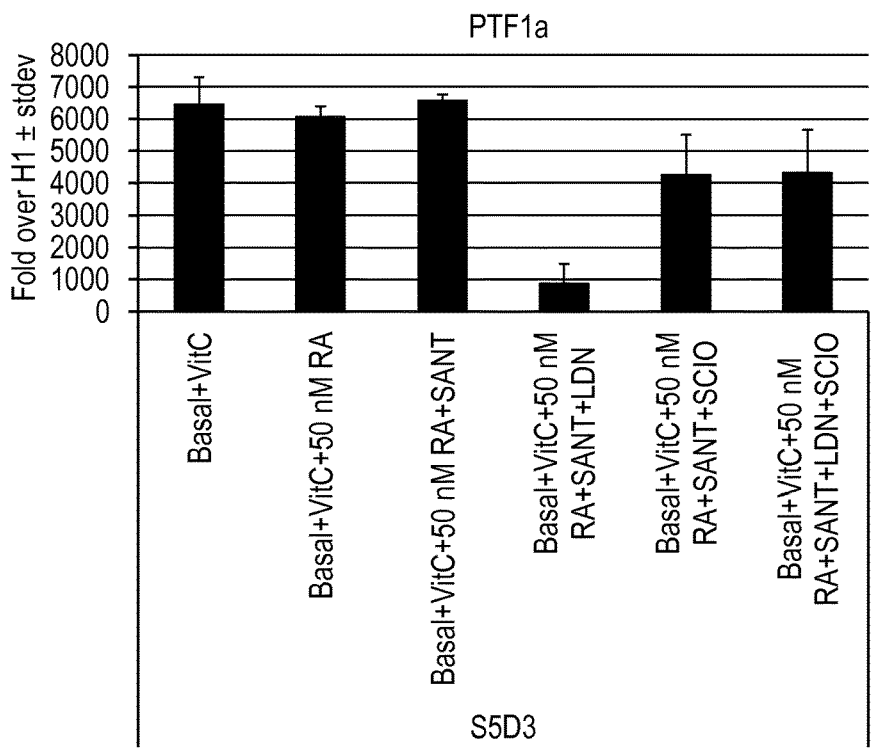
Figure 22L:
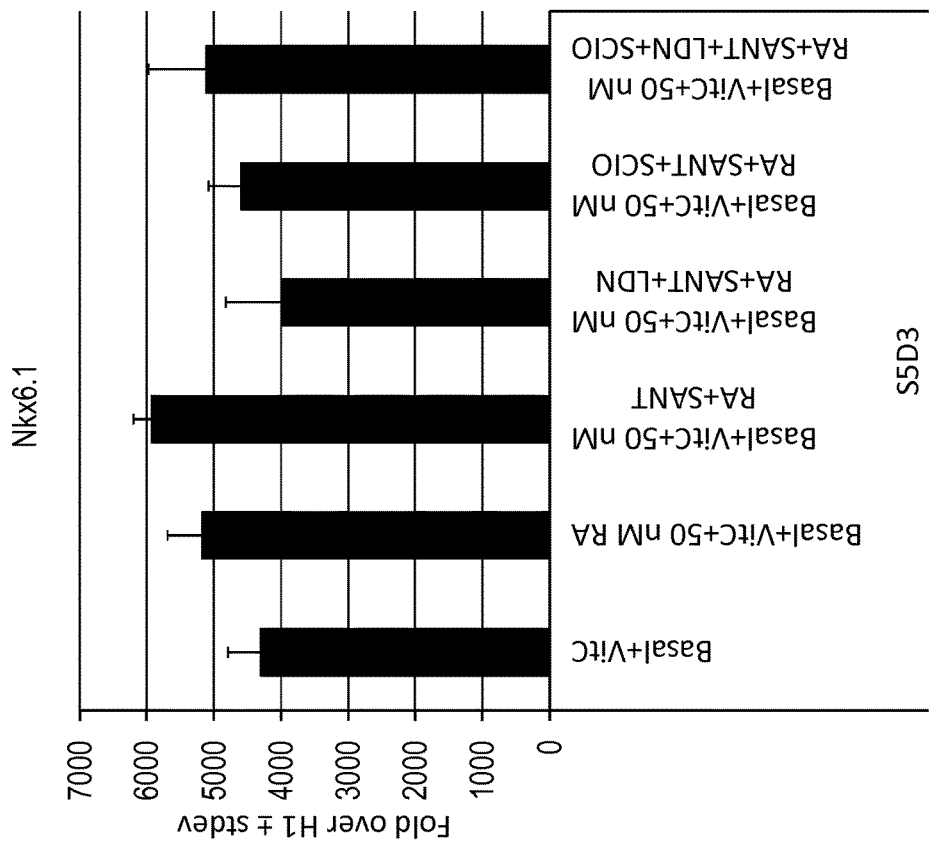
Figure 22K:
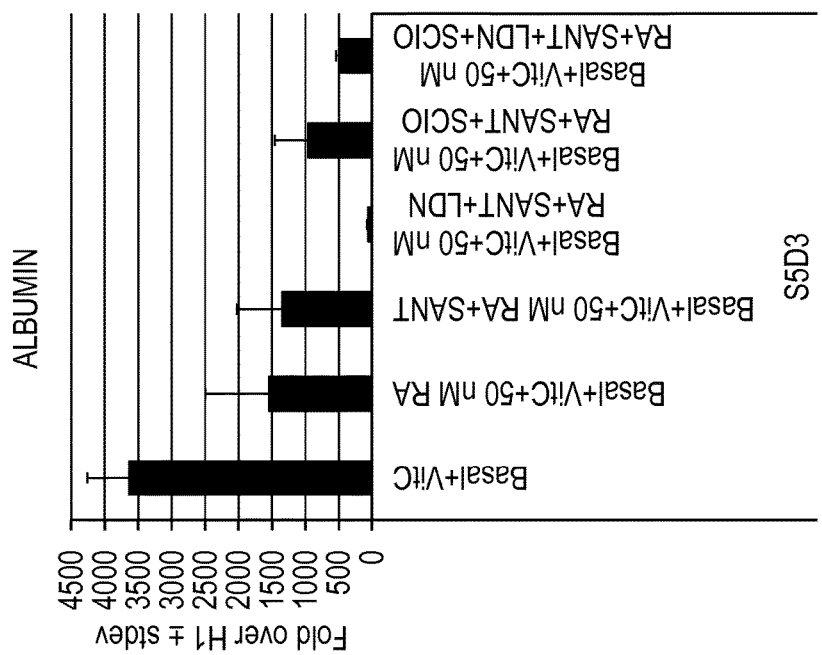

FIG. 22A through FIG. 22L show data from real-time PCR analyses of the expression of Pax4 (FIG. 22A); Pax6 (FIG. 22B); PDX1 (FIG. 22C); PTF1a (FIG. 22D); glucagon (FIG. 22E); insulin (FIG. 22F); NeuroD (FIG. 22G); ngn3 (FIG. 22H); Zic1 (FIG. 22I); CDX2 (FIG. 22J); albumin (FIG. 22K); NKX6.1 (FIG. 22L) in cells of the embryonic stem cell line H1 differentiated according to example 13 and harvested at S5 day 3.

At end of stage 5, cultures treated with combinations listed above were immune stained for insulin, glucagon, and somatostatin hormones. Table VIII summarizes average percentage of insulin positive cells, glucagon and somatostatin positive cells, and polyhormonal cells (two more hormone expression in one cell).

As shown in FIG. 22 and Table VIII, below, addition of low dose retinoic acid plus ascorbic acid at stage 5 significantly reduced overall number of hormone positive cells while increasing percentage of single hormonal insulin positive cells as compared to cultures treated only with vitamin C at S5. Furthermore, combination of retinoic acid, ascorbic acid, sonic hedgehog inhibitor, and ALK5 inhibitor further increased number of single hormonal insulin positive cells as compared to cultures treated only with ascorbic acid (Vitamin C). This data indicates that a unique combination of factors is needed to generate single hormonal insulin positive cells.

TABLE VIII

Expression of hormones as a percentage of the entire hormone count at S5 day 3.

| Treatment at S5 | % single hormonal Insulin+ | % glucagon + Plus % somatostatin+ | % Polyhormonal |
|---|---|---|---|
| +Vitamin C | 12 | 44 | 44 |
| +RA + Vitamin C | 27 | 26 | 43 |
| RA + Vitamin C + Alk5 inh + Shh Inh | 44 | 21 | 34 |

What is claimed is:

1. An in vitro culture comprising a differentiated population of human pancreatic endoderm cells in which greater than 10% of the cells are single hormonal insulin positive cells and a population of human pancreatic foregut cells in a differentiation medium, wherein the differentiation medium differentiates pancreatic foregut cells into the differentiated population of pancreatic endoderm cells in which greater than 10% of the cells are single hormonal insulin positive cells and wherein said differentiation medium comprises one of the following:
   a retinoid, ascorbic acid, and a shh-inhibitor,
   a retinoid, ascorbic acid and SANT-1,
   a retinoid, ascorbic acid, a shh-inhibitor and a TGF-β ligand,
   a retinoid, ascorbic acid, a shh-inhibitor and ALK5 inhibitor,
   a retinoid, ascorbic acid, SANT-1 and a TGF-β ligand,
   a retinoid, ascorbic acid, a shh-inhibitor, ALK5 inhibitor, and a BMP inhibitor,
   a retinoid, ascorbic acid, SANT-1, a TGF-β ligand and a BMP inhibitor; or
   a retinoid, ascorbic acid, a shh-inhibitor, a TGF-β ligand, and LDN-19318,
   wherein the presence of ascorbic acid in the differentiation medium increases the number of insulin positive cells and decreases the number of glucagon positive cells and somatostatin positive cells compared to differentiation medium without ascorbic acid.

2. The in vitro culture of claim 1, wherein the human pancreatic foregut cells are obtained by stepwise differentiation of human embryonic stem cells cultured in a medium supplemented with a TGF-β ligand.

3. The in vitro culture of claim 2, wherein the medium in said stepwise differentiation further comprises a WNT activator.

4. The in vitro culture of claim 1, wherein the human pancreatic foregut cells are obtained by stepwise differentiation of human definitive endoderm cells cultured in a medium supplemented with an FGF ligand.

5. The method of claim 1, wherein the differentiation medium further comprises a PKC activator.

6. The method of claim 1, wherein the differentiation medium comprises the retinoid, ascorbic acid, and the shh-inhibitor, and further comprises a PKC activator.

7. The in vitro culture of claim 4, wherein the medium in said stepwise differentiation further comprises ascorbic acid.

8. The in vitro culture of claim 2, wherein the human pancreatic foregut cells are obtained by stepwise differentiation of human pluripotent stem cells cultured in a medium supplemented with a TGF-β ligand.

9. The in vitro culture of claim 2, wherein the medium in said stepwise differentiation further comprises GDF-8.

10. The in vitro culture of claim 9, wherein the medium in said stepwise differentiation further comprises GSK3β inhibitor.

11. The in vitro culture of claim 10, wherein the medium in said stepwise differentiation further comprises MCX compound.

12. An in vitro culture comprising human pancreatic foregut cells in a differentiation medium supplemented with one of the following:
   a retinoid, ascorbic acid, and a shh-inhibitor;
   a retinoid, ascorbic acid and SANT-1;
   a retinoid, ascorbic acid, a shh-inhibitor, and a TGF-β ligand;

a retinoid, ascorbic acid, a shh-inhibitor and ALK5 inhibitor;

a retinoid, ascorbic acid, SANT-1 and a TGF-β ligand;

a retinoid, ascorbic acid, a shh-inhibitor, ALK5 inhibitor, and a BMP inhibitor;

a retinoid, ascorbic acid, SANT-1, a TGF-β ligand, and a BMP inhibitor; or wherein the differentiation medium differentiates the human pancreatic foregut cells into a differentiated population of human pancreatic endoderm cells in which greater than 10% of the cells are single hormonal insulin positive cells, and wherein the presence of the ascorbic acid in the differentiation medium increases the number of insulin positive cells and decreases the number of glucagon positive cells and somatostatin positive cells compared to differentiation medium without ascorbic acid.

13. The in vitro culture of claim 12, wherein the pancreatic foregut cells are obtained from stepwise differentiation of human pluripotent stem cells.

14. The in vitro culture of claim 13, wherein the stepwise differentiation comprises culturing human pluripotent stem cells in medium supplemented with GDF-8.

15. The in vitro culture of claim 14, wherein the medium in said stepwise differentiation further comprises a GSK3β inhibitor.

16. The in vitro culture of claim 15, wherein the medium in said stepwise differentiation further comprises MCX compound.

17. An in vitro culture of a differentiated population of human pancreatic endoderm cells in which greater than 10% of the cells are single hormonal insulin positive cells and a population of human pancreatic foregut cells in a differentiation medium supplemented with a retinoid, ascorbic acid and SANT-1, wherein the differentiation medium differentiates pancreatic foregut cells into the differentiated population of pancreatic endoderm cells in which greater than 10% of the cells are single hormonal insulin positive cells, and wherein the presence of the ascorbic acid in the differentiation medium increases the number of insulin positive cells and decreases the number of glucagon positive cells and somatostatin positive cells compared to differentiation medium without ascorbic acid.

18. The in vitro culture of pancreatic endoderm cells of claim 17, wherein the pancreatic foregut cells are obtained from stepwise differentiation of human pluripotent stem cells.

19. The in vitro culture of claim 18, wherein the stepwise differentiation comprises culturing human embryonic stem cells in medium supplemented with GDF-8.

20. The in vitro culture of claim 19, wherein the medium in said stepwise differentiation further comprises a GSK3β inhibitor.

21. The in vitro culture of claim 20, wherein the medium in said stepwise differentiation further comprises MCX compound.

22. The in vitro culture of claim 17, wherein the differentiation medium is further supplemented with a TGF-β ligand, a BMP inhibitor or both a TGF-β ligand and a BMP inhibitor.

23. The in vitro culture of claim 22, wherein the TGF-β ligand is ALK5 inhibitor.

24. The in vitro culture of claim 22, wherein the BMP inhibitor is LDN-193189.

25. The in vitro culture of claim 1, wherein greater than 30% of the differentiated population of pancreatic endoderm cells are PDX-1+, NKX6.1+, SOX2−, and CDX2−.

26. The in vitro culture of claim 12, wherein greater than 30% of the differentiated population of pancreatic endoderm cells are PDX-1+, NKX6.1+, SOX2−, and CDX2−.

27. The in vitro culture of claim 17, wherein greater than 30% of the differentiated population of pancreatic endoderm cells are PDX-1+, NKX6.1+, SOX2−, and CDX2−.

28. The in vitro culture of claim 1, wherein the differentiation medium comprises the retinoid, ascorbic acid, and the shh-inhibitor.

29. The in vitro culture of claim 1, wherein the differentiation medium comprises the retinoid, ascorbic acid and SANT-1.

30. The in vitro culture of claim 1, wherein the differentiation medium comprises the retinoid, ascorbic acid, the shh-inhibitor and the TGF-β ligand.

31. The in vitro culture of claim 1, wherein the differentiation medium comprises the retinoid, ascorbic acid, the shh-inhibitor and the ALK5 inhibitor.

32. The in vitro culture of claim 1, wherein the differentiation medium comprises the retinoid, ascorbic acid, SANT-1 and the TGF-β ligand.

33. The in vitro culture of claim 1, wherein the differentiation medium comprises the retinoid, ascorbic acid, the shh-inhibitor, the ALK5 inhibitor, and the BMP inhibitor.

34. The in vitro culture of claim 1, wherein the differentiation medium comprises the retinoid, ascorbic acid, SANT-1, the TGF-β ligand and the BMP inhibitor.

35. The in vitro culture of claim 1, wherein the differentiation medium comprises the retinoid, ascorbic acid, the shh-inhibitor, the TGF-β ligand, and LDN-19318.

* * * * *

UNITED STATES PATENT AND TRADEMARK OFFICE
CERTIFICATE OF CORRECTION

PATENT NO. : 10,358,628 B2
APPLICATION NO. : 14/831115
DATED : July 23, 2019
INVENTOR(S) : Rezania Page 1 of 1

It is certified that error appears in the above-identified patent and that said Letters Patent is hereby corrected as shown below:

In the Claims

In Claim 5, replace "The method" with --The *in vitro* culture--.

In Claim 6, replace "The method" with --The *in vitro* culture--.

Signed and Sealed this
Thirty-first Day of March, 2020

Andrei Iancu
*Director of the United States Patent and Trademark Office*